(12) United States Patent
Nowak et al.

(10) Patent No.: US 7,579,349 B2
(45) Date of Patent: Aug. 25, 2009

(54) 4-(PYRAZOL-3-YLAMINO) PYRIMIDINE DERIVATIVES FOR USE IN THE TREATMENT OF CANCER

(75) Inventors: Thorsten Nowak, Macclesfield (GB); Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 413 days.

(21) Appl. No.: 10/595,390

(22) PCT Filed: Oct. 11, 2004

(86) PCT No.: PCT/GB2004/004307

§ 371 (c)(1), (2), (4) Date: Sep. 6, 2006

(87) PCT Pub. No.: WO2005/040159

PCT Pub. Date: May 6, 2005

(65) Prior Publication Data

US 2007/0037888 A1    Feb. 15, 2007

(30) Foreign Application Priority Data

Oct. 17, 2003 (GB) .................. 0324335.9
Jun. 2, 2004 (GB) .................. 0412194.3

(51) Int. Cl.
C07D 413/14 (2006.01)
A61K 31/506 (2006.01)

(52) U.S. Cl. .............. 514/235.8; 514/252.18; 514/252.19; 514/255.05; 514/275; 544/122; 544/295; 544/296; 544/324

(58) Field of Classification Search ............ 544/122, 544/295, 296, 324; 514/235.8, 252.18, 252.19, 514/255.05, 275
See application file for complete search history.

(56) References Cited

U.S. PATENT DOCUMENTS 4,038,240 A    7/1977    Hugl et al.

FOREIGN PATENT DOCUMENTS

| DE | 2426180 A1 | 12/1975 |
|---|---|---|
| WO | 97/19065 A1 | 5/1997 |
| WO | 00/12485 A1 | 3/2000 |
| WO | 00/35455 A1 | 6/2000 |
| WO | 00/39101 A1 | 7/2000 |
| WO | 00/63182 A2 | 10/2000 |
| WO | 01/22938 A1 | 4/2001 |
| WO | 01/60816 A1 | 8/2001 |
| WO | 01/64655 A1 | 9/2001 |
| WO | 01/64656 A1 | 9/2001 |
| WO | 01/85699 A2 | 11/2001 |
| WO | 02/22601 A1 | 3/2002 |
| WO | 02/22602 A2 | 3/2002 |
| WO | 02/22603 A1 | 3/2002 |
| WO | 02/22604 A1 | 3/2002 |
| WO | 02/22605 A1 | 3/2002 |
| WO | 02/22606 A1 | 3/2002 |
| WO | 02/22607 A1 | 3/2002 |
| WO | 02/22608 A1 | 3/2002 |
| WO | 02/50065 A2 | 6/2002 |
| WO | 03/048133 A1 | 6/2003 |

OTHER PUBLICATIONS

Simone, Oncology: Introduction, Cecil Textbook of Medicine, 20$^{th}$ Edition, vol. 1, pp. 1004-1010, 1996.*
LeRoith et al., The insulin-like growth factor system and cancer, Cancer Letters, 195 (2003), pp. 127-137.*
Breault, Gloria A., et al., "Cyclin-Dependent Kinase 4 Inhibitors as a Treatment for Cancer. Part 2: Identification and Optimisation of Substituted 2,4-Bis Anilino Pyrimidines", Bioorganic & Medicinal Chemistry Letters, 2003, 2961-2966, vol. 13.
Pierce, Albert C. et al., "CH . . . O and CH . . . N Hydrogen Bonds in Ligand Design: A Novel Quinazolin-4-ylthiazol-2-ylamine Protein Kinase Inhibitor", J. Med. Chem, 2005, 1278-1281, vol. 48.

* cited by examiner

*Primary Examiner*—Deepak Rao

(57) ABSTRACT

A compound of Formula (I); wherein the substituents are as defined in the text for use in modulating insulin-like growth factor 1 receptor activity in a warm blooded animal such as man.

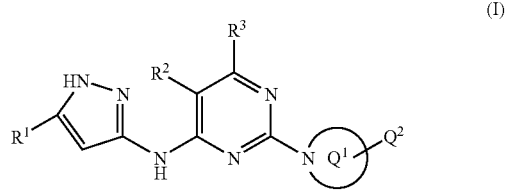

(I)

33 Claims, No Drawings

4-(PYRAZOL-3-YLAMINO) PYRIMIDINE DERIVATIVES FOR USE IN THE TREATMENT OF CANCER

CROSS-REFERENCE TO RELATED APPLICATIONS

This application is a US National Stage under 35 U.S.C § 371 of International Application No. PCT/GB2004/004307 (filed 11 Oct. 2004) which claims priority under 35 U.S.C. § 119(a)-(d) to Application No. GB 0324335.9 filed on 17 Oct. 2003 and GB 0412194.3 filed on 2 Jun. 2004.

The present invention relates to novel pyrimidine derivatives, processes for their preparation, pharmaceutical compositions containing them and their use in therapy.

The insulin-like growth factor (IGF) axis consists of ligands, receptors, binding proteins and proteases. The two ligands, IGF-I and IGF-II, are mitogenic peptides that signal through interaction with the type 1 insulin-like growth factor receptor (IGF-1R), a hetero-tetrameric cell surface receptor. Binding of either ligand stimulates activation of a tyrosine kinase domain in the intracellular region of the β-chain and results in phosphorylation of several tyrosine residues resulting in the recruitment and activation of various signalling molecules. The intracellular domain has been shown to transmit signals for mitogenesis, survival, transformation, and differentiation in cells. The structure and function of the IGF-1R has been reviewed by Adams et al (*Cellular and Molecular Life Sciences*, 57, 1050-1093, 2000). The IGF-IIR (also known as mannose 6-phosphate receptor) has no such kinase domain and does not signal mitogenesis but may act to regulate ligand availability at the cell surface, counteracting the effect of the IGF-1R. The IGF binding proteins (IGFBP) control availability of circulating IGF and release of IGF from these can be mediated by proteolytic cleavage. These other components of the IGF axis have been reviewed by Collett-Solberg and Cohen (*Endocrine*, 12, 121-136, 2000).

There is considerable evidence linking IGF signalling with cellular transformation and the onset and progression of tumours. IGF has been identified as the major survival factor that protects from oncogene induced cell death (Harrington et al, *EMBO J*, 13, 3286-3295, 1994). Cells lacking IGF-1R have been shown to be refractory to transformation by several different oncogenes (including SV40T antigen and ras) that efficiently transform corresponding wild-type cells (Sell et al., *Mol. Cell Biol.*, 14, 3604-12, 1994). Upregulation of components of the IGF axis has been described in various tumour cell lines and tissues, particularly tumours of the breast (Surmacz, *Journal of Mammary Gland Biology & Neoplasia*, 5, 95-105, 2000), prostate (Djavan et al, *World J. Urol.*, 19, 225-233, 2001, and O'Brien et al, *Urology*, 58, 1-7, 2001) and colon (Guo et al, *Gastroenterology*, 102, 1101-1108, 1992). Conversely, IGF-IIR has been implicated as a tumour suppressor and is deleted in some cancers (DaCosta et al, *Journal of Mammary Gland Biology & Neoplasia*, 5, 85-94, 2000). There is a growing number of epidemiological studies linking increased circulating IGF (or increased ratio of IGF-1 to IGFBP3) with cancer risk (Yu and Rohan, *J. Natl. Cancer Inst.*, 92, 1472-1489, 2000). Transgenic mouse models also implicate IGF signalling in the onset of tumour cell proliferation (Lamm and Christofori, *Cancer Res.* 58, 801-807, 1998, Foster et al, *Cancer Metas. Rev.*, 17, 317-324, 1998, and DiGiovanni et al, *Proc. Natl. Acad. Sci.*, 97, 3455-3460, 2000).

Several in vitro and in vivo strategies have provided the proof of principal that inhibition of IGF-1R signalling reverses the transformed phenotype and inhibits tumour cell growth. These include neutralizing antibodies (Kalebic et al *Cancer Res.*, 54, 5531-5534, 1994), antisense oligonucleotides (Resnicoff et al, *Cancer Res.*, 54, 2218-2222, 1994), triple-helix forming oligonucleotides (Rinninsland et al, *Proc. Natl. Acad. Sci.*, 94, 5854-5859, 1997), antisense mRNA (Nakamura et al, *Cancer Res.*, 60, 760-765, 2000) and dominant negative receptors (D'Ambrosio et al., *Cancer Res.*, 56, 4013-4020, 1996). Antisense oligonucleotides have shown that inhibition of IGF-1R expression results in induction of apoptosis in cells in vivo (Resnicoff et al, *Cancer Res.*, 55, 2463-2469, 1995) and have been taken into man (Resnicoff et al, *Proc. Amer. Assoc. Cancer Res.*, 40 Abs 4816, 1999). However, none of these approaches is particularly attractive for the treatment of major solid tumour disease.

Since increased IGF signalling is implicated in the growth and survival of tumour cells, and blocking IGF-1R function can reverse this, inhibition of the IGF-1R tyrosine kinase domain is an appropriate therapy by which to treat cancer. In vitro and in vivo studies with the use of dominant-negative IGF-1R variants support this. In particular, a point mutation in the ATP binding site which blocks receptor tyrosine kinase activity has proved effective in preventing tumour cell growth (Kulik et al, *Mol. Cell. Biol.*, 17, 1595-1606, 1997). Several pieces of evidence imply that normal cells are less susceptible to apoptosis caused by inhibition of IGF signalling, indicating that a therapeutic margin is possible with such treatment (Baserga, *Trends Biotechnol.*, 14, 150-2, 1996).

There are few reports of selective IGF-1R tyrosine kinase inhibitors. Parrizas et al. described tyrphostins that had some efficacy in vitro and in vivo (Parrizas et al., *Endocrinology*, 138:1427-33 (1997)). These compounds were of modest potency and selectivity over the insulin receptor. Telik Inc. have described heteroaryl-aryl ureas which have selectivity over insulin receptors but potency against tumour cells in vitro is still modest (Published PCT Patent Application No. WO 00/35455).

Pyrimidine derivatives substituted at the 2- and 4-positions by a substituted amino group having IGF-IR tyrosine kinase inhibitory activity are described in WO 03/048133. Compounds in which the nitrogen atom of the amino substituent forms part of a heterocyclic ring are not disclosed.

WO 02/50065 discloses that certain pyrazolyl-amino substituted pyrimidine derivatives have protein kinase inhibitory activity, especially as inhibitors of Aurora-2 and glycogen synthase kinase-3 (GSK-3), and are useful for treating diseases such as cancer, diabetes and Alzheimer's disease. The compounds disclosed have a substituted amino substituent at the 2-position of the pyrimidine ring but again there is no disclosure of compounds in which the nitrogen atom of the amino substituent forms part of a heterocyclic ring.

Pyrazolyl-amino substituted pyrimidine derivatives having Aurora-2 and glycogen synthase kinase-3 (GSK-3) inhibitory activity in which the 2-position of the pyrimidine ring is substituted by an N-linked heterocyclic ring are disclosed generically in WO 02/22601, WO 02/22602, WO 02/22603, WO 02/22604, WO 02/22605, WO 02/22606, WO 02/22607 and WO 02/22608. In the large majority of the over four hundred compounds exemplified, the pyrimidine ring is present as part of a fused ring system, however, and in none of the exemplified compounds is the heterocyclic substituent at this position itself substituted by another ring substituent.

WO 01/60816 discloses that certain substituted pyrimidine derivatives have protein kinase inhibitory activity. There is no disclosure in WO 01/60816 of pyrimidine derivatives having a pyrazolyl-amino substituent at the 4-position on the pyrimidine ring and a substituted N-linked saturated monocyclic ring at the 2-position on the pyrimidine ring.

The present invention provides a compound of formula (I):

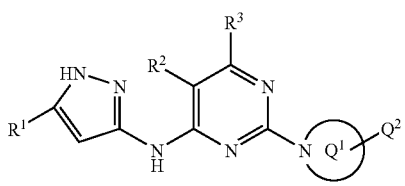

or a pharmaceutically acceptable salt thereof, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen, hydroxyl or halogen, or a (C1-C6)alkyl, (C2-C6)alkenyl, (C2-6)alkynyl, (C3-C8)cycloalkyl, (C3-C8)cycloalkyl(C1-C6)alkyl, (C1-C6)alkoxy, (C3-8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)$R^{3b}$, —O$R^{3b}$, —S$R^{3b}$, —NH$R^{3b}$, —N[(C1-C6)alkyl]$R^{3b}$, —S(O)$_m$$R^{3a}$ or —N($R^{3c}$)C(O)$R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, $R^{3b}$ represents a saturated monocyclic 4-, 5- or 6-membered heterocyclic ring comprising at least one ring heteroatom selected from nitrogen, oxygen and sulphur and $R^{3c}$ represents hydrogen or (C1-C6)alkyl, or $R^3$ represents a saturated monocyclic 5- to 6-membered heterocyclic ring comprising at least one ring heteroatom selected from nitrogen, oxygen and sulphur, or $R^3$ represents a 5- to 6-membered heteroaromatic ring comprising at least one ring heteroatom selected from nitrogen, oxygen and sulphur, or $R^3$ represents a 2,7-diazaspiro[3.5]nonane group, each of which groups or rings within $R^3$ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino(C1-C6)alkyl, di-[(C1-C6)alkyl]amino(C1-C6)alkyl, (C3-C8)cycloalkylamino(C1-C6)alkyl, (C3-C6)cycloalkyl(C1-C3)alkylamino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N($R^{3c}$)C(O)$R^{3a}$ wherein $R^{3a}$ and $R^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;

—NQ$^1$ represents an N-linked saturated monocyclic 5- to 6-membered ring containing one nitrogen heteroatom and optionally comprising one or more additional ring heteroatoms selected from nitrogen, oxygen and sulphur;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —N$R^4R^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)N$R^6R^7$ and —SO$_2$N$R^8R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —N$R^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)N$R^{12}R^{13}$ and —SO$_2$N$R^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2;

and wherein any saturated monocyclic ring optionally bears 1 or 2 oxo or thioxo substituents.

According to a further aspect of the present invention, there is provided a compound of formula (I) or a pharmaceutically acceptable salt thereof, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —C(O)$R^{3b}$, —O$R^{3b}$, —S$R^{3b}$, —NH$R^{3b}$, —N[(C1-C6)alkyl]$R^{3b}$ or —S(O)$_m$$R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, and $R^{3b}$ represents a saturated monocyclic 5- to 6-membered ring containing one or more heteroatoms selected from nitrogen, oxygen and sulphur, or $R^3$ represents a saturated monocyclic 5- to 6-membered heterocyclic ring, which ring comprises at least one ring heteroatom selected from nitrogen, oxygen and sulphur, each of which groups or rings within $R^3$ may be optionally substituted by one or more substituents independently selected from (C1-C6)alkyl, (C1-C6)alkoxy, (C1-C6)alkoxy(C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-6)alkanoylamino or a saturated monocyclic 4-, 5-, 6- or 7-membered ring, which ring may optionally comprise one or more heteroatoms selected from nitrogen, oxygen and sulphur;

—$NQ^1$ represents an N-linked saturated monocyclic 5- to 6-membered ring containing one nitrogen heteroatom and optionally comprising one or more additional ring heteroatoms selected from nitrogen, oxygen and sulphur;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —$NR^4R^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —$S(O)_p$(C1-C4)alkyl, —$C(O)NR^6R^7$ and —$SO_2NR^8R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —$NR^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —$S(O)_n$(C1-C6)alkyl, —$C(O)NR^{12}R^{13}$ and —$SO_2NR^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2.

According to a further aspect of the present invention, there is provided a compound of formula (I) or a pharmaceutically acceptable salt thereof, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by halogen or a (C1-C6)alkoxy group;

$R^2$ represents hydrogen, halogen or trifluoromethyl;

$R^3$ represents hydrogen or a (C1-C6)alkyl, (C3-C8)cycloalkyl, (C3-C8)cycloalkyl(C1-C6)alkyl, (C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, (C1-C6)alkylamino, (C3-C8)cycloalkylamino, (C3-C8)cycloalkyl(C1-C6)alkylamino, (C1-C6)alkoxyamino or —$S(O)_mR^{3a}$ group, each of which groups within $R^3$ may be optionally substituted by at least one substituent selected from (C1-C6)alkoxy, (C1-C6)alkoxy(C1-C6)alkoxy, halogen, hydroxyl, trifluoromethyl, or a saturated monocyclic 4-, 5-, 6- or 7-membered ring, which ring may optionally comprise one or more heteroatoms selected from nitrogen, oxygen and sulphur, wherein $R^{3a}$ represents a (C1-C6)alkyl, (C3-C8)cycloalkyl, (C3-C8)cycloalkyl(C1-C6)alkyl or (C1-C6)alkoxy group and m is 0, 1 or 2;

—$NQ^1$ represents an N-linked saturated monocyclic 5- to 6-membered ring containing one nitrogen heteroatom and optionally comprising one or more additional ring heteroatoms selected from nitrogen, oxygen and sulphur;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents, which may be the same or different, selected from (C1-C6)alkyl or (C1-C6)alkoxy (either of which may be optionally substituted by at least one substituent selected from halogen, amino, hydroxyl and trifluoromethyl), halogen, nitro, cyano, —$NR^4R^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —$S(O)_p$(C1-C4)alkyl, —$C(O)NR^6R^7$ and —$SO_2NR^8R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by at least one substituent selected from (C1-C6)alkyl or (C1-C6)alkoxy (either of which may be optionally substituted by at least one substituent selected from halogen, amino, hydroxyl and trifluoromethyl), halogen, nitro, cyano, —$NR^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —$S(O)_n$(C1-C6)alkyl, —$C(O)NR^{12}R^{13}$ and —$SO_2NR^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2.

Unless otherwise indicated, the term 'alkyl' when used alone or in combination, refers to a straight chain or branched chain alkyl moiety. A (C1-C6)alkyl group has from one to six carbon atoms including methyl, ethyl, n-propyl, isopropyl, tert-butyl, n-pentyl, n-hexyl and, the like. References to '(C1-C4)alkyl' will be understood accordingly to mean a straight or branched chain alkyl moiety having from 1 to 4 carbon atoms. References to individual alkyl groups such as "propyl" are specific for the straight-chain version only, references to individual branched-chain alkyl groups such as "isopropyl" are specific for the branched-chain version only.

Analogously, the terms '(C1-C6)alkoxy' and '(C1-C4)alkoxy', when used alone or in combination, will be understood to refer to straight or branched chain groups having from one to six or from one to four carbon atoms respectively and includes such groups as methoxy, ethoxy, propoxy, isopropoxy and butoxy.

A '(C2-C6)alkenyl' group refers to a straight or branched chain group having from two to six carbon atoms such as vinyl, isopropenyl, allyl and but-2-enyl. Similarly, a '(C2-C6)alkynyl' group refers to a straight or branched chain group having from two to six carbon atoms such as ethynyl, 2-propynyl and but-2-ynyl.

The term 'cycloalkyl', when used alone or in combination, refers to a saturated alicyclic moiety having from three to eight carbon atoms and includes, for example, cyclopropyl, cyclobutyl, cyclopentyl, cyclohexyl and cycloheptyl. References to (C3-C6)cycloalkyl will be understood accordingly to mean a saturated alicyclic moiety having from 3 to 6 carbon atoms, representative examples of which are listed above.

As used herein, the term 'halogen' includes fluorine, chlorine, bromine and iodine.

The term 'optionally substituted' is used herein to indicate optional substitution by the group or groups specified at any suitable available position.

Suitable values for any of the substituents herein, for example the 'R' groups ($R^1$ to $R^{15}$, $R^{3a}$, $R^{3b}$ or $R^{3c}$) or for various groups within a —$NQ^1$, $Q^2$ or $Q^3$ group include:— for halogen: fluoro, chloro, bromo and iodo;

for (C1-C6)alkyl: methyl, ethyl, propyl, isopropyl, tert-butyl, n-pentyl and n-hexyl;

for (C2-C6)alkenyl: vinyl, isopropenyl, allyl and but-2-enyl;

for (C2-C6)alkynyl: ethynyl, 2-propynyl and but-2-ynyl;

for (C1-C6)alkoxy: methoxy, ethoxy, propoxy, isopropoxy and butoxy;

for (C1-C6)alkoxy(C1-C6)alkoxy: methoxymethoxy, methoxyethoxy, ethoxymethoxy, propoxymethoxy and butoxymethoxy;

for (C1-C6)alkoxy(C1-C6)alkyl: methoxymethyl, methoxyethyl, ethoxymethyl, propoxymethyl and butoxymethyl;

for tri-[(C1-C4)alkyl]silyl trimethylsilyl, triethylsilyl, dimethyl-ethylsilyl and methyl-diethylsilyl;

for (C1-C6)alkylthio: methylthio, ethylthio and propylthio;

for (C1-C6)alkylamino: methylamino, ethylamino, propylamino, isopropylamino and butylamino;

for di-[(C1-C6)alkyl]amino: dimethylamino, diethylamino, N-ethyl-N-methylamino and diisopropylamino;

for amino(C1-C6)alkyl: aminomethyl, aminoethyl, aminopropyl and aminobutyl;

for (C1-C6)alkylamino(C1-C6)alkyl: methylaminomethyl, methylaminoethyl, methylaminopropyl, ethylaminomethyl, ethylaminoethyl, propylaminomethyl, isopropylaminoethyl and butylaminomethyl;

for di-[(C1-C6)alkyl]amino(C1-C6)alkyl: dimethylaminomethyl, dimethylaminoethyl, dimethylaminobutyl, diethylaminomethyl, diethylaminoethyl, diethylaminopropyl, N-ethyl-N-methylaminomethyl, N-ethyl-N-methylaminomethyl and diisopropylaminoethyl;

for (C1-C6)alkylcarbonyl: methylcarbonyl, ethylcarbonyl, propylcarbonyl and tert-butylcarbonyl;

for (C1-C6)alkoxycarbonyl: methoxycarbonyl, ethoxycarbonyl, propoxycarbonyl and tert-butoxycarbonyl;

for N—(C1-C6)alkylcarbamoyl: N-methylcarbamoyl, N-ethylcarbamoyl and N-propylcarbamoyl;

for N,N-di-[(C1-C6)alkyl]carbamoyl: N,N-dimethylcarbamoyl, N-ethyl-N-methylcarbamoyl and N,N-diethylcarbamoyl;

for (C3-C8)cycloalkyl: cyclopropyl, cyclobutyl, cyclopentyl, cyclohexyl and cycloheptyl;

for (C3-C8)cycloalkyl(C1-C6)alkyl: cyclopropylmethyl, cyclobutylmethyl, cyclopentylmethyl, cyclohexylmethyl and cycloheptylmethyl;

for (C3-C8)cycloalkyl(C1-C6)alkoxy: cyclopropylmethoxy, cyclobutylmethoxy, cyclopentylmethoxy, cyclohexylmethoxy and cycloheptylmethoxy;

for (C3-C8)cycloalkylcarbonyl: cyclopropylcarbonyl, cyclobutylcarbonyl, cyclopentylcarbonyl, cyclohexylcarbonyl and cycloheptylcarbonyl;

for (C3-C8)cycloalkyl(C1-C6)alkylcarbonyl: cyclopropylmethylcarbonyl, cyclobutylmethylcarbonyl, cyclopentylmethylcarbonyl and cyclohexylmethylcarbonyl;

for (C3-C8)cycloalkylamino: cyclopropylamino, cyclobutylamino, cyclopentylamino, cyclohexylamino and cycloheptylamino;

for (C3-C8)cycloalkylamino(C1-C6)alkyl: cyclopropylaminomethyl, cyclopropylaminoethyl, cyclopropylaminopropyl, cyclobutylaminomethyl, cyclopentylaminoethyl, cyclopentylaminopropyl cyclohexylaminoethyl and cycloheptylaminoethyl;

for (C3-C8)cycloalkyl(C1-C6)alkylamino: cyclopropylmethylamino, cyclopropylethylamino, cyclopentylmethylamino and cyclohexylmethylamino;

for (C3-C8)cycloalkyl(C1-C6)alkylamino(C1-C6)alkyl: cyclopropylmethylaminomethyl, cyclopropylmethylaminoethyl, cyclopropylmethylaminopropyl, cyclopropylethylaminoethyl, cyclopropylethylaminobutyl, cyclopentylmethylaminoethyl, cyclopentylmethylaminobutyl and cyclohexylmethylaminoethyl;

for (C1-C6)alkoxyamino: methoxyamino, ethoxyamino, propoxyamino and butoxyamino;

for (C1-C6)alkanoyl: formyl, acetyl, propionyl, butyryl and isobuyryl;

for (C2-C6)alkanoylamino: acetamido and propionamido;

for (C1-C6)alkylsulphonyl: methylsulphonyl and ethylsulphonyl; and for (C1-C6)alkylsulphinyl: methylsulphinyl and ethylsulphinyl.

A 'heteroatom' is a nitrogen, sulphur or oxygen atom. Where rings include nitrogen atoms, these may be substituted as necessary to fulfil the bonding requirements of nitrogen or they may be linked to the rest of the structure by way of the nitrogen atom. Nitrogen atoms may also be in the form of N-oxides. Sulphur atoms may be in the form of S, S(O) or $SO_2$.

A 'saturated monocyclic 3-, 4-, 5-, 6- or 7-membered ring, which ring may optionally comprise one or more heteroatoms selected from nitrogen, oxygen and sulphur' may be a carbocyclic ring (that is an alicyclic ring having ring carbon atoms only) or is a heterocyclic ring containing three to seven atoms of which at least one is a heteroatom selected from nitrogen, oxygen and sulphur and which ring may, unless otherwise specified, be carbon or nitrogen linked. When the 'saturated monocyclic 3-, 4-, 5-, 6- or 7-membered ring, which ring may optionally comprise one or more heteroatoms selected from nitrogen, oxygen and sulphur' is a heterocyclic ring, the heterocyclic ring preferably contains from one to four, more preferably from one to three, even more preferably from one to two, heteroatoms independently selected from nitrogen, oxygen and sulphur. Unless specified otherwise, the heterocyclic ring may be carbon or nitrogen linked. Examples of suitable carbocyclic rings include cyclopropyl, cyclobutyl, cyclopentyl, cyclohexyl and cycloheptyl. A saturated monocyclic 3-, 4-, 5-, 6- or 7-membered heterocyclic ring may suitably be selected from oxiranyl, azetidinyl, dioxanyl, trioxanyl, oxepanyl, dithianyl, trithianyl, oxathianyl, thiomorpholinyl, pyrrolidinyl, piperidinyl, imidazolidinyl, morpholinyl, tetrahydrofuranyl, tetrahydropyranyl and piperazinyl (particularly azetidinyl, pyrrolidinyl, piperidinyl, morpholinyl, tetrahydrofuranyl, tetrahydropyranyl and piperazinyl). A saturated heterocyclic ring that bears 1 or 2 oxo or thioxo substituents may, for example, be 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Where reference is made to a 'saturated monocyclic 5- to 6-membered ring' or to a 'saturated monocyclic 5- to 6-membered heterocyclic ring', it will be understood that this refers to rings containing five or six ring atoms, representative examples of which are listed above. Where reference is made to a 'saturated monocyclic 4-, 5- or 6-membered ring' or to a 'saturated monocyclic 4-, 5- or 6-membered heterocyclic ring', it will be understood that this refers to rings containing four, five or six ring atoms, representative examples of which are listed above.

An 'N-linked saturated monocyclic 5- to 6-membered ring containing one nitrogen heteroatom, and optionally comprising one or more additional ring heteroatoms selected from nitrogen, oxygen and sulphur' is a saturated monocyclic heterocyclic ring containing five or six ring atoms which, in addition to the nitrogen atom through which it is linked to the rest of the structure, optionally comprises at least one heteroatom selected from nitrogen, oxygen and sulphur. The saturated monocyclic heterocyclic ring containing five or six ring atoms preferably comprises from one to three, more preferably from one to two, heteroatoms independently selected from nitrogen, oxygen and sulphur in addition to the nitrogen atom through which it is linked to the rest of the structure. Particular examples of such ring systems include pyrrolidinyl, piperidinyl, morpholinyl and piperazinyl.

A '5- to 6-membered heteroaromatic ring comprising at least one ring heteroatom selected from nitrogen, oxygen and sulphur' is a fully unsaturated, aromatic monocyclic ring containing five or six atoms of which at least one is a heteroatom selected from nitrogen, oxygen and sulphur, which ring may, unless otherwise specified, be carbon or nitrogen linked. Preferably, the 5- to 6-membered heteroaromatic ring contains from one to four heteroatoms independently selected from nitrogen, oxygen and sulphur. Particular examples of such ring systems include pyridyl, imidazolyl, isoxazolyl, pyrazolyl, furyl, pyrazinyl, pyridazinyl, pyrimidinyl, pyrrolyl, thiazolyl, oxazolyl, oxadiazolyl, isothiazolyl, triazolyl, tetrazolyl or thienyl.

A 'saturated or unsaturated 5- to 6-membered monocyclic ring which may comprise at least one ring heteroatom selected from nitrogen, oxygen and sulphur' is a saturated or fully or partially unsaturated monocyclic ring containing five or six atoms of which optionally at least one is a heteroatom selected from nitrogen, oxygen and sulphur, which ring may, unless otherwise specified, be carbon or nitrogen linked. The ring may have alicyclic or aromatic properties. An aromatic monocyclic ring may be aryl (such as phenyl) or heteroaromatic, representative examples of which are listed above.

As used herein, the term 'heterocyclic ring' refers to a saturated monocyclic ring system having from 3 to 8 ring atoms in which one or more ring carbons is replaced by a heteroatom selected from nitrogen, oxygen and sulphur. Preferably, the heterocyclic ring contains from one to four, more preferably from one to three, even more preferably from one to two, heteroatoms independently selected from nitrogen, oxygen and sulphur. Examples include pyrrolidinyl and piperidinyl.

When $R^3$ is a 2,7-diazaspiro[3.5]nonane group, it is preferably linked to the pyrimidine ring via. a nitrogen atom, particularly via. the nitrogen atom at the 7-position. When the 2,7-diazaspiro[3.5]nonane group carries a substituent, this may be at any available carbon or nitrogen atom, for example at any nitrogen atom that is not attached to the pyrimidine ring. A particular substituted 2,7-diazaspiro[3.5]nonane group may, for example, be 2-(tert-butoxycarbonyl)-2,7-diazaspiro[3.5]nonane.

Where $R^4$ and $R^5$, or $R^6$ and $R^7$, or $R^8$ and $R^9$, or $R^{10}$ and $R^{11}$, or $R^{12}$ and $R^{13}$, or $R^{14}$ and $R^{15}$ form a saturated heterocyclic ring, the only heteroatom present is the nitrogen atom to which $R^4$ and $R^5$, or $R^6$ and $R^7$, or $R^8$ and $R^9$, or $R^{10}$ and $R^{11}$, or $R^{12}$ and $R^{13}$, or $R^{14}$ and $R^{15}$ are attached. The saturated heterocyclic ring is preferably a 4- to 7-membered ring, including the nitrogen atom to which $R^4$ and $R^5$, or $R^6$ and $R^7$, or $R^8$ and $R^9$, or $R^{10}$ and $R^{11}$, or $R^{12}$ and $R^{13}$, or $R^{14}$ and $R^{15}$ are attached.

$R^1$ is suitably an optionally substituted (C3-C8)cycloalkyl(C1-C6)alkyl group (such as cyclopropylmethyl, cyclopentylmethyl, cyclohexylmethyl) but is preferably an optionally substituted (C1-C6)alkyl group (particularly a (C1-C4)alkyl group, for example methyl, ethyl, propyl, isopropyl, tert-butyl) or an optionally substituted (C3-C8)cycloalkyl group (particularly a (C3-C6)cycloalkyl group, such as cyclopropyl, cyclopentyl, cyclohexyl). In particular, $R^1$ is an unsubstituted (C1-C6) (preferably (C1-C4)) alkyl group or an unsubstituted (C3-C8) (preferably (C3-C6)) cycloalkyl group.

In one embodiment of the invention, $R^1$ represents a (C1-C4)alkyl group, especially methyl, ethyl or tert-butyl, more especially methyl or tert-butyl, even more especially methyl.

In another embodiment, $R^1$ represents a (C3-C6)cycloalkyl group, especially cyclopropyl.

$R^2$ may be hydrogen or trifluoromethyl but is preferably halogen (such as fluorine, chlorine, bromine or iodine).

In one preferred embodiment, $R^2$ represents chlorine or fluorine (particularly chlorine). In another preferred embodiment, $R^2$ is hydrogen.

In one embodiment, $R^3$ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)$R^{3b}$, —O$R^{3b}$, —NH$R^{3b}$, —N[(C1-C6)alkyl]$R^{3b}$, S(O)$_m$$R^{3a}$ or N($R^{3c}$)C(O)$R^{3a}$ group, wherein $R^{3a}$ represents a (C1-C6)alkyl or (C1-C6)alkoxy group, m is 0, 1 or 2, $R^{3b}$ represents a saturated monocyclic 4-, 5- or 6-membered heterocyclic ring comprising at least one ring heteroatom selected from nitrogen, oxygen and sulphur and $R^{3c}$ represents hydrogen or (C1-C6)alkyl, or $R^3$ represents a saturated monocyclic 5- to 6-membered heterocyclic ring comprising at least one ring heteroatom selected from nitrogen, oxygen and sulphur, or $R^3$ represents a 5- to 6-membered heteroaromatic ring comprising at least one ring heteroatom selected from nitrogen, oxygen and sulphur, or $R^3$ represents a 2,7-diazaspiro[3.5]nonane group. Each of these groups or rings within $R^3$ may be optionally substituted by one or more (for example one or two, particularly one) substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, amino(C1-C6)alkyl, (C1-C6)alkylamino(C1-C6)alkyl, di-[(C1-C6)alkyl]amino(C1-C6)alkyl, (C1-C6)alkoxycarbonyl, carbamoyl, (C1-C6)alkylcarbamoyl, di-

[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N($R^{3c}$)C(O)$R^{3a}$ wherein $R^{3a}$ and $R^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (for example one or two, particularly one) (C1-C4)alkyl, hydroxyl or cyano groups. Any saturated monocyclic ring within $R^3$ optionally bears 1 or 2 oxo or thioxo substituents.

In another embodiment, $R^3$ represents hydrogen, hydroxyl or halogen, or a (C1-C6)alkyl, (C2-C6)alkenyl, (C2-C6)alkynyl, (C3-C8)cycloalkyl, (C1-C6)alkoxy, (C1-C6)alkoxycarbonyl, amino, (C1-C6)alkylamino, di-[(C1-C6)alkyl]amino, (C3-C8)cycloalkylamino, carbamoyl, (C1-C6)alkylcarbamoyl, di-[(C1-C6)alkyl]carbamoyl, —C(O)$R^{3b}$, —O$R^{3b}$, —NH$R^{3b}$ or —S(O)$_m$$R^{3a}$ group, wherein $R^{3a}$ represents a (C1-C6)alkyl group, m is 0 and $R^{3b}$ represents a saturated monocyclic 4-, 5- or 6-membered heterocyclic ring comprising at least one ring heteroatom selected from nitrogen, oxygen and sulphur, or $R^3$ represents a saturated monocyclic 5- to 6-membered heterocyclic ring comprising at least one ring heteroatom selected from nitrogen and oxygen, or $R^3$ represents a 5- to 6-membered heteroaromatic ring comprising at least one ring heteroatom selected from nitrogen and oxygen, or $R^3$ represents a 2,7-diazaspiro[3.5]nonane group. Each of these groups or rings within $R^3$ may be optionally substituted by one or more (for example one or two, particularly one) substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, amino, (C1-C6)alkylamino, di-[(C1-C6)alkyl]amino, amino(C1-C6)alkyl, (C1-C6)alkoxycarbonyl, carbamoyl, (C1-C6)alkylcarbamoyl, (C1-C6)alkylthio, (C1-C6)alkylsulphonyl, (C1-C6)alkanoyl, an alkanoylamino group —N($R^{3c}$)C(O)$R^{3a}$ wherein $R^{3a}$ represents a (C1-C6) alkyl or (C1-C6)alkoxy group and $R^{3c}$ represents hydrogen or (C1-C6)alkyl, or a saturated monocyclic 3-, 4-, 5- or 6-membered ring, which ring may optionally comprise one or more heteroatoms selected from nitrogen, oxygen and sulphur, any of which substituents may be optionally substituted by one or more (for example one or two, particularly one) (C1-C4) alkyl, hydroxyl or cyano groups. Any saturated monocyclic ring within $R^3$ optionally bears 1 or 2 oxo substituents.

In another embodiment, $R^3$ represents hydrogen, hydroxyl or halogen, or a (C1-C4)alkyl, (C2-C4)alkenyl, (C2-C4)alkynyl, (C1-C3)alkoxy, amino, (C1-C3)alkylamino, di-[(C1-C3) alkyl]amino, (C3-C6)cycloalkylamino, carbamoyl, (C1-C3) alkylcarbamoyl, di-[(C1-C3)alkyl]carbamoyl, —C(O)$R^{3b}$, —O$R^{3b}$, —NH$R^{3b}$ or —S(O)$_m$$R^{3a}$ group, wherein $R^{3a}$ represents a (C1-C3)alkyl group, m is 0 and $R^{3b}$ represents a saturated monocyclic 4-, 5- or 6-membered heterocyclic ring comprising at least one ring heteroatom selected from nitrogen, oxygen and sulphur, or $R^3$ represents a saturated monocyclic 5- to 6-membered heterocyclic ring comprising at least one ring heteroatom selected from nitrogen and oxygen, or $R^3$ represents a 5- to 6-membered heteroaromatic ring comprising at least one ring heteroatom selected from nitrogen and oxygen. Each of these groups or rings within $R^3$ may be optionally substituted by one or more substituents as defined above, in particular by one or more (for example one or two, particularly one) substituents independently selected from (C1-C3)alkyl, (C1-C3)alkoxy, (C1-C3)alkoxy(C1-C3)alkyl, (C1-C3)alkoxy(C1-C3)alkoxy, halogen, hydroxyl, trifluoromethyl, amino, (C1-C3)alkylamino, di-[(C1-C3)alkyl] amino, amino(C1-C3)alkyl, carbamoyl, (C1-C3)alkylcarbamoyl, (C1-C3)alkylthio, (C1-C3)alkylsulphonyl, (C1-C3) alkanoyl, an alkanoylamino group —N($R^{3c}$)C(O)$R^{3a}$ wherein $R^{3a}$ represents a (C1-C3)alkyl or (C1-C3)alkoxy group and $R^{3c}$ represents hydrogen or (C1-C3)alkyl, or a saturated monocyclic 3-, 4-, 5- or 6-membered ring, which ring may optionally comprise one or more heteroatoms selected from nitrogen, oxygen and sulphur, any of which substituents may be optionally substituted by one or more (for example one or two, particularly one) (C1-C2)alkyl, hydroxyl or cyano groups. Any saturated monocyclic ring within $R^3$ optionally bears 1 oxo substituent.

In another embodiment, $R^3$ represents hydrogen or a (C1-C4)alkyl, (C1-C3)alkoxy or (C3-C5)cycloalkyl group or $R^3$ represents a saturated monocyclic 5- to 6-membered heterocyclic ring comprising at least one ring heteroatom selected from nitrogen and oxygen. Each of these groups or rings within $R^3$ may be optionally substituted by one or more (for example one or two, particularly one) substituents as defined above, in particular by one or more substituents independently selected from hydroxyl and (C1-C3)alkoxy.

Suitable values for $R^3$ include, for example, hydrogen, hydroxyl, chloro, fluoro or iodo, or a methyl, ethyl, n-propyl, iso-propyl, n-butyl, tert-butyl, ethenyl, propenyl, butenyl, pentenyl, ethynyl, propynyl, butynyl, methoxy, ethoxy, propoxy, tert-butoxy, cyclopropyl, cyclobutyl, methoxycarbonyl, ethoxycarbonyl, propoxycarbonyl, tert-butoxycarbonyl, methylamino, ethylamino, propylamino, dimethylamino, diethylamino, cyclobutylamino, cyclohexylamino, carbamoyl, N-methylcarbamoyl, N-ethylcarbamoyl, N-propylcarbamoyl, N-butylcarbamoyl, N,N-dimethylcarbamoyl, N-ethyl-N-methylcarbamoyl, pyrrolidinylcarbonyl, morpholinylcarbonyl, azetidinylcarbonyl, methylthio, ethylthio, piperidinylamino, tetrahydropyranylamino, tetrahydropyranyloxy, pyrrolidinyl, morpholinyl, piperazinyl, oxadiazolyl or 2,7-diazaspiro[3.5]nonan-7-yl group. Each of these groups or rings may be optionally substituted by one or more (for example one or two, particularly one) substituents as defined above.

In particular, suitable values for $R^3$ include, for example, hydrogen, hydroxyl, chloro, fluoro, bromo, iodo, methyl, ethyl, propyl, iso-propyl, butyl, tert-butyl, cyclopropyl, cyclobutyl, cyclopentyl, cyclohexyl, trifluoromethyl, hydroxymethyl, methoxymethyl, ethoxymethyl, (2-methoxyethoxy)methyl, aminomethyl, methylaminomethyl, ethylaminomethyl, morpholinomethyl, piperazin-1-ylmethyl, 4-methylpiperazin-1-ylmethyl, pyrrolidin-1-ylmethyl, 2-hydroxyethyl, 2-methoxyethyl, 2-ethoxyethyl, 2-(ethoxycarbonyl)ethyl, 2-(N-methylcarbamoyl)ethyl, 3-hydroxypropyl, 3-methoxypropyl, 3-ethoxypropyl, 3-aminoprop-1-yl, 3-N,N-dimethylaminopropyl, 3-tert-butoxycarbonylamino)prop-1-yl, 3-pyrrolidin-1-ylpropyl, ethenyl, propenyl, butenyl, pentenyl, 3-hydroxyprop-1-en-1-yl, 3-aminoprop-1-en-1-yl, 2-(methoxycarbonyl)ethen-1-yl, 3-(tert-butoxycarbonylamino)prop-1-en-1-yl, ethynyl, propynyl, butynyl, pentynyl, 3-hydroxyprop-1-yn-1-yl, 3-methoxyprop-1-yn-1-yl, 2-(trimethylsilyl)ethynyl, 3-aminoprop-1-yn-1-yl, 3-methylaminoprop-1-yn-1-yl, 3-(dimethylamino)prop-1-yn-1-yl, 3-(N-methylacetamido)prop-1-yn-1-yl, 3-acetamidoprop-1-yn-1-yl, methoxy, ethoxy, propoxy, butoxy, pentoxy, (5-oxopyrrolidin-2-yl)methoxy, tetrahydrofuran-3-ylmethoxy, 2-hydroxyethoxy, 2-ethoxyethoxy, 2-(2-hydroxyethoxy)ethoxy, 2-methoxyethoxy, (2-methoxyethoxy)ethoxy, 2-{N-[2-hydroxyethyl]-N-methyl-amino}ethoxy, 2-morpholinoethoxy, 2-(2-oxopyrrolidin-1-yl)ethoxy, 2-(imidazolid-2-on-1-yl)ethoxy, 3-hydroxypropyloxy, 2-hydroxyprop-1-yloxy, 3-methoxyprop-1-yloxy, 2-methoxyprop-1-yloxy, 3-morpholinoprop-1-yloxy, 3-(methylthio)

prop-1-yloxy, 3-(methylsulphonyl)propyl-1-oxy, methoxycarbonyl, tert-butoxycarbonyl, N-(tert-butoxycarbonyl)amino, methylamino, 2-methoxyethylamino, 2-aminoethylamino, 2-(dimethylamino)ethylamino, (N-2-methoxyethyl)-N-methylamino, 3-isopropoxyprop-1-ylamino, 2-(2-hydroxyethoxy)ethylamino, 2-(acetoamido)ethylamino, 2-(morpholin-4-yl)ethylamino, 2-methylprop-1-ylamino, 2-hydroxyprop-1-ylamino, 3-methoxypropylamino, 3-ethoxypropylamino, 2-isopropoxyethylamino, tetrahydrofuran-2-ylmethylamino, dimethylamino, N-(2-hydroxyethyl)-N-ethylamino, cyclopropylamino, cyclobutylamino, cyclopentylamino, 4-methylcyclohexylamino, 4-hydroxycyclohexylamino, carbamoyl, N-hydroxycarbamoyl, N-cyclopropylcarbamoyl, N-cyclopentylcarbamoyl, N-aminocarbamoyl, N-(acetylamino)carbamoyl, N-methylcarbamoyl, 2-hydroxyethylcarbamoyl, N-(2-hydroxypropyl)carbamoyl, N-(2,3-dihydroxypropyl)carbamoyl, N-(4-hydroxybutyl)carbamoyl, N-(2-methoxyethyl)carbamoyl, N-(2-(acetylamino)ethyl)carbamoyl, N-[2-(2-hydroxyethoxy)ethyl]carbamoyl, N-(carbamoylmethyl)carbamoyl, N-[2-(methylthio)ethyl]carbamoyl, N-(2-methoxyethyl)-N-methylcarbamoyl, pyrrolidin-1-ylcarbonyl, morpholinocarbonyl, azetidin-1-ylcarbonyl, (3-hydroxypyrrolidin-1-yl)carbonyl, methylthio, ethylthio, propylthio, 2,2,6,6-tetramethylpiperidin-4-ylamino, 4-tetrahydropyranylamino, tetrahydropyran-4-yloxy, pyrrolidin-1-yl, morpholino, piperazin-1-yl, 4-methylpiperazin-1-yl, 4-ethylpiperazin-1-yl, 4-isopropylpiperazin-1-yl, 4-(2-hydroxyethyl)piperazin-1-yl, 4-(3-hydroxypropyl)piperazin-1-yl, 4-(2-methoxyethyl)piperazin-1-yl, 4-(2-aminoethyl)piperazin-1-yl, 4-[2-(2-hydroxyethoxy)ethyl]piperazin-1-yl, 4-(2-cyanoethyl)piperazin-1-yl, 4-(tert-butoxycarbonyl)piperazin-1-yl, 1-formyl-piperazin-4-yl, 4-acetylpiperazin-1-yl, 4-(ethylsulphonyl)piperazin-1-yl, 4-aminopiperidin-1-yl, 4-(N-tert-butoxycarbonylamino)piperidin-1-yl, 3-hydroxypyrrolidin-1-yl, 3-dimethylamino-pyrrolidin-1-yl, cis-3,4-dihydroxypyrrolidin-1-yl, 5-methyl-[1,3,4]-oxadiazol-2-yl, 2,7-diazaspiro[3.5]nonan-7-yl and (tert-butoxycarbonyl)-2,7-diazaspiro[3.5]nonan-7-yl.

More particularly, suitable values for $R^3$ include, for example, hydrogen, hydroxyl, chloro, iodo, methyl, ethyl, propyl, cyclopropyl, trifluoromethyl, hydroxymethyl, methoxymethyl, ethoxymethyl, (2-methoxyethoxy)methyl, aminomethyl, methylaminomethyl, morpholinomethyl, 4-methylpiperazin-1-ylmethyl, pyrrolidin-1-ylmethyl, 2-methoxyethyl, 2-(ethoxycarbonyl)ethyl, 2-(N-methylcarbamoyl)ethyl, 3-hydroxypropyl, 3-methoxypropyl, 3-aminoprop-1-yl, 3-N,N-dimethylaminopropyl, 3-(tert-butoxycarbonylamino)prop-1-yl, 3-pyrrolidin-1-ylpropyl, ethenyl, pent-3-en-1-yl, 3-hydroxyprop-1-en-1-yl, 3-aminoprop-1-en-1-yl, 2-(methoxycarbonyl)ethen-1-yl, 3-(tert-butoxycarbonylamino)prop-1-en-1-yl, ethynyl, 3-hydroxyprop-1-yn-1-yl, 3-methoxyprop-1-yn-1-yl, 2-(trimethylsilyl)ethynyl, 3-aminoprop-1-yn-1-yl, 3-methylaminoprop-1-yn-1-yl, 3-(dimethylamino)prop-1-yn-1-yl, 3-(N-methylacetamido)prop-1-yn-1-yl, 3-acetamidoprop-1-yn-1-yl, methoxy, ethoxy, (5-oxopyrrolidin-2-yl)methoxy (for example (2S)-(5-oxopyrrolidin-2-yl)methoxy or (2R)-(5-oxopyrrolidin-2-yl)methoxy), tetrahydrofuran-3-ylmethoxy, 2-hydroxyethoxy, 2-ethoxyethoxy, 2-(2-hydroxyethoxy)ethoxy, 2-methoxyethoxy, (2-methoxyethoxy)ethoxy, 2-{N-[2-hydroxyethyl]-N-methyl-amino}ethoxy, 2-morpholinoethoxy, 2-(2-oxopyrrolidin-1-yl)ethoxy, 2-(imidazolid-2-on-1-yl)ethoxy, 3-hydroxypropyloxy, 2-hydroxyprop-1-yloxy (for example (2R)-2-hydroxyprop-1-yloxy), 3-methoxyprop-1-yloxy, 2-methoxyprop-1-yloxy (for example (2S)-2-methoxyprop-1-yloxy), 3-morpholinoprop-1-yloxy, 3-(methylthio) prop-1-yloxy, 3-(methylsulphonyl)propyl-1-oxy, methoxycarbonyl, N-(tert-butoxycarbonyl)amino, methylamino, 2-methoxyethylamino, 2-aminoethylamino, 2-(dimethylamino)ethylamino, (N-2-methoxyethyl)-N-methylamino, 3-isopropoxyprop-1-ylamino, 2-(2-hydroxyethoxy)ethylamino, 2-(acetoamido)ethylamino, 2-(morpholin-4-yl)ethylamino, 2-methylprop-1-ylamino, 2-hydroxyprop-1-ylamino (for example (2R)-2-hydroxyprop-1-ylamino or (2S)-2-hydroxyprop-1-ylamino), 3-methoxypropylamino, 3-ethoxypropylamino, 2-isopropoxyethylamino, tetrahydrofuran-2-ylmethylamino (for example (2R)-tetrahydrofuran-2-ylmethylamino), dimethylamino, N-(2-hydroxyethyl)-N-ethylamino, cyclobutylamino, 4-methylcyclohexylamino, 4-hydroxycyclohexylamino, carbamoyl, N-hydroxycarbamoyl, N-cyclopropylcarbamoyl, N-cyclopentylcarbamoyl, N-aminocarbamoyl, N-(acetylamino)carbamoyl, N-methylcarbamoyl, 2-hydroxyethylcarbamoyl, N-(2-hydroxypropyl)carbamoyl (for example N—((R)-2-hydroxypropyl)carbamoyl), N-(2,3-dihydroxypropyl)carbamoyl (for example N—((2R)-2,3-dihydroxypropyl)carbamoyl), N-(4-hydroxybutyl)carbamoyl, N-(2-methoxyethyl)carbamoyl, N-(2-(acetylamino)ethyl)carbamoyl, N-[2-(2-hydroxyethoxy)ethyl]carbamoyl, N-(carbamoylmethyl)carbamoyl, N-[2-(methylthio)ethyl]carbamoyl, N-(2-methoxyethyl)-N-methylcarbamoyl, pyrrolidin-1-ylcarbonyl, morpholinocarbonyl, azetidin-1-ylcarbonyl, (3-hydroxypyrrolidin-1-yl)carbonyl (for example (3R)-3-hydroxypyrrolidin-1-ylcarbonyl), methylthio, 2,2,6,6-tetramethylpiperidin-4-ylamino, 4-tetrahydropyranylamino, tetrahydropyran-4-yloxy, pyrrolidin-1-yl, morpholino, piperazin-1-yl, 4-methylpiperazin-1-yl, 4-ethylpiperazin-1-yl, 4-isopropylpiperazin-1-yl, 4-(2-hydroxyethyl)piperazin-1-yl, 4-(3-hydroxypropyl)piperazin-1-yl, 4-(2-methoxyethyl)piperazin-1-yl, 4-(2-aminoethyl)piperazin-1-yl, 4-[2-(2-hydroxyethoxy)ethyl]piperazin-1-yl, 4-(2-cyanoethyl)piperazin-1-yl, 4-(tert-butoxycarbonyl)piperazin-1-yl, 1-formyl-piperazin-4-yl, 4-acetylpiperazin-1-yl, 4-(ethylsulphonyl)piperazin-1-yl, 4-aminopiperidin-1-yl, 4-(N-tert-butoxycarbonylamino)piperidin-1-yl, 3-hydroxypyrrolidin-1-yl (for example (3R)-3-hydroxypyrrolidin-1-yl), 3-dimethylamino-pyrrolidin-1-yl (for example (3R)-3-dimethylamino-pyrrolidin-1-yl), cis-3,4-dihydroxypyrrolidin-1-yl, 5-methyl-[1,3,4]-oxadiazol-2-yl, 2,7-diazaspiro[3.5]nonan-7-yl and (tert-butoxycarbonyl)-2,7-diazaspiro[3.5]nonan-7-yl.

More particularly, suitable values for $R^3$ include, for example, hydrogen, chloro, iodo, methyl, ethyl, trifluoromethyl, hydroxymethyl, methoxymethyl, ethoxymethyl, (2-methoxyethoxy)methyl, morpholinomethyl, 3-hydroxypropyl, 3-methoxypropyl, 3-N,N-dimethylaminopropyl, ethenyl, 3-hydroxyprop-1-en-1-yl, ethynyl, 3-hydroxyprop-1-yn-1-yl, 3-methoxyprop-1-yn-1-yl, 3-aminoprop-1-yn-1-yl, 3-methylaminoprop-1-yn-1-yl, 3-(dimethylamino)prop-1-yn-1-yl, 3-(N-methylacetamido)prop-1-yn-1-yl, 3-acetamidoprop-1-yn-1-yl, methoxy, ethoxy, (5-oxopyrrolidin-2-yl)methoxy (for example (2S)-(5-oxopyrrolidin-2-yl)methoxy or (2R)-(5-oxopyrrolidin-2-yl)methoxy), tetrahydrofuran-3-ylmethoxy, 2-hydroxyethoxy, 2-ethoxyethoxy, 2-(2-hydroxyethoxy)ethoxy, 2-methoxyethoxy, (2-methoxyethoxy)ethoxy, 2-{N-[2-hydroxyethyl]-N-methyl-amino}ethoxy, 2-morpholinoethoxy, 2-(2-oxopyrrolidin-1-yl)ethoxy, 2-(imidazolid-2-on-1-yl)ethoxy, 3-hydroxypropyloxy, 2-hydroxyprop-1-yloxy (for example (2R)-2-hydroxyprop-1-yloxy), 3-methoxyprop-1-yloxy, 2-methoxyprop-1-yloxy (for example (2S)-2-methoxyprop-1-yloxy), 3-morpholinoprop-1-yloxy, 3-(methylthio)prop-1-yloxy, 3-(methylsulphonyl)propyl-1-oxy, methylamino, 2-methoxyethylamino, 2-(methoxyethyl)amino, 2-(2-hydroxyethoxy)ethylamino, 2-(morpholin-4-yl)ethylamino, 2-methylprop-1-ylamino, 2-hydroxyprop-1-ylamino (for example (2R)-2-hydroxyprop-1-ylamino or (2S)-2-hydroxyprop-1-ylamino), 3-methoxypropylamino, 3-ethoxypropylamino, 2-isopropoxyethylamino, tetrahydrofuran-2-ylmethylamino (for example (2R)-tetrahydrofuran-2-ylmethylamino), dimethylamino, N-(2-hydroxyethyl)-N-ethylamino, cyclobutylamino, carbamoyl, N-cyclopropylcarbamoyl, N-methylcarbamoyl, 2-hydroxyethylcarbamoyl, N-(2-hydroxypropyl)carbamoyl (for example N—((R)-2-hydroxypropyl)carbamoyl), N-(2-methoxyethyl)carbamoyl, N-[2-(methylthio)ethyl]carbamoyl, pyrrolidin-1-ylcarbonyl, azetidin-1-ylcarbonyl, methylthio, 4-tetrahydropyranylamino, tetrahydropyran-4-yloxy, pyrrolidin-1-yl, morpholino, piperazin-1-yl, 4-methylpiperazin-1-yl, 4-ethylpiperazin-1-yl, 4-isopropylpiperazin-1-yl, 4-(2-hydroxyethyl)piperazin-1-yl, 4-(3-hydroxypropyl)piperazin-1-yl, 4-(2-methoxyethyl)piperazin-1-yl, 4-(2-cyanoethyl)piperazin-1-yl, 4-acetylpiperazin-1-yl, 4-(ethylsulphonyl)piperazin-1-yl, 3-hydroxypyrrolidin-1-yl (for example (3R)-3-hydroxypyrrolidin-1-yl), 3-dimethylamino-pyrrolidin-1-yl (for example (3R)-3-dimethylamino-pyrrolidin-1-yl) and 1-formyl-piperazin-4-yl.

In one embodiment, $R^3$ is suitably selected from hydrogen or halogen, or a (C1-C6)alkyl, (C2-C6)alkenyl, (C2-C6)alkynyl, (C1-C6)alkoxy, (C1-C6)alkylcarbonyl, (C1-C6)alkoxycarbonyl, amino, (C1-C6)alkylamino, di-[(C1-C6)alkyl]amino, carbamoyl, —C(O)$R^{3b}$, —O$R^{3b}$, —S$R^{3b}$, —NH$R^{3b}$, —N[(C1-C6)alkyl]$R^{3b}$ or —S(O)$_m$$R^{3a}$ group (wherein $R^{3a}$ and $R^{3b}$ are as defined above), or a saturated monocyclic 5- or 6-membered heterocyclic ring, which ring comprises at least one ring heteroatom selected from nitrogen, oxygen and sulphur, each of which groups or rings may be optionally substituted by one or more (for example one or two, particularly one) substituents as defined hereinbefore.

In another embodiment, $R^3$ is suitably selected from hydrogen or a substituted or unsubstituted group selected from (C1-C6)alkyl (preferably (C1-C4)alkyl) such as methyl, ethyl, propyl, isopropyl, tert-butyl, (C3-C8)cycloalkyl (preferably (C3-C6)cycloalkyl) such as cyclopropyl, cyclopentyl, cyclohexyl, (C3-C8)cycloalkyl(C1-C6)alkyl (preferably (C3-C6)cycloalkyl(C1-C4)alkyl) such as cyclopropylmethyl, (C1-C6)alkoxy (preferably (C1-C4)alkoxy) such as methoxy, ethoxy, propoxy, isopropoxy and butoxy, (C1-C6)alkylcarbonyl such as methylcarbonyl, (C3-C8)cycloalkylcarbonyl such as cyclopropylcarbonyl, (C3-C8)cycloalkyl(C1-C6)alkylcarbonyl such as cyclopropylmethylcarbonyl, (C1-C6)alkoxycarbonyl, (C1-C6)alkylamino such as methylamino or ethylamino, (C3-C8)cycloalkylamino, (C3-C8)cycloalkyl(C1-C6)alkylamino, (C1-C6)alkoxyamino or —S(O)$_m$$R^{3a}$.

Suitable substituents on $R^3$ include one or more (for example, one, two or three, particularly one or two, more particularly one) substituents independently selected from (C1-C6)alkoxy (such as methoxy or ethoxy), (C1-C6)alkoxy (C1-C6)alkoxy (such as methoxyethoxy) or a saturated monocyclic 3-, 4-, 5-, 6- or 7-membered (for example 4- to 7-membered) ring, which ring may optionally comprise one or more heteroatoms selected from nitrogen, oxygen and sulphur (such as cyclopentyl, cyclohexyl, pyrrolidinyl, piperidinyl, dioxanyl, morpholinyl, tetrahydrofuranyl, piperazinyl).

Particular substituents for the group $R^3$, when it is substituted, include, for example, one or more (for example one or two, particularly one) substituents independently selected from (C1-C6)alkyl, (C1-C6)alkoxy, halogen, hydroxyl, trifluoromethyl, amino, (C1-C6)alkylamino and di-[(C1-C6)alkyl]amino, or a saturated monocyclic 3-, 4-, 5-, 6- or 7-membered (for example 4- to 7-membered) ring, which ring may optionally comprise one or more heteroatoms selected from nitrogen, oxygen and sulphur.

When $R^3$ carries a substituent that is a saturated monocyclic 3-, 4-, 5-, 6- or 7-membered (for example 4- to 7-membered) ring, which ring may optionally comprise one or more heteroatoms selected from nitrogen, oxygen and sulphur, that ring preferably comprises nitrogen and, optionally, one or two additional heteroatoms selected from nitrogen, oxygen and sulphur. For example, the saturated monocyclic 3-, 4-, 5-, 6- or 7-membered (for example 4- to 7-membered) ring substituent on $R^3$ may comprise pyrrolidine.

In one embodiment, $R^3$ represents hydrogen.

Preferably, —NQ$^1$ represents a saturated monocyclic five or six membered ring containing one nitrogen heteroatom and optionally at least one additional ring heteroatom (for example, one, two, three or four ring heteroatoms, which may be the same or different) selected from nitrogen, oxygen and sulphur.

In one embodiment, the N-linked saturated monocyclic 5- to 6-membered ring containing one nitrogen heteroatom of —NQ$^1$ optionally comprises one or two additional ring heteroatoms (which may be the same or different) selected from nitrogen, oxygen and sulphur.

In a further embodiment, —NQ$^1$ represents a saturated monocyclic five or six membered ring containing one nitrogen heteroatom.

In a particularly preferred embodiment, —NQ$^1$ represents pyrrolidinyl or piperidinyl (most preferably pyrrolidinyl).

Ring NQ$^1$ may be substituted at any substitutable position in the ring by the ring Q$^2$. Preferably, NQ$^1$ is substituted by Q$^2$ at a ring atom adjacent to the nitrogen atom linking —NQ$^1$ to the pyrimidine ring of the compounds of the invention.

Q$^2$ suitably represents a 5- to 6-membered heteroaromatic ring comprising at least one ring heteroatom (for example, one, two, three or four ring heteroatoms, which may be the same or different) selected from nitrogen, oxygen and sulphur and may be, for example, thienyl, pyrazolyl, oxazolyl, isoxazolyl, thiadiazolyl, pyrrolyl, furanyl, thiazolyl, triazolyl, tetrazolyl, imidazolyl, pyrazinyl, pyridazinyl, pyrimidinyl or pyridyl.

Preferably, Q$^2$ represents a five or six membered heteroaromatic ring comprising one or two ring heteroatoms, which may be the same or different, selected from nitrogen and oxygen, such as pyridyl, pyrimidyl, pyrazinyl, pyridazinyl, imidazolyl, oxazolyl, tetrazolyl or isoxazolyl (particularly tetrazolyl or isoxazolyl).

In a further embodiment, Q$^2$ represents a five or six membered heteroaromatic ring comprising a nitrogen and an oxygen ring heteroatom.

In a particularly preferred embodiment, Q$^2$ represents an isoxazolyl ring.

In a further embodiment, Q$^2$ represents a five or six membered heteroaromatic ring comprising from one to four nitrogen ring heteroatoms, for example, Q$^2$ may represent pyrrolyl, pyrazolyl, triazolyl, tetrazolyl, imidazolyl, pyrazinyl, pyridazinyl, pyrimidinyl or pyridyl.

Q$^2$ may suitably be linked to ring NQ$^1$ through any available ring atom, for example it may be linked via a ring carbon or nitrogen atom. Where Q$^2$ comprises at least one ring heteroatom then preferably Q$^2$ is linked to ring NQ$^1$ via a ring carbon atom adjacent to a heteroatom.

In addition to being substituted by Q$^3$, Q$^2$ is optionally substituted by at least one substituent (for example, one, two, three or four substituents, which may be the same or different)

independently selected from (C1-C6)alkyl, particularly (C1-C4)alkyl (such as methyl, ethyl, n-propyl, isopropyl, n-butyl, isobutyl, tert-butyl, n-pentyl or n-hexyl), (C1-C6)alkoxy, particularly (C1-C4)alkoxy (such as methoxy, ethoxy, n-propoxy, n-butoxy, tert-butoxy, n-pentoxy or n-hexoxy), (each of the (C1-C6)alkyl and (C1-C6)alkoxy substituent groups being optionally substituted by at least one substituent, e.g. one, two, three or four substituents, independently selected from halogen (such as fluorine, chlorine, bromine or iodine), amino, hydroxyl and trifluoromethyl), halogen (such as fluorine, chlorine, bromine or iodine), nitro, cyano, —$NR^4R^5$, carboxyl, hydroxyl, (C2-C6)alkenyl, particularly (C2-C4) alkenyl (such as ethenyl), (C3-C8)cycloalkyl (for example, cyclopropyl, cyclobutyl, cyclopentyl and cyclohexyl), (C3-C8)cycloalkyl(C1-C6)alkyl (such as cyclopropylmethyl), (C1-C4)alkoxycarbonyl, particularly (C1-C3)alkoxycarbonyl (such as methoxycarbonyl or ethoxycarbonyl), (C1-C4) alkylcarbonyl, particularly (C1-C3)alkylcarbonyl (such as methylcarbonyl, ethylcarbonyl, n-propylcarbonyl, isopropylcarbonyl or n-butylcarbonyl), (C1-C4)alkylcarbonylamino, particularly (C1-C3)alkylcarbonylamino (such as methylcarbonylamino or ethylcarbonylamino), phenylcarbonyl, —$S(O)_p$(C1-C4), particularly (C1-C2)alkyl (such as methylthio, ethylthio, methylsulphinyl, ethylsulphinyl, mesyl and ethylsulphonyl), —$C(O)NR^6R^7$ and —$SO_2NR^8R^9$ (where p, $R^6$, $R^7$, $R^8$ and $R^9$ are as defined above)

$R^4$, $R^5$, $R^6$, $R^7$, $R^8$ and $R^9$ may each suitably independently represent hydrogen or (C1-C6)alkyl, preferably (C1-C4) alkyl such as methyl, ethyl, propyl or butyl, or suitably $R^4$ and $R^5$, or $R^6$ and $R^7$, or $R^8$ and $R^9$, when taken together with the nitrogen atom to which they are attached, may each independently form a saturated heterocyclic ring such as pyrrolidinyl or piperidinyl.

In one embodiment, $Q^2$ is optionally substituted by at least one substituent independently selected from (C1-C6)alkyl, (C1-C6)alkoxy, halogen and (C3-C8)cycloalkyl.

$Q^3$ is suitably a substituted or unsubstituted (C1-C6)alkyl (preferably (C1-C4)alkyl) group such as methyl, ethyl, propyl or butyl, a (C3-C8)cycloalkyl (preferably (C3-C6)cycloalkyl) group such as cyclopropyl, cyclobutyl, cyclopentyl or cyclohexyl, a (C3-C8)cycloalkyl(C1-C6)alkyl group such as cyclopropylmethyl or a saturated or unsaturated 5- to 6-membered monocyclic ring comprising optionally at least one ring heteroatom (for example, one, two, three or four heteroatoms) selected from nitrogen, oxygen and sulphur such as phenyl, pyridyl, imidazolyl, isoxazolyl, pyrazolyl, furyl, pyrazinyl, pyridazinyl, pyrimidinyl, pyrrolyl, thiazolyl, oxazolyl, isothiazolyl, triazolyl, tetrahydrofuranyl or thienyl (particularly pyridyl, pyrazinyl, thiazolyl, tetrahydrofuranyl or pyrimidinyl).

In one embodiment, $Q^3$ represents a substituted or unsubstituted group selected from (C1-C6)alkyl, (C3-C8)cycloalkyl or a substituted or unsubstituted saturated or unsaturated 5- to 6-membered monocyclic ring comprising optionally at least one ring heteroatom selected from nitrogen, oxygen and sulphur. For example, $Q^3$ may represent a substituted or unsubstituted group selected from methyl, cyclopropyl, pyridyl, pyrazinyl, thiazolyl, tetrahydrofuranyl or pyrimidinyl.

In a further embodiment, $Q^3$ is preferably a substituted or unsubstituted group selected from (C1-C4)alkyl (especially methyl), (C3-C6)cycloalkyl (especially cyclopropyl) or an optionally substituted unsaturated 5- to 6-membered monocyclic ring comprising one or two ring heteroatoms, which may be the same or different, selected from nitrogen, oxygen and sulphur, such as imidazolyl, isoxazolyl, pyrazolyl, furyl, pyrazinyl (especially pyrazin-2-yl), pyridazinyl, pyrimidinyl (especially pyrimidin-2-yl), pyrrolyl, oxazolyl, isothiazolyl, triazolyl, tetrahydrofuranyl or thienyl, especially pyridyl (preferably pyrid-2-yl or pyrid-3-yl) or thiazolyl (especially thiazol-2-yl or thiazol-4-yl) or tetrahydrofuranyl (especially tetrahydrofuran-3-yl).

Suitable optional substituents for $Q^3$ are one or more (for example, one, two, three or four) substituents independently selected from (C1-C6)alkyl or (C1-C6)alkoxy (either of which may be optionally substituted by at least one substituent (for example, one, two, three or four substituents) independently selected from halogen, amino, hydroxyl and trifluoromethyl), halogen, nitro, cyano, —$NR^{10}R^{11}$, carboxyl, hydroxyl, (C2-C6)alkenyl, (C3-C8)cycloalkyl, (C1-C6) alkoxycarbonyl, (C1-C6)alkylcarbonyl, (C1-C6)alkylcarbonylamino, phenylcarbonyl, —$S(O)_n$(C1-C6)alkyl, —$C(O)NR^{12}R^{13}$ and —$SO_2NR^{14}R^{15}$ (where n, $R^{10}$, $R^{11}$, $R^{12}$, $R^{13}$, $R^{14}$ and $R^{15}$ are as defined above).

Suitably, $R^{10}$, $R^{11}$, $R^{12}$, $R^{13}$, $R^{14}$ and $R^{15}$ each independently represent hydrogen or (C1-C6)alkyl such as methyl, or $R^{10}$ and $R^{11}$, or $R^{12}$ and $R^{13}$, or $R^{14}$ and $R^{15}$, when taken together with the nitrogen atom to which they are attached, may each suitably form a saturated heterocyclic ring such as pyrrolidinyl or piperidinyl.

It will be appreciated that the number and nature of substituents on rings in the compounds of the invention will be selected so as to avoid sterically undesirable combinations.

In one preferred group of compounds of formula (I) according to the invention, $R^1$ represents a (C1-C4)alkyl or (C3-C6)cycloalkyl group; $R^2$ represents halogen; $R^3$ represents hydrogen; —$NQ^1$ represents a saturated monocyclic 5- or 6-membered ring containing one nitrogen heteroatom and optionally at least one additional ring heteroatom selected from nitrogen, oxygen and sulphur; $Q^2$ represents a substituted 5- or 6-membered heteroaromatic ring comprising one or two ring heteroatoms, which may be the same or different, selected from nitrogen and oxygen; and $Q^3$ represents a (C1-C4)alkyl or (C3-C6)cycloalkyl group or an optionally substituted unsaturated 5- to 6-membered monocyclic ring comprising one or two ring heteroatoms, which may be the same or different, selected from nitrogen, oxygen and sulphur.

Particularly preferred compounds within this group are those in which —$NQ^1$ represents pyrrolidinyl or piperidinyl (particularly pyrrolidinyl); $Q^2$ represents isoxazolyl or tetrazolyl (particularly isoxazolyl); and $Q^3$ represents methyl, cyclopropyl, tetrahydrofuranyl, pyrazinyl, thiazolyl, pyrimidinyl or pyridyl.

Other particularly preferred compounds within this group are those in which —$NQ^1$ represents pyrrolidinyl or piperidinyl; $Q^2$ represents isoxazolyl or tetrazolyl; and $Q^3$ represents methyl, cyclopropyl, thiazolyl, tetrahydrofuranyl or pyridyl.

Other particularly preferred compounds within this group are those in which —$NQ^1$ represents pyrrolidinyl or piperidinyl; $Q^2$ represents isoxazolyl; and $Q^3$ represents methyl, cyclopropyl, thiazolyl or pyridyl.

Other particularly preferred compounds within this group are those in which —$NQ^1$ represents pyrrolidinyl; $Q^2$ represents isoxazolyl; and $Q^3$ represents cyclopropyl, thiazolyl, pyrazinyl, pyrimidinyl or pyridyl.

Suitable values for the group of sub-formula (i) (which is attached to the 2-position of the pyrimidine ring of formula (I)):

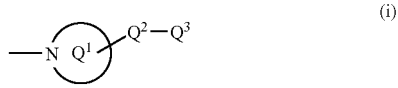

include, for example, 2-[3-(pyrid-2-yl)isoxazol-5-yl]pyrrolidin-1-yl, 2-(3-methylisoxazol-5-yl)pyrrolidin-1-yl, 3-cyclopropylisoxazol-5-yl]pyrrolidin-1-yl, 2-[3-(thiazol-2-yl)isoxazol-5-yl]pyrrolidin-1-yl, 2-[3-(thiazol-4-yl)isoxazol-5-yl]pyrrolidin-1-yl, 2-[3-(pyrid-3-yl)isoxazol-5-yl]pyrrolidin-1-yl, 2-(3-(pyrid-2-yl)isoxazol-5-yl)piperidin-1-yl, 2-(3-{tetrahydrofuran-3-yl}isoxazol-5-yl)pyrrolidin-1-yl, 2-[3-(2-methoxypyrid-3-yl)isoxazol-5-yl]pyrrolidin-1-yl, 2-(2-methyl-2H-tetrazol-5-yl)pyrrolidin-1-yl, 2-[3-(pyrazin-2-yl)isoxazol-5-yl]pyrrolidin-1-yl, 2-{3-(pyrimid-2-yl)isoxazol-5-yl}pyrrolidin-1-yl, 2-{3-(3-methoxypyrazin-2-yl)isoxazol-5-yl}pyrrolidin-1-yl and 2-{3-(3-hydroxypyrazin-2-yl)isoxazol-5-yl}pyrrolidin-1-yl (where, for the avoidance of any doubt, it is the pyrrolidin-1-yl or piperidin-1-yl group that is attached to the 2-position of the pyrimidine ring in Formula (I)).

In particular, suitable values for the group of sub-formula (i) above include, for example, 2-[3-(pyrid-2-yl)isoxazol-5-yl]pyrrolidin-1-yl, 3-cyclopropylisoxazol-5-yl]pyrrolidin-1-yl, 2-[3-(thiazol-2-yl)isoxazol-5-yl]pyrrolidin-1-yl, 2-[3-(thiazol-4-yl)isoxazol-5-yl]pyrrolidin-1-yl, 2-[3-(pyrid-3-yl)isoxazol-5-yl]pyrrolidin-1-yl, 2-(3-{tetrahydrofuran-3-yl}isoxazol-5-yl)pyrrolidin-1-yl, 2-[3-(2-methoxypyrid-3-yl)isoxazol-5-yl]pyrrolidin-1-yl, 2-[3-(pyrazin-2-yl)isoxazol-5-yl]pyrrolidin-1-yl, 2-{3-(pyrimid-2-yl)isoxazol-5-yl}pyrrolidin-1-yl, 2-{3-(3-methoxypyrazin-2-yl)isoxazol-5-yl}pyrrolidin-1-yl and 2-{3-(3-hydroxypyrazin-2-yl)isoxazol-5-yl}pyrrolidin-1-yl.

A particular embodiment of the present invention is a compound of formula (Ia):

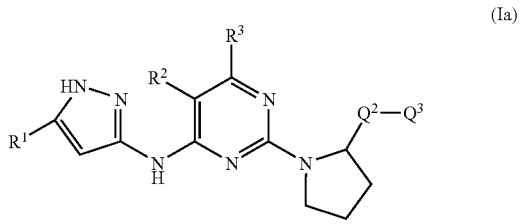

or a pharmaceutically acceptable salt thereof,
wherein:
$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)$R^{3b}$, —OR$^{3b}$, —SR$^{3b}$, —NHR$^{3b}$, —N[(C1-C6)alkyl]R$^{3b}$, —S(O)$_m$R$^{3a}$ or N(R$^{3c}$)C(O)R$^{3a}$ group, wherein R$^{3a}$ represents a (C1-C6)alkyl, (C3-C8)cycloalkyl, (C3-C8)cycloalkyl(C1-C6)alkyl or (C1-C6)alkoxy group, m is 0, 1 or 2, R$^{3b}$ represents a saturated monocyclic 4-, 5- or 6-membered heterocyclic ring comprising at least one ring heteroatom selected from nitrogen, oxygen and sulphur and R$^{3c}$ represents hydrogen or (C1-C6)alkyl, or $R^3$ represents a saturated monocyclic 5- to 6-membered heterocyclic ring comprising at least one ring heteroatom selected from nitrogen, oxygen and sulphur, or $R^3$ represents a 5- to 6-membered heteroaromatic ring comprising at least one ring heteroatom selected from nitrogen, oxygen and sulphur, or $R^3$ represents a 2,7-diazaspiro[3.5]nonane group, each of which groups or rings within $R^3$ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino(C1-C6)alkyl, di-[(C1-C6)alkyl]amino(C1-C6)alkyl, (C3-C8)cycloalkylamino(C1-C6)alkyl, (C3-C6)cycloalkyl(C1-C3)alkylamino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N(R$^{3c}$)C(O)R$^{3a}$ wherein R$^{3a}$ and R$^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^4$R$^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)NR$^6$R$^7$ and —SO$_2$NR$^8$R$^9$, wherein R$^4$, R$^5$, R$^6$, R$^7$, R$^8$ and R$^9$ each independently represent hydrogen or (C1-C6)alkyl, or R$^4$ and R$^5$, or R$^6$ and R$^7$, or R$^8$ and R$^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^{10}$R$^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)NR$^{12}$R$^{13}$ and —SO$_2$NR$^{14}$R$^{15}$, wherein R$^{10}$, R$^{11}$, R$^{12}$, R$^{13}$, R$^{14}$ and R$^{15}$ each independently represent hydrogen or (C1-C6)alkyl, or R$^{10}$ and R$^{11}$, or R$^{12}$ and R$^{13}$, or R$^{14}$ and R$^{15}$, when taken together with the nitrogen atom to which they are attached, may each independently form a saturated heterocyclic ring and n is 0, 1 or 2;

and wherein any saturated monocyclic ring optionally bears 1 or 2 oxo or thioxo substituents.

According to another embodiment of the present invention, there is provided a compound of formula (Ia), or a pharmaceutically acceptable salt thereof, wherein:

R$^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

R$^2$ represents hydrogen, halogen or trifluoromethyl;

R$^3$ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —C(O)R$^{3b}$, —OR$^{3b}$, —SR$^{3b}$, —NHR$^{3b}$, —N[(C1-C6)alkyl]R$^{3b}$ or —S(O)$_m$R$^{3a}$ group, wherein R$^{3a}$ represents a (C1-C6)alkyl, (C3-C8)cycloalkyl, (C3-C8)cycloalkyl(C1-C6)alkyl or (C1-C6)alkoxy group, m is 0, 1 or 2, and R$^{3b}$ represents a saturated monocyclic 5- to 6-membered ring containing one or more heteroatoms selected from nitrogen, oxygen and sulphur, or R$^3$ represents a saturated monocyclic 5- to 6-membered heterocyclic ring, which ring comprises at least one ring heteroatom selected from nitrogen, oxygen and sulphur, each of which groups or rings within R$^3$ may be optionally substituted by one or more substituents independently selected from (C1-C6)alkyl, (C1-C6)alkoxy, (C1-C6)alkoxy(C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-6)alkanoylamino or a saturated monocyclic 4-, 5-, 6- or 7-membered ring, which ring may optionally comprise one or more heteroatoms selected from nitrogen, oxygen and sulphur;

Q$^2$ represents a 5- to 6-membered heteroaromatic ring comprising at least one ring heteroatom selected from nitrogen, oxygen and sulphur, which ring is substituted by Q$^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^4$R$^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)NR$^6$R$^7$ and —SO$_2$NR$^8$R$^9$, wherein R$^4$, R$^5$, R$^6$, R$^7$, R$^8$ and R$^9$ each independently represent hydrogen or (C1-C6)alkyl, or R$^4$ and R$^5$, or R$^6$ and R$^7$, or R$^8$ and R$^9$, when taken together with the nitrogen atom to which they are attached, may each independently form a saturated heterocyclic ring and p is 0, 1 or 2;

Q$^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q$^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^{10}$R$^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)NR$^{12}$R$^{13}$ and —SO$_2$NR$^{14}$R$^{15}$, wherein R$^{10}$, R$^{11}$, R$^{12}$, R$^{13}$, R$^{14}$ and R$^{15}$ each independently represent hydrogen or (C1-C6)alkyl, or R$^{10}$ and R$^{11}$, or R$^{12}$ and R$^{13}$, or R$^{14}$ and R$^{15}$, when taken together with the nitrogen atom to which they are attached, may each independently form a saturated heterocyclic ring and n is 0, 1 or 2.

In this embodiment, Q$^2$ particularly represents a 5- to 6-membered heteroaromatic ring comprising at least one ring nitrogen and, optionally, at least one further ring heteroatom selected from nitrogen, oxygen and sulphur. More particularly, Q$^2$ represents a 5- to 6-membered heteroaromatic ring comprising at least one ring nitrogen and, optionally, at least one further ring heteroatom selected from nitrogen and oxygen. For example, Q$^2$ may represent isoxazolyl (particularly isoxazol-5-yl) or tetrazolyl (particularly tetrazol-5-yl). In particular, Q$^2$ is isoxazolyl (for example isoxazol-5-yl). The ring Q$^2$ is substituted by Q$^3$ as hereinbefore defined and, optionally, is further substituted, on any available ring atom, by one or more further substituents as hereinbefore defined.

Another particular embodiment of the present invention is a compound of formula (Ib):

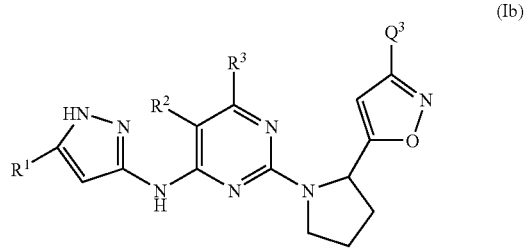

(Ib)

or a pharmaceutically acceptable salt thereof, wherein:

R$^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

R$^2$ represents hydrogen, halogen or trifluoromethyl;

R$^3$ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)R$^{3b}$, OR$^{3b}$, —SR$^{3b}$, —NHR$^{3b}$, —N[(C1-C6)alkyl]R$^{3b}$, —S(O)$_m$R$^{3a}$ or —N(R$^{3c}$)C(O)R$^{3a}$ group, wherein R³ᵃ represents a (C1-C6)alkyl, (C3-C8)cycloalkyl, (C3-C8)cycloalkyl(C1-C6)alkyl or (C1-C6)alkoxy group, m is 0, 1 or 2, R³ᵇ represents a saturated monocyclic 4-, 5- or 6-membered heterocyclic ring comprising at least one ring heteroatom selected from nitrogen, oxygen and sulphur and R³ᶜ represents hydrogen or (C1-C6)alkyl, or R³ represents a saturated monocyclic 5- to 6-membered heterocyclic ring comprising at least one ring heteroatom selected from nitrogen, oxygen and sulphur, or R³ represents a 5- to 6-membered heteroaromatic ring comprising at least one ring heteroatom selected from nitrogen, oxygen and sulphur, or R³ represents a 2,7-diazaspiro[3.5]nonane group, each of which groups or rings within R³ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino(C1-C6)alkyl, di-[(C1-C6)alkyl]amino(C1-C6)alkyl, (C3-C8)cycloalkylamino(C1-C6)alkyl, (C3-C6)cycloalkyl(C1-C3)alkylamino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N(R³ᶜ)C(O)R³ᵃ wherein R³ᵃ and R³ᶜ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;

Q³ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q³ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR¹⁰R¹¹, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)ₙ(C1-C6)alkyl, —C(O)NR¹²R¹³ and —SO₂NR¹⁴R¹⁵, wherein R¹⁰, R¹¹, R¹², R¹³, R¹⁴ and R¹⁵ each independently represent hydrogen or (C1-C6)alkyl, or R¹⁰ and R¹¹, or R¹² and R¹³, or R¹⁴ and R¹⁵, when taken together with the nitrogen atom to which they are attached, may each independently form a saturated heterocyclic ring and n is 0, 1 or 2;

and wherein any saturated monocyclic ring optionally bears 1 or 2 oxo or thioxo substituents.

According to another embodiment of the present invention, there is provided a compound of formula (Ib), or a pharmaceutically acceptable salt thereof, wherein:

R¹ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

R² represents hydrogen, halogen or trifluoromethyl;

R³ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —C(O)R³ᵇ, —OR³ᵇ, —SR³ᵇ, NR³ᵇ, —N[(C1-C6)alkyl]R³ᵇ or —S(O)ₘR³ᵃ group, wherein R³ᵃ represents a (C1-C6)alkyl, (C3-C8)cycloalkyl, (C3-C8)cycloalkyl(C1-C6)alkyl or (C1-C6)alkoxy group, m is 0, 1 or 2, and R³ᵇ represents a saturated monocyclic 5- to 6-membered ring containing one or more heteroatoms selected from nitrogen, oxygen and sulphur;

or R³ represents a saturated monocyclic 5- or 6-membered heterocyclic ring, which ring comprises at least one ring heteroatom selected from nitrogen, oxygen and sulphur, each of which groups or rings within R³ may be optionally substituted by one or more substituents independently selected from (C1-C6)alkyl, (C1-C6)alkoxy, (C1-C6)alkoxy(C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-6)alkanoylamino or a saturated monocyclic 4-, 5-, 6- or 7-membered ring, which ring may optionally comprise one or more heteroatoms selected from nitrogen, oxygen and sulphur;

Q³ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q³ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR¹⁰R¹¹, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)ₙ(C1-C6)alkyl, —C(O)NR¹²R¹³ and —SO₂NR¹⁴R¹⁵, wherein R¹⁰, R¹¹, R¹², R¹³, R¹⁴ and R¹⁵ each independently represent hydrogen or (C1-C6)alkyl, or R¹⁰ and R¹¹, or R¹² and R¹³, or R¹⁴ and R¹⁵, when taken together with the nitrogen atom to which they are attached, may each independently form a saturated heterocyclic ring and n is 0, 1 or 2.

In this embodiment, Q³ is particularly selected from a (C1-C6)alkyl or (C3-C6)cycloalkyl group, or a saturated or unsaturated 5- to 6-membered monocyclic ring which may comprise at least one ring heteroatom selected from nitrogen, oxygen and sulphur, and wherein Q³ is optionally substituted by one or more substituents as hereinbefore defined.

A particular embodiment of the present invention is a compound of formula (Ic):

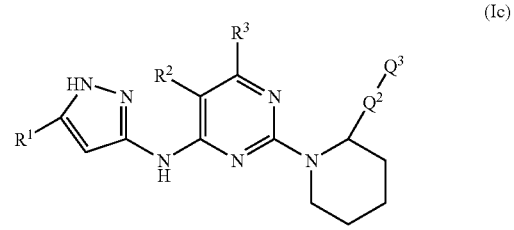

(Ic)

or a pharmaceutically acceptable salt thereof, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen, hydroxyl or halogen, or a (C1-C6) alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)$R^{3b}$, —O$R^{3b}$, —S$R^{3b}$, —NH$R^{3b}$, —N[(C1-C6)alkyl]$R^{3b}$, —S(O)$_m R^{3a}$ or —N($R^{3c}$)C(O)$R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, $R^{3b}$ represents a saturated monocyclic 4-, 5- or 6-membered heterocyclic ring comprising at least one ring heteroatom selected from nitrogen, oxygen and sulphur and $R^{3c}$ represents hydrogen or (C1-C6)alkyl, or $R^3$ represents a saturated monocyclic 5- to 6-membered heterocyclic ring comprising at least one ring heteroatom selected from nitrogen, oxygen and sulphur, or $R^3$ represents a 5- to 6-membered heteroaromatic ring comprising at least one ring heteroatom selected from nitrogen, oxygen and sulphur, or $R^3$ represents a 2,7-diazaspiro[3.5]nonane group, each of which groups or rings within $R^3$ may be optionally substituted by one or more substituents independently selected from (C1-C6)alkyl, (C1-C6)alkoxy, (C1-C6)alkoxy (C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino(C1-C6) alkyl, di-[(C1-C6)alkyl]amino(C1-C6)alkyl, (C3-C8)cycloalkylamino(C1-C6)alkyl, (C3-C6)cycloalkyl(C1-C3) alkylamino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6) alkylsulphinyl, (C1-C6)alkanoyl, an alkanoylamino group —N($R^{3c}$)C(O)$R^{3a}$ wherein $R^{3a}$ and $R^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —N$R^4 R^5$, carboxyl, hydroxyl, (C2-C6)alkenyl, (C3-C8)cycloalkyl, (C3-C8)cycloalkyl(C1-C6) alkyl, (C1-C4)alkoxycarbonyl, (C1-C4)alkylcarbonyl, (C1-C4)alkylcarbonylamino, phenylcarbonyl, —S(O)$_p$(C1-C4) alkyl, —C(O)N$R^6 R^7$ and —SO$_2$N$R^8 R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6) alkyl or (C1-C6)alkoxy (either of which may be optionally substituted by one or more substituents independently selected from halogen, amino, hydroxyl and trifluoromethyl), halogen, nitro, cyano, —N$R^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)N$R^{12}R^{13}$ and —SO$_2$N$R^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2;

and wherein any saturated monocyclic ring optionally bears 1 or 2 oxo or thioxo substituents.

According to another embodiment of the present invention, there is provided a compound of formula (Ic), or a pharmaceutically acceptable salt thereof, wherein:

$R^1$ represents trifluoromethyl, or a (C1-C6)alkyl, (C3-C8) cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —C(O)$R^{3b}$, —O$R^{3b}$, —S$R^{3b}$, —NH$R^{3b}$, —N[(C1-C6)alkyl]$R^{3b}$ or —S(O)$_m R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, and $R^{3b}$ represents a saturated monocyclic 5- to 6-membered ring containing one or more heteroatoms selected from nitrogen, oxygen and sulphur;

or $R^3$ represents a saturated monocyclic 5- or 6-membered heterocyclic ring, which ring comprises at least one ring heteroatom selected from nitrogen, oxygen and sulphur, each of which groups or rings within $R^3$ may be optionally substituted by one or more substituents independently selected from (C1-C6)alkyl, (C1-C6)alkoxy, (C1-C6)alkoxy (C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-6)alkanoylamino or a saturated monocyclic 4- to 7-membered ring, which ring may optionally comprise one or more heteroatoms selected from nitrogen, oxygen and sulphur;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^4$R$^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)NR$^6$R$^7$ and —SO$_2$NR$^8$R$^9$, wherein R$^4$, R$^5$, R$^6$, R$^7$, R$^8$ and R$^9$ each independently represent hydrogen or (C1-C6)alkyl, or R$^4$ and R$^5$, or R$^6$ and R$^7$, or R$^8$ and R$^9$, when taken together with the nitrogen atom to which they are attached, may each independently form a saturated heterocyclic ring and p is 0, 1 or 2;

Q$^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q$^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^{10}$R$^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)NR$^{12}$R$^{13}$ and —SO$_2$NR$^{14}$R$^{15}$, wherein R$^{10}$, R$^{11}$, R$^{12}$, R$^{13}$, R$^{14}$ and R$^{15}$ each independently represent hydrogen or (C1-C6)alkyl, or R$^{10}$ and R$^{11}$, or R$^{12}$ and R$^{13}$, or R$^{14}$ and R$^{15}$, when taken together with the nitrogen atom to which they are attached, may each independently form a saturated heterocyclic ring and n is 0, 1 or 2.

In this embodiment, Q$^2$ particularly represents a 5- to 6-membered heteroaromatic ring comprising at least one ring nitrogen and, optionally, at least one further ring heteroatom selected from nitrogen, oxygen and sulphur. More particularly, Q$^2$ represents a 5- to 6-membered heteroaromatic ring comprising at least one ring nitrogen and, optionally, at least one further ring heteroatom selected from nitrogen and oxygen. For example, Q$^2$ may represent isoxazolyl (particularly isoxazol-5-yl). The ring Q$^2$ is substituted by Q$^3$ and, optionally, is further substituted, on any available ring atom, by one or more further substituents as hereinbefore defined.

Another particular embodiment of the present invention is a compound of formula (Id):

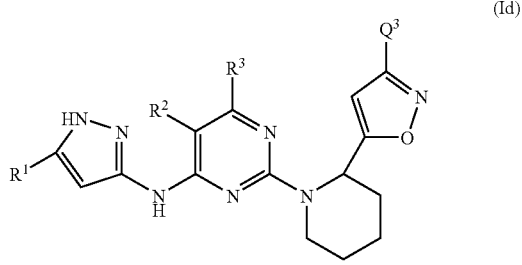

(Id)

or a pharmaceutically acceptable salt thereof,
wherein:

R$^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

R$^2$ represents hydrogen, halogen or trifluoromethyl;

R$^3$ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)R$^{3b}$, OR$^{3b}$, —SR$^{3b}$, —NHR$^{3b}$, —N[(C1-C6)alkyl]R$^{3b}$, —S(O)$_m$R$^{3a}$ or —N(R$^{3c}$)C(O)R$^{3a}$ group, wherein R$^{3a}$ represents a (C1-C6)alkyl, (C3-C8)cycloalkyl, (C3-C8)cycloalkyl(C1-C6)alkyl or (C1-C6)alkoxy group, m is 0, 1 or 2, R$^{3b}$ represents a saturated monocyclic 4-, 5- or 6-membered heterocyclic ring comprising at least one ring heteroatom selected from nitrogen, oxygen and sulphur and R$^{3c}$ represents hydrogen or (C1-C6)alkyl, or R$^3$ represents a saturated monocyclic 5- to 6-membered heterocyclic ring comprising at least one ring heteroatom selected from nitrogen, oxygen and sulphur, or R$^3$ represents a 5- to 6-membered heteroaromatic ring comprising at least one ring heteroatom selected from nitrogen, oxygen and sulphur, or R$^3$ represents a 2,7-diazaspiro[3.5]nonane group, each of which groups or rings within R$^3$ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino(C1-C6)alkyl, di-[(C1-C6)alkyl]amino(C1-C6)alkyl, (C3-C8)cycloalkylamino(C1-C6)alkyl, (C3-C6)cycloalkyl(C1-C3)alkylamino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N(R$^{3c}$)C(O)R$^{3a}$ wherein R$^{3a}$ and R$^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;

Q$^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q$^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —NR$^{10}$R$^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)NR$^{12}$R$^{13}$ and —SO$_2$NR$^{14}$R$^{15}$, wherein R$^{10}$, R$^{11}$, R$^{12}$, R$^{13}$, R$^{14}$ and R$^{15}$ each independently represent hydrogen or (C1-C6)alkyl, or R$^{10}$ and R$^{11}$, or R$^{12}$ and R$^{13}$, or R$^{14}$ and R$^{15}$, when taken together with the nitrogen atom to which they are attached, may each independently form a saturated heterocyclic ring and n is 0, 1 or 2;

and wherein any saturated monocyclic ring optionally bears 1 or 2 oxo or thioxo substituents.

According to another embodiment of the present invention, there is provided a compound of formula (Id), or a pharmaceutically acceptable salt thereof, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —C(O)$R^{3b}$, —O$R^{3b}$, —S$R^{3b}$, —NH$R^{3b}$, —N[(C1-C6)alkyl]$R^{3b}$ or —S(O)$_m$$R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, and $R^{3b}$ represents a saturated monocyclic 5- to 6-membered ring containing one or more heteroatoms selected from nitrogen, oxygen and sulphur;

or $R^3$ represents a saturated monocyclic 5- or 6-membered heterocyclic ring, which ring comprises at least one ring heteroatom selected from nitrogen, oxygen and sulphur, each of which groups or rings within $R^3$ may be optionally substituted by one or more substituents independently selected from (C1-C6)alkyl, (C1-C6)alkoxy, (C1-C6)alkoxy(C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoylamino or a saturated monocyclic 4- to 7-membered ring, which ring may optionally comprise one or more heteroatoms selected from nitrogen, oxygen and sulphur;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, $NR^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)$_n$(C1-C6)alkyl, —C(O)$NR^{12}R^{13}$ and —SO$_2$$NR^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2.

In this embodiment, $Q^3$ is particularly selected from a (C1-C6)alkyl or (C3-C6)cycloalkyl group, or a saturated or unsaturated 5- or 6-membered monocyclic ring which may comprise at least one ring heteroatom selected from nitrogen, oxygen and sulphur, and wherein $Q^3$ is optionally substituted by one or more substituents as hereinbefore defined.

Particular compounds of the invention include, for example, any one or more compounds of formula (I) selected from:—

5-Chloro-2-{2-[3-(pyrid-2-yl)isoxazol-5-yl]pyrrolidin-1-yl}-4-(5-methyl-1H-pyrazol-3-ylamino)pyrimidine;
5-Chloro-2-[2-(3-methylisoxazol-5-yl)pyrrolidin-1-yl]-4-(5-tert-butyl-1H-pyrazol-3-ylamino)pyrimidine;
5-Chloro-2-[2-(3-methylisoxazol-5-yl)pyrrolidin-1-yl]-4-(5-cyclopropyl-1H-pyrazol-3-ylamino)pyrimidine;
5-Chloro-2-[2-(3-cyclopropylisoxazol-5-yl)pyrrolidin-1-yl]-4-(5-cyclopropyl-1H-pyrazol-3-ylamino)pyrimidine;
5-Chloro-2-[2-(3-cyclopropylisoxazol-5-yl)pyrrolidin-1-yl]-4-(5-methyl-1H-pyrazol-3-ylamino)pyrimidine;
5-Chloro-2-[2-(3-methylisoxazol-5-yl)pyrrolidin-1-yl]-4-(5-methyl-1H-pyrazol-3-ylamino)pyrimidine;
5-Chloro-2-{2-[3-(thiazol-2-yl)isoxazol-5-yl]pyrrolidin-1-yl}-4-(5-methyl-1H-pyrazol-3-ylamino)pyrimidine;
5-Chloro-2-{2-[3-(thiazol-2-yl)isoxazol-5-yl]pyrrolidin-1-yl}-4-(5-cyclopropyl-1H-pyrazol-3-ylamino)pyrimidine;
5-Chloro-2-{2-[3-(pyrid-2-yl)isoxazol-5-yl]pyrrolidin-1-yl}-4-(5-cyclopropyl-1H-pyrazol-3-ylamino)pyrimidine;
-Chloro-2-{2-[3-(pyrid-3-yl)isoxazol-5-yl]pyrrolidin-1-yl}-4-(5-methyl-1H-pyrazol-3-ylamino)pyrimidine;
5-Chloro-2-{2-[3-(pyrid-3-yl)isoxazol-5-yl]pyrrolidin-1-yl}-4-(5-cyclopropyl-1H-pyrazol-3-ylamino)pyrimidine;
2-[2-(3-Cyclopropylisoxazol-5-yl)pyrrolidin-1-yl]-6-methoxymethyl-4-(5-methyl-1H-pyrazol-3-ylamino)pyrimidine;
2-[2-(3-Cyclopropylisoxazol-5-yl)pyrrolidin-1-yl]-6-methoxymethyl-4-(5-cyclopropyl-1H-pyrazol-3-ylamino)pyrimidine;
5-Chloro-2-(2-(3-(pyrid-2-yl)isoxazol-5-yl)piperidin-1-yl)-4-(5-methyl-1H-pyrazol-3-ylamino)pyrimidine;
5-Chloro-2-[2-(3-{tetrahydrofuran-3-yl)isoxazol-5-yl]pyrrolidin-1-yl}-4-(5-methyl-1H-pyrazol-3-ylamino)pyrimidine;
5-Chloro-4-(5-cyclopropyl-1H-pyrazol-3-ylamino)-2-[2-(3-{tetrahydrofuran-3-yl}isoxazol-5-yl]pyrrolidin-1-yl]-pyrimidine;
6-Chloro-4-(5-methyl-1H-pyrazol-3-ylamino)-2-{2-[3-(pyrid-2-yl)isoxazol-5-yl]pyrrolidin-1-yl}pyrimidine;
5-Chloro-4-(5-cyclopropyl-1H-pyrazol-3-ylamino)-2-{2-[3-(pyrid-2-yl)isoxazol-5-yl]piperidin-1-yl}pyrimidine;
5-Chloro-2-{2-[3-(2-methoxypyrid-3-yl)isoxazol-5-yl]pyrrolidin-1-yl}-4-(5-methyl-1H-pyrazol-3-ylamino)pyrimidine;
5-Fluoro-4-(5-methyl-1H-pyrazol-3-ylamino)-2-{2-[3-(pyrid-2-yl)isoxazol-5-yl]pyrrolidin-1-yl}-pyrimidine;
4-(5-Cyclopropyl-1H-pyrazol-3-ylamino)-5-fluoro-2-{2-[3-(pyrid-2-yl)isoxazol-5-yl]pyrrolidin-1-yl}pyrimidine;
S-5-Chloro-2-{2-[3-methylisoxazol-5-yl]pyrrolidin-1-yl}-4-(5-cyclopropyl-1H-pyrazol-3-ylamino)pyrimidine;
4-(5-Methyl-1H-pyrazol-3-ylamino)-2-{2-[3-(pyrid-2-yl)isoxazol-5-yl]pyrrolidin-1-yl}pyrimidine;
4-(5-Cyclopropyl-1H-pyrazol-3-ylamino)-2-{2-[3-(pyrid-2-yl)isoxazol-5-yl]pyrrolidin 1-yl}pyrimidine;
4-(5-Cyclopropyl-1H-pyrazol-3-ylamino)-6-methyl-2-[2-{3-(pyrid-2-yl)isoxazol-5-yl}pyrrolidin-1-yl]pyrimidine;
4-(5-Methyl-1H-pyrazol-3-ylamino)-6-methyl-2-[2-{3-(pyrid-2-yl)isoxazol-5-yl}pyrrolidin-1-yl]pyrimidine;
4-(5-Cyclopropyl-1H-pyrazol-3-ylamino)-6-methyl-2-[2-(3-methylisoxazol-5-yl)pyrrolidin-1-yl]pyrimidine;
6-Ethyl-4-(5-methyl-1H-pyrazol-3-ylamino)-2-[2-{3-(pyrid-2-yl)isoxazol-5-yl}pyrrolidin-1-yl]pyrimidine;
6-(3-Methoxypropyl)-4-(5-methyl-1H-pyrazol-3-ylamino)-2-[2-{3-(pyrid-2-yl)isoxazol-5-yl}pyrrolidin-1-yl]pyrimidine;

6-Methoxymethyl-4-(5-methyl-1H-pyrazol-3-ylamino)-2-[2-{3-(pyrid-2-yl)isoxazol-5-yl}pyrrolidin-1-yl]pyrimidine;

4-(5-Cyclopropyl-1H-pyrazol-3-ylamino)-6-methoxymethyl-2-[2-{3-(pyrid-2-yl)isoxazol-5-yl}pyrrolidin-1-yl]pyrimidine;

6-Methoxymethyl-4-(5-methyl-1H-pyrazol-3-ylamino)-2-{2-[3-(thiazol-2-yl)isoxazol-5-yl]pyrrolidin-1-yl}pyrimidine;

6-Methoxymethyl-4-(5-methyl-1H-pyrazol-3-ylamino)-2-[2-{3-(pyrid-3-yl)isoxazol-5-yl}pyrrolidin-1-yl]pyrimidine;

4-(5-Methyl-1H-pyrazol-3-ylamino)-6-(pent-3-en-1-yl)-2-[2-{3-(pyrid-2-yl)isoxazol-5-yl}pyrrolidin-1-yl]pyrimidine;

4-(5-Methyl-1H-pyrazol-3-ylamino)-2-{2-[3-(pyrid-2-yl)isoxazol-5-yl]pyrrolidin-1-yl}-6-trifluoromethylpyrimidine;

4-(5-Cyclopropyl-1H-pyrazol-3-ylamino)-2-{2-[3-(pyrid-2-yl)isoxazol-5-yl]pyrrolidin-1-yl}-6-trifluoromethylpyrimidine;

S-6-Ethyl-4-(5-methyl-1H-pyrazol-3-ylamino)-2-[2-{3-(pyrid-2-yl)isoxazol-5-yl}pyrrolidin-1-yl]pyrimidine;

S-5-Chloro-2-{2-[3-(thiazol-2-yl)isoxazol-5-yl]pyrrolidin-1-yl}-4-(5-methyl-1H-pyrazol-3-ylamino)pyrimidine;

S-5-Chloro-2-{2-[3-(pyrid-2-yl)isoxazol-5-yl]pyrrolidin-1-yl}-4-(5-cyclopropyl-1H-pyrazol-3-ylamino)pyrimidine;

S-4-(5-Methyl-1H-pyrazol-3-ylamino)-6-methyl-2-[2-{3-(pyrid-2-yl)isoxazol-5-yl}pyrrolidin-1-yl]pyrimidine;

S-5-Chloro-2-{2-[3-(pyrid-2-yl)isoxazol-5-yl]pyrrolidin-1-yl}-4-(5-methyl-1H-pyrazol-3-ylamino)pyrimidine;

S-5-Chloro-2-{2-[3-(2-methoxypyrid-3-yl)isoxazol-5-yl]pyrrolidin-1-yl}-4-(5-methyl-1H-pyrazol-3-ylamino)pyrimidine;

6-(3-N,N-Dimethylaminopropyl)-4-(5-methyl-1H-pyrazol-3-ylamino)-2-[2-{3-(pyrid-2-yl)isoxazol-5-yl}pyrrolidin-1-yl]pyrimidine;

6-(3-Pyrrolidin-1-ylpropyl)-4-(5-methyl-1H-pyrazol-3-ylamino)-2-[2-{3-(pyrid-2-yl)isoxazol-5-yl}pyrrolidin-1-yl]pyrimidine;

6-Methoxycarbonyl-4-(5-methyl-1H-pyrazol-3-ylamino)-2-{2-[3-(pyrid-2-yl)isoxazol-5-yl]pyrrolidin-1-yl}pyrimidine;

6-(2-Hydroxyethylcarbamoyl)-4-(5-methyl-1H-pyrazol-3-ylamino)-2-{2-[3-(pyrid-2-yl)isoxazol-5-yl]pyrrolidin-1-yl}pyrimidine;

4-(5-Methyl-1H-pyrazol-3-ylamino)-2-{2-[3-(pyrid-2-yl)isoxazol-5-yl]pyrrolidin-1-yl}-6-(pyrrolidin-1-ylcarbonyl)pyrimidine;

6-Methoxy-4-(5-methyl-1H-pyrazol-3-ylamino)-2-{2-[3-(pyrid-2-yl))isoxazol-5-yl]pyrrolidin-1-yl}pyrimidine;

5-Chloro-4-(3-cyclopropyl-1H-pyrazol-5-ylamino)-2-[2-(2-methyl-2H-tetrazol-5-yl)pyrrolidin-1-yl]pyrimidine;

6-N-Ethylpiperazinyl-4-(5-methyl-1H-pyrazol-3-ylamino)-2-{2-[3-(pyrid-2-yl)isoxazol-5-yl]pyrrolidin-1-yl}pyrimidine;

6-N-Methylpiperazyl-2-{2-[3-(pyrid-2-yl)isoxazol-5-yl]pyrrolidin-1-yl}-4-(5-methyl-1H-pyrazol-3-ylamino)pyrimidine;

6-Morpholino-4-(5-methyl-1H-pyrazol-3-ylamino)-2-{2-[3-(pyrid-2-yl)isoxazol-5-yl]pyrrolidin-1-yl}pyrimidine;

6-(3-(N,N-Dimethylamino)propyn-1-yl)-4-(5-methyl-1H-pyrazol-3-ylamino)-2-(2-(3-(pyrid-2-yl)isoxazol-5-yl)pyrrolidin-1-yl)pyrimidine;

6-Methylamino-4-(5-methyl-1H-pyrazol-3-ylamino)-2-[2-(3-pyridin-2-yl)isoxazol-5-yl)pyrrolidin-1-yl]pyrimidine;

6-(2-Methoxyethyl)amino-4-(5-methyl-1H-pyrazol-3-ylamino)-2-{2-[3-(pyrid-2-yl)isoxazol-5-yl]pyrrolidin-1-yl}pyrimidine;

6-Methoxycarbonyl-2-{2-[3-(pyrid-2-yl)isoxazol-5-yl]pyrrolidin-1-yl}-4-(5-methyl-1H-pyrazol-3-ylamino)pyrimidine;

6-(N-Methylcarbamoyl)-2-{2-[3-(pyrid-2-yl)isoxazol-5-yl]pyrrolidin-1-yl}-4-(5-methyl-1H-pyrazol-3-ylamino)pyrimidine;

6-Morpholinocarbonyl-2-{2-[3-(pyrid-2-yl)isoxazol-5-yl]pyrrolidin-1-yl}-4-(5-methyl-1H-pyrazol-3-ylamino)pyrimidine;

6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine;

6-(N-Hydroxycarbamoyl)-2-{2-[3-(pyrid-2-yl)isoxazol-5-yl]pyrrolidin-1-yl}-4-(5-methyl-1H-pyrazol-3-ylamino)pyrimidine;

6-Carbamoyl-2-{2-[3-(pyrid-2-yl)isoxazol-5-yl]pyrrolidin-1-yl}-4-(5-methyl-1H-pyrazol-3-ylamino)pyrimidine;

S-6-Methoxycarbonyl-2-{2-[3-(pyrid-2-yl)isoxazol-5-yl]pyrrolidin-1-yl}-4-(5-methyl-1H-pyrazol-3-ylamino)pyrimidine;

S-6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine;

S-6-[N-(2-Methoxyethyl)-N-methylcarbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-(2-(Acetylamino)ethyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-{N-[2-(2-Hydroxyethoxy)ethyl]carbamoyl}-2-{2-[3-(pyrid-2-yl)isoxazol-5-yl]pyrrolidin-1-yl}-4-(5-methyl-1H-pyrazol-3-ylamino)pyrimidine;

S-6-[N—((R)-2-Hydroxypropyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-(4-Hydroxybutyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-((2R)-2,3-Dihydroxypropyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-(Carbamoylmethyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-((3R)-3-Hydroxypyrrolidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine;

S-6-{N-[2-(Methylthio)ethyl]carbamoyl}-2-{2-[3-(pyrid-2-yl)isoxazol-5-yl]pyrrolidin-1-yl}-4-(5-methyl-1H-pyrazol-3-ylamino)pyrimidine;

S-6-(N-Cyclopropylcarbamoyl)-2-{2-[3-(pyrid-2-yl)isoxazol-5-yl]pyrrolidin-1-yl}-4-(5-methyl-1H-pyrazol-3-ylamino)pyrimidine;

S-6-(N-Cyclopentylcarbamoyl)-2-{2-[3-(pyrid-2-yl)isoxazol-5-yl]pyrrolidin-1-yl}-4-(5-methyl-1H-pyrazol-3-ylamino)pyrimidine;

S-6-(Azetidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine;

S-6-(N-Methylcarbamoyl)-2-{2-[3-(pyrid-2-yl)isoxazol-5-yl]pyrrolidin-1-yl}-4-(5-methyl-1H-pyrazol-3-ylamino)pyrimidine;

6-(N-Aminocarbamoyl)-2-{2-[3-(pyrid-2-yl)isoxazol-5-yl]pyrrolidin-1-yl}-4-(5-methyl-1H-pyrazol-3-ylamino)pyrimidine;

6-[N-(Acetylamino)carbamoyl]-2-{2-[3-(pyrid-2-yl)isoxazol-5-yl]pyrrolidin-1-yl}-4-(5-methyl-1H-pyrazol-3-ylamino)pyrimidine;

6-(5-Methyl-[1,3,4]-oxadiazol-2-yl)-2-{2-[3-(pyrid-2-yl)isoxazol-5-yl]pyrrolidin-1-yl}-4-(5-methyl-1H-pyrazol-3-ylamino)pyrimidine;

6-Hydroxymethyl-2-{2-[3-(pyrid-2-yl)isoxazol-5-yl]pyrrolidin-1-yl}-4-(5-methyl-1H-pyrazol-3-ylamino)pyrimidine;

6-(Morpholinomethyl)-2-{2-[3-(pyrid-2-yl)isoxazol-5-yl]pyrrolidin-1-yl}-4-(5-methyl-1H-pyrazol-3-ylamino)pyrimidine;

6-(4-Methylpiperazin-1-ylmethyl)-2-{2-[3-(pyrid-2-yl)isoxazol-5-yl]pyrrolidin-1-yl}-4-(5-methyl-1H-pyrazol-3-ylamino)pyrimidine;

6-(Methylaminomethyl)-2-{2-[3-(pyrid-2-yl)isoxazol-5-yl]pyrrolidin-1-yl}-4-(5-methyl-1H-pyrazol-3-ylamino)pyrimidine;

6-(Pyrrolidin-1-ylmethyl)-2-{2-[3-(pyrid-2-yl)isoxazol-5-yl]pyrrolidin-1-yl}-4-(5-methyl-1H-pyrazol-3-ylamino)pyrimidine;

6-Aminomethyl-2-{2-[3-(pyrid-2-yl)isoxazol-5-yl]pyrrolidin-1-yl}-4-(5-methyl-1H-pyrazol-3-ylamino)pyrimidine;

S-6-Hydroxymethyl-2-{2-[3-(pyrid-2-yl)isoxazol-5-yl]pyrrolidin-1-yl}-4-(5-methyl-1H-pyrazol-3-ylamino)pyrimidine;

S-6-Ethoxymethyl-2-{2-[3-(pyrid-2-yl)isoxazol-5-yl]pyrrolidin-1-yl}-4-(5-methyl-1H-pyrazol-3-ylamino)pyrimidine;

S-6-[(2-Methoxyethoxy)methyl]-2-{2-[3-(pyrid-2-yl)isoxazol-5-yl]pyrrolidin-1-yl}-4-(5-methyl-1H-pyrazol-3-ylamino)pyrimidine;

S-5-Chloro-2-{2-[3-(pyrazin-2-yl)isoxazol-5-yl]pyrrolidin-1-yl}-4-(5-cyclopropyl-1H-pyrazol-3-ylamino)pyrimidine;

S-6-Methyl-4-(5-methyl-1H-pyrazol-3-ylamino)-2-{2-[3-(pyrazin-2-yl)isoxazol-5-yl]pyrrolidin-1-yl}pyrimidine;

S-6-Chloro-4-(5-cyclopropyl-1H-pyrazol-3-ylamino)-2-{2-[3-(pyrazin-2-yl)isoxazol-5-yl]pyrrolidin-1-yl}pyrimidine;

S-4-(5-Cyclopropyl-1H-pyrazol-3-ylamino)-2-{2-[3-(pyrazin-2-yl)isoxazol-5-yl]pyrrolidin-1-yl}-6-(2-methoxyethylamino)pyrimidine;

S-6-Methylamino-{2-[3-(pyrazin-2-yl)isoxazol-5-yl]pyrrolidin-1-yl)-4-(5-cyclopropyl-1H-pyrazol-3-ylamino)pyrimidine;

S-4-(5-Cyclopropyl-1H-pyrazol-3-ylamino)-6-methoxy-{2-[3-(pyrazin-2-yl)isoxazol-5-yl]pyrrolidin-1-yl}pyrimidine;

6-Pyrrolidin-1-yl-2-{2-[3-(pyrid-2-yl)isoxazol-5-yl]pyrrolidin-1-yl}-4-(5-methyl-1H-pyrazol-3-ylamino)pyrimidine;

S-6-Chloro-4-(5-methyl-1H-pyrazol-3-ylamino)-2-[2-{3-(pyrid-2-yl)isoxazol-5-yl}pyrrolidin-1-yl]pyrimidine;

S-6-(2,2,6,6-Tetramethylpiperidin-4-ylamino)-2-{2-[3-(pyrid-2-yl)isoxazol-5-yl]pyrrolidin-1-yl}-4-(5-methyl-1H-pyrazol-3-ylamino)pyrimidine;

S-6-Iodo-4-(5-methyl-1H-pyrazol-3-ylamino)-2-[2-{3-(pyrid-2-yl)isoxazol-5-yl}pyrrolidin-1-yl]pyrimidine;

S-E-6-[3-(tert-Butoxycarbonylamino)prop-1-en-1-yl]-4-(5-methyl-1H-pyrazol-3-ylamino)-2-[2-{3-(pyrid-2-yl)isoxazol-5-yl}pyrrolidin-1-yl]pyrimidine;

S-6-Ethenyl-4-(5-methyl-1H-pyrazol-3-ylamino)-2-[2-{3-(pyrid-2-yl)isoxazol-5-yl}pyrrolidin-1-yl]pyrimidine;

S-E-6-(3-Hydroxyprop-1-en-1-yl)-4-(5-methyl-1H-pyrazol-3-ylamino)-2-[2-{3-(pyrid-2-yl)isoxazol-5-yl}pyrrolidin-1-yl]pyrimidine;

S-6-[3-(tert-Butoxycarbonylamino)prop-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Aminoprop-1-yl]-4-(5-methyl-1H-pyrazol-3-ylamino)-2-[2-{3-(pyrid-2-yl)isoxazol-5-yl}pyrrolidin-1-yl]pyrimidine;

S-E-6-[3-Aminoprop-1-en-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Methylaminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Methoxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Hydroxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(Trimethylsilyl)ethynyl]-4-(5-methyl-1H-pyrazol-3-ylamino)-2-[2-{3-(pyrid-2-yl)isoxazol-5-yl}pyrrolidin-1-yl]pyrimidine;

S-6-[3-(N-Methylacetamido)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-(Dimethylamino)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Acetamidoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(Ethoxycarbonyl)ethyl]-4-(5-methyl-1H-pyrazol-3-ylamino)-2-[2-{3-(pyrid-2-yl)isoxazol-5-yl}pyrrolidin-1-yl]pyrimidine;

S-E-6-[2-(Methoxycarbonyl)ethen-1-yl]-4-(5-methyl-1H-pyrazol-3-ylamino)-2-[2-{3-(pyrid-2-yl)isoxazol-5-yl}pyrrolidin-1-yl]pyrimidine;

S-6-Ethynyl-4-(5-methyl-1H-pyrazol-3-ylamino)-2-[2-{3-(pyrid-2-yl)isoxazol-5-yl}pyrrolidin-1-yl]pyrimidine;

6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine;

S-6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine;

S-6-Methoxymethyl-4-(5-methyl-1H-pyrazol-3-ylamino)-2-[2-{3-(pyrid-2-yl)isoxazol-5-yl}pyrrolidin-1-yl]pyrimidine;

S-6-[3-Aminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(N-Methylcarbamoyl)ethyl]-4-(5-methyl-1H-pyrazol-3-ylamino)-2-[2-{3-(pyrid-2-yl)isoxazol-5-yl}pyrrolidin-1-yl]pyrimidine;

S-4-(5-Ethyl-1H-pyrazol-3-ylamino)-2-[2-[3-(2-methoxypyrid-3-yl)isoxazol-5-yl]pyrrolidin-1-yl]pyrimidine;

S-4-(5-Methyl-1H-pyrazol-3-ylamino)-2-[2-[3-(2-methoxypyrid-3-yl)isoxazol-5-yl]pyrrolidin-1-yl]pyrimidine;

S-4-(5-Cyclopropyl-1H-pyrazol-3-yl no)-2-[2-[3-(2-methoxypyrid-3-yl)isoxazol-5-yl]pyrrolidin-1-yl]pyrimidine;

6-(N-tert-Butoxycarbonyl)amino-2-{2-[3-(pyrid-2-yl)isoxazol-5-yl]pyrrolidin-1-yl}-4-(5-methyl-1H-pyrazol-3-ylamino)pyrimidine;

6-(4-Aminopiperidin-1-yl)2-{2-[3-(pyrid-2-yl)isoxazol-5-yl]pyrrolidin-1-yl}-4-(5-methyl-1H-pyrazol-3-ylamino)pyrimidine;

6-(4-(N-tert-Butoxycarbonylamino)piperidin-1-yl)-2-{2-[3-(pyrid-2-yl)isoxazol-5-yl]pyrrolidin-1-yl}-4-(5-methyl-1H-pyrazol-3-ylamino)pyrimidine;

6-piperazin-1-yl-2-{2-[3-(pyrid-2-yl)isoxazol-5-yl]pyrrolidin-1-yl}-4-(5-methyl-1H-pyrazol-3-ylamino)pyrimidine;

S-6-{4-[2-(2-Hydroxyethoxy)ethyl]piperazin-1-yl}-2-{2-[3-(pyrid-2-yl)isoxazol-5-yl]pyrrolidin-1-yl}-4-(5-methyl-1H-pyrazol-3-ylamino)pyrimidine;

S-6-(1-Formyl-piperazin-4-yl)-2-{2-[3-(pyrid-2-yl)isoxazol-5-yl]pyrrolidin-1-yl}-4-(5-methyl-1H-pyrazol-3-ylamino)pyrimidine;

S-6-piperazin-1-yl-2-{2-[3-(pyrid-2-yl)isoxazol-5-yl]pyrrolidin-1-yl}-4-(5-methyl-1H-pyrazol-3-yl amino)pyrimidine;

S-6-(4-Isopropylpiperazin-1-yl)-2-{2-[3-(pyrid-2-yl)isoxazol-5-yl]pyrrolidin-1-yl}-4-(5-methyl-1H-pyrazol-3-ylamino)pyrimidine;

S-6-[(4-(2-Hydroxyethyl)piperazin-1-yl)]-2-{2-[3-(pyrid-2-yl)isoxazol-5-yl]pyrrolidin-1-yl}-4-(5-methyl-1H-pyrazol-3-ylamino)pyrimidine;

S-6-[(3R)-3-Hydroxypyrrolidin-1-yl]-2-{2-[3-(pyrid-2-yl)isoxazol-5-yl]pyrrolidin-1-yl}-4-(5-methyl-1H-pyrazol-3-ylamino)pyrimidine;

S-6-[(3R)-3-Dimethylamino-pyrrolidin-1-yl]-2-{2-[3-(pyrid-2-yl)isoxazol-5-yl]pyrrolidin-1-yl}-4-(5-methyl-1H-pyrazol-3-ylamino)pyrimidine;

S-6-(4-Tetrahydropyranylamino)-2-{2-[3-(pyrid-2-yl)isoxazol-5-yl]pyrrolidin-1-yl}-4-(5-methyl-1H-pyrazol-3-ylamino)pyrimidine;

S-6-Morpholino-2-{2-[3-(pyrid-2-yl)isoxazol-5-yl]pyrrolidin-1-yl}-4-(5-methyl-1H-pyrazol-3-ylamino)pyrimidine;

S-6-(2-Methoxyethyl)amino-2-{2-[3-(pyrid-2-yl)isoxazol-5-yl]pyrrolidin-1-yl}-4-(5-methyl-1H-pyrazol-3-ylamino)pyrimidine;

S-6-[(N-2-Methoxyethyl)-N-methylamino]-2-{2-[3-(pyrid-2-yl)isoxazol-5-yl]pyrrolidin-1-yl}-4-(5-methyl-1H-pyrazol-3-ylamino)pyrimidine;

S-6-((2R)-2-Hydroxyprop-1-ylamino)-2-{2-[3-(pyrid-2-yl)isoxazol-5-yl]pyrrolidin-1-yl}-4-(5-methyl-1H-pyrazol-3-ylamino)pyrimidine;

S-6-[N-(2-Hydroxyethyl)-N-ethylamino]-2-{2-[3-(pyrid-2-yl)isoxazol-5-yl]pyrrolidin-1-yl}-4-(5-methyl-1H-pyrazol-3-ylamino)pyrimidine;

S-6-Dimethylamino-2-{2-[3-(pyrid-2-yl)isoxazol-5-yl]pyrrolidin-1-yl}-4-(5-methyl-1H-pyrazol-3-ylamino)pyrimidine;

S-6-Methylamino-2-{2-[3-(pyrid-2-yl)isoxazol-5-yl]pyrrolidin-1-yl}-4-(5-methyl-1H-pyrazol-3-ylamino)pyrimidine;

S-6-Chloro-2-{2-[3-(pyrazin-2-yl)isoxazol-5-yl]pyrrolidin-1-yl}-4-(5-methyl-1H-pyrazol-3-ylamino)pyrimidine;

6-Mopholino-2-{2-[3-(pyrazin-2-yl)isoxazol-5-yl]pyrrolidin-1-yl}-4-(5-methyl-1H-pyrazol-3-ylamino)pyrimidine;

6-Chloro-2-[2-[3-(pyrid-2-yl)isoxazol-5-yl]pyrrolidin-1-yl}-4-(5-cyclopropyl-1H-pyrazol-3-ylamino)pyrimidine;

6-(2-Hydroxyethoxy)-2-{2-[3-(pyrid-2-yl)isoxazol-5-yl]pyrrolidin-1-yl}-4-(5-cyclopropyl-1H-pyrazol-3-ylamino)pyrimidine;

6-[4-(tert-Butoxycarbonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine;

6-[2-(tert-Butoxycarbonyl)-2,7-diazaspiro[3.5]nonan-7-yl]-4-(5-methyl-1H-pyrazol-3-ylamino)-2-[2-{3-(pyrid-2-yl)isoxazol-5-yl}pyrrolidin-1-yl]pyrimidine;

6-(2,7-Diazaspiro[3.5]nonan-7-yl)-4-(5-methyl-1H-pyrazol-3-ylamino)-2-[2-{3-(pyrid-2-yl)isoxazol-5-yl}pyrrolidin-1-yl]pyrimidine;

S-6-[4-(2-Aminoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(3-Hydroxypropyl)piperazin-{-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(2-Cyanoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(2-Methoxyethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine;

S-6-[4-(Ethylsulphonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(2-Hydroxyethoxy)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[2-(Acetoamido)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[2-Aminoethylamino]-4-(5-methyl-1H-pyrazol-3-ylamino)-2-[2-{3-(pyrid-2-yl)isoxazol-5-yl}pyrrolidin-1-yl]pyrimidine;

S-6-[4-Methylcyclohexylamino]-4-(5-methyl-1H-pyrazol-3-ylamino)-2-[2-{3-(pyrid-2-yl)isoxazol-5-yl}pyrrolidin-1-yl]pyrimidine;

S-6-[4-Hydroxycyclohexylamino]-4-(5-methyl-1H-pyrazol-3-ylamino)-2-[2-{3-(pyrid-2-yl)isoxazol-5-yl}pyrrolidin-1-yl]pyrimidine;

S-6-[cis-3,4-Dihydroxypyrrolidin-1-yl]-4-(5-methyl-1H-pyrazol-3-ylamino)-2-[2-{3-(pyrid-2-yl)isoxazol-5-yl}pyrrolidin-1-yl]pyrimidine;

S-6-Chloro-4-(5-methyl-1H-pyrazol-3-ylamino)-2-[2-{3-(pyrimid-2-yl)isoxazol-5-yl}pyrrolidin-1-yl]pyrimidine;

S-6-Chloro-4-(5-methyl-1H-pyrazol-3-ylamino)-2-[2-{3-(3-methoxypyrazin-2-yl)isoxazol-5-yl}pyrrolidin-1-yl]pyrimidine;

S-6-Morpholino-4-(5-methyl-1H-pyrazol-3-ylamino)-2-[2-{3-(pyrimid-2-yl)isoxazol-5-yl}pyrrolidin-1-yl]pyrimidine;

S-6-Morpholino-4-(5-methyl-1H-pyrazol-3-ylamino)-2-[2-{3-(3-methoxypyrazin-2-yl)isoxazol-5-yl}pyrrolidin-1-yl]pyrimidine;

S-6-Morpholino-4-(5-methyl-1H-pyrazol-3-ylamino)-2-[2-{3-(3-hydroxypyrazin-2-yl)isoxazol-5-yl}pyrrolidin-1-yl]pyrimidine;

S-6-[4-Methylpiperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[Cyclobutylamino]-4-(5-methyl-1H-pyrazol-3-ylamino)-2-[2-{3-(pyrid-2-yl)isoxazol-5-yl}pyrrolidin-1-yl]pyrimidine;

S-6-[3-Isopropoxyprop-1-ylamino]-4-(5-methyl-1H-pyrazol-3-ylamino)-2-[2-{3-(pyrid-2-yl)isoxazol-5-yl}pyrrolidin-1-yl]pyrimidine;

S-6-[2-(Morpholin-4-yl)ethylamino]-4-(5-methyl 1H-pyrazol-3-ylamino)-2-[2-{3-(pyrid-2-yl)isoxazol-5-yl}pyrrolidin-1-yl]pyrimidine;

S-6-[2-(Dimethylamino)ethylamino]-4-(5-methyl 1H-pyrazol-3-ylamino)-2-[2-{3-(pyrid-2-yl)isoxazol-5-yl}pyrrolidin-1-yl]pyrimidine;

S-6-[(2S)-2-Hydroxyprop-1-ylamino]-4-(5-methyl-1H-pyrazol-3-ylamino)-2-[2-(3-(pyrid-2-yl)isoxazol-5-yl}pyrrolidin-1-yl]pyrimidine;

S-6-[2-Methylprop-1-ylamino]-4-(5-methyl-1H-pyrazol-3-ylamino)-2-[2-{3-(pyrid-2-yl)isoxazol-5-yl}pyrrolidin-1-yl]pyrimidine;

S-6-[3-Methoxypropylamino]-4-(5-methyl-1H-pyrazol-3-ylamino)-2-[2-{3-(pyrid-2-yl)isoxazol-5-yl}pyrrolidin-1-yl]pyrimidine;

S-6-[4-Ethylpiperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Ethoxypropylamino]-4-(5-methyl-1H-pyrazol-3-ylamino)-2-[2-{3-(pyrid-2-yl)isoxazol-5-yl}pyrrolidin-1-yl]pyrimidine;

S-6-[(2R)-Tetrahydrofuran-2-ylmethylamino]-4-(5-methyl-1H-pyrazol-3-ylamino)-2-[2-{3-(pyrid-2-yl)isoxazol-5-yl}pyrrolidin-1-yl]pyrimidine;

S-6-(2-Isopropoxyethylamino)-4-(5-methyl-1H-pyrazol-3-ylamino)-2-[2-{3-(pyrid-2-yl)isoxazol-5-yl}pyrrolidin-1-yl]pyrimidine;

S-6-Morpholino-4-(5-cyclopropyl-1H-pyrazol-3-ylamino)-2-[2-{3-(pyrimid-2-yl)isoxazol-5-yl}pyrrolidin-1-yl]pyrimidine;

S-6-Methylamino-4-(5-cyclopropyl-1H-pyrazol-3-ylamino)-2-[2-{3-(pyrimid-2-yl)isoxazol-5-yl}pyrrolidin-1-yl]pyrimidine;

S-6-Chloro-4-(5-cyclopropyl-1H-pyrazol-3-ylamino)-2-[2-{3-(pyrimid-2-yl)isoxazol-5-yl}pyrrolidin-1-yl]pyrimidine;

S-6-Methyl-4-(5-methyl-1H-pyrazol-3-ylamino)-2-[2-{3-(3-methoxypyrazin-2-yl)isoxazol-5-yl}pyrrolidin-1-yl]pyrimidine;

S-6-Methoxy-4-(5-cyclopropyl-1H-pyrazol-3-ylamino)-2-[2-{3-(pyrimidin-2-yl)isoxazol-5-yl}pyrrolidin-1-yl]pyrimidine;

S-6-(2-Methoxyethoxy)-4-(5-cyclopropyl-1H-pyrazol-3-ylamino)-2-[2-{3-(pyrimidin-2-yl)isoxazol-5-yl}pyrrolidin-1-yl]pyrimidine;

S-4-(5-Ethyl-1H-pyrazol-3-ylamino)-2-{2-[3-(pyrid-2-yl)isoxazol-5-yl]pyrrolidin-1-yl}pyrimidine;

S-4-(5-Cyclopropyl-1H-pyrazol-3-ylamino)-2-{2-[3-(pyrid-2-yl)isoxazol-5-yl]pyrrolidin-1-yl}pyrimidine;

S-4-(5-Ethyl-1H-pyrazol-3-ylamino)-5-fluoro-2-{2-[3-(pyrid-2-yl)isoxazol-5-yl]pyrrolidin-1-yl}pyrimidine;

S-4-(5-Cyclopropyl-1H-pyrazol-3-ylamino)-5-fluoro-2-{2-[3-(pyrid-2-yl)isoxazol-5-yl]pyrrolidin-1-yl}pyrimidine;

4-(5-Cyclopropyl-1H-pyrazol-3-ylamino)-6-methyl-2-{2-[3-(pyrimid-2-yl)isoxazol-5-yl]pyrrolidin-1-yl}pyrimidine;

4-(5-Cyclopropyl-1H-pyrazol-3-ylamino)-6-methyl-2-{2-[3-(pyrazin-2-yl)isoxazol-5-yl]pyrrolidin-1-yl}pyrimidine;

4-(5-Cyclopropyl-1H-pyrazol-3-ylamino)-6-methyl-2-{2-[3-(pyrid-2-yl)isoxazol-5-yl]pyrrolidin-1-yl}pyrimidine;

6-(3-Hydroxypropyl)-4-(5-methyl-1H-pyrazol-3-ylamino)-2-{2-[3-(pyrid-2-yl)isoxazol-5-yl]pyrrolidin-1-yl}pyrimidine;

S-6-(3-Hydroxypropyl)-4-(5-methyl-1H-pyrazol-3-ylamino)-2-{2-[3-(pyrid-2-yl)isoxazol-5-yl]pyrrolidin-1-yl}pyrimidine;

S-6-Propyl-2-{2-[3-(pyrid-2-yl)isoxazol-5-yl]pyrrolidin-1-yl}-4-(5-methyl-1H-pyrazol-3-ylamino)pyrimidine;

S-6-Chloro-4-(5-ethyl-1H-pyrazol-3-ylamino)-2-[2-{3-(pyrid-2-yl)isoxazol-5-yl}pyrrolidin-1-yl]pyrimidine;

S-6-(2-Hydroxyethoxy)-4-(5-ethyl-1H-pyrazol-3-ylamino)-2-[2-{3-(pyrid-2-yl)isoxazol-5-yl}pyrrolidin-1-yl]pyrimidine;

S-6-(2-Methoxyethoxy)-4-(5-ethyl-1H-pyrazol-3-ylamino)-2-[2-{3-(pyrid-2-yl)isoxazol-5-yl}pyrrolidin-1-yl]pyrimidine;

S-6-Morpholino-4-(5-ethyl-1H-pyrazol-3-ylamino)-2-[2-{3-(pyrid-2-yl)isoxazol-5-yl}pyrrolidin-1-yl]pyrimidine;

S-6-(4-Methylpiperazin-1-yl)-4-(5-ethyl-1H-pyrazol-3-ylamino)-2-[2-{3-(pyrid-2-yl)isoxazol-5-yl}pyrrolidin-1-yl]pyrimidine;

S-6-Chloro-4-(5-ethyl-1H-pyrazol-3-ylamino)-2-[2-{3-(2-pyrazinyl)isoxazol-5-yl}pyrrolidin-1-yl]pyrimidine;

S-6-Methoxy-4-(5-methyl-1H-pyrazol-3-ylamino)-2-[2-{3-(pyrid-2-yl)isoxazol-5-yl}pyrrolidin-1-yl)pyrimidine;

S-6-(2-Methoxyethoxy)-4-(5-methyl-1H-pyrazol-3-ylamino)-2-[2-{3-(pyrid-2-yl)isoxazol-5-yl}pyrrolidin-1-yl]pyrimidine;

S-6-Pyrrolidin-1-yl-4-(5-methyl-1H-pyrazol-3-ylamino)-2-[2-{3-(pyrid-2-yl)isoxazol-5-yl}pyrrolidin-1-yl]pyrimidine;

S-6-Methoxymethyl-4-(5-methyl-1H-pyrazol-3-ylamino)-2-[2-{3-(pyrid-2-yl)isoxazol-5-yl}pyrrolidin-1-yl]pyrimidine;

S-6-Morpholinocarbonyl-4-(5-methyl-1H-pyrazol-3-ylamino)-2-[2-{3-(pyrid-2-yl)isoxazol-5-yl}pyrrolidin-1-yl]pyrimidine;

S-6-Carbamoyl-4-(5-methyl-1H-pyrazol-3-ylamino)-2-[2-{3-(pyrid-2-yl)isoxazol-5-yl}pyrrolidin-1-yl]pyrimidine;

S-5-Fluoro-4-(5-methyl-1H-pyrazol-3-ylamino)-2-[2-{3-(pyrid-2-yl)isoxazol-5-yl}pyrrolidin-1-yl]pyrimidine;

S-4-(5-Methyl-1H-pyrazol-3-ylamino)-2-[2-{3-(pyrid-2-yl)isoxazol-5-yl}pyrrolidin-1-yl]pyrimidine;

S-4-(5-Methyl-1H-pyrazol-3-ylamino)-6-(2-hydroxyethoxy)-2-[2-{3-(pyrid-2-yl)isoxazol-5-yl}pyrrolidin-1-yl]pyrimidine;

S-4-(5-Methyl-1H-pyrazol-3-ylamino)-6-(2-{N-[2-hydroxyethyl]-N-methyl-amino}ethoxy)-2-[2-{3-(pyrid-2-yl)isoxazol-5-yl}pyrrolidin-1-yl]pyrimidine;

S-4-(5-Methyl-1H-pyrazol-3-ylamino)-6-(2-morpholinoethoxy)-2-[2-(3-(pyrid-2-yl)isoxazol-5-yl)pyrrolidin-1-yl]pyrimidine;

S-4-(5-Methyl-1H-pyrazol-3-ylamino)-6-(methylthio)-2-[2-{3-(pyrid-2-yl)isoxazol-5-yl}pyrrolidin-1-yl]pyrimidine;

4-(5-Methyl-1H-pyrazol-3-ylamino)-6-(tetrahydrofuran-3-ylmethoxy)-2-[2-{3-(pyrid-2-yl)isoxazol-5-yl}pyrrolidin-1-yl]pyrimidine;

S-4-(5-Methyl-1H-pyrazol-3-ylamino)-6-(2-(2-hydroxyethoxy)ethoxy)-2-[2-{3-(pyrid-2-yl)isoxazol-5-yl}pyrrolidin-1-yl]pyrimidine;

4-(5-Methyl-1H-pyrazol-3-ylamino)-6-(2-methoxyethoxy)-2-[2-{3-(pyrid-2-yl)isoxazol-5-yl}pyrrolidin-1-yl]pyrimidine;

S-4-(5-Methyl-1H-pyrazol-3-ylamino)-6-(3-hydroxypropyloxy)-2-[2-{3-(pyrid-2-yl)isoxazol-5-yl}pyrrolidin-1-yl]pyrimidine;

S-4-(5-Methyl-1H-pyrazol-3-ylamino)-6-[2-(2-methoxyethoxy)ethoxy]-2-[2-{3-(pyrid-2-yl)isoxazol-5-yl}pyrrolidin-1-yl]pyrimidine;

S-4-(5-Methyl-1H-pyrazol-3-ylamino)-6-(2-ethoxyethoxy)-2-[2-{3-(pyrid-2-yl)isoxazol-5-yl}pyrrolidin-1-yl]pyrimidine;

S-4-(5-Methyl-1H-pyrazol-3-ylamino)-6-(3-morpholinoprop-1-yloxy)-2-[2-{3-(pyrid-2-yl)isoxazol-5-yl}pyrrolidin-1-yl]pyrimidine;

S-4-(5-Methyl-1H-pyrazol-3-ylamino)-6-(3-methoxyprop-1-yloxy)-2-[2-{3-(pyrid-2-yl)isoxazol-5-yl}pyrrolidin-1-yl]pyrimidine;

S-4-(5-Methyl-1H-pyrazol-3-ylamino)-6-[2-(2-oxopyrrolidin-1-yl)ethoxy]-2-[2-{3-(pyrid-2-yl)isoxazol-5-yl}pyrrolidin-1-yl]pyrimidine;

S-4-(5-Methyl-1H-pyrazol-3-ylamino)-6-[(2S)-2-methoxyprop-1-yloxy]-2-[2-{3-(pyrid-2-yl)isoxazol-5-yl}pyrrolidin-1-yl]pyrimidine;

S-4-(5-Methyl-1H-pyrazol-3-ylamino)-6-[3-(methylthio)prop-1-yloxy]-2-[2-{3-(pyrid-2-yl)isoxazol-5-yl}pyrrolidin-1-yl]pyrimidine;

S-4-(5-Methyl-1H-pyrazol-3-ylamino)-6-[(2S)-5-oxopyrrolidin-2-yl)methoxy]-2-[2-{3-(pyrid-2-yl)isoxazol-5-yl}pyrrolidin-1-yl]pyrimidine;

S-4-(5-Methyl-1H-pyrazol-3-ylamino)-6-[(2R)-5-oxopyrrolidin-2-yl)methoxy]-2-[2-{3-(pyrid-2-yl)isoxazol-5-yl}pyrrolidin-1-yl]pyrimidine;

S-4-(5-Methyl-1H-pyrazol-3-ylamino)-6-[2-(imidazolid-2-on-1-yl)ethoxy]-2-[2-{3-(pyrid-2-yl)isoxazol-5-yl}pyrrolidin-1-yl]pyrimidine;

S-4-(5-Methyl-1H-pyrazol-3-ylamino)-6-ethoxy-2-[2-{3-(pyrid-2-yl)isoxazol-5-yl}pyrrolidin-1-yl]pyrimidine;

S-4-(5-Methyl-1H-pyrazol-3-ylamino)-6-hydroxy-2-[2-{3-(pyrid-2-yl)isoxazol-5-yl}pyrrolidin-1-yl]pyrimidine;

S-4-(5-Methyl-1H-pyrazol-3-ylamino)-6-(2-methoxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-(2-hydroxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-[(2R)-2-hydroxyprop-1-yloxy]-2-[2-{3-(pyrid-2-yl)isoxazol-5-yl}pyrrolidin-1-yl]pyrimidine;

S-4-(5-Ethyl-1H-pyrazol-3-ylamino)-6-(2-methoxyethoxy)-2-[2-{3-(pyrazin-2-yl)isoxazol-5-yl}pyrrolidin-1-yl]pyrimidine;

S-4-(5-Ethyl-1H-pyrazol-3-ylamino)-6-methoxy-2-[2-{3-(pyrazin-2-yl)isoxazol-5-yl}pyrrolidin-1-yl]pyrimidine;

S-4-(5-Cyclopropyl-1H-pyrazol-3-ylamino)-6-(2-hydroxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-(tetrahydropyran-4-yloxy)-2-[2-{3-(pyrid-2-yl)isoxazol-5-yl}pyrrolidin-1-yl]pyrimidine;

S-5-Fluoro-4-(5-methyl-1H-pyrazol-3-ylamino)-2-[2-{3-(thiazol-2-yl)isoxazol-5-yl}pyrrolidin-1-yl]pyrimidine;

S-5-Chloro-4-(5-methyl-1H-pyrazol-3-ylamino)-2-[2-{3-(thiazol-4-yl)isoxazol-5-yl}pyrrolidin-1-yl]pyrimidine;

S-5-Fluoro-4-(5-ethyl-1H-pyrazol-3-ylamino)-2-[2-{3-(thiazol-2-yl)isoxazol-5-yl}pyrrolidin-1-yl]pyrimidine;

S-4-(5-Methyl-1H-pyrazol-3-ylamino)-2-[2-{3-(thiazol-2-yl)isoxazol-5-yl}pyrrolidin-1-yl]pyrimidine;

S-4-(5-Ethyl-1H-pyrazol-3-ylamino)-2-[2-{3-(thiazol-2-yl)isoxazol-5-yl}pyrrolidin-1-yl]pyrimidine;

S-4-(5-Cyclopropyl-1H-pyrazol-3-ylamino)-2-[2-{3-(thiazol-2-yl)isoxazol-5-yl}pyrrolidin-1-yl]pyrimidine;

S-4-(5-Cyclopropyl-1H-pyrazol-3-ylamino)-5-fluoro-2-[2-{3-(thiazol-2-yl)isoxazol-5-yl}pyrrolidin-1-yl]pyrimidine;

S-6-Chloro-4-(5-methyl-1H-pyrazol-3-ylamino)-2-[2-{3-(thiazol-2-yl)isoxazol-5-yl}pyrrolidin-1-yl]pyrimidine;

S-6-Chloro-4-(5-cyclopropyl-1H-pyrazol-3-ylamino)-2-[2-{3-(thiazol-2-yl)isoxazol-5-yl}pyrrolidin-1-yl]pyrimidine;

S-6-Morpholino-4-(5-methyl-1H-pyrazol-3-ylamino)-2-[2-{3-(thiazol-2-yl)isoxazol-5-yl}pyrrolidin-1-yl]pyrimidine;

S-6-Morpholino-4-(5-ethyl-1H-pyrazol-3-ylamino)-2-[2-{3-(pyrazin-2-yl)isoxazol-5-yl}pyrrolidin-1-yl]pyrimidine;

S-6-(2-Methoxyethylamino)-4-(5-methyl-1H-pyrazol-3-ylamino)-2-[2-{3-(thiazol-2-yl)isoxazol-5-yl}pyrrolidin-1-yl]pyrimidine;

S-6-Methylamino-4-(5-methyl-1H-pyrazol-3-ylamino)-2-[2-{3-(thiazol-2-yl)isoxazol-5-yl}pyrrolidin-1-yl]pyrimidine;

S-6-(4-Methylpiperazin-1yl)-4-(5-methyl-1H-pyrazol-3-ylamino)-2-[2-{3-(thiazol-2-yl)isoxazol-5-yl}pyrrolidin-1-yl]pyrimidine;

S-6-Methyl-4-(5-methyl-1H-pyrazol-3-ylamino)-2-[2-{3-(thiazol-2-yl)isoxazol-5-yl}pyrrolidin-1-yl]pyrimidine;

S-6-[3-(Methylsulphonyl)propyl-1-oxy]-4-(5-methyl-1H-pyrazol-3-ylamino)-2-[2-{3-(pyrid-2-yl)isoxazol-5-yl}pyrrolidin-1-yl]pyrimidine;

S-4-(5-Cyclopropyl-1H-pyrazol-3-ylamino)-6-(2-methoxyethoxy)-2-[2-{3-(pyrazin-2-yl)isoxazol-5-yl}pyrrolidin-1-yl]pyrimidine;

S-6-Methyl-4-(5-Ethyl-1H-pyrazol-3-ylamino)-2-[2-{3-(3-methoxypyrazin-2-yl)isoxazol-5-yl}pyrrolidin-1-yl]pyrimidine;

S-6-Chloro-4-(5-Ethyl-1H-pyrazol-3-ylamino)-2-[2-{3-(3-methoxypyrazin-2-yl)isoxazol-5-yl}pyrrolidin-1-yl]pyrimidine;

S-6-Chloro-4-(5-ethyl-1H-pyrazol-3-ylamino)-2-[2-{3-(pyrimid-2-yl)isoxazol-5-yl}pyrrolidin-1-yl]pyrimidine;

S-6-Methoxy-4-(5-ethyl-1H-pyrazol-3-ylamino)-2-[2-{3-(pyrimid-2-yl)isoxazol-5-yl}pyrrolidin-1-yl]pyrimidine;

S-6-Ethyl-4-(5-ethyl-1H-pyrazol-3-ylamino)-2-[2-{3-(pyrimid-2-yl)isoxazol-5-yl}pyrrolidin-1-yl]pyrimidine;

S-6-Methylamino-4-(5-ethyl-1H-pyrazol-3-ylamino)-2-[2-{3-(pyrimid-2-yl)isoxazol-5-yl}pyrrolidin-1-yl]pyrimidine;

S-6-Ethyl-4-(5-cyclopropyl-1H-pyrazol-3-ylamino)-2-[2-{3-(pyrimid-2-yl)isoxazol-5-yl}pyrrolidin-1-yl]pyrimidine;

S-6-Cyclopropyl-4-(5-cyclopropyl-1H-pyrazol-3-ylamino)-2-[2-{3-(pyrimid-2-yl)isoxazol-5-yl}pyrrolidin-1-yl]pyrimidine;

S-6-Cyclopropyl-4-(5-ethyl-1H-pyrazol-3-ylamino)-2-[2-{3-(pyrimid-2-yl)isoxazol-5-yl}pyrrolidin-1-yl]pyrimidine;

S-6-(2-Methoxyethoxy)-4-(5-ethyl-1H-pyrazol-3-ylamino)-2-[2-{3-(pyrimid-2-yl)isoxazol-5-yl}pyrrolidin-1-yl]pyrimidine;

S-6-Methyl-4-(5-Methyl-1H-pyrazol-3-ylamino)-2-[2-[3-(2-methoxypyrid-3-yl)isoxazol-5-yl]pyrrolidin-1-yl]pyrimidine;

S-5-Fluoro-4-(5-cyclopropyl-1H-pyrazol-3-ylamino)-2-[2-[3-(2-methoxypyrid-3-yl)isoxazol-5-yl]pyrrolidin-1-yl]pyrimidine;

S-5-Fluoro-4-(5-ethyl-1H-pyrazol-3-ylamino)-2-[2-[3-(2-methoxypyrid-3-yl)isoxazol-5-yl]pyrrolidin-1-yl]pyrimidine;

S-6-(2-Hydroxyethoxy)-4-(5-methyl-1H-pyrazol-3-ylamino)-2-[2-[3-(2-methoxypyrid-3-yl)isoxazol-5-yl]pyrrolidin-1-yl]pyrimidine;

S-6-Chloro-4-(5-cyclopropyl-1H-pyrazol-3-ylamino)-2-[2-[3-(2 methoxypyrid-3-yl)isoxazol-5-yl]pyrrolidin-1-yl]pyrimidine;
S-6-Chloro-4-(5-ethyl-1H-pyrazol-3-ylamino)-2-[2-[3-(2-methoxypyrid-3-yl)isoxazol-5-yl]pyrrolidin-1-yl]pyrimidine;
S-6-(2-Hydroxyethoxy)-4-(5-cyclopropyl-1H-pyrazol-3-ylamino)-2-[2-[3-(2-methoxypyrid-3-yl)isoxazol-5-yl]pyrrolidin-1-yl]pyrimidine;
S-5-Fluoro-4-(5-methyl-1H-pyrazol-3-ylamino)-2-[2-[3-(2-methoxypyrid-3-yl)isoxazol-5-yl]pyrrolidin-1-yl]pyrimidine;
S-6-(2-Hydroxyethoxy)-4-(5-ethyl-1H-pyrazol-3-ylamino)-2-[2-[3-(2-methoxypyrid-3-yl)isoxazol-5-yl]pyrrolidin-1-yl]pyrimidine;
S-6-Methyl-4-(5-cyclopropyl-1H-pyrazol-3-ylamino)-2-[2-{3-(3-methoxypyrazin-2-yl)isoxazol-5-yl}pyrrolidin-1-yl]pyrimidine;
S-6-Morpholino-4-(5-ethyl-1H-pyrazol-3-ylamino)-2-[2-{3-(3-methoxypyrazin-2-yl)isoxazol-5-yl}pyrrolidin-1-yl]pyrimidine;
S-6-Chloro-4-(5-methyl-1H-pyrazol-3-ylamino)-2-[2-[3-(2-methoxypyrid-3-yl)isoxazol-5-yl]pyrrolidin-1-yl]pyrimidine;
S-6-Methyl-4-(5-ethyl-1H-pyrazol-3-ylamino)-2-[2-{3-(pyrimid-2-yl)isoxazol-5-yl}pyrrolidin-1-yl]pyrimidine;
S-6-Methyl-4-(5-ethyl-1H-pyrazol-3-ylamino)-2-[2-{3-(pyrid-2-yl)isoxazol-5-yl}pyrrolidin-1-yl]pyrimidine;
S-6-Morpholino-4-(5-ethyl-1H-pyrazol-3-ylamino)-2-[2-{3-(3-hydroxypyrazin-2-yl)isoxazol-5-yl}pyrrolidin-1-yl]pyrimidine; and
S-6-(3-Methoxypropyl)-4-(5-methyl-1H-pyrazol-3-ylamino)-2-[2-{3-(pyrid-2-yl)isoxazol-5-yl}pyrrolidin-1-yl]pyrimidine;

and pharmaceutically acceptable salts thereof.

Where the compounds according to the invention contain one or more asymmetrically substituted carbon atoms, the invention includes all stereoisomers, including enantiomers and diastereomers, and mixtures including racemic mixtures thereof. Tautomers and mixtures thereof are also included.

Racemates may be separated into individual enantiomers using known procedures (cf. Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species.

It is to be understood that certain compounds of formula (I) may exist in solvated as well as unsolvated forms such as, for example, hydrated forms. It is to be understood that the invention encompasses all such solvated forms which modulate insulin-like growth factor 1 receptor activity in a human or animal.

It is also to be understood that certain compounds of formula (I) may exhibit polymorphism and that the invention encompasses all such forms which modulate insulin-like growth factor 1 receptor activity in a human or animal.

The compounds according to the invention may be provided as pharmaceutically acceptable salts. Suitable pharmaceutically acceptable salts include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid.

The present invention further provides a process for the preparation of a compound of formula (I) as defined above, or a pharmaceutically acceptable salt thereof, which comprises:

(i) reacting a compound of formula (II)

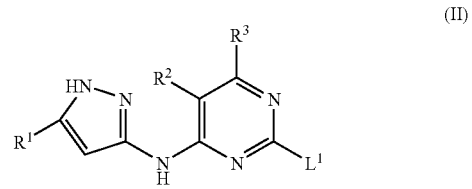

wherein $L^1$ represents a leaving group (e.g. halogen or sulphonyloxy such as methanesulphonyloxy or toluene-4-sulphonyloxy) and $R^1$, $R^2$ and $R^3$ are as defined in formula (I) except that any functional group is protected if necessary, with a compound of formula (III),

wherein $Q^1$ and $Q^2$ are as defined in formula (I) except that any functional group is protected if necessary;

or (ii) reacting a compound of formula (IV)

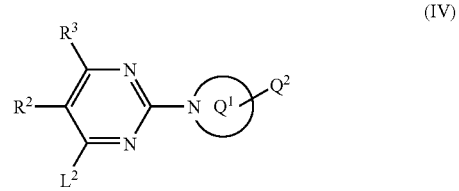

wherein $L^2$ represents a leaving group (e.g. halogen or sulphonyloxy such as methanesulphonyloxy or toluene-4-sulphonyloxy) and $R^2$, $R^3$, $Q^1$ and $Q^2$ are as defined in formula (I) except that any functional group is protected if necessary, with a compound of formula (V),

wherein $R^1$ is as defined in formula (I) except that any functional group is protected if necessary;

or (iii) reacting a compound of formula (VI)

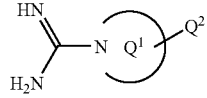
(VI)

wherein $Q^1$ and $Q^2$ are as defined in formula (I) except that any functional group is protected if necessary, with a compound of formula (VII)

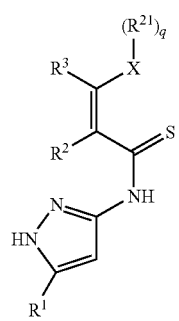
(VII)

wherein X represents an oxygen atom and q is 1 or X represents a nitrogen atom and q is 2, $R^{21}$ independently represents a (C1-C6)alkyl group and $R^2$ and $R^3$ are as defined in formula (I) except that any functional group is protected if necessary;

or (iv) reacting a compound of formula (VIII)

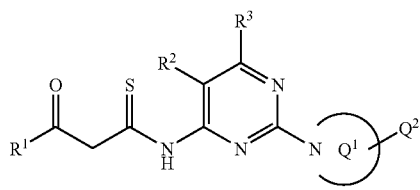
(VIII)

wherein $R^1$, $R^2$, $R^3$, $NQ^1$ and $Q^2$ are as defined in formula (I) except that any functional group is protected if necessary with hydrazine;

or (v) for compounds of formula (I) wherein $R^3$ is a (C1-C6) alkoxy, amino, (C1-C6)alkylamino, di-[(C1-C6)alkyl]amino, amino, —$OR^{3b}$, —$SR^{3b}$, —$NHR^{3b}$, —$N[(C1-C6)$ alkyl]$R^{3b}$ or —$S(O)_mR^{3a}$ group wherein m is 0 and $R^{3a}$ and $R^{3b}$ are as defined above (and the group $R^3$ is optionally substituted by at least one group as defined above), reacting a compound of formula (IX)

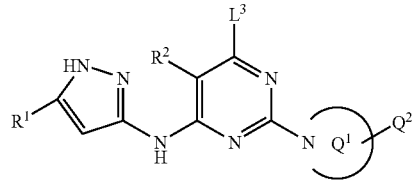
(IX)

wherein $L^3$ represents a leaving group (e.g. halogen or sulphonyloxy such as methanesulphonyloxy or toluene-4-sulphonyloxy) and $R^1$, $R^2$, $Q^1$ and $Q^2$ are as defined in formula (I) except that any functional group is protected if necessary, with a compound of formula H—Xa, wherein Xa is selected from $OR^{22}$, $NH_2$, $NHR^{22}$, $N(R^{22})_2$, $NH_2$, $OR^{3b}$, $SR^{3b}$, $NHR^{3b}$, $N[(C1-C6)alkyl]R^{3b}$ and $SR^{3a}$, wherein $R^{22}$ is an, optionally substituted, (C1-C6)alkyl group and $R^{3a}$ and $R^{3b}$ are each as defined above except that any functional group is protected if necessary;

or (vi) for compounds of formula (I) wherein $R^3$ is an, optionally substituted, saturated monocyclic 5- or 6-membered heterocyclic ring comprising at least one ring nitrogen and, optionally, one or more additional heteroatoms selected from nitrogen, oxygen and sulphur, reacting a compound of formula (IX), with a compound of formula (Xb)

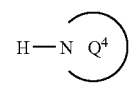
(Xb)

wherein $Q^4$ is a saturated monocyclic 5- or 6-membered heterocyclic ring optionally comprising one or more heteroatoms selected from nitrogen, oxygen and sulphur in addition to the nitrogen atom shown above, which ring is optionally substituted by at least one group as defined above, or with an optionally substituted 2,7-diazaspiro[3.5]nonane group;

or (vii) for compounds of formula (I) wherein $R^3$ is a (C2-C6) alkenyl or (C2-C6)alkynyl group, and the group $R^3$ is optionally substituted by at least one group as defined above, reacting a compound of formula (IX), with a compound of formula (Xc) or of formula (Xc')

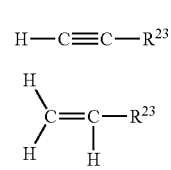
(Xc)
(Xc')

wherein $R^{23}$ is selected from hydrogen and an, optionally substituted, (1-4C)alkyl or (C1-C4)alkoxycarbonyl group;

or (viii) for compounds of formula (I) wherein $R^3$ is attached to the pyrimidine ring through a carbon atom, reacting a compound of formula (IX), with a compound of the formula M-R³, wherein R³ is appropriately selected from the R³ groups as defined above and M is a metallic group, such as ZnBr, B(OH)₂, CuCN or SnBu₃;

(ix) for compounds of formula (I) wherein R³ is a (C1-C6) alkoxycarbonyl group (and the group R³ is optionally substituted by at least one group as defined above), reacting a compound of formula (X)

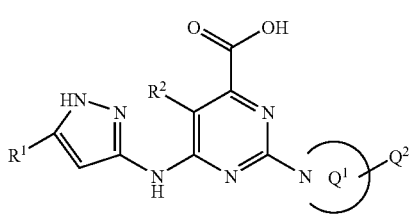

(X)

wherein R¹, R², Q¹ and Q² are as defined in formula (I) except that any functional group is protected if necessary, with a compound of formula H—O—(C1-C6)alkyl, wherein the (C1-C6)alkyl group is optionally substituted by at least one group as defined above and any functional group is protected if necessary; or (x) for compounds of formula (I) wherein R³ is a 5-membered heteroaromatic ring comprising at least one heteroatom selected from nitrogen, oxygen and sulphur (and the group R³ is optionally substituted by at least one group as defined above), conducting an internal condensation reaction using an appropriate starting material and a suitable dehydrating agent. For example, for compounds of formula (I) wherein R³ is a 1,3,4-oxadiazole group, reacting a compound of formula (XI)

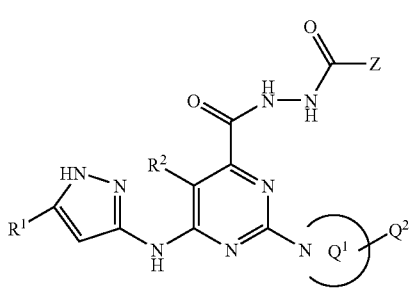

(XI)

wherein Z represents any suitable substituent for R³ as defined above and R¹, R², Q¹ and Q² are as defined in formula (I) except that any functional group is protected if necessary, with a suitable dehydrating agent, such as (methoxycarbonylsulphamoyl)triethylammonium hydroxide; or (xi) for compounds of formula (I) wherein R³ is a (C1-C6) alkyl, (C3-C6)alkenyl, (C3-C6)alkynyl or (C1-C6)alkoxy group substituted by at least one group as defined above, reacting a compound of formula (XII)

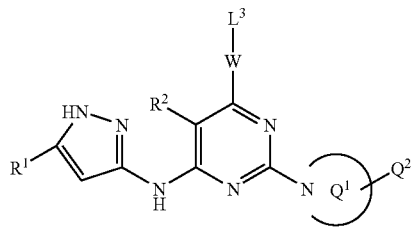

(XII)

wherein L³ represents a leaving group as defined above, W represents an optionally substituted (C1-C6)alkyl, (C3-C6)alkenyl, (C3-C6)alkynyl or (C1-C6)alkoxy group and R¹, R², Q¹ and Q² are as defined in formula (I) except that any functional group is protected if necessary, with a compound of formula H—Xa, (Xb), (Xc), (Xc') or M-R³ as defined above;

and optionally after (i), (ii), (iii), (iv) (v), (vi), (vii), (viii), (ix), (x) or (xi) carrying out one or more of the following:
converting the compound obtained to a further compound of the invention
forming a pharmaceutically acceptable salt of the compound.

Process (i) may conveniently be carried out in the presence of a suitable inert solvent or diluent for example a ketone such as acetone or an alcohol such as ethanol, butanol or n-hexanol or an aromatic hydrocarbon such as toluene or N-methylpyrrolid-2-one, optionally in the presence of a suitable base, for example an organic amine base such as diisopropylethylamine, and at a temperature in the range from 0° C. to reflux, particularly reflux.

Process (ii) may conveniently be carried out in the presence of a suitable inert solvent or diluent for example a ketone such as acetone or an alcohol such as ethanol, butanol or n-hexanol or an aromatic hydrocarbon such as toluene or N-methylpyrrolid-2-one, optionally in the presence of a suitable acid for example an inorganic acid such as anhydrous hydrogen chloride and at a temperature in the range from 0° C. to reflux, particularly reflux Processes (i) and (ii) may each alternatively conveniently be carried out under standard Buchwald conditions (for example see J. Am. Chem. Soc., 118, 7215; J. Am. Chem. Soc., 119, 8451; J. Org. Chem., 62, 1568 and 6066) for example in the presence of palladium acetate, in a suitable inert solvent or diluent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range from 25 to 80° C.

Process (iii) may conveniently be carried out in a suitable inert solvent or diluent such as N-methylpyrrolidinone or butanol at a temperature in the range from 100 to 200° C., in particular in the range from 150 to 170° C. The reaction is preferably conducted in the presence of a suitable base such as, for example, sodium methoxide or potassium carbonate.

Process (iv) may be carried out in a suitable inert solvent or diluent, for example, an alcohol such as ethanol or butanol at a temperature in the range from 50 to 120° C., in particular in the range from 70 to 100° C.

Processes (v) and (vi) may conveniently be carried out in the presence of a suitable inert solvent or diluent for example a ketone such as acetone or an alcohol such as methanol, ethanol, butanol or n-hexanol or an aromatic hydrocarbon such as toluene or N-methyl pyrrolid-2-one, optionally in the presence of a suitable base. A suitable base would be sodium hydride or an organic amine base such as diisopropylethylamine. Another suitable base would be an alkali metal alkoxide, for example sodium methoxide or sodium ethoxide. Processes (v) and (vi) may conveniently be carried out at a temperature in the range from 0° C. to reflux, particularly reflux. Conveniently, these processes may also be performed by heating the reactants in a sealed vessel using a suitable heating apparatus such as a microwave heater.

Process (vii) may conveniently be carried out in the presence of a suitable inert solvent or diluent for example acetonitrile, THF or dioxane, in the presence of a suitable base and a suitable catalyst. A suitable base would be an organic amine base, for example triethylamine or diisopropylethylamine. A suitable catalyst would be, for example, copper iodide/palladium (II) chloride-bis(triphenyl)phosphine. Process (vii) may conveniently be carried out at a temperature in the range from 0° C. to reflux, particularly reflux. Conveniently, this process may also be performed by heating the reactants in a sealed vessel using a suitable heating apparatus such as a microwave heater.

Process (viii) may conveniently be carried out in the presence of a suitable inert solvent or diluent for example THF or dioxane, in the presence of a suitable catalyst. A suitable catalyst would be a palladium (0) catalyst, for example tetrakis(triphenyl)phosphine palladium(0). As the skilled person would appreciate, the palladium (0) catalyst may be prepared in situ. Process (viii) may conveniently be carried out at a temperature in the range from 0° C. to reflux, particularly reflux.

Process (ix) may conveniently be carried out in the absence of an inert solvent or diluent and at a temperature in the range from room temperature to reflux, particularly reflux. Process (ix) is conveniently carried out in the presence of a suitable acid, for example concentrated sulphuric acid.

Process (x) may conveniently be carried out in the presence of a suitable inert solvent or diluent, for example dichloromethane, THF or dioxane. Process (x) may conveniently be carried out at a temperature in the range from 0° C. to reflux, particularly reflux.

Process (xi) may conveniently be carried out under the conditions discussed above for process (v).

Compounds of formulae (II), (III), (IV), (V), (VI), (VII), (VI), HXa, (Xb), (Xc), (Xc') and M-$R^3$ are either commercially available, are known in the literature or may be prepared using known techniques, for example by analogy with the processes described in WO 03/048133. Compounds of the formula (IX), (X), (XI) and (XII) may be prepared using processes (i) and (ii) above. Examples of preparation methods for certain of these compounds are given hereinafter in the examples.

Compounds of formula (I) can be converted into further compounds of formula (I) using standard procedures conventional in the art.

Examples of the types of conversion reactions that may be used include introduction of a substituent by means of an aromatic substitution reaction or of a nucleophilic substitution reaction, reduction of substituents, alkylation of substituents and oxidation of substituents. The reagents and reaction conditions for such procedures are well known in the chemical art.

Particular examples of aromatic substitution reactions include the introduction of a nitro group using concentrated nitric acid; the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of nucleophilic substitution reactions include the introduction of an alkoxy group or of an alkylamino group, a dialkyamino group or a N-containing heterocycle using standard conditions. Particular examples of reduction reactions include the reduction of a carbonyl group to a hydroxyl group with sodium borohydride or of a nitro group to an amino group by catalytic hydrogenation with a nickel catalyst or by treatment with iron in the presence of hydrochloric acid with heating; and particular examples of oxidation reactions include oxidation of alkylthio to alkylsulphinyl or alkylsulphonyl. Other conversion reactions that may be used include the acid catalysed esterification of carboxylic acids with alcohols.

An example of a suitable conversion reaction is the conversion of a compound of formula (I) wherein $R^3$ is a (C1-C6)alkenyl group to a compound of formula (I) wherein $R^3$ is a (C1-C6)alkyl group substituted by a di-[(C1-C6)alkyl] amino group or by a saturated monocyclic 4- to 7-membered ring, which ring comprises nitrogen and one or more heteroatoms independently selected from nitrogen, oxygen and sulphur. Such a conversion may be achieved using standard procedures, for example by conversion of the alkenyl group to a dihydroxyalkyl group with osmium tetroxide, oxidation to the corresponding ketone with a suitable oxidising agent (for example sodium periodate) and conversion of the ketone group to the desired substituent as defined above by reaction with the appropriate amine in the presence of a suitable reducing agent (for example sodium cyanoborohydride).

Another example of a suitable conversion reaction is the conversion of a compound of formula (I) wherein $R^3$ is an optionally substituted (C1-C6)alkoxycarbonyl group to a compound of formula (I) wherein $R^3$ is an optionally substituted carbamoyl, (C1-C6)alkylcarbamoyl or di-[(C1-C6)alkyl]carbamoyl group or an optionally substituted —C(O)$R^{3b}$ group, wherein $R^{3b}$ is as defined above. Such a conversion may be achieved using standard procedures, for example by reaction of the compound of formula (I) wherein $R^3$ is an optionally substituted (C1-C6)alkoxycarbonyl group with ammonia, with an optionally substituted primary, secondary or tertiary amine or with an optionally substituted H—$R^{3b}$ group. As the skilled person would appreciate, this conversion could be conducted starting from the carboxylic acid and preparing an activated ester, for example using 4-(4,6-dimethoxy[1,3,5]triazin-2-yl)-4-methyl-morpholinium chloride, which may then be reacted with the necessary amine.

Another example of a suitable conversion reaction is the conversion of a compound of formula (I) wherein $R^3$ is a (C1-C6)alkoxycarbonyl group to a compound of formula (I) wherein $R^3$ is a hydroxyl-(C1-C6)alkyl group. Such a conversion may be achieved using standard procedures, for example by reduction using lithium borohydride or lithium aluminium hydride.

It will be appreciated that the preparation of compounds of formula (I) may involve, at various stages, the addition and removal of one or more protecting groups. The protection and deprotection of functional groups is described in 'Protective Groups in Organic Synthesis', 2nd edition, T. W. Greene and P. G. M. Wuts, Wiley-Interscience (1991).

When a pharmaceutically acceptable salt of a compound of formula (I) is required, for example an acid-addition salt, it may be obtained by, for example, reaction of said compound with a suitable acid using a conventional procedure.

As mentioned hereinbefore some of the compounds according to the present invention may contain one or more chiral centers and may therefore exist as stereoisomers. Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

In the section above relating to the preparation of the compounds of formula (I), the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The compounds of formula (I) have activity as pharmaceuticals, in particular as modulators or inhibitors of insulin-like growth factor-1 receptor (IGF-1R) activity, and may be used in the treatment of proliferative and hyperproliferative diseases/conditions, examples of which include the following cancers:

(1) carcinoma, including that of the bladder, brain, breast, colon, kidney, liver, lung, ovary, pancreas, prostate, stomach, cervix, colon, thyroid and skin;
(2) hematopoietic tumours of lymphoid lineage, including acute lymphocytic leukaemia, B-cell lymphoma and Burketts lymphoma;
(3) hematopoietic tumours of myeloid lineage, including acute and chronic myelogenous leukaemias and promyelocytic leukaemia;
(4) tumours of mesenchymal origin, including fibrosarcoma and rhabdomyosarcoma; and
(5) other tumours, including melanoma, seminoma, tetratocarcinoma, neuroblastoma and glioma.

The compounds of the invention are especially useful in the treatment of tumours of the breast and prostate.

According to a further aspect, therefore, the present invention provides a compound of formula (I), or a pharmaceutically acceptable salt thereof, as defined above for use in therapy of the human or animal body.

In particular, the invention provides the use of a compound of formula (I), or a pharmaceutically acceptable salt thereof, as defined above in modulating insulin-like growth factor-1 receptor (IGF-1R) activity in a human or animal.

The invention also provides the use of a compound of formula (I), or a pharmaceutically acceptable salt thereof, as hereinbefore defined in the manufacture of a medicament for use in therapy, in particular in modulating insulin-like growth factor-1 receptor (IGF-1R) activity in a human or animal.

It will be appreciated that "therapy" also includes "prophylaxis" unless otherwise indicated. The terms "therapeutic" and "therapeutically" will be understood accordingly.

In a further aspect the present invention provides a method of treating cancer which comprises administering to a patient in need thereof a therapeutically effective amount of a compound of formula (I), or a pharmaceutically acceptable salt thereof, as hereinbefore defined.

The invention further provides a method of modulating insulin-like growth factor-1 receptor (IGF-1R) activity which comprises administering to a patient in need thereof a therapeutically effective amount of a compound of formula (I), or a pharmaceutically acceptable salt thereof, as hereinbefore defined.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

It will be appreciated that the dosage administered will vary depending on the compound employed, the mode of administration, the treatment desired and the disorder indicated. Typically a daily dose of active ingredient in the range of from 0.5 mg to 75 mg active ingredient per kg body weight is received, given if required in divided doses, the precise amount of compound received and the route of administration depending on the weight, age, sex of the patient being treated and on the particular disease condition being treated according to principles known in the art.

The anti-proliferative treatment defined hereinbefore may be applied as a sole therapy or may involve, in addition to the compounds of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adtiamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbB2 antibody trastuzumab [Herceptin™] and the anti-erbB1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a compound of formula (I), or a pharmaceutically acceptable salt thereof, as defined hereinbefore and an additional anti-tumour agent as defined hereinbefore for the conjoint treatment of cancer.

The activity and selectivity of compounds according to the invention may be determined using an appropriate assay as described, for example, in WO 03/048133, and detailed below.

EXAMPLES

The invention will now be further described with reference to the following illustrative examples—in which, unless stated otherwise:

(i) temperatures are given in degrees Celsius (° C.); operations were carried out at room or ambient temperature, that is, at a temperature in the range of 18 to 25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz, in DMSO-$d_6$ unless otherwise indicated. The following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$;

(xi) the following abbreviations have been used:

| | |
|---|---|
| THF | tetrahydrofuran; |
| EtOAc | ethyl acetate; |
| DCM | dichloromethane; |
| DMSO | dimethylsulphoxide; |
| DIPEA | diisopropylethylamine; |
| NMP | N-methylpyrrolid-2-one; |
| tBuOH | tert-butyl alcohol; |
| TFA | trifluoroacetic acid; |
| DMF | N,N-dimethylformamide; and |
| DMA | N,N-dimethylacetamide. |

Example 1

5-Chloro-2-{2-[3-(pyrid-2-yl)isoxazol-5-yl]pyrrolidin-1-yl}-4-(5-methyl-1H-pyrazol-3-ylamino)pyrimidine A mixture of 2,5-dichloro-4-(5-methyl-1H-pyrazol-3-ylamino)pyrimidine (Method 10 of WO 03/048133) (158 mg, 0.648 mmol), 2-[3-(pyrid-2-yl)isoxazol-5-yl]pyrrolidine (Method 12) (212 mg, 0.972 mmol) and di-isopropylethylamine (282 μL, 1.62 mmol) was stirred and heated at 140° C. in n-hexanol (7.0 ml) under nitrogen for 9 hours. The bulk of the hexanol was then removed by evaporation and the residue partitioned between ethyl acetate and water. The ethyl acetate layer was separated, washed with 1.0 molar phosphate buffer pH 4 (×2), then water and finally brine. The organic layer was dried ($Na_2SO_4$), filtered and evaporated and the crude product was absorbed onto a 10 g isolute SCX2 ion exchange column. The column was eluted with DCM/methanol (4:1) to remove neutrals and then with dichloromethane/2M methanolic ammonia (4:1) to elute the product. The purified product was dissolved in the minimum volume of DCM and to the stirred solution a slight excess of 1.0 M ethereal hydrogen chloride was added. Further diethyl ether was added and the solid product collected by filtration, washed with diethyl ether and dried to give the hydrochloride salt of the title compound (300 mg, 100%).

NMR (DMSO-$d_6$+$d_4$ acetic acid at 100° C.): 2.13 (m, 3H), 2.4 (m, 1H), 3.7 (m, 1H), 3.86 (m, 1H), 3.86 (m, 1H), 5.45 (d, 1H), 6.12 (s, 1H) 6.75 (s, 1H), 7.45 (t, 1H), 7.9 (m, 2H), 8.07 (s, 1H), 8.65 (d, 1H); m/z 423 [MH]+.

Examples 2 to 11 were prepared using the same method as Example 1:

| Ex No | Starting materials | Compound name | $Q^3$ | $R^1$ | NMR DMSO-$d_6$ + $d_4$ acetic acid at 100° C. | m/z $(MH)^+$ |
|---|---|---|---|---|---|---|
| 2 | Method 13 below and A | 5-Chloro-2-[2-(3-methylisoxazol-5-yl]pyrrolidin-1-yl]-4-(5-methyl-1H-pyrazol-3-ylamino)pyrimidine | Methyl | Methyl | 1.93-2.0 (m, 2H), 2.15 (s, 3H), 2.20-2.36 (m, 3H), 3.46-3.55 (m, 1H), 3.66-3.78 (m, 1H), 5.19-5.22 (m, 1H), 5.80 (s, 1H), 6.02 (s, 1H), 8.0 (s, 3H), 8.50 (s, 1H). | 360 |
| 3 | Method 13 below and B | 5-Chloro-2-[2-(3-methylisoxazol-5-yl]pyrrolidin-1-yl]-4-(5-cyclopropyl-1H-pyrazol-3-ylamino)pyrimidine | Methyl | Cyclopropyl | 0.68 (d, 2H), 0.92 (d, 2H), 1.80-2.05 (m, 4H), 2.15 (s, 3H), 2.22-2.35 (m, 1H), 3.44-3.58 (m, 1H), 3.62-3.79 (m, 1H), 5.22 (d, 1H), 5.82 (s, 1H), 6.0 (s, 1H), 7.98 (s, 1H), 12.4 (s, 1H) | 386 |
| 4 | Method 13 below and C | 5-Chloro-2-[2-(3-methylisoxazol-5-yl]pyrrolidin-1-yl]-4-(5-tert-butyl-1H-pyrazol-3-ylamino)pyrimidine | Methyl | tert-butyl | 1.35 (s, 9H), 2.30-2.40 (m, 1H), 1.98-2.10 (m, 3H), 2.14 (s, 3H), 3.65-3.75 (m, 2H), 5.32 (d, 1H), 5.99 (s, 1H), 6.35 (s, 1H), 7.99 (s, | 402 |

-continued

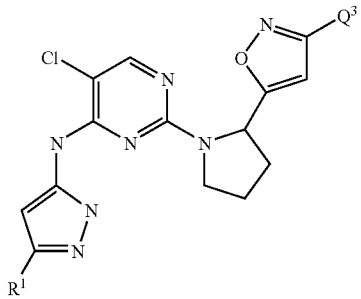

| Ex No | Starting materials | Compound name | Q³ | R¹ | NMR DMSO-d₆ + d₄ acetic acid at 100° C. | m/z (MH)⁺ |
|---|---|---|---|---|---|---|
| | | | | | 1H), 8.10 (s, 1H), 11.75 (s, 1H). | |
| 5 | Method 14 below and B | 5-Chloro-2-[2-(3-cyclopropylisoxazol-5-yl]pyrrolidin-1-yl]-4-(5-cyclopropyl-1H-pyrazol-3-ylamino)phyrimidine | Cyclo-propyl | Cyclo-propyl | 0.65 (m, 4H), 0.90 (m, 4H), 1.97 (m, 5H), 2.28 (m, 1H), 3.62 (m, 2H), 5.25 (d, 1H), 5.80 (s, 1H), 6.06 (s, 1H), 7.93 (s, 1H) | 412 |
| 6 | Method 14 below and A | 5-Chloro-2-[2-(3-cyclopropylisoxazol-5-yl]pyrrolidin-1-y]-4-(5-methyl-1H-pyrazol-3-ylamino)pyrimidine | Cyclo-propyl | Methyl | 0.65 (m, 2H), 0.87 (m, 2H), 1.95 (m, 4H), 2.18 (s, 3H), 2.25 (m, 1H), 3.66 (m, 2H), 5.22 (d, 1H), 5.81 (s, 1H), 6.13 (s, 1H), 7.95 (s, 1H) | 386 |
| 7 | Method 15 below and A | 5-Chloro-2-{2-[3-(thiazol-2-yl)isoxazol-5-yl]pyrrolidin-1-yl}-4-(5-methyl-1H-pyrazol-3-ylamino)pyrimidine | 2-thiazole | Methyl | 2.1 (m, 3H), 2.28 (s, 3H), 2.47 (m, 1H), 3.65 (m, 1H), 3.76 (m, 1H), 5.36 (d, 1H), 6.22 (s, 1H), 6.61 (s, 1H), 7.77 (d, 1H), 7.94 (d, 1H), 7.96 (s, 1H) | 429 |
| 8 | Method 15 below and B | 5-Chloro-2-{2-[3-(thiazol-2-yl)isoxazol-5-yl]pyrrolidin-1-yl}-4-(5-cyclopropyl-1H-pyrazol-3-ylamino)pyrimidine | 2-thiazole | Cyclo-propyl | 0.7 (m, 2H), 0.9 (m, 2H), 1.87 (m, 1H), 2.21 (m, 3H), 2.4 (m, 1H), 3.65 (m, 1H), 3.79 (m, 1H), 5.4 (d, 1H), 6.11 (s, 1H), 6.65 (s, 1H), 7.85 (d, 1H), 7.99 (d, 1H), 8.01 (s, 1H) | 455 |
| 9 | Method 12 below and B | 5-Chloro-2-{2-[3-(pyrid-2-yl)isoxazol-5-yl]pyrrolidin-1-yl}-4-(5-cyclopropyl-1H-pyrazol-3-ylamino)pyrimidine | 2-pyridine | Cyclo-propyl | 0.66 (m, 2H), 0.88 (m, 2H), 1.82 (m, 1H), 2.1 (m, 3H), 2.36 (m, 1H), 3.67 (m, 1H), 3.77 (m, 1H), 5.4 (d, 1H), 6.1 (s, 1H), 6.61 (s, 1H), 7.87 (t, 1H), 7.92 (d, 1H), | 449 |

-continued

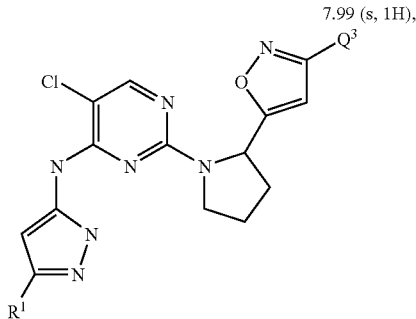

7.99 (s, 1H),

| Ex No | Starting materials | Compound name | Q³ | R¹ | NMR DMSO-d₆ + d₄ acetic acid at 100° C. | m/z (MH)⁺ |
|---|---|---|---|---|---|---|
| 10 | Method 16 below and A | 5-Chloro-2-{2-[3-(pyrid-3-yl)isoxazol-5-yl]pyrrolidin-1-yl}-4-(5-methyl-1H-pyrazol-3-ylamino)pyrimidine | 3-pyridine | Methyl | 8.63 (d, 1H) 2.1 (m, 3H), 2.2 (s, 3H), 2.4 (m, 1H), 3.68 (m, 1H), 3.8 (m, 1H), 3.57 (d, 1H), 6.12 (s, 1H), 6.73 (s, 1H), 7.45 (t, 1H), 8.0 (s, 2H), 8.15 (d, 1H), 8.65 (d, 1H), 8.97 (s, 1H), 11.7 (s, 1H). | 423 |
| 11 | Method 16 below and B | 5-Chloro-2-{2-[3-(pyrid-3-yl)isoxazol-5-yl]pyrrolidin-1-yl}-4-(5-cyclopropyl-1H-pyrazol-3-ylamino)pyrimidine | 3-pyridine | Cyclopropyl | 0.66 (m, 2H), 0.90 (m, 2H), 1.90 (m, 1H), 2.1 (m, 3H), 2.38 (m, 1H), 3.67 (m, 1H), 3.80 (m, 1H), 5.38 (d, 1H), 6.12 (s, 1H), 6.70 (s, 1H), 7.45 (t, 1H), 7.97 (s, 1H), 8.10 (d, 1H), 8.62 (d, 1H), 8.95 (s, 1H) | 449 |

A: 2,5-Dichloro-4-(5-methyl-1H-pyrazol-3-ylamino)pyrimidine
B: 2,5-Dichloro-4-(5-cyclopropyl-1H-pyrazol-3-ylamino)pyriinidine
C: 2,5-Dichloro-4-(5-tert-butyl-1H-pyrazol-3-ylamino)pyrimidine
The preparation of compounds A-C is described in WO 03/048133.

Example 12

2-[2-(3-Cyclopropylisoxazol-5-yl)pyrrolidin-1-yl]-methoxymethyl-4-(5-methyl-1H-pyrazol-3-ylamino)pyrimidine A mixture of 4-chloro-2-[2-(3-cyclopropylisoxazol-5-yl)pyrrolidin-1-yl]-6-methoxymethylpyrimidine (Method 19) (250 mg, 0.746 mmol), 3-amino-5-methyl-1H-pyrazole (109 mg, 1.2 mmol) and hydrogen chloride (0.56 ml of a 4M solution in dioxane, 2.24 mmol) in NMP (5 ml) was heated at 120° C. for 18 hours. The mixture was allowed to cool then directly applied to an isolute SCX2 ion exchange column. The column was eluted with DCM/methanol (4:1) to remove neutrals and then with 7M methanolic ammonia to elute the product. The partially purified product was then purified by chromatography on silica gel eluting with DCM/methanol (100:0 increasing in polarity to 95:5). The product was triturated with diethyl ether/DCM and the solid product collected by filtration to give the title compound (100 mg, 34%) as a white solid.

NMR (DMSO-d₆+d₄-acetic acid at 100° C.): 0.65 (m, 2H), 0.88 (m, 2H), 1.97 (m, 4H), 2.17 (s, 3H), 2.25 (m, 1H), 3.35 (s, 3H), 3.63 (m, 2H), 4.13 (dd, 2H), 5.28 (d, 1H), 5.85 (s, 1H), 6.00 (s, 1H), 6.33 (s, 1H); m/z 396 [MH]+.

Example 13

2-[2-(3-Cyclopropylisoxazol-5-yl)pyrrolidin-1-yl]-6-methoxymethyl-4-(5-cyclopropyl-1H-pyrazol-3-ylamino)pyrimidine The title compound was prepared by the same method as described for Example 12 starting from 3-amino-5-cyclopropyl-1H-pyrazole (Method 7 of WO 03/048133) (130 mg, 41%).

NMR (DMSO-d$_6$+d$_4$-acetic acid at 100° C.): 0.65 (m, 4H), 0.86 (m, 4H), 1.85 (m, 2H), 2.00 (m, 3H), 2.25 (m, 1H), 3.32 (s, 3H), 3.63 (m, 2H), 4.12 (dd, 2H), 5.30 (d, 1H), 5.86 (s, 1H), 5.95 (s, 1H), 6.32 (s, 1H); m/z 422 [MH]+.

Example 14

5-Chloro-2-{2-[3-(pyrid-2-yl)isoxazol-5-yl]piperidin-1-yl}-4-(5-methyl-1H-pyrazol-3-ylamino)pyrimidine 2-[3-(Pyrid-2-yl)isoxazol-5-yl]piperidine (Method 16(a)) (137 mg, 0.6 mmol) was treated as described in Example 1 except that the reaction mixture was heated at 140° C. for 18 hours and then treated with ethylene diaminopropyl silica based scavenger prior to workup as described in Example 1 to give the title compound (35 mg, 16%).

NMR (DMSOd6, 100° C., 400 MHz): 1.53 (m, 2H), 1.75 (m, 2H), 1.93 (m, 1H), 2.2 (s, 3H), 2.25 (m, 1H), 2.9 (m, 1H), 4.6 (d, 1H), 6.13 (s, 2H), 6.7 (s, 1H), 7.4 (t, 1H), 7.85 (m, 2H), 8.05 (s, 1H), 8.17 (s, 1H), 8.68 (d, 1H), 11.75 (s, 1H); m/z 437 [MH]+.

Examples 15 to 24

Examples 15 to 24 were prepared using the method of Example 1:

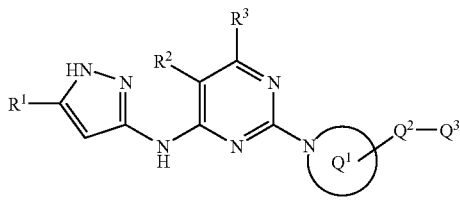

| Ex No | Starting materials | Compound name | R$^1$ | R$^2$ | R$^3$ | Q$^1$ | Q$^2$ | Q$^3$ | NMR (DMSO 373K + d4AcOH) | m/z (MH)+ |
|---|---|---|---|---|---|---|---|---|---|---|
| 15 | A and Method 24 below | 5-Chloro-2-[2-(3-{tetrahydrofuran-3-yl}isoxazol-5-yl]pyrrolidin-1-yl]-4-(5-methyl-1H-pyrazol-3-ylamino)pyrimidine | Me | Cl | H | pyrrolidin-1-yl | isoxazol-5-yl | tetrahydrofuran-3-yl | 2.02 (m, 4H), 2.21 (m, 1H), 2.32 (m, 1H), 3.41 (m, 1H), 3.6 (m, 2H), 3.72 (m, 2H), 3.8 (m, 1H), 3.92 (t, 1H), 5.38 (d, 1H), 6.05 (s, 1H), 6.1 (s, 1H), 7.96 (s, 1H) | 416 |
| 16 | B and Method 24 below | 5-Chloro-4-(5-cyclopropyl-1H-pyrazol-3-ylamino)-2-[2-(3-{tetrahydrofuran-3-yl}isoxazol-5-yl]pyrrolidin-1-yl]-pyrimidine | cyclopropyl | Cl | H | pyrrolidin-1-yl | isoxazol-5-yl | tetrahydrofuran-3-yl | 0.69 (m, 2H), 0.89 (m, 2H), 1.9-2.1 (m, 5H), 2.21 (m, 1H), 2.3 (m, 1H), 3.4 (m, 1H), 3.6 (m, 2H), 3.65-3.83 (m, 3H), 3.94 (t, 1H), 5.3 (d, 1H), 6.05 (s, 1H), 6.09 (s, 1H), 7.96 (s, 1H) | 442 |
| 17 | Method 29 and Method 12 below | 6-Chloro-4-(5-methyl-1H-pyrazol-3-ylamino)-2-{2-[3-(pyrid-2-yl)isoxazol-5-yl]pyrrolidin-1-yl}pyrimidine | Me | H | Cl | pyrrolidin-1-yl | isoxazol-5-yl | pyridin-2-yl | 2.08 (m, 2H), 2.18 (m, 4H), 3.74 (m, 2H), 5.47 (d, 1H), 5.98 (s, 1H), 6.4 (s, 1H), 6.67 (s, 1H), 7.43 (m, 1H), 7.9 (m, 2H), 8.65 (d, 1H), 8.88 (br s, 1H), 11.44 (br s, 1H) (not deuterated) | 423 |
| 18 | B and Method 16(a) below | 5-Chloro-4-(5-cyclopropyl-1H-pyrazol-3-ylamino)-2-{2-[3-(pyrid-2-yl)isoxazol-5-yl]piperidin-1-yl}pyrimidine | cyclopropyl | Cl | H | piperidin-1-yl | isoxazol-5-yl | pyridin-2-yl | 0.6 (m, 2H), 0.87 (m, 2H), 1.53 (m, 2H), 1.73 (m, 2H), 1.85 (m, 1H), 1.95 (m, 1H), 2.26 (m, 1H), 3.0 (d, 1H), 4.6 (d, 1H), 6.05 (s, 1H), 6.13 (d, 1H), 6.66 (s, 1H), 7.4 (t, 1H), 7.87 (t, 1H), 7.94 (d, 1H), 8.03 (s, 1H), 8.62 (d, 1H). | 463 |
| 19 | A and Method 25 below | 5-Chloro-2-(2-[3-(2-methoxypyrid-3-yl)isoxazol-5-yl]pyrrolidin-1-yl}-4-(5-methyl-1H-pyrazol-3-ylamino)pyrimidine | Me | Cl | H | pyrrolidin-1-yl | isoxazol-5-yl | 2-methoxypyridin-3-yl | 2.06 (m, 3H), 2.2 (s, 3H), 2.37 (m, 1H), 3.65 (m, 1H), 3.75 (m, 1H), 3.9 (s, 3H), 5.37 (d, 1H), 6.15 (s, 1H), 6.55 (s, 1H), 7.03 (t, 1H), 8.0 (s, 1H), 8.07 (d, 1H), 8.25 (d, 1H) | 453 |
| 20 | Method 27(b) and Method 12 below | 5-Fluoro-4-(5-methyl-1H-pyrazol-3-ylamino)-2-{2-[3-(pyrid-2-yl)isoxazol-5-yl]pyrrolidin-1-yl}-pyrimidine | Me | F | H | pyrrolidin-1-yl | isoxazol-5-yl | pyridin-2-yl | 2.1 (m, 3H), 2.2 (s, 3H), 2.4 (m, 1H), 3.6 (m, 1H), 3.77 (m, 1H), 5.35 (d, 1H), 6.15 (s, 1H), 6.63 (s, 1H), 7.42 (t, 1H), 7.9 (m, 3H), 8.63 (s, 1H), 8.83 (s, 1H), 11.53 (s, 1H). | 407 |
| 21 | Method 27 and | 4-(5-Cyclopropyl-1H-pyrazol-3- | cyclopropyl | F | H | pyrrolidin-1-yl | isoxazol-5-yl | pyridin-2-yl | 0.7 (2H, m), 0.9 (2H, m), 1.9 (m, 1H), 2.12 (m, 3H), | 433 |

-continued

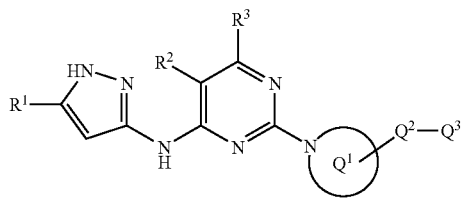

| Ex No | Starting materials | Compound name | R¹ | R² | R³ | Q¹ | Q² | Q³ | NMR (DMSO 373K + d4AcOH) | m/z (MH)⁺ |
|---|---|---|---|---|---|---|---|---|---|---|
|  | Method 12 below | ylamino)-5-fluoro-2-{2-[3-(pyrid-2-yl)isoxazol-5-yl]pyrrolidin-1-yl}pyrimidine |  |  |  |  |  |  | 2.38 (m, 1H), 3.63 (m, 1H), 3.74 (m, 1H), 5.4 (d, 1H), 6.1 (s, 1H), 6.63 (s, 1H), 7.43 (t, 1H), 7.88 (m, 3H), 8.62 (d, 1H), 8.83 (s, 1H), 11.63 (s, 1H). |  |
| 22[1] | B and Method 40 below | S-5-Chloro-2-{2-[3-methylisoxazol-5-yl]pyrrolidin-1-yl}-4-(5-cyclopropyl-1H-pyrazol-3-ylamino)pyrimidine | cyclo-propyl | Cl | H | pyrrolidin-1-yl | isoxazol-5-yl | methyl | 0.68 (d, 2H), 0.92 (d, 2H), 1.80-2.05 (m, 4H), 2.15 (s, 3H), 2.22-2.35 (m, 1H), 3.44-3.58 (m, 1H), 3.62-3.79 (m, 1H), 5.22 (d, 1H), 5.82 (s, 1H), 6.0 (s, 1H), 7.98 (s, 1H), 12.4 (s, 1H) | 386 |
| 23 | Method 26 and Method 42 below | 4-(5-Methyl-1H-pyrazol-3-ylamino)-2-{2-[3-(pyrid-2-yl)isoxazol-5-yl]pyrrolidin-1-yl}pyrimidine | Me | H | H | pyrrolidin-1-yl | isoxazol-5-yl | pyridin-2-yl | 2.00 (m, 3H), 2.15 (s, 3H), 2.32 (m, 1H), 3.54 (m, 1H), 3.80 (m, 1H), 5.38 (d, 1H), 6.20 (m, 1H), 6.66 (s, 1H), 7.45 (m, 1H), 7.90 (m, 4H), 8.62 (d, 1H), 9.38 (br s, 1H), 11.76 (br s, 1H) | 389 |
| 24 | Method 28 and Method 12 below | 4-(5-Cyclopropyl-1H-pyrazol-3-ylamino)-2-{2-[3-(pyrid-2-yl)isoxazol-5-yl]pyrrolidin-1-yl}pyrimidine | cyclo-propyl | H | H | pyrrolidin-1-yl | isoxazol-5-yl | pyridin-2-yl | 0.60 (m, 2H), 0.85 (m, 2H), 1.80 (m, 2.00 (m, 3H), 2.30 (m, 1H), 3.56 (m, 1H), 3.80 (m, 1H), 5.40 (d, 1H), 6.20 (br s, 1H), 6.64 (s, 1H), 7.45 (m, 1H), 7.90 (m, 3H), 8.62 (d, 1H), 9.40 (br s, 1H), 11.84 (br s, 1H) | 415 |

A: 2,5-Dichloro-4-(5-methyl-1H-pyrazol-3-ylamino)pyrimidine
B: 2,5-Dichloro-4-(5-cyclopropyl-1H-pyrazol-3-ylamino)pyrimidine
The preparation of compounds A and B is described in WO 03/048133.
[1]Purified by chromatography on silica gel eluting with DCM / methanol (98:2 increasing in polarity to 95:5).

Example 25

4-(5-Cycloprop-yl-1H-pyrazol-3-ylamino)-6-methyl-2-[2-{3-(pyrid-2-yl)isoxazol-5-yl}pyrrolidin-1-yl]pyrimidine A mixture of 4-hydroxy-6-methyl-2-[2-{3-(pyrid-2-yl)isoxazol-5-yl}pyrrolidin-1-yl]pyrimidine (Method 30) (200 mg, 0.62 mmol) in phosphoryl chloride (7 ml) was heated at 70° C., under nitrogen for 30 minutes. The volatiles were removed by evaporation and the residue dissolved in DCM, washed with saturated sodium hydrogen carbonate solution, dried (MgSO₄) and the solvent removed by evaporation. The crude product was then treated as described in Example 12, with 3-amino-5-cyclopropyl-1H-pyrazole (Method 7 of WO-03/048133) (120 mg, 0.98 mmol), and 4M hydrogen chloride solution in dioxane (0.65 ml) in NMP (5 ml) to give the title compound (100 mg, 37%).

NMR (DMSO): 0.64 (m, 2H), 0.84 (m, 2H), 1.76-1.82 (m, 1H), 1.96-2.15 (m, 7H), 2.25-2.36 (m, 1H), 3.45-3.55 (m, 1H), 3.72-3.80 (m, 1H), 5.40 (d, 1H), 5.87 (s, 1H), 6.08 (s, 1H), 6.61 (s, 1H), 7.44 (dd, 1H), 7.86-7.95 (m, 2H), 8.60 (d, 1H), 9.30 (s, 1H); m/z 429 [M]+.

Examples 26 to 36

Examples 26 to 36 were prepared by an analogous method to that described in Example 25.

Example 26

4-(5-Methyl-1H-pyrazol-3-ylamino)-6-methyl-2-[2-{3-(pyrid-2-yl)isoxazol-5-yl}pyrrolidin-1-yl]pyrimidine Starting materials: 4-hydroxy-6-methyl-2-[2-{3-(pyrid-2-yl)isoxazol-5-yl}pyrrolidin-1-yl]pyrimidine (Method 30) and 3-amino-5-methyl-1H-pyrazole.

Purified by chromatography on silica gel eluting with methanol/DCM (8:92) to give the title compound (42 mg, 22%).

NMR (DMSO): 1.99-2.15 (m, 10H), 2.25-2.38 (m, 1H), 3.52-3.60 (m, 1H), 3.72-3.80 (m, 1H), 5.39 (d, 1H), 6.10 (s, 1H), 6.64 (s, 1H), 7.45 (dd, 1H), 7.86-7.98 (m, 2H), 8.62 (d, 1H), 9.22 (s, 1H); m/z 403 [MH]+.

Example 27

4-(5-Cyclopropyl-1H-pyrazol-3-ylamino)-6-methyl-2-[2-(3-methylisoxazol-5-yl)pyrrolidin-1-yl]pyrimidine Starting materials: 4-hydroxy-6-methyl-2-[2-{3-(methyl)isoxazol-5-yl}pyrrolidin-1-yl]pyrimidine (Method 31) and 3-amino-5-cyclopropyl-1H-pyrazole (Method 7 of WO-03/048133).

Yield: 70 mg, 25%.

NMR (DMSO): 0.62 (m, 2H), 0.89 (d, 2H), 1.84-1.78 (m, 1H), 2.0-1.94 (m, 3H), 2.08 (s, 3H), 2.12 (s, 3H), 3.48-3.55 (m, 1H), 3.63-3.73 (m, 1H), 5.30 (d, 1H), 6.0 (s, 1H), 6.08 (s, 1H), 9.21 (s, 1H), 11.8 (s, 1H); m/z 364 [MH]−.

Example 28

6-Ethyl-4-(5-methyl-1H-pyrazol-3-ylamino)-2-[2-{3-(pyrid-2-yl)isoxazol-5-yl}pyrrolidin-1-yl]pyrimidine Starting materials: 4-hydroxy-6-ethyl-2-[2-{3-(pyrid-2-yl)isoxazol-5-yl}pyrrolidin-1-yl]pyrimidine (Method 32) and 3-amino-5-methyl-1H-pyrazole.

Yield: 150 mg, 38%.

NMR (DMSO): 1.02-1.15 (m, 3H), 1.99-2.09 (m, 3H), 2.14 (s, 3H), 2.28-2.41 (m, 3H), 3.58-3.62 (m, 1H), 3.75-3.80 (m, H), 5.38 (d, 1H), 6.14 (s, 1H), 6.68 (s, 1H), 7.45 (dd, 1H), 7.87-7.95 (m, 2H), 8.62 (d, 1H), 9.22 (s, 1H); m/z 417 [MH]+.

Example 29

6-(3-Methoxypropyl)-4-(5-methyl-1H-pyrazol-3-ylamino)-2-[2-{3-(pyrid-2-yl)isoxazol-5-yl}pyrrolidin-1-yl]pyrimidine Starting materials: 4-hydroxy-6-(3-methoxypropyl)-2-[2-{3-(pyrid-2-yl)isoxazol-5-yl}pyrrolidin-1-yl]pyrimidine (Method 33) and 3-amino-5-methyl-1H-pyrazole.

Yield: 56 mg, 14%.

NMR (DMSO): 1.78-1.82 (m, 1H), 2.0-2.12 (m, 3H), 2.18 (s, 3H), 2.28-2.40 (m, 2H), 2.58-2.64 (m, 2H), 3.04-3.20 (m, 2H), 3.30 (s, 3H), 3.58-3.62 (m, 1H), 3.73-3.82 (m, 1H), 5.38 (d, 1H), 5.90 (s, 1H), 6.10 (s, 1H), 6.65 (s, 1H), 7.48 (dd, 1H), 7.87-7.98 (m, 2H), 8.62 (d, 1H), 9.24 (s, 1H); m/z 461 [MH]+.

Example 30

6-Methoxymethyl-4-(5-methyl-1H-pyrazol-3-ylamino)-2-[2-{3-(pyrid-2-yl)isoxazol-5-yl}pyrrolidin-1-yl]pyrimidine Starting materials: 4-hydroxy-6-methoxymethyl-2-[2-{3-(pyrid-2-yl)isoxazol-5-yl}pyrrolidin-1-yl]pyridine (Method 34) and 3-amino-5-methyl-1H-pyrazole.

Yield: 260 mg, 49%.

NMR (DMSO): 2.0-2.15 (m, 3H), 2.20 (s, 3H), 3.30 (s, 3H), 3.65-3.8 (m, 2H), 4.15 (q, 2H), 5.45 (d, 1H), 6.04 (s, 1H), 6.38 (s, 1H), 6.64 (s, 1H), 7.44 (dd, 1H), 7.88-7.90 (m, 2H), 8.65 (d, 1H), 8.90 (s, 1H).

Example 31

4-(5-Cycloprop-yl-1H-pyrazol-3-ylamino)-6-methoxymethyl-2-[2-{3-(pyrid-2-yl)isoxazol-5-yl}pyrrolidin-1-yl]pyrimidine Starting materials: 4-hydroxy-6-methoxymethyl-2-[2-{3-(pyrid-2-yl)isoxazol-5-yl}pyrrolidin-1-yl]pyrimidine (Method 34) and 3-amino-5-cyclopropyl-1H-pyrazole (Method 7 of WO-03/048133).

Yield: 245 mg, 48%.

NMR (DMSO): 0.63-0.65 (m, 2H), 0.84-0.9 (m, 3H), 1.80-1.89 (m, 1H), 2.04-2.10 (m, 2H), 2.11-2.18 (m, 1H), 2.32-2.40 (m, 1H), 3.35 (s, 3H), 3.68-3.80 (m, 2H), 4.18 (q, 2H), 5.45 (d, 1H), 6.0 (s, 1H), 6.38 (s, 1H), 6.65 (s, 1H), 7.44 (dd, 1H), 7.78-7.97 (m, 2H), 8.65 (d, 1H), 8.92 (s, 1H); m/z 459 [MH]+.

Example 32

6-Methoxymethyl-4-(5-methyl-1H-pyrazol-3-ylamino)-2-{2-[3-(thiazol-2-yl)isoxazol-5-yl]pyrrolidin-1-yl}pyrimidine Starting materials: 4-hydroxy-6-methoxymethyl-2-[2-{3-(thiazol-2-yl)isoxazol-5-yl}pyrrolidin-1-yl]pyrimidine (Method 36) and 3-amino-5-methyl-1H-pyrazole.

Yield: 32 mg, 12%.

NMR (DMSO): 2.0-2.15 (m, 3H), 2.16 (s, 3H), 2.37 (m, 1H), 3.33 (s, 3H), 3.65-3.79 (m, 2H), 4.14 (m, 2H), 5.44 (d, 1H), 6.0 (s, 1H), 6.37 (s, 1H), 6.63 (s, 1H), 7.79 (d, 1H), 7.95 (d, 1H); m/z 439 [MH]+.

Example 33

6-Methoxymethyl-4-(5-methyl-1H-pyrazol-3-ylamino)-2-[2-{3-(pyrid-3-yl)isoxazol-5-yl}pyrrolidin-1-yl]pyrimidine Starting materials: 4-hydroxy-6-methoxymethyl-2-{3-(pyrid-3-yl)isoxazol-5-yl}pyrrolidin-1-yl]pyrimidine (Method 35(a)) and 3-amino-5-methyl-1H-pyrazole.

Yield: 30 mg, 21%.

NMR (DMSO): 2.07 (m, 3H), 2.17 (s, 3H), 2.36 (m, 1H), 3.33 (s, 3H), 3.7 (m, 2H), 4.16 (t, 2H), 5.43 (d, 1H), 6.03 (s, 1H), 6.37 (s, 1H), 6.77 (s, 1H), 7.47 (t, 1H), 8.13 (d, 1H), 8.65 (d, 1H), 8.87 (s, 1H), 8.98 (s, 1H), 11.5 (s, 1H); m/z 433 [MH]+.

Example 34

4-(5-Methyl-1H-pyrazol-3-ylamino)-6-(pent-3-en-1-yl)-2-[2-{3-(pyrid-2-yl)isoxazol-5-yl}pyrrolidin-1-yl]pyrimidine Starting materials: 4-hydroxy-6-(pent-3-en-1-yl)-2-[2-{3-(pyrid-2-yl)isoxazol-5-yl}pyrrolidin-1-yl]pyrimidine (Method 35) and 3-amino-5-methyl-1H-pyrazole.

Yield: 341 mg, 56%.

NMR (DMSO): 1.55 (d, 3H), 2.02-2.18 (m, 3H), 2.18 (s, 3H), 2.23-2.28 (m, 1H), 2.32-2.45 (m, 3H), 3.68-3.8 (m, 2H), 5.34-5.40 (m, 3H), 6.05 (s, 1H), 6.18 (s, 1H), 6.65 (s, 1H), 7.43 (dd, 1H), 7.88-7.96 (m, 2H), 8.65 (d, 1H), 8.75 (s, 1H), 11.50 (s, 1H); m/z 457 [MH]+.

Example 35

4-(5-Methyl-1H-pyrazol-3-ylamino)-2-{2-[3-(pyrid-2-yl)isoxazol-5-yl]pyrrolidin-1-yl}-6-trifluoromethylpyrimidine Starting materials: 4-hydroxy-6-trifluoromethyl-2-[2-{3-(pyrid-2-yl)isoxazol-5-yl}pyrrolidin-1-yl]pyrimidine (Method 37) and 3-amino-5-methyl-1H-pyrazole.

Yield: 115 mg, 38%.

NMR (DMSO): 2.20 (m, 7H), 3.70 (br m, 2H), 5.42 (br d, 1H), 5.95 (br s, 1H), 6.62 (br m, 1H), 6.80 (br s, 1H), 7.50 (m, 1H), 7.95 (m, 2H), 8.64 (m, 1H); m/z 457 [MH]+.

Example 36

4-(5-Cyclopropyl-1H-pyrazol-3-ylamino)-2-{2-[3-(pyrid-2-yl)isoxazol-5-yl]pyrrolidin-1-yl}-6-trifluoromethylpyrimidine Starting materials: 4-hydroxy-6-trifluoromethyl-2-[2-{3-(pyrid-2-yl)isoxazol-5-yl}pyrrolidin-1-yl]pyrimidine (Method 37) and 3-amino-5-cyclopropyl-1H-pyrazole (Method 7 of WO-03/048133).

Yield: 60 mg, 17%.

NMR (DMSO): 0.70 (m, 2H), 0.90 (m, 2H), 1.90 (m, 1H), 2.15 (m, 4H), 3.78 (m, 2H), 5.50 (d, 1H), 6.05 (s, 1H), 6.70 (s, 1H), 7.45 (m, 1H), 7.95 (m, 2H), 8.68 (d,1H), 9.58 (br s, 1H), 11.78 (br s, 1H); m/z 483 [MH]+.

Examples 37 to 42

The following single enantiomers of Examples 37 to 42 were prepared by separation of the racemic compound by chiral HPLC using a Chiralpak AD column using methanol or methanol/ethanol mixtures as eluent.

Example 37

S-6-Ethyl-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 28).

Example 38

S-5-Chloro-2-{2-[3-(thiazol-2-yl)isoxazol-5-yl]pyrrolidin-1-yl}-4-(5-methyl-1H-pyrazol-3-ylamino) pyrimidine The title compound was prepared by separation of the racemic compound (Example 7).

Example 39

S-5-Chloro-2-{2-[3-(pyrid-2-yl)isoxazol-5-yl]pyrrolidin-1-yl}-4-(5-cyclopropyl-1H-pyrazol-3-ylamino) pyrimidine The title compound was prepared by separation of the racemic compound (Example 9).

Example 40

S-4-(5-Methyl-1H-pyrazol-3-ylamino)-6-methyl-2-[2-{3-(pyrid-2-yl)isoxazol-5-yl}pyrrolidin-1-yl]pyrimidine The title compound was prepared by separation of the racemic compound (Example 26).

Example 41

S-5-Chloro-2-{2-[3-(pyrid-2-yl)isoxazol-5-yl]pyrrolidin-1-yl}-4-(5-methyl-1H-pyrazol-3-ylamino)pyrimidine The title compound was prepared by separation of the racemic compound (Example 1).

Example 42

S-5-Chloro-2-{2-[3-(2-methoxypyrid-3-yl)isoxazol-5-yl]pyrrolidin-1-yl}-4-(5-methyl-1H-pyrazol-3-ylamino)pyrimidine The title compound was prepared by separation of the racemic compound (Example 19).

Example 43

6-(3-N,N-Dimethylaminopropyl)-4-(5-methyl-1H-pyrazol-3-ylamino)-2-[2-{3-(pyrid-2-yl)isoxazol-5-yl}pyrrolidin-1-yl]pyrimidine Osmium tetroxide (0.070 ml of 2.5% wt solution in tBuOH) followed by water (0.38 ml) was added to a stirred solution of 4-(5-methyl-1H-pyrazol-3-ylamino)-6-(pent-3-en-1-yl)-2-[2-{3-(pyrid-2-yl)isoxazol-5-yl}pyrrolidin-1-yl]pyrimidine (Example 34) (100 mg, 2.2 mmol) in THF (2 ml), under nitrogen. Sodium periodate (150 mg, 6.5 mmol) was added and the mixture stirred for 1 hour. The mixture was diluted with water and extracted with ethyl acetate. The extracts were combined, dried (MgSO$_4$) and the volatiles removed by evaporation. The residue was dissolved in methanol and acetic acid (0.066 ml) and 2M solution of dimethylamine in THF (0.55 ml) added. Sodium cyanoborohydride (28 mg) was quickly added and the mixture stirred at ambient temperature for 18 hours. The volatiles were then removed by evaporation, the residue dissolved in ethyl acetate, washed with saturated aqueous sodium carbonate solution and then brine. The volatiles were removed by evaporation, and the residue purified by chromatography on silica gel eluting with DCM/methanol/aqueous ammonia (100:0:0 increasing in polarity to 85:15:0.3) to give the title compound (8 mg, 11%).

NMR (DMSO): 1.28-1.35 (m, 2H), 1.70-1.78 (m, 2H), 2.07-2.10 (m2H), 2.1(s, 6H), 2.20 (s, 3H), 2.30-2.45 (m, 4H), 3.70-3.82 (m, 2H), 5.47 (d, 1H), 6.08 (s, 1H), 6.20 (s, 1H), 6.65 (s, 1H), 7.45 (dd, 1H), 7.87-7.99 (m, 2H), 8.68 (d, 1H); m/z 472 [MH]−.

Example 44

6-(3-Pyrrolidin-1-ylpropyl)-4-(5-methyl-1H-pyrazol-3-ylamino)-2-[2-{3-(pyrid-2-yl)isoxazol-5-yl}pyrrolidin-1-yl]pyrimidine Example 44 was prepared by an analogous method to that described in Example 43 starting from 4-(5-methyl-1H-pyrazol-3-ylamino)-6-(pent-3-en-1-yl)-2-[2-{3-(pyrid-2-yl)isoxazol-5-yl}pyrrolidin-1-yl]pyrimidine (Example 34) and pyrrolidine.

Yield: 6 mg, 18%.

NMR (DMSO): 1.55-1.68 (m, 4H), 1.68-1.78 (m, 2H), 2.0-2.17 (m, 4H), 2.18 (s, 3H), 2.28-2.45 (m, 8H), 3.65-3.80 (m, 2H), 5.43 (d, 1H), 6.04 (s, 1H), 6.18 (s, 1H), 6.64 (s, 1H), 7.42 (dd, 1H), 7.85-7.97 (m, 2H), 8.63 (d, 1H), 8.74 (s, 1H); m/z 500 [MH]+.

Example 45

6-Methoxycarbonyl-4-(5-meth-1-1H-pyrazol-3-ylamino)-2-{2-[3-(pyrid-2-yl)isoxazol-5-yl]pyrrolidin-1-yl}pyrimidine A mixture of 2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 43) (100 mg 0.21 mmol), methanol (10 ml) and 1 drop of 98% sulphuric acid was heated at reflux for 18 hours. The volatiles were removed by evaporation and the residue dissolved in water. The resulting solution was adjusted to pH 12 by careful addition of 10M aqueous sodium hydroxide solution and then extracted with DCM. The extracts were combined and the volatiles removed by evaporation. The residue was purified by chromatography on silica gel eluting with DCM/methanol (100:0 increasing in polarity to 95:5). The purified product was triturated with diethylether and the resulting solid collected by filtration to give the title compound (10 mg, 8.8%).

NMR (DMSO-$d_6$+$d_4$-acetic acid at 100° C.): 2.05 (m, 3H), 2.15 (s, 3H), 2.35 (m, 1H), 3.75 (m, 5H), 5.50 (dd, 1H), 6.05 (s, 1H), 6.70 (s, 1H), 6.88 (s, 1H), 7.40 (m, 1H), 7.88 (t, 1H), 7.95 (d, 1H), 8.65 (d, 1H); m/z 447 [MH]+.

Example 46

6-(2-Hydroxyethylcarbamoyl)-4-(5-methyl-1H-pyrazol-3-ylamino)-2-{2-[3-(pyrid-2-yl)isoxazol-5-yl]pyrrolidin-1-yl}pyrimidine A mixture of 6-methoxycarbonyl-4-(5-methyl-1H-pyrazol-3-ylamino)-2-{2-[3-(pyrid-2-yl)isoxazol-5-yl]pyrrolidin-1-yl}pyrimidine (Example 45) (49.5 mg, 0.11 mmol) and ethanolamine (2.0 ml, 33.7 mmol) in methanol (4 ml) was heated at 88° C. for 2 hours. The volatiles were removed by evaporation and the residue was purified by reverse phase HPLC using a C18 column eluting with water/acetonitrile/TFA (95:5:0.2 decreasing in polarity to 0:100:0.2) the fractions containing product were combined and passed through a 50 g isolute SCX-2 ion exchange column. The column was eluted with methanol to elute any neutral impurities, followed by 7M methanolic ammonia to elute the product. The solvent was removed by evaporation, the residue triturated with diethylether and the resulting solid collected by filtration to give the title compound (27 mg, 57%).

NMR (DMSO-$d_6$+$d_4$-acetic acid at 100° C.): 2.10 (m, 3H), 2.20 (s, 3H), 2.40 (m, 1H), 3.35 (m, 2H), 3.55 (t, 2H), 3.75 (m, 1H), 3.85 (m, 1H), 5.50 (dd, 1H), 6.10 (s, 1H), 6.72 (s, 1H), 6.88 (s, 1H), 7.40 (m, 1H), 7.85 (t, 1H), 7.90 (d, 1H), 8.62 (d, 1H); m/z 476 [MH]+.

Example 47

4-(5-Methyl-1H-pyrazol-3-ylamino)-2-{2-[3-(pyrid-2-yl)isoxazol-5-yl]pyrrolidin-1-yl}-6-(pyrrolidin-1-ylcarbonyl)pyrimidine Example 47 was prepared by an analogous method to that described in Example 46 except that the starting material was treated with neat pyrrolidine and the product was purified by chromatography on silica gel eluting with DCM/methanol (100:0 increasing in polarity to 90:10) to give the title compound (10 mg, 2.8%).

NMR (DMSO-$d_6$+$d_4$-acetic acid at 100° C.): 1.75 (m, 4H), 2.10 (m, 3H), 2.20 (s, 3H), 2.40 (m, 1H), 3.45 (m, 4H), 3.70 (m, 1H), 3.85 (m, 1H), 5.40 (dd, 1H), 6.10 (s, 1H), 6.55 (s, 1H), 6.65 (s, 1H), 7.40 (m, 1H), 7.88 (t, 1H), 7.95 (d, 1H), 8.65 (d, 1H); m/z 486 [MH]+.

Example 48

6-Methoxy-4-(5-methyl-1H-pyrazol-3-ylamino)-2-{2-[3-(pyrid-2-yl))isoxazol-5-yl]pyrrolidin-1-yl}pyrimidine A mixture of 6-chloro-4-(5-methyl-1H-pyrazol-3-ylamino)-2-{2-[3-(pyrid-2-yl)isoxazol-5-yl]pyrrolidin-1-yl}pyrimidine (Example 17) (200 mg, 0.47 mmol), 25% NaOMe/MeOH solution (0.54 ml, 2.3 mmol) in methanol (3 ml) was heated under sealed conditions at 140° C. for one hour. The mixture was allowed to cool and then adjusted to pH 7 by careful addition of 2M ethereal hydrogen chloride. The mixture was then diluted with water and the aqueous mixture extracted with DCM, the extracts combined, dried (MgSO$_4$) and the solvent removed by evaporation. The residue was triturated with diethyl ether the product collected by filtration to give the title compound (98 mg, 50%) as a white solid.

NMR (DMSO): 2.14-2.2 (m, 6H), 2.38 (m, 1H), 3.75 (m, 5H), 5.44 (d, 1H), 5.75 (s, 1H), 5.94 (s, 1H), 6.66 (s, 1H), 7.4 (m, 1H), 7.88 (m, 1H), 7.91 (m, 1H), 8.63 (m, 1H); m/z 419 [MH]+.

Example 49

5-Chloro-4-(3-cyclopropyl-1H-pyrazol-5-ylamino)-2-[2-(2-methyl-2H-tetrazol-5-yl)pyrrolidin-1-yl]pyrimidine 1-tert-Butyloxy-2-(2-methyl-2H-tetrazol-5-yl)pyrrolidine (Method 46) (160 mg, 0.63 mmol) was stirred for one hour in TFA (2 ml) at ambient temperature. The TFA was removed by evaporation and the resulting product was added to a mixture of 2,5-dichloro-4(3-cyclopropyl-1H-pyrazol-5-ylamino)pyrimidine (Method 20 of WO 03/048133) (152 mg, 0.57 mmol) and di-isopropylethylamine (330 μL, 1.9 mmol) in n-hexanol (4.0 ml). The resulting mixture was stirred and heated at 120° C. under nitrogen for 12 hours. 3-(1,2-diaminoethyl)propyl functionalised silica gel (40 mg, 0.11 mmol) was added and the mixture was then heated at 140° C. for 12 hours. The mixture was allowed to cool, filtered and the filtrate directly applied to an isolute SCX2 ion exchange column. The column was eluted with DCM/methanol (4:1) to remove neutrals and then with 7M methanolic ammonia to elute the product. The product was triturated with diethyl ether and the solid product collected by filtration, washed with diethyl ether and dried to give the title compound (82 mg, 38%).

NMR (DMSO-d₆ at 100° C.): 0.72 (m, 2H), 093 (m, 2H), 1.87 (m, 1H), 2.06 (m, 3H), 2.41 (m, 1H), 3.71 (m, 2H), 4.27 (s, 3H) 5.47 (dd, 1H), 6.11 (br s, 1H), 7.92 (s, 1H); m/z 387 [MH]+.

Example 50

6-N-Ethylpiperazinyl-4-(5-methyl-1H-pyrazol-3-ylamino)-2-{2-[3-(pyrid-2-yl)isoxazol-5-yl]pyrrolidin-1-yl}pyrimidine A mixture of 6-chloro-2-{2-[3-(pyrid-2-yl)isoxazol-5-yl]pyrrolidin-1-yl}-4-(5-methyl-1H-pyrazol-3-ylamino)pyrimidine (Example 17) (250 mg, 0.59 mmol) and N-ethylpiperazine (674 mg, 5.9 mmol) in anhydrous 1,4-dioxane (5 ml) was heated at 150° C. for 40 minutes in a sealed vessel under microwave irradiation. The volatiles were removed by evaporation and the residue was purified by reverse phase HPLC using a C18 column eluting with water/acetonitrile/trifluoroacetic acid (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation and the residue re-purified by chromatography on silica gel eluting with DCM/methanol/aqueous ammonia (100:0:0 increasing polarity to 89:20:1) to give the title compound (200 mg, 68%).

NMR (DMSO-d₆+d₄-acetic acid at 100° C.): 1.08 (t, 3H), 2.05 (m, 3H), 2.18 (s, 3H), 2.87 (m, 6H), 2.35 (m, 1H), 2.87 (m, 6H), 3.57 (s, 4H), 3.65 (m, 1H), 3.75 (m, 1H), 5.35 (d, 1H), 5.55 (s, 1H), 5.95 (s, 1H), 6.60 (s, 1H), 7.40 (m, 1H), 7.85 (m, 1H), 7.95 (d, 1H), 8.60 (d, 1H); m/z 501 [MH]+.

Examples 51 and 52

Examples 51 and 52 were prepared by an analogous method to that described in Example 50, however, normal phase chromatography was not required, and the compounds were isolated by trituration with diethylether/DCM and collection by filtration.

Example 51

6-N-Methylpiperazyl-2-{2-[3-(pyrid-2-yl)isoxazol-5-yl]pyrrolidin-1-yl}-4-(5-methyl-1H-pyrazol-3-ylamino)pyrimidine Staring materials: 6-chloro-2-{2-[3-(pyrid-2-yl)isoxazol-5-yl]pyrrolidin-1-yl}-4-(5-methyl-1H-pyrazol-3-ylamino)pyrimidine (Example 17) and N-methylpiperazine.

Yield: 201 mg, 70%.

NMR (DMSO-d₆+d₄-acetic acid at 100° C.): 2.00-2.15 (m, 3H), 2.20 (s, 3H), 2.35 (m, 1H), 2.60 (s, 3H), 2.95 (m, 4H), 3.6 (m, 4H), 3.70 (m, 1H), 3.75 (m, 1H), 5.35 (d, 1H), 5.95 (s, 1H), 6.65 (s, 1H), 7.40 (m, 1H), 7.85 (m, 1H), 7.95 (d, 1H), 8.60 (d, 1H); m/z 487 [MH]⁺.

Example 52

6-Morpholino-4-(5-methyl-1H-pyrazol-3-ylamino)-2-{2-[3-(pyrid-2-yl)isoxazol-5-yl]pyrrolidin-1-yl}pyrimidine Staring materials: 6-chloro-2-{2-[3-(pyrid-2-yl)isoxazol-5-yl]pyrrolidin-1-yl}-4-(5-methyl-1H-pyrazol-3-ylamino)pyrimidine (Example 17) and morpholine.

Yield: 239 mg, 85%.

NMR (DMSO-d₆+d₄-acetic acid at 100° C.): 2.00-2.20 (m, 3H), 2.25 (s, 3H), 2.35 (m, 1H), 3.35 (m, 4H), 3.55 (m, 4H), 3.60-3.75 (m, 2H), 5.35 (d, 1H), 5.60 (s, 1H), 5.70 (s, 1H), 5.95 (s, 1H), 6.67 (s, 1H), 7.40 (m, 1H), 7.85 (m, 1H), 7.95 (d, 1H), 8.60 (d, 1H); m/z 474 [MH]+.

Example 53

6-(3-(N,N-Dimethylamino)propyn-1-yl)-4-(5-methyl-1H-pyrazol-3-ylamino)-2-(2-(3-(pyrid-2-yl)isoxazol-5-yl)pyrrolidin-1-yl)pyrimidine A mixture of 6-bromo-4-(5-methyl-1H-pyrazol-3-ylamino)-2-(2-(3-(pyrid-2-yl)isoxazol-5-yl)pyrrolidine)pyrimidine (Method 49) (200 mg, 0.43 mmol), palladium(II) chloride-bis(triphenylphosphine) (12 mg, 0.02 mmole), copper(I)iodide (2 mg, 0.02 mmol), triethylamine (0.300 ml, 2.1 mmol), 3-(N,N-dimethylamino)propyne (0.070 ml, 0.64 mmol) in acetonitrile (2 ml) were heated at 75° C. for 15 minute in a sealed vessel under microwave irradiation. The mixture was dissolved in ethyl acetate, the solution decanted from the insolubles, the solution washed with water, dried (MgSO₄), and the solvent removed by evaporation. The residue was purified by chromatography on silica gel eluting with DCM/methanol (90:10 increasing in polarity to 85:15). The purified product was triturated with ether and collected by filtration to give the title compound (44 mg, 25%).

NMR (DMSO): 2.10 (m, 3H), 2.20 (s, 3H), 2.29 (s, 6H), 2.32-2.45 (m, 1H), 3.45 (s, 2H), 3.66-3.80 (m, 2H), 5.45 (d, 1H), 6.08 (s, 1H), 6.47 (s, 1H), 6.68 (s, 1H), 7.46 (d, 1H), 7.88-7.98 (m, 2H), 8.66 (d, 1H), 9.04 (s, 1H), 11.55 (s, 1H); m/z 470 [MH]+.

Example 54

6-Methylamino-4-(5-methyl-1H-pyrazol-3-ylamino)-2-[2-(3-pyridin-2-ylisoxazol-5-yl)pyrrolidin-1-yl]pyrimidine A mixture of 6-chloro-2-{2-[3-(pyrid-2-yl)isoxazol-5-yl]pyrrolidin-1-yl}-4-(5-methyl-1H-pyrazol-3-ylamino)pyrimidine (Example 17) (250 mg, 0.59 mmol) and methylamine (4 ml of a 2M in methanol, 8.0 mmol) was heated at 130° C. for 90 minutes in a sealed vessel under microwave irradiation. The volatiles were removed by evaporation and the residue was purified by reverse phase HPLC using a C18 column eluting with water/acetonitrile/trifluoroacetic acid (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (126 mg, 50%) as a yellow solid.

NMR (DMSO-d₆ at 100° C.): 2.05 (m, 3H), 2.15 (s, 3H). 2.35 (m, 1H), 2.74 (s, 3H), 3.70 (m, 2H), 5.43 (d, 1H), 5.51 (br s, 1H), 5.91 (br s, 2H), 6.60 (s, 1H), 7.40 (m, 1H), 7.85 (m, 1H), 7.95 (d, 1H), 8.04 (br s, 1H), 8.60 (d, 1H), 11.33 (br s, 1H); m/z 418 [MH]+.

Example 55

6-(2-Methoxyethyl)amino-4-(5-methyl-1H-pyrazol-3-ylamino)-2-{2-[3-(pyrid-2-yl)isoxazol-5-yl]pyrrolidin-1-yl}pyrimidine A mixture of 6-chloro-2-{2-[3-(pyrid-2-yl)isoxazol-5-yl]pyrrolidin-1-yl}-4-(5-methyl-1H-pyrazol-3-ylamino)pyrimidine (Example 17) (250 mg, 0.59 mmol) and 2-methoxyethylamine (443 mg, 5.9 mmol) in anhydrous 1,4-dioxane (5 ml) was heated at 150° C. for 40 minutes in a sealed vessel under microwave irradiation. The reaction was worked up as described in Example 54 to give the title compound (108 mg, 40%) as a cream solid.

NMR (DMSO-$d_6$+$d_4$-acetic acid at 100° C.): 2.00-2.15 (m, 3H), 2.18 (s, 3H), 2.35 (m, 1H), 3.15 (s, 1H), 3.20-3.40 (m, 4H), 3.65 (m, 1H), 3.75 (m, 1H), 5.35 (d, 1H), 5.55 (s, 1H), 5.85 (s, 1H), 6.55 (s, 1H), 7.40 (m, 1H), 7.85 (m, 1H), 7.95 (d, 1H), 8.60 (d, 1H); m/z 462 [MH]+.

Example 56

6-Methoxycarbonyl-2-{2-[3-(pyrid-2-yl)isoxazol-5-yl]pyrrolidin-1-yl}-4-(5-methyl-1H-pyrazol-3-ylamino)pyrimidine A mixture of 2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 43) (1.73 g, 4.0 mmol), methanol (300 ml) and 98% sulphuric acid (1 ml) was heated at reflux for 18 hours. The volatiles were removed by evaporation, the residue dissolved in water and the pH of the resulting solution adjusted to pH 12 with 10M sodium hydroxide. The aqueous solution was extracted with DCM and purified by chromatography on silica gel, eluting with DCM/methanol (100:0 increasing in polarity to 90:10) to give the title compound (904 mg, 51%).

NMR (DMSO-$d_6$+$d_4$-acetic acid at 100° C.): 2.05 (m, 3H), 2.15 (s, 3H), 2.35 (m, 1H), 3.75 (m, 5H), 5.50 (dd, 1H), 6.05 (s, 1H), 6.70 s, 1H), 6.88 (s, 1H), 7.40 (m, 1H), 7.88 (t, 1H), 7.95 (d, 1H), 8.65 (d, 1H); m/z 447 [MH]+.

Example 57

6-(N-Methylcarbamoyl)-2-{2-[3-(pyrid-2-yl)isoxazol-5-yl]pyrrolidin-1-yl}-4-(5-methyl-1H-pyrazol-3-ylamino)pyrimidine A mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine Example 56) (62.5 mg, 0.14 mmol), 2N solution of methylamine in methanol (2.0 ml, 4.00 mmol) and methanol (3.0 ml) was heated at 65° C. for 1 hour under microwave irradiation. The volatiles were removed by evaporation and the residue dissolved in DCM and purified by chromatography on silica gel eluting with DCM/methanol (100:0 increasing in polarity to 90:10). The purified product was triturated with diethylether and the resulting solid collected by filtration to give the title compound (21 mg, 34%).

NMR (DMSO-$d_6$+$d_4$-acetic acid at 100° C.): 2.10 (m, 3H), 2.20 (s, 3H), 2.40 (m, 1H), 3.75 (m, 1H), 3.85 (m, 1H), 5.50 (dd, 1H), 6.10 (s, 1H), 6.70 (s, 1H), 6.90 (s, 1H), 7.40 (m, 1H), 7.87 (t, 1H), 7.93 (d, 1H), 8.65 (d, 1H); m/z 446 [MH]+.

Example 58

6-Morpholinocarbonyl-2-{2-[3-(pyrid-2-yl)isoxazol-5-yl]pyrrolidin-1-yl}-4-(5-methyl-1H-pyrazol-3-ylamino)pyrimidine A mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (200 mg, 0.45 mmol) and morpholine (0.5 ml, 5.73 mmol) in anhydrous methanol (5.0 ml) was heated at 120° C. for 18 hours. The volatiles were removed by evaporation and the residue was purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation and the residue was triturated with diethylether. The resulting solid was collected by filtration to give the title compound (120 mg, 52%).

NMR (DMSO-$d_6$+$d_4$-acetic acid at 100° C.): 2.10 (m, 3H), 2.20 (s, 3H), 2.40 (m, 1H), 3.47 (m, 8H), 3.65 (m, 1H), 3.76 (m, 1H), 5.42 (dd, 1H), 6.07 (s, 1H), 6.45 (s, 1H), 6.65 (s, 1H), 7.40 (m, 1H), 7.85 (t, 1H), 7.95 (d, 1H), 8.60 (d, 1H); m/z 502 [MH]+.

Example 59

6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine A mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (200 mg, 0.45 mmol) and 2-methoxyethylamine (5 ml, 57.2 mmol) was heated at reflux for 18 hours. The reaction mixture was evaporated, the residue dissolved in methanol and passed through a 50 g isolute SCX-2 ion exchange column. The column was eluted with methanol to elute any neutrals, followed by 7M methanolic ammonia to elute the product. The solvent was removed by evaporation and the residue was purified by chromatography on silica gel eluting with DCM/methanol (100:0 increasing in polarity to 90:10). The purified product was triturated with diethylether and the resulting solid collected by filtration to give the title compound (78 mg, 36%).

NMR (DMSO-$d_6$+$d_4$-acetic acid at 100° C.): 2.10 (m, 3H), 2.20 (s, 3H), 2.40 (m, 1H), 3.25 (s, 3H), 3.40 (m, 4H), 3.75 (m, 1H), 3.85 (m, 1H), 5.45 (dd, 1H), 6.10 (s, 1H), 6.70 (s, 1H), 6.90 (s, 1H), 7.40 (m, 1H), 7.85 (t, 1H), 7.92 (d, 1H), 8.65 (d, 1H); m/z 490 [MH]+.

Example 60

6-N-Hydroxycarbamoyl-2-{2-[3-(pyrid-2-yl)isoxazol-5-yl]pyrrolidin-1-yl}-4-(5-methyl-1H-pyrazol-3-ylamino)pyrimidine A mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (200 mg, 0.45 mmol), hydroxylamine mono-hydrochloride (340 mg, 4.86 mmol) and triethylamine (0.80 ml, 5.40 mmol) in anhydrous methanol (5 ml) was heated at reflux for 18 hours. The volatiles were removed by evaporation and the residue was purified by reverse phase HPLC using a C18 column eluting with water/ acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (40 mg, 20%) as a foam.

NMR (DMSO-$d_6$+$d_4$-acetic acid at 100° C.): 2.08 (m, 3H), 2.15 (s, 3H), 2.37 (m, 1H), 3.74 (m, 1H), 3.80 (m, 1H), 5.54 (dd, 1H), 6.08 (s, 1H), 6.70 (s, 1H), 6.85 (s, 1H), 7.40 (m, 1H), 7.85 (t, 1H), 7.92 (d, 1H), 8.63 (d, 1H); m/z 448 [MH]+.

Example 61

6-Carbamoyl-2-{2-[3-(pyrid-2-yl)isoxazol-5-yl]pyrrolidin-1-yl}-4-(5-methyl-1H-pyrazol-3-ylamino)pyrimidine A mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (200 mg, 0.45 mmol) and a solution of 7N ammonia in methanol (7 ml, 49 mmol) was heated at 65° C. in a sealed vessel under microwave irradiation for 1 hour. The reaction mixture was evaporated, dissolved in methanol and passed through a 50 g isolute SCX-2 ion exchange column. The column was eluted with methanol to elute any neutrals, followed by 7M methanolic ammonia to elute the product. The solvent was removed by evaporation and the residue triturated with diethylether. The resulting solid was collected by filtration to give the title compound (180.0 mg, 93%).

NMR (DMSO-$d_6$+$d_4$-acetic acid at 100° C.): 2.10 (m, 3H), 2.18 (s, 3H), 2.40 (m, 1H), 3.78 (m, 1H), 3.84 (m, 1H), 5.48 (dd, 1H), 6.10 (s, 1H), 6.70 (s, 1H), 6.90 (s, 1H), 7.40 (m, 1H), 7.85 (t, 1H), 7.92 (d, 1H), 8.62 (d, 1H); m/z 432 [MH]+.

Example 62

S-6-Methoxycarbonyl-2-{2-[3-(pyrid-2-yl)isoxazol-5-yl]pyrrolidin-1-yl}-4-(5-methyl-1H-pyrazol-3-ylamino)pyrimidine A mixture of S-2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 50) (1.73 g, 4.0 mmol), methanol (300 ml) and 98% sulphuric acid (1 ml) was heated at reflux for 18 hours. The volatiles were removed by evaporation, the residue dissolved in water and the pH of the resulting solution adjusted to pH 12 with 10M sodium hydroxide. The aqueous solution was extracted with DCM and purified by chromatography on silica gel, eluting with DCM/methanol (100:0 increasing in polarity to 90:10) to give the title compound (904.0 mg, 51%).

NMR (DMSO-$d_6$+$d_4$-acetic acid at 100° C.): 2.05 (m, 3H), 2.15 (s, 3H), 2.35 (m, 1H), 3.75 (m, 5H), 5.50 (dd, 1H), 6.05 (s, 1H), 6.70 s, 1H), 6.88 (s, 1H), 7.40 (m, 1H), 7.88 (t, 1H), 7.95 (d, 1H), 8.65 (d, 1H); m/z 447 [MH]+.

Example 63

S-6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine 4-(4,6-Dimethoxy[1,3,5]triazin-2-yl)-4-methyl-morpholinium chloride (149.3 mg, 0.54 mmol) was added to a mixture of S-2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 50) (200 mg, 0.46 mmol) and anhydrous DMF (10 ml) and the reaction mixture stirred at ambient temperature for 0.5 hour until a clear solution formed (indicative of successful activated ester formation). 2-Methoxyethylamine (0.50 ml, 5.75 mmol) was added and the reaction stirred at ambient temperature for a further 2 hours. The reaction mixture was then passed through a 50 g isolute SCX-2 ion exchange column. The column was eluted with methanol to elute any neutrals, followed by 7M methanolic ammonia to elute the product. The solvent was removed by evaporation and the residue purified by chromatography on silica gel eluting with DCM/methanol (100:0 increasing in polarity to 90:10). The purified product was triturated with diethylether and the resulting solid collected by filtration to give the title compound (136 mg, 58%).

NMR (DMSO-$d_6$+$d_4$-acetic acid at 100° C.): 2.10 (m, 3H), 2.18 (s, 3H), 2.40 (m, 1H), 3.25 (s, 3H), 3.42 (m, 4H), 3.75 (m, 1H), 3.83 (m, 1H), 5.46 (dd, 1H), 6.10 (s, 1H), 6.70 (s, 1H), 6.90 (s, 1H), 7.40 (m, 1H), 7.85 (t, 1H), 7.92 (d, 1H), 8.62 (d, 1H); m/z 490 [MH]+.

Example 64

S-6-[N-(2-Methoxyethyl)-N-methylcarbamoyl]-2-{2-[3-(pyrid-2-yl)isoxazol-5-yl]pyrrolidin-1-yl}-4-(5-methyl-1H-pyrazol-3-ylamino)pyrimidine 4-(4,6-Dimethoxy[1,3,5]triazin-2-yl)-4-methyl-morpholinium chloride (149.3 mg, 0.54 mmol) was added to a mixture of S-2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 50) (200 mg, 0.46 mmol) and anhydrous DMF (10 ml) and the reaction mixture stirred at ambient temperature for 0.5 hour until a clear solution formed. N-(2-Methoxyethyl)-N-methylamine (0.5 ml) was added and the reaction stirred at ambient temperature for a further 2 hours. The reaction mixture was then passed through a 50 g isolute SCX-2 ion exchange column. The column was eluted with methanol to elute any neutrals, followed by 7M methanolic ammonia to elute the product. The solvent was removed by evaporation and the residue was purified by chromatography on silica gel eluting with DCM/methanol (100:0 increasing in polarity to 90:10). The purified product was then repurified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (90 mg, 37%).

NMR (DMSO-$d_6$+$d_4$-acetic acid at 100° C.): 2.08 (m, 3H), 2.18 (s, 3H), 2.37 (m, 1H), 2.95 (s, 2H), 3.18 (s, 3H), 3.40 (m, 3H), 3.50 (m, 1H), 3.69 (m, 1H), 3.76 (m, 1H), 5.45 (dd, 1H), 6.38 (s, 1H), 6.60 (s, 1H), 7.38 (m, 1H), 7.85 (t, 1H), 7.88 (d, 1H), 8.58 (d, 1H); m/z 504 [MH]+.

Example 65

S-6-[N-(2-(Acetylamino)ethyl)carbamoyl]-2-{2-[3-(pyrid-2-yl)isoxazol-5-yl]pyrrolidin-1-yl}-4-(5-methyl-1H-pyrazol-3-ylamino)pyrimidine 4-(4,6-Dimethoxy[1,3,5]triazin-2-yl)-4-methyl-morpholinium chloride (149.3 mg, 0.54 mmol) was added to a mixture of S-2-{2-[3-(pyrid-2-yl)isoxazol-5-yl]pyrrolidin-1-yl}-

4-(5-methyl-1H-pyrazol-3-ylamino)pyrimidin-6-yl carboxylic acid (Method 50) (200 mg, 0.46 mmol) and anhydrous DMF (5 ml) and the reaction mixture stirred at room temperature for 0.5 hour until a clear solution formed. N-Acetyl-1,2-ethylenediamine (0.22 ml, 2.29 mmol) was added and the reaction stirred at room temperature for a further 2 hours. The reaction mixture was filtered, the volatiles were removed from the filtrate by evaporation and the residue was purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation and the residue triturated with diethylether and collected by filtration to give the title compound (115.7 mg, 49%).

NMR (DMSO-$d_6$+$d_4$-acetic acid at 100° C.): 1.80 (s, 3H), 2.10 (m, 3H), 2.19 (s, 3H), 2.40 (m, 1H), 3.25 (m, 2H) 3.35 (m, 2H), 3.77 (m, 1H), 3.85 (m, 1H), 5.53 (dd, 1H), 6.10 (s, 1H), 6.71 (s, 1H), 6.88 (s, 1H), 7.40 (m, 1H), 7.85 (t, 1H), 7.93 (d, 1H), 8.61 (d, 1H); m/z 517 [MH]+.

Examples 66 to 76

Examples 66 to 76 were prepared by an analogous method to that described for Example 65 using S-2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 50) and the appropriate amine.

Example 66

S-6-{N-[2-(2-Hydroxyethoxy)ethyl]carbamoyl}-2-{2-[3-(pyrid-2-yl)isoxazol-5-yl]pyrrolidin-1-yl}-4-(5-methyl-1H-pyrazol-3-ylamino)pyrimidine Amine starting material: 2-(2-hydroxyethoxy)ethylamine. Yield: 123 mg, 49%.

NMR (DMSO-$d_6$+$d_4$-acetic acid at 100° C.): 2.10 (m, 3H), 2.19 (s, 3H), 2.40 (m, 1H), 3.40 (m, 2H) 3.45 (m, 2H), 3.55 (m, 2H), 3.75 (m, 1H), 3.85 (m, 1H), 5.47 (dd, 1H), 6.10 (s, 1H), 6.71 (s, 1H), 6.90 (s, 1H), 7.40 (m, 1H), 7.85 (t, 1H), 7.93 (d, 1H); m/z 520 [MH]+.

Example 67

S-6-[N-((R)-2-Hydroxypropyl)carbamoyl]-2-{2-[3-(pyrid-2-yl)isoxazol-5-yl]pyrrolidin-1-yl}-4-(5-methyl-1H-pyrazol-3-ylamino)pyrimidine Amine starting material: (R)-2-hydroxypropylamine. Yield: 137 mg, 61%.

NMR (DMSO-$d_6$+$d_4$-acetic acid at 100° C.): 1.05 (d, 3H), 2.10 (m, 3H), 2.19 (s, 3H), 2.40 (m, 1H), 3.46 (m, 2H), 3.75 (m, 1H), 3.85 (m, 1H), 3.90 (m, 1H), 5.44 (dd, 1H), 6.12 (s, 1H), 6.71 (s, 1H), 6.90 (s, 1H), 7.40 (m, 1H), 7.85 (t, 1H), 7.93 (d, 1H), 8.62 (d, 1H); m/z 490 [MH]+.

Example 68

S-6-[N-(4-Hydroxybutyl)carbamoyl]-2-{2-[3-(pyrid-2-yl)isoxazol-5-yl]pyrrolidin-1-yl}-4-(5-methyl-1H-pyrazol-3-ylamino)pyrimidine Amine starting material: 4-hydroxybutylamine. This product was isolated without trituration (153 mg, 66%).

NMR (DMSO-$d_6$+$d_4$-acetic acid at 100° C.): 1.45 (m, 2H), 1.55 (m, 2H), 2.10 (m, 3H), 2.19 (s, 3H), 2.40 (m, 1H), 3.25 (m, 2H), 3.40 (t, 2H), 3.76 (m, 1H), 3.84 (m, 1H), 5.44 (dd, 1H), 6.12 (s, 1H), 6.70 (s, 1H), 6.88 (s, 1H), 7.39 (m, 1H), 7.85 (t, 1H), 7.93 (d, 1H), 8.61 (d, 1H); m/z 504 [MH]+.

Example 69

S-6-[N-((2R)-2,3-Dihydroxypropyl)carbamoyl]-2-{2-[3-(pyrid-2-yl)isoxazol-5-yl]pyrrolidin-1-yl}-4-(5-methyl-1H-pyrazol-3-ylamino)pyrimidine Amine starting material: (2R)-2,3-dihydroxypropylamine. This product was isolated by trituration with water (135 mg, 58%).

NMR (DMSO-$d_6$+$d_4$-acetic acid at 100° C.): 2.15 (m, 3H), 2.19 (s, 3H), 2.43 (m, 1H), 3.25 (m, 1H), 3.43 (m, 3H), 3.65 (m, 1H), 3.76 (m, 1H), 3.85 (m, 1H), 5.50 (dd, 1H), 6.11 (s, 1H), 6.76 (s, 1H), 6.92 (s, 1H), 7.42 (m, 1H), 7.87 (t, 1H), 7.95 (d, 1H), 8.65 (d, 1H); m/z 506 [MH]+.

Example 70

S-6-[N-(Carbamoylmethyl)carbamoyl]-2-{2-[3-(pyrid-2-yl)isoxazol-5-yl]-pyrrolidin-1-yl}-4-(5-methyl-1H-pyrazol-3-ylamino)pyrimidine This product was prepared using glycinimide hydrochloride and triethylamine (7.0 equivalents) and was isolated without trituration (141 mg, 62%).

NMR (DMSO-$d_6$+$d_4$-acetic acid at 100° C.): 2.10 (m, 3H), 2.18 (s, 3H), 2.40 (m, 1H), 3.80 (m, 2H), 3.85 (m, 2H), 5.50 (dd, 1H), 6.08 (s, 1H), 6.74 (s, 1H), 6.90 (s, 1H), 7.40 (m, 1H), 7.85 (t, 1H), 7.93 (d, 1H), 8.62 (d, 1H); m/z 506 [MH]+.

Example 71

S-6-((3R)-3-Hydroxypyrrolidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine Amine starting material: (2R)-3-hydroxypyrrolidine. This product was isolated with trituration (129 mg, 56%).

NMR (DMSO-$d_6$+$d_4$-acetic acid at 100° C.): 1.70 (m, 2H), 2.10 (m, 3H), 2.18 (s, 3H), 2.38 (m, 1H), 3.50 (m, 2H), 3.65 (m, 2H), 3.81 (m, 2H), 4.23 (s, 1H), 5.40 (dd, 1H), 6.07 (s, H), 6.56 (s, 1H), 6.65 (s, 1H), 7.40 (m, 1H), 7.85 (t, 1H), 7.93 (d, 1H), 8.62 (d, 1H); m/z 502 [MH]+.

Example 72

S-6-{N-[2-(Methylthio)ethyl]carbamoyl}-2-{2-[3-(pyrid-2-yl)isoxazol-5-yl]pyrrolidin-1-yl}-4-(5-methyl-1H-pyrazol-3-ylamino)pyrimidine Amine starting material: 2-(methylthio)ethylamine. This product was isolated with trituration (147 mg, 63%).

NMR (DMSO-$d_6$+$d_4$-acetic acid at 100° C.): 2.02 (s, 3H), 2.10 (m, 3H), 2.17 (s, 3H), 2.38 (m, 1H), 2.60 (t, 2H), 3.45 (m, 2H), 3.75 (m, 1H), 3.83 (m, 1H), 5.46 (dd, 1H), 6.07 (s, 1H), 6.70 (s, 1H), 6.89 (s, 1H), 7.40 (m, 1H), 7.85 (t, 1H), 7.90 (d, 1H), 8.61 (d, 1H); m/z 506 [MH]+.

Example 73

S-6-(N-Cyclopropylcarbamoyl)-2-{2-[3-(pyrid-2-yl)isoxazol-5-yl]pyrrolidin-1-yl}-4-(5-methyl-1H-pyrazol-3-ylamino)pyrimidine Amine starting material: cyclopropylamine. This product was isolated with trituration (113 mg, 52%).

NMR (DMSO-$d_6$+$d_4$-acetic acid at 100° C.): 0.50 (m, 1H), 0.60 (m, 1H), 0.67 (m, 2H), 2.10 (m, 3H), 2.19 (s, 3H), 2.40 (m, 1H), 2.77 (m, 1H), 3.75 (m, 1H), 3.83 (m, 1H), 5.43 (dd, 1H), 6.12 (s, 1H), 6.70 (s, 1H), 6.88 (s, 1H), 7.40 (m, 1H), 7.85 (t, 1H), 7.92 (d, 1H), 8.62 (d, 1H); m/z 472 [MH]+.

Example 74

S-6-(N-Cyclopentylcarbamoyl)-2-{2-[3-(pyrid-2-yl)isoxazol-5-yl]pyrrolidin-1-yl}-4-(5-methyl-1H-pyrazol-3-ylamino)pyrimidine Amine starting material: cyclopentylamine. This product was isolated with trituration (162 mg, 70%).

NMR (DMSO-$d_6$+$d_4$-acetic acid at 100° C.): 1.30-1.91 (m, 8H), 2.12 (m, 3H), 2.19 (s, 3H), 2.43 (m, 1H), 3.75 (m, 1H), 3.85 (m, 1H), 4.11 (m, 1H), 5.43 (dd, 1H), 6.15 (s, 1H), 6.70 (s, 1H), 6.88 (s, 1H), 7.40 (m, 1H), 7.86 (t, 1H), 7.92 (d, 1H), 8.63 (d, 1H); m/z 500 [MH]+.

Example 75

S-6-(Azetidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine Amine starting material: azetidine. This product was isolated with trituration (153 mg, 70%).

NMR (DMSO-$d_6$+$d_4$-acetic acid at 100° C.): 2.08 (m, 3H), 2.10 (s, 5H), 2.40 (m, 1H), 3.70 (m, 1H), 3.85 (m, 1H), 4.02 (m, 2H), 4.40 (m, 1H), 4.57 (m, 1H), 5.45 (dd, 1H), 6.10 (s, 1H), 6.65 (s, 1H), 6.80 (s, 1H), 7.44 (m, 1H), 7.78 (t, 1H), 7.95 (d, 1H), 8.65 (d, 1H); m/z 472 [MH]+.

Example 76

S-6-(N-Methylcarbamoyl)-2-{2-[3-(pyrid-2-yl)isoxazol-5-yl]pyrrolidin-1-yl}-4-(5-methyl 1H-pyrazol-3-ylamino)pyrimidine This product was prepared using a 2N methylamine solution in THF (10.0 equivalents) and was isolated without trituration (145 mg, 70%).

NMR (DMSO-$d_6$+$d_4$-acetic acid at 100° C.): 2.08 (m, 3H), 2.18 (s, 3H), 2.38 (m, 1H), 2.77 (s, 3H), 3.75 (m, 1H), 3.85 (m, 1H), 5.47 (dd, 1H), 6.08 (s, 1H), 6.67 (s, 1H), 6.85 (s, 1H), 7.38 (m, 1H), 7.82 (t, 1H), 7.90 (d, 1H), 8.58 (d, 1H); m/z 446 [MH]+.

Example 77

6-(N-Aminocarbamoyl)-2-{2-[3-(pyrid-2-yl)isoxazol-5-yl]pyrrolidin-1-yl}-4-(5-methyl-1H-pyrazol-3-ylamino)pyrimidine Hydrazine mono-hydrate (1.6 ml, 20.6 mmol) was added to a mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (1.54 g, 3.45 mmol) in methanol (20.0 ml) at ambient temperature. The resulting reaction mixture was heated at reflux for 1 hour then allowed to cool. The resulting solid was collected by filtration and washed with methanol to give the title compound (1.05 g, 68.3%).

NMR (DMSO-$d_6$+$d_4$-acetic acid at 100° C.): 2.10 (m, 3H), 2.17 (s, 3H), 2.38 (m, 1H), 3.75 (m, 1H), 3.82 (m, 1H), 5.50 (dd, 1H), 6.06 (s, 1H), 6.68 (s, 1H), 6.86 (s, 1H), 7.38 (m, 1H), 7.85 (t, 1H), 7.95 (d, 1H), 8.61 (d, 1H); m/z 447 [MH]+.

Example 78

6-[N-(Acetylamino)carbamoyl]-2-{2-[3-(pyrid-2-yl)isoxazol-5-yl]pyrrolidin-yl}-4-(5-methyl-1H-pyrazol-3-ylamino)pyrimidine A solution of 6-[N-(acetylamino)carbamoyl]-2-{2-[3-(pyrid-2-yl)isoxazol-5-yl]pyrrolidin-1-yl}-4-(2-acetyl-5-methyl-1H-pyrazol-3-ylamino)pyrimidine (Method 51) (170 mg, 0.32 mmol) in methanol (10 ml) and 2N sodium hydroxide (0.5 ml, 1.0 mmol) was stirred at room temperature for 0.5 hour. The resulting precipitate was collected by filtration to give the title compound (150 mg, 96%).

NMR (DMSO-$d_6$+$d_4$-acetic acid at 100° C.): 1.88 (s, 3H), 2.08 (m, 3H), 2.18 (s, 3H), 2.40 (m, 1H), 3.75 (m, 1H), 3.84 (m, 1H), 5.55 (dd, 1H), 6.10 (s, 1H), 6.70 (s, 1H), 6.90 (s, 1H), 7.40(m, 1H), 7.85 (t, 1H), 7.93 (d, 1H), 8.62 (d, 1H); m/z 489 [MH]+.

Example 79

6-(5-Methyl-[1,3,4]-oxadiazol-2-yl)-2-{2-[3-(pyrid-2-yl)isoxazol-5-yl]pyrrolidin-1-yl}-4-(5-methyl-1H-pyrazol-3-ylamino)pyrimidine (Methoxycarbonylsulfamoyl)triethylammonium hydroxide (internal salt) (90 mg, 3.76 mmol) was added to a solution of 6-[N-(acetylamino)carbamoyl]-2-{2-[3-(pyrid-2-yl)isoxazol-5-yl]pyrrolidin-1-yl}-4-(2-acetyl-5-methyl-1H-pyrazol-3-ylamino)pyrimidine (Method 51) (500 mg, 0.94 mmol) in anhydrous THF (20 ml) and the reaction heated at reflux for 18 hours. The volatiles were removed by evaporation and the residue was dissolved in methanol (5 ml) and 2N aqueous sodium hydroxide solution (11.0 ml) and stirred at ambient temperature for 15 minutes. The methanol was removed by evaporation and the pH of the resulting solution adjusted to pH 7 with 1N hydrochloric acid. The volatiles were removed evaporation and the residue purified by chromatography on silica gel eluting with DCM/methanol (100:0 increasing in polarity to 90:10). The purified product was then triturated with diethylether and collected by filtration to give the title compound (200 mg, 52%).

NMR (DMSO-$d_6$+$d_4$-acetic acid at 100° C.): 2.08 (m, 3H), 2.18 (s, 3H), 2.38 (m, 1H), 2.53 (s, 3H), 3.76 (m, 1H), 3.84 (m, 1H), 5.50 (dd, 1H), 6.08 (s, 1H), 6.72 (s, 1H), 7.02 (s, 1H), 7.39 (m, 1H), 7.85 (t, 1H), 7.92 (d, 1H), 8.61 (d, 1H); m/z 471 [MH]+.

Example 80

6-Hydroxymethyl-2-{2-[3-(pyrid-2-yl)isoxazol-5-yl]pyrrolidin-1-yl}-4-(5-methyl-1H-pyrazol-3-ylamino)pyrimidine A 2M solution of lithium borohydride in THF (22.4 ml, 44.8 mmol) was added to a mixture of 6-methoxycarbonyl-2-{2-[3-(pyrid-2-yl)isoxazol-5-yl]pyrrolidin-1-yl}-4-(5-methyl-1H-pyrazol-3-ylamino)pyrimidine (Example 56) (4.0 mg, 8.96 mmol) in anhydrous THF (200 ml). The reaction mixture was stirred at ambient temperature for 3 hours and then heated at reflux for 1 hour. The mixture allowed to cool and methanol was added until effervescence ceased, a 4M solution hydrogen chloride in dioxane (30 ml) was then added and the mixture heated at reflux for 1 hour. The volatiles were removed by evaporation, the residue was dissolved in water and the resulting solution adjusted to pH 9 by careful addition of 10M aqueous sodium hydroxide solution. The aqueous mixture was extracted with DCM and purification by chromatography on silica gel, eluting with DCM/methanol (100:0 increasing in polarity to 90:10) to give the title compound (3.4 g, 91%).

NMR (DMSO-$d_6$+$d_4$-acetic acid at 100° C.): 2.10 (m, 3H), 2.18 (s, 3H), 2.35 (m, 1H), 3.70 (m, 1H), 3.77 (m, 1H), 4.23 (dd, 2H), 5.45 (dd, 1H), 6.01 (s, 1H), 6.41 (s, 1H), 6.65 (s, 1H), 7.40 (m, 1H), 7.85 (t, 1H), 7.95 (d, 1H), 8.62 (d, 1H); m/z 419 [MH]+.

Example 81

6-(Morpholinomethyl)-2-{2-[3-(pyrid-2-yl)isoxazol-5-yl]pyrrolidin-1-yl}-4-(5-methyl-1H-pyrazol-3-ylamino)pyrimidine A mixture of 6-[(4-methylphenylsulphonyloxy)methyl]-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine (Method 52) (214 mg, 0.295 mmol) and morpholine (5 ml, 83.2 mmol) was heated at reflux for 2 hours. The volatiles were removed by evaporation and the residue was dissolved in methanol (10 ml) and 10M aqueous sodium hydroxide solution (3 ml). The mixture was heated at 60° C. for 1 hour. The volatiles were removed by evaporation and the residue dissolved in water, extracted with dichloromethane. The extracts were combined and the solvent removed by evaporation. The residue was purified by chromatography on silica gel, eluting with dichloromethane (100%) and then diethylether (100%). The purified product was triturated with diethylether and collected by filtration to give the title compound (125 mg).

NMR (DMSO-$d_6$+$d_4$-acetic acid at 100° C.): 2.05 (m, 3H), 2.18 (s, 3H), 2.35 (m, 1H), 2.57 (m, 4H), 3.40 (m, 2H), 3.55 (m, 4H), 3.68 (m, 1H), 3.78 (m, 1H), 5.45 (dd, 1H), 6.05 (s, 1H), 6.38 (s, 1H), 6.64 (s, 1H), 7.40 (m, 1H), 7.85 (t, 1H), 7.93 (d, 1H), 8.62 (d, 1H); m/z 488 [MH]+.

Example 82

6-(4-Methylpiperazin-1-ylmethyl)-2-{2-[3-(pyrid-2-yl)isoxazol-5-yl]pyrrolidin-1-yl}-4-(5-methyl-1H-pyrazol-3-ylamino)pyrimidine A mixture of 6-[(4-methylphenylsulphonyloxy)methyl]-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine (Method 52) (214 mg, 0.295 mmol) and 1-methylpiperazine (3.0 ml, 27.1 mmol) was heated at reflux for 4 hours. The volatiles were removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation of give the title compound (107 mg, 71%).

NMR (DMSO-$d_6$+$d_4$-acetic acid at 100° C.): 2.08 (m, 3H), 2.18 (s, 3H), 2.35 (m, 4H), 2.60 (m, 8H), 3.34 (d, 2H), 3.67 (m, 1H), 3.77 (m, 1H), 5.43 (dd, 1H), 6.06 (s, 1H), 6.33 (s, 1H), 6.62 (s, 1H), 7.40 (m, 1H), 7.86 (t, 1H), 7.92 (d, 1H), 8.63 (d, 1H); m/z 501 [MH]+.

Example 83

6-(Methylaminomethyl)-2-{2-[3-(pyrid-2-yl)isoxazol-5-yl]pyrrolidin-1-yl}-4-(5-methyl-1H-pyrazol-3-ylamino)pyrimidine A mixture of 6-[(4-methylphenylsulphonyloxy)methyl]-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine (Method 52) (190 mg, 0.26 mmol) and a solution of 2N methylamine in THF (5 ml, 10 mmol) were heated at 90° C. in a sealed vessel under microwave irradiation for 1 hour. The volatiles were removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation of give the title compound (87.1 mg, 77%).

NMR (DMSO-$d_6$+$d_4$-acetic acid at 100° C.): 2.08 (m, 3H), 2.18 (s, 3H), 2.35 (m, 1H), 2.60 (s, 3H), 3.75 (m, 1H), 3.82 (m, 1H), 3.92 (dd, 2H), 5.53 (dd, 1H), 6.06 (s, 1H), 6.30 (s, 1H), 6.67 (s, 1H), 7.40 (m, 1H), 7.86 (t, 1H), 7.93 (d, 1H), 8.62 (d, 1H); m/z 432 [MH]+.

Example 84

6-(Pyrrolidin-1-ylmethyl)-2-{2-[3-(pyrid-2-ylisoxazol-5-yl]pyrrolidin-1-yl}-4-(5-methyl-1H-pyrazol-3-ylamino)pyrimidine A mixture of 6-[(4-methylphenylsulphonyloxy)methyl]-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine (Method 52) (214 mg, 0.295 mmol) and pyrrolidine (3.0 ml, 27 mmol) was heated at 95° C. for 24 hours. The volatiles were removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation of give the title compound (77.6 mg, 52%).

NMR (DMSO-$d_6$+$d_4$-acetic acid at 100° C.): 2.08 (m, 3H), 2.18 (s, 3H), 2.36 (m, 1H), 3.22 (m, 4H), 3.70 (m, 1H), 3.80 (m, 1H), 4.05 (dd, 2H), 5.49 (dd, 1H), 6.07 (s, 1H), 6.35 (s, 1H), 6.67 (s, 1H), 7.40 (m, 1H), 7.86 (t, 1H), 7.93 (d, 1H), 8.62 (d, 1H); m/z 472 [MH]+.

Example 85

6-Aminomethyl-2-{2-[3-(pyrid-2-yl)isoxazol-5-yl]pyrrolidin-1-yl}-4-(5-methyl-1H-pyrazol-3-ylamino)pyrimidine Sodium azide (44 mg, 0.68 mmol) was added to a solution of 6-[(4-methylphenylsulphonyloxy)methyl]-2-{2-[3-(pyrid-2-yl)isoxazol-5-yl]pyrrolidin-1-yl}-4-(5-methyl-1-N-[4-methylphenylsulphonyl]-1H-pyrazol-3-ylamino)pyrimidine (Method 52) (159 mg, 0.22 mmol) in anhydrous DMF (2.0 ml) and the mixture heated at 110° C. for 1.5 hours. Triphenylphosphine (282.0 mg, 1.08 mmol) and water (0.10 ml) were then added and the reaction mixture heated at 100° C. for 1 hour. The mixture allowed to cool and was then passed through a 50 g isolute SCX-2 ion exchange column. The column was eluted with methanol to elute any neutrals, followed by 7M methanolic ammonia to elute the product. The volatiles were removed by evaporation and the residue dissolved in methanol (5 ml) and 10M aqueous sodium hydroxide solution (0.5 ml) and stirred for 1 hour. The volatiles were removed by evaporation and the residue dissolved in water, and extracted with DCM. The extracts were combined, the solvent removed by evaporation and the residue purified by chromatography on silica gel, eluting with DCM/methanol/aqueous ammonia (100:0:0 increasing in polarity to 80:20:1) to give the title compound (48.5 mg, 53%) as a solid.

NMR (DMSO-$d_6$+$d_4$-acetic acid at 100° C.): 2.08 (m, 3H), 2.19 (s, 3H), 2.35 (m, 1H), 3.75 (m, 1H), 3.82 (m, 3H), 5.55 (dd, 1H), 6.05 (s, 1H), 6.32 (s, 1H), 6.69 (s, 1H), 7.42 (m, 1H), 7.87 (t, 1H), 7.95 (d, 1H), 8.63 (d, 1H); m/z 418 [MH]+.

Example 86

S-6-Hydroxymethyl-2-{2-[3-(pyrid-2-yl)isoxazol-5-yl]pyrrolidin-1-yl}-4-(5-methyl-1H-pyrazol-3-ylamino)pyrimidine S-6-Methoxycarbonyl-2-{2-[3-(pyrid-2-yl)isoxazol-5-yl]pyrrolidin-1-yl}-4-(5-methyl-1H-pyrazol-3-ylamino)pyrimidine (Example 62) was treated by the method described in Example 80 to give the title compound.

NMR (DMSO-$d_6$+$d_4$-acetic acid at 100° C.): 2.10 (m, 3H), 2.18 (s, 3H), 2.35 (m, 1H), 3.70 (m, 1H), 3.77 (m, 1H), 4.23 (dd, 2H), 5.45 (dd, 1H), 6.01 (s, 1H), 6.41 (s, 1H), 6.65 (s, 1H), 7.40 (m, 1H), 7.85 (t, 1H), 7.95 (d, 1H), 8.62 (d, 1H); m/z 419 [MH]+.

Example 87

S-6-Ethoxymethyl-2-{2-[3-(pyrid-2-yl)isoxazol-5-yl]pyrrolidin-1-yl}-4-(5-methyl-1H-pyrazol-3-ylamino)pyrimidine A 1M solution of lithium bis(trimethylsilyl)amide in THF (5.0 ml, 5.0 mmol) was added to a mixture of S-6-chloromethyl-2-{2-[3-(pyrid-2-yl)isoxazol-5-yl]pyrrolidin-1-yl}-4-(5-methyl-2-N-[4-methylphenylsulphonylamino]-1H-pyrazol-3-ylamino)pyrimidine (Method 53) (240 mg, 0.41 mmol) in anhydrous ethanol (30 ml). The reaction mixture was then heated at 100° C. for 48 hours and allowed to cool. A small volume of water was added, the volatiles removed by evaporation. The residue was purified by chromatography on silica gel, eluting with DCM/methanol (100:0 increasing in polarity to 90:10) to give the title compound (29 mg, 16%).

NMR (DMSO-$d_6$+$d_4$-acetic acid at 100° C.): 1.15 (t, 3H), 2.05 (m, 3H), 2.18 (s, 3H), 2.35 (s, 1H), 3.52 (q, 2H), 3.67 (m, 1H), 3.76 (m, 1H), 4.20 (dd, 2H), 5.42 (dd, 1H), 6.02 (s, 1H), 6.38 (s, 1H), 6.62 (s, 1H), 7.40 (m, 1H), 7.86 (t, 1H), 7.92 (m, 1H), 8.62 (d, 1H); m/z 447 [MH]+.

Example 88

S-6-[(2-Methoxyethoxy)methyl]-2-{2-[3-(pyrid-2-yl)isoxazol-5-yl]pyrrolidin-1-yl}-4-(5-methyl-1H-pyrazol-3-ylamino)pyrimidine A 1M solution of lithium bis(trimethylsilyl)amide in THF (5.0 ml, 5.0 mmol) was added to a mixture of S-6-chloromethyl-2-{2-[3-(pyrid-2-yl)isoxazol-5-yl]pyrrolidin-1-yl}-4-(5-methyl-2-N-[4-methylphenylsulphonyl amino]-1H-pyrazol-3-ylamino)pyrimidine (Method 53) (240 mg, 0.41 mmol) in anhydrous 2-methoxyethanol (30 ml). The reaction mixture was then heated at 150° C. for 1.5 hours in a sealed vessel under microwave irradiation. A small volume of water was added, the volatiles removed by evaporation. The residue was purified by chromatography on silica gel, eluting with DCM/methanol (100:0 increasing in polarity to 90:10) to give the title compound (69.0 mg, 43%).

NMR (DMSO-$d_6$+$d_4$-acetic acid at 100° C.): 2.05 (m, 3H), 2.18 (s, 3H), 2.35 (s, 1H), 3.25 (s, 2H), 3.48 (t, 2H), 3.60 (t, 2H), 3.68 (m, 1H), 3.76 (m, 1H), 4.25 (dd, 2H), 5.42 (dd, 1H), 6.05 (s, 1H), 6.38 (s, 1H), 6.65 (s, 1H), 7.42 (m, 1H), 7.86 (t, 1H), 7.92 (m, 1H), 8.63 (d, 1H); m/z 477 [MH]+.

Example 89

S-5-Chloro-2-{2-[3-(pyrazin-2-yl)isoxazol-5-yl]pyrrolidin-1-yl}-4-(5-cyclopropyl-1H-pyrazol-3-ylamino)pyrimidine A mixture of 2,5-dichloro-4-(5-cyclopropyl-1H-pyrazol-3-ylamino)pyrimidine (Method 20 of WO 03/04133) (195 mg, 0.72 mmol), S-2-[3-(2-pyrazinyl)isoxazol-5-yl]pyrrolidine (Method 55) (171.5 mg, 0.79 mmol), N,N-diisopropylethylamine (0.28 ml, 1.58 mmol) and n-hexanol (10.0 ml) was heated at 125° C. for 18 hours. 3-(2-Aminoethylamino)propyl functionalised silica gel (500 mg) was then added and the reaction mixture heated at 140° C. for a further 2 hours. The reaction mixture was passed through a 50 g isolute SCX-2 ion exchange column. The column was eluted with methanol to elute any neutrals, followed by 7M methanolic ammonia to elute the product. The solvent was removed by evaporation and the residue purified by chromatography on silica gel eluting with DCM/methanol (100:0 increasing in polarity to 90:10). The purified product was triturated with diethylether and collected by filtration to give the title compound (100 mg, 31%)

NMR (DMSO-$d_6$+$d_4$-acetic acid at 100° C.): 1.28 (m, 2H), 1.48 (m, 2H), 2.68 (m, 2H), 2.78 (m, 1H), 3.01 (m, 1H), 4.27 (m, 1H), 4.41 (m, 1H), 6.05 (d, 1H), 7.29 (s, 1H), 8.60 (s, 1H), 9.25 (m, 2H), 9.73 (s, 1H); m/z 450 [MH]+.

Example 90

S-6-Methyl-4-(5-methyl-1H-pyrazol-3-ylamino)-2-{2-[3-(pyrazin-2-yl)isoxazol-5-yl]pyrrolidin-1-yl}pyrimidine A mixture of S-2-chloro-6-methyl-4-(5-methyl-1H-pyrazol-3-ylamino)pyrimidine (Method 56) (250 mg, 1.12 mmol), S-2-[3-(2-pyrazinyl)isoxazol-5-yl]pyrrolidine (Method 55) (266 mg, 1.23 mmol) and N,N-diisopropylethylamine (0.22 ml, 2.52 mmol) in n-hexanol (5 ml) was heated at 150° C. in a sealed vessel under microwave irradiation for 6 hours. The solvent was removed by evaporation and the residue was dissolved in methanol and poured onto a 50 g isolute SCX-2 ion exchange column. The column was eluted with methanol to elute any neutrals, followed by 7M methanolic ammonia to elute the product. The solvent was removed by evaporation to give the title compound (319.6 mg, 71%).

NMR (DMSO-$d_6$+$d_4$-acetic acid at 100° C.): 2.05 (m, 3H), 2.12 (s, 3H), 2.17 (s, 3H), 2.36 (m, 1H), 3.69 (m, 1H), 3.78 (m, 1H), 5.45 (dd, 1H), 5.98 (s, 1H), 6.18 (s, 1H), 6.71 (s, 1H), 8.68 (m, 2H), 9.12 (s, 1H); m/z 404 [MH]+.

Example 91

S-6-Chloro-4-(5-cyclopropyl-1H-pyrazol-3-ylamino)-2-{2-[3-(pyrazin-2-yl)isoxazol-5-yl]pyrrolidin-1-yl}pyrimidine A mixture of S-2,6-dichloro-4-(5-cyclopropyl-1H-pyrazol-3-ylamino)pyrimidine (Method 57) (1.5 g, 5.55 mmol), S-2-[3-(2-pyrazinyl)isoxazol-5-yl]pyrrolidine (Method 55) (1.32 g, 6.11 mmol) and N,N-diisopropylethylamine (0.92 ml, 6.66 mmol) in n-butanol (25 ml) heated at 80° C. for 4 hours. The solvent was removed by evaporation and the residue purified by chromatography on silica gel eluting with DCM/methanol (100:0 increasing in polarity to 90:10) to give the title compound (750 mg, 30%).

NMR (DMSO-$d_6$+$d_4$-acetic acid at 100° C.): 0.63 (m, 2H), 0.85 (m, 2H), 1.82 (m, 1H), 2.05 (m, 2H), 2.15 (m, 1H), 2.38 (m, 1H), 3.67 (m, 1H), 3.77(m, 1H), 5.43 (dd, 1H), 5.92 (s, 1H), 6.35 (s, 1H), 6.72 (s, 1H), 8.68 (m, 2H), 9.12 (s, 1H); m/z 450 [MH]+.

Example 92

S-4-(5-Cyclopropyl-1H-pyrazol-3-ylamino)-2-{2-[3-(pyrazin-2-yl)isoxazol-5-yl]pyrrolidin-1-yl}-6-(2-methoxyethylamino)pyrimidine A mixture of S-6-chloro-4-(5-cyclopropyl-1H-pyrazol-3-ylamino)-2-{2-[3-(pyrazin-2-yl)isoxazol-5-yl]pyrrolidin-1-yl}pyrimidine (Example 91) (215 mg, 0.48 mmol) and 2-methoxyethylamine (4.0 ml, 46.1 mmol)) were heated at 150° C. in a sealed vessel under microwave irradiation for 2 hours. The solvent was removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (78 mg, 33%).

NMR (DMSO-$d_6$+$d_4$-acetic acid at 100° C.): 0.63 (m, 2H), 0.85 (m, 2H), 1.80 (m, 1H), 2.10 (m, 3H), 2.35 (m, 1H), 3.20 (s, 3H), 3.35 (m, 4H), 3.65 (m, 1H), 3.77 (m, 1H), 5.43 (dd, 1H), 5.52 (s, 1H), 5.80 (s, 1H), 6.72 (s, 1H), 8.68 (m, 2H), 9.12 (s, 1H); m/z 489 [MH]+.

Example 93

S-6-Methylamino-{2-[3-(pyrazin-2-yl)isoxazol-5-yl]pyrrolidin-1-yl}-4-(5-cyclopropyl-1H-pyrazol-3-ylamino)pyrimidine A mixture of S-6-chloro-4-(5-cyclopropyl-1H-pyrazol-3-ylamino)-2-{2-[3-(pyrazin-2-yl)isoxazol-5-yl]pyrrolidin-1-yl}pyrimidine (example 91) (215 mg, 0.48 mmol) and a 2M solution of methylamine in THF (5.0 ml) were heated at 150° C. in a sealed vessel under microwave irradiation for 1.5 hours. The solvent was removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (100 mg, 50%).

NMR (DMSO-$d_6$+$d_4$-acetic acid at 100° C.): 0.63 (m, 2H), 0.85 (m, 2H), 1.82 (m, 1H), 2.10 (m, 3H), 2.36 (m, 1H), 2.68 (s, 3H), 3.67 (m, 1H), 3.75 (m, 1H), 5.44 (dd, 1H), 5.60 (s, 1H), 5.80 (s, 1H), 6.72 (s, 1H), 8.68 (m, 2H), 9.13 (s, 1H); m/z 445 [MH]+.

Example 94

S-4-(5-Cyclopropyl-1H-pyrazol-3-ylamino)-6-methoxy-{2-[3-(pyrazin-2-yl)isoxazol-5-yl]pyrrolidin-1-yl}pyrimidine A 1.33M solution of sodium methoxide in anhydrous methanol (3.0 ml, 2.25 mmol) was added to a mixture of S-6-chloro-4-(5-cyclopropyl-1H-pyrazol-3-ylamino)-2-{2-[3-(pyrazin-2-yl)isoxazol-5-yl]pyrrolidin-1-yl}pyrimidine (Example 91) (200 mg, 0.45 mmol) in anhydrous methanol (2.0 ml) and the reaction mixture was heated at 120° C. in a sealed vessel under microwave irradiation for 1.5 hours. The solvent was removed by evaporation and the residue was purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (87.5 mg, 44%).

NMR (DMSO-$d_6$+$d_4$-acetic acid at 100° C.): 0.64 (m, 2H), 0.85 (m, 2H), 1.82 (m, 1H), 2.10 (m, 3H), 2.40 (m, 1H), 3.71 (m, 4H), 3.78 (m, 1H), 5.45 (dd, 1H), 5.72 (s, 1H), 5.89 (s, 1H), 6.72 (s, 1H), 8.68 (m, 2H), 9.15 (s, 1H); m/z 446 [MH]+.

Example 95

6-Pyrrolidin-1-yl-2-{2-[3-(pyrid-2-yl)isoxazol-5-yl]pyrrolidin-1-yl}-4-(5-methyl-1H-pyrazol-3-ylamino)pyrimidine A mixture of 6-chloro-4-(5-methyl-1H-pyrazol-3-ylamino)-2-{2-[3-(pyrid-2-yl)isoxazol-5-yl]pyrrolidin-1-yl}pyrimidine (Example 17) (250 mg, 0.59 mmol), pyrrolidine (0.5 ml, 5.98 mmol) and anhydrous 1,4-dioxane (5.0 ml) was heated at 100° C. in a sealed vessel under microwave irradiation for 1 hour. The volatiles were removed by evaporation and the residue was purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation and the residue triturated with diethylether and collected by filtration to give the title compound (145 mg, 54%).

NMR (DMSO-d₆+d₄-acetic acid at 100° C.): 1.85 (s, 4H), 2.08 (m, 3H), 2.17 (s, 3H), 2.35 (m, 1H), 3.25 (m, 2H) 3.33 (m, 2H), 3.69 (m, 1H), 3.80 (m, 1H), 5.40 (dd, 1H), 5.85 (s, 1H), 6.71 (s, 1H), 7.38 (m, 1H), 7.85 (t, 1H), 7.90 (d, 1H), 8.61 (d, 1H); m/z 458 [MH]+.

Example 96

S-6-Chloro-4-(5-methyl-1H-pyrazol-3-ylamino)-2-[2-{3-(pyrid-2-yl)isoxazol-5-yl}pyrrolidin-1-yl]pyrimidine A mixture of 2,6-dichloro-4-(5-methyl-1H-pyrazol-3-ylamino)pyrimidine (Method 29) (14.36 g, 59 mmol), S-2-[3-(pyrid-2-yl)isoxazol-5-yl]pyrrolidine (Method 42) (12.69 g, 59 mmol) and N,N-diisopropylethylamine (14.5 ml, 83 mmol) in xylene (380 ml) was heated at 80° C. for 2 days. The solvent was removed by evaporation. The residue was triturated with ether and water and the crude solid product collected by filtration washed with water and dried. The ether was evaporated from the filtrate and DCM added to aqueous mixture. Insoluble material was removed by filtration, the DCM layer was separated and dried (MgSO₄). The originally isolated crude solid product was dissolved in DCM and was added to this solution. The solution concentrated by evaporation and left to stand for 2 days. The resulting solid was collected by filtration, washed with the minimum DCM and dried to give title compound. (13.3 g, 53%) as white crystals.

NMR (DMSO): 2.08 (m, 2H), 2.18 (m, 4H), 3.74 (m, 2H), 5.47 (d, 1H), 5.98 (s, 1H), 6.4 (s, 1H), 6.67 (s, 1H), 7.43 (m, 1H), 7.9 (m, 2H), 8.65 (d, 1H), 8.88 (br s, 1H), 11.44 (br s, 1H); m/z 423 [MH]+.

Example 97

S-6-(2,2,6,6-Tetramethylpiperidin-4-ylamino)-2-{2-[3-(pyrid-2-yl)isoxazol-5-yl]pyrrolidin-1-yl}-4-(5-methyl-1H-pyrazol-3-ylamino)pyrimidine A mixture of S-6-chloro-2-{2-[3-(pyrid-2-yl)isoxazol-5-yl]pyrrolidin-1-yl}-4-(5-methyl-1H-pyrazol-3-ylamino)pyrimidine (Example 96) (200 mg, 0.47 mmol), 4-amino-2,2,6,6-tetramethylpiperidine (0.4 ml, 2.33 mmol) and anhydrous 1,4-dioxane (5.0 ml) was heated at 150° C. in a sealed vessel under microwave irradiation for 4 hours. The volatiles was removed by evaporation and the residue purified by reverse phase HPLC using a C18 column eluting with water/acetonitrile/TFA (95:5:0.2 decreasing in polarity to 0:100:0.2). Product containing fractions were combined and passed through a 50 g isolute SCX-2 ion exchange column. The column was eluted with methanol to elute any neutrals, followed by 7M methanolic ammonia to elute the product. The solvent was removed by evaporation to give the title compound (122 mg, 47%).

NMR (DMSO-d₆+d₄-acetic acid at 100° C.): 1.25-1.45 (m, 12H), 2.01 (m, 3H), 2.17 (s, 3H), 2.35 (m, 1H), 3.65 (m, 1H), 3.75 (m, 1H), 4.23 (m, 1H), 5.40 (dd, 1H), 5.89 (s, 1H), 6.60 (s, 1H), 7.40 (m, 1H), 7.87 (t, 1H), 7.93 (d, 1H), 8.63 (d, 1H); m/z 543 [MH]+.

Example 98

S-6-Iodo-4-(5-methyl-1H-pyrazol-3-ylamino)-2-[2-{3-(pyrid-2-yl)isoxazol-5-yl}pyrrolidin-1-yl]pyrimidine S-6-Chloro-4-(5-methyl-1H-pyrazol-3-ylamino)-2-[2-{3-(pyrid-2-yl)isoxazol-5-yl}pyrrolidin-1-yl]pyrimidine (Example 96) (2.0 g, 4.7 mmol), sodium iodide (3.9 g, 26 mmol) in hydroiodic acid (25 ml) was heated at 50° C. for 3 days. The reaction mixture was allowed to cool and poured onto ice and basified with 20% aqueous sodium hydroxide solution and extracted with DCM. The extracts were combined, dried (MgSO₄) and the solvent evaporated to give the title compound (2 g, 83%).

NMR (DMSO): 1.9-2.1 (m, 3H), 2.16 (s, 3H), 2.28-2.40 (m, 1H), 3.45-3.60 (m, 1H), 3.68-3.80 (m, 1H), 5.35 (d, 1H), 5.75 (s, 1H), 5.84 (s, 1H), 6.75 (s, 1H), 7.45 (dd, 1H), 7.86-8.0 (m, 2H), 8.63 (d, 1H), 9.52(s, 1H); m/z 515 [MH]+.

Example 99

S-E-6-[3-(tert-Butoxycarbonylamino)prop-1-en-1-yl]-4-(5-methyl-1H-pyrazol-3-ylamino)-2-[2-{3-(pyrid-2-yl)isoxazol-5-yl}pyrrolidin-1-yl]pyrimidine 3-(tert-Butoxycarbonylamino)prop-1-en-1-yl boronate[2,3-dihydroxy-2,3-dimethylbutane]ester (Method 58) (938 mg, 3.5 mmol) was added to a mixture of S-6-iodo-4-(5-methyl-1H-pyrazol-3-ylamino)-2-[2-{3-(pyrid-2-yl)isoxazol-5-yl}pyrrolidin-1-yl]pyrimidine (Example 98) (300 mg, 0.6 mmol), tetrakis(triphenylphosphine)palladium(0) (27 mg, 0.02 mmol) and 2M aqueous sodium carbonate solution (1.5 ml) in toluene (8 ml) and ethanol (4 ml) and the mixture heated at 140° C. in a sealed vessel under microwave irradiation for 15 minutes. The mixture was extracted with EtOAc and the extracts combined, washed with water and dried (MgSO₄). The solvent was removed by evaporation and the residue purified by column chromatography on silica gel eluting with DCM/methanol (100:0 increasing in polarity to 96:4) to give the title compound (188 mg, 60%).

NMR (DMSO): 1.45 (s, 9H), 2.05-2.18 (m, 2H), 2.20 (s, 3H), 2.35-2.46 (m, 1H), 2.95-3.0 (m, 2H), 3.74-3.9 (m, 4H), 5.5 (d, 1H), 6.10 (s, 1H), 6.22 (d, 1H), 6.30 (s, 1H), 6.58-6.71 (m, 3H), 7.45 (dd, 1H), 7.90-8.0 (dd, 2H), 8.65 (d, 1H), 8.90 (s, 1H), 11.55 (s, 1H); m/z 544 [MH]+.

Examples 100 and 101

Examples 100 and 101 were prepared by an analogous method to that described in Example 99.

Example 100

S-6-Ethenyl-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and vinylboronate[2,3-dihydroxy-2,3-dimethylbutane]ester. The product was triturated with ether/DCM/hexane to give the title compound (82 mg, 47%).

NMR (DMSO): 2.02-2.12 (m, 3H), 2.21 (s, 3H), 2.35-2.40 (m, 1H), 3.69-3.80 (m, 2H), 5.40 (d, 1H), 5.49 (dd, 1H), 6.08 (s, 1H), 6.15 (d, 1H), 6.29 (s, 1H), 6.40-6.50 (m, 1H), 6.66 (s,

1H), 7.44 (dd, 1H), 7.95 (m, 2H), 8.61 (s, 1H), 8.90 (s, 1H), 11.50 (s, 1H); m/z 415 [MH]+.

Example 101

S-E-6-(3-Hydroxyprop-1-en-1-yl)-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-acetoxyprop-1-en-1-ylbboronate[2,3-dihydroxy-2,3-dimethylbutane]ester. The product was purified by reverse phase HPLC using a C18 column eluting with water/acetonitrile/TFA (95:5:0.2 decreasing in polarity to 0:100:0.2) to give the title compound (19 mg, 7%).

NMR (DMSO): 2.05-2.16 (m, 3H), 2.19 (s, 3H), 2.34-2.42 (m, 1H), 3.70-3.85 (m, 2H), 4.16 (dd, 2H), 4.50 (t, 1H), 5.49 (d, 1H), 6.08 (s, 1H), 6.25-6.32 (m, 2H), 6.69 (s, 1H), 6.75-6.82 (m, 1H), 7.45 (dd, 1H), 7.88-7.96 (m, 2H), 8.67 (d, 1H), 8.88 (s, 1H), 11.52 (s, 1H); m/z 445 [MH]+.

Example 102

S-6-[3-(tert-Butoxycarbonylamino)prop-1-yl]-4-(5-methyl-1H-pyrazol-3-ylamino)-2-[2-{3-(pyrid-2-yl)isoxazol-5-yl}pyrrolidin-1-yl]pyrimidine A solution of S-E-6-[3-(tert-butoxycarbonylamino)prop-1-en-1-yl]-4-(5-methyl-1H-pyrazol-3-ylamino)-2-[2-{3-(pyrid-2-yl)isoxazol-5-yl}pyrrolidin-1-yl]pyrimidine (Example 99) (84 mg, 0.15 mmol), p-toluenesulphonylhydrazide (259 mg, 1.4 mmol) in dimethyl ethyl ether (5 ml) was warmed to reflux and sodium acetate (240 mg, 2.9 mmol) in water (5 ml) was added over 2 hours and the mixture heated at reflux for 18 hours. The mixture was diluted with EtOAc and washed with water, and then brine, dried (MgSO$_4$) and the solvent removed by evaporation. The residue was dissolved in methanol and poured onto a SCX2 (10 g) ion exchange column. The impurities were eluted with methanol and then the product was eluted with 7M methanolic ammonia. The solvent was removed by evaporation to give the title compound (80 mg, 95%).

NMR (DMSO): 1.38 (s, 9H), 1.68-1.78 (m, 2H), 2.04-2.18 (m, 3H), 2.20 (s, 3H), 2.30-2.40 (m, 3H), 3.65-3.80 (m, 2H), 5.45 (d, 1H), 6.02 (s, 1H), 6.20 (s, 1H), 6.28 (s, 1H), 6.68 (s, 1H), 7.45 (dd, 1H), 7.88-7.98 (m, 2H), 8.68 (d, 1H), 8.76 (s, 1H), 11.5 (s, 1H); m/z 546 [MH]+.

Example 103

S-6-[3-Aminoprop-1-yl]-4-(5-methyl-1H-pyrazol-3-ylamino)-2-[2-{3-(pyrid-2-yl)isoxazol-5-yl}pyrrolidin-1-yl]pyrimidine S-6-[3-(tert-Butoxycarbonylamino)prop-1-yl]-4-(5-methyl-1H-pyrazol-3-ylamino)-2-[2-{3-(pyrid-2-yl)isoxazol-5-yl}pyrrolidin-1-yl]pyrimidine (Example 102) (80 mg, 0.15 mmol) in DCM was cooled to about 0 to 5° C. Trifluoroacetic acid (TFA) (1 ml) was added and the mixture stirred at 5° C. for 1 hour and then for 1.5 hours at ambient temperature. The volatiles were removed by evaporation and the residue dissolved in methanol and poured onto a SCX2 (10 g) ion exchange column. The impurities were eluted with methanol and then the product was eluted with 7M methanolic ammonia. The solvent was removed by evaporation to give the title compound (40 mg, 63%).

NMR (DMSO): 1.62-1.70 (m, 2H), 2.04-2.15 (m, 2H), 2.19 (s, 3H), 2.32-2.48 (m, 3H), 2.50-2.60 (m, 2H), 3.68-3.80 (m, 2H), 5.49 (d, 1H), 6.05 (s, 1H), 6.20 (s, 1H), 6.65 (s, 1H), 7.45 (dd, 1H), 7.85-7.95 (m, 2H), 8.66 (d, 1H), 8.73 (s, 1H); m/z 446 [MH]+.

Example 104

S-E-6-[3-Aminoprop-1-en-1-yl]-4-(5-methyl-1H-pyrazol-3-ylamino)-2-[2-{3-(pyrid-2-yl)isoxazol-5-yl}pyrrolidin-1-yl]pyrimidine S-E-6-[3-(tert-Butoxycarbonylamino)prop-1-en-1-yl]-4-(5-methyl-1H-pyrazol-3-ylamino)-2-[2-{3-(pyrid-2-yl)isoxazol-5-yl}pyrrolidin-1-yl]pyrimidine (Example 99) (50 mg, 0.09 mmol) in DCM (5 ml) was cooled to 5° C. TFA (1 ml) was added and the mixture stirred at 5° C. for 1 hour, then ambient temperature for 4 hours. The volatiles were removed by evaporation, the residue dissolved in methanol, and poured onto a SCX2 (10 g) ion exchange column. The impurities were eluted with methanol and then the product was eluted with 7M methanolic ammonia. The solvent was removed by evaporation and triturated with ether to give the title compound (25 mg, 63%).

NMR (DMSO): 2.07-2.12 (m, 3H), 2.20 (s, 3H), 2.32-2.44 (m, 1H), 3.35 (d, 2H), 3.70-3.85 (m, 2H), 5.48 (d, 1H), 6.05 (s, 1H), 6.20-6.28 (m, 2H), 6.68 (s, 1H), 6.75-6.82 (m, 1H), 7.45 (dd, 1H), 7.89-7.95 (m, 2H), 8.65 (d, 1H), 8.85 (s, 1H), 11.50 (s, 1H); m/z 444 [MH]+.

Example 105

S-6-[3-Methylaminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine A mixture of S-6-iodo-4-(5-methyl-1H-pyrazol-3-ylamino)-2-[2-{3-(pyrid-2-yl)isoxazol-5-yl}pyrrolidin-1-yl]pyrimidine Example 98) (500 mg, 0.97 mmol), 3-methylaminoprop-1-yne (134 mg, 1.9 mmol) bis(triphenylphosphine)palladium (II) chloride (27 mg, 0.04 mmol), copper (I) iodide (4 mg, 0.02 mmol), triethylamine (0.7 ml, 5 mmol) in acetonitrile (12 ml) was heated at 75° C. in a sealed vessel under microwave irradiation for 15 minutes. The reaction mixture was extracted with EtOAc, the extracts combined and washed with water, dried (MgSO$_4$) and the solvent removed by evaporation. The residue was purified by column chromatography on silica gel eluting with DCM/methanol/aqueous ammonia (100:0:0 increasing in polarity to 85:15:1) to give the title compound (219 mg, 50%).

NMR (DMSO): 2.00-2.12 (m, 3H), 2.20 (s, 3H), 2.32 (m, 2H), 2.35 (s, 3H), 3.5 (s, 2H), 3.65-3.8 (m, 2H), 5.46 (d, 1H), 6.02 (s, 1H), 6.45 (s, 1H), 6.65 (s, 1H), 7.45 (dd, 1H), 7.87-7.98 (m, 2H), 8.67 (d, 1H), 9.05 (s, 1H), 11.6 (s, 1H); m/z 456 [MH]+.

Examples 106 to 111

Examples 106 to 111 were prepared by an analogous method to that described in Example 105.

Example 106

S-6-[3-Methoxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-methoxyprop-1-yne. The product was purified by reverse phase HPLC using a C18 column eluting with water/acetonitrile/TFA (95:5:0.2 decreasing in polarity to 0:100:0.2). Yield: 70 mg, 53%.

NMR (DMSO): 2.0-2.18 (m, 3H), 2.19 (s, 3H), 2.30-2.42 (m, 2H), 3.33 (s, 3H), 3.63-3.70 (m, 1H), 3.73-3.80 (m, 1H), 4.30 (s, 3H), 5.45 (d, 1H), 6.03 (s, 1H), 6.45 (s, 1H), 6.67 (s, 1H), 7.45 (dd, 1H), 7.88-7.96 (m, 2H), 8.66 (d, 1H); m/z 457 [MH]+.

Example 107

S-6-[3-Hydroxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and prop-2-yn-1-ol. The product was purified by reverse phase HPLC using a C18 column eluting with water/acetonitrile/TFA (95:5:0.2 decreasing in polarity to 0:100:0.2). Yield: 50 mg, 30%.

NMR (DMSO): 2.01-2.15 (m, 4H), 2.18 (s, 3H), 2.30-2.40 (m, 1H), 3.62-3.70 (m, 1H), 3.72-3.8 (m, 1H), 4.25 (s, 3H), 5.04 (t, 1H), 6.04 (s, 3H), 6.45 (s, 1H), 6.65 (s, 1H), 7.45 (m, 1H), 7.88-7.97 (m, 2H), 8.65 (d, 1H), 9.08 (s, 1H), 11.55 (s, 1H); m/z 443 [MH]+.

Example 108

S-6-[2-(Trimethylsilyl)ethynyl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and trimethylsilyacetylene. Yield: 225 mg, 50%.

NMR (DMSO): 0.25 (s, 9H), 2.02-2.19 (m, 3H), 2.20 (s, 3H), 2.30-2.42 (m, 1H), 3.62-3.80 (m, 2H), 5.45 (d, 1H), 6.04 (s, 1H), 6.45 (s, 1H), 6.69 (s, 1H), 7.48 (dd, 1H), 7.85-7.98 (m, 2H), 8.65 (s, 1H), 9.05 (s, 1H), 11.60 (s, 1H); m/z 485 [MH]+.

Example 109

S-6-[3-(N-Methylacetamido)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-(N-methylacetamido)prop-1-yne (Method 59). Yield: 50 mg, 26%.

NMR (DMSO): 2.02-2.15 (m, 5H), 2.20 (s, 3H), 2.31-2.40 (m, 1H), 2.93 (s, 3H), 2.97-3.01 (m, 1H), 3.64-3.71 (m, 1H), 3.73-3.80 (m, 1H), 4.38 (s, 2H), 5.45 (d, 1H), 6.04 (s, 1H), 6.45 (s, 1H), 6.65 (s, 1H), 7.45 (dd, 1H), 7.88-7.96 (m, 2H), 8.66 (d, 1H), 9.08 (s, 1H); m/z 498 [MH]+.

Example 110

S-6-[3-(Dimethylamino)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-(dimethylamino)prop-1-yne. The product was purified by reverse phase HPLC using a C18 column eluting with water/acetonitrile/TFA (95:5:0.2 decreasing in polarity to 0:100:0.2). Yield: 32 mg, 18%.

NMR (DMSO): 2.01-2.15 (m, 3H), 2.19 (s, 3H), 2.28 (s, 6H), 2.32-2.42 (m, 1H), 3.42 (s, 2H), 3.64-3.71 (m, 1H), 3.72-3.80 (m, 1H), 5.45 (d, 1H), 6.05 (s, 1H), 6.45 (s, 1H), 6.68 (s, 1H), 7.45 (d, 1H), 7.86-7.95 (m, 2H), 8.66 (d, 1H), 9.05 (s, 1H), 11.55 (s, 1H).

Example 111

S-6-[3-Acetamidoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-acetamidoprop-1-yne (prepared by a analogous method to that described in Method 59). Yield: 44 mg, 24%.

NMR (DMSO): 1.88 (s, 3H), 2.02-2.17 (m, 3H), 2.20 (s, 3H), 2.30-2.42 (m, 1H), 3.62-3.70 (m, 1H), 3.72-3.80 (m, 1H), 4.1 (d, 2H), 5.45 (d, 1H), 6.05 (s, 1H), 6.45 (s, 1H), 6.65 (s, 1H), 7.45 (dd, 1H), 7.88-7.96 (m, 2H), 8.05 (s, 1H), 8.75 (d, 1H), 9.08 (s, 1H), 11.55 (s, 1H); m/z 484 [MH]+.

Example 112

S-6-[2-(Ethoxycarbonyl)ethyl]-4-(5-methyl-1H-pyrazol-3-ylamino)-2-[2-{3-(pyrid-2-yl)isoxazol-5-yl}pyrrolidin-1-yl]pyrimidine S-6-iodo-4-(5-methyl-1H-pyrazol-3-ylamino)-2-[2-{3-(pyrid-2-yl)isoxazol-5-yl}pyrrolidin-1-yl]pyrimidine (Example 98) (70 mg, 0.14 mmol), 3-(ethoxycarbonyl)ethyl zinc bromide (0.82 ml of 1M solution in ether), bis(triphenylphosphine)palladium (II) chloride (7 mg, 0.01 mmol) in THF (2 ml) and dimethylacetamide (DMA) (1 ml) were heated at 70° C. in a sealed vessel under microwave irradiation for 30 minutes. The mixture was diluted with EtOAc, washed with water, dried (MgSO$_4$) and the volatiles removed by evaporation. The residue was purified by chromatography on silica gel eluting with methanol/DCM (3:97) and then further purified by reverse phase HPLC using a C18 column eluting with water/acetonitrile/TFA (95:5:0.2 decreasing in polarity to 0:100:0.2) to give the title compound (20 mg, 30%).

NMR (DMSO): 1.12 (t, 3H), 2.0-2.2 (m, 3H), 2.19 (s, 3H), 2.30-2.40 (m, 1H), 2.55-2.60 (m, 1H), 2.66-2.70 (m, 3H), 3.64-3.80 (m, 2H), 4.05 (q, 2H), 5.44 (d, 1H), 6.0 (s, 1H), 6.16 (s, 1H), 6.65 (s, 1H), 7.45 (dd, 1H), 7.87-7.95 (m, 2H), 8.65 (s, M1); m/z 489 [MH]+.

Example 113

S-E-6-[2-(Methoxycarbonyl)ethen-1-yl]-4-(5-methyl-1H-pyrazol-3-ylamino)-2-[2-{3-(pyrid-2-yl)isoxazol-5-yl}pyrrolidin-1-yl]pyrimidine A mixture of S-6-iodo-4-(5-methyl-1H-pyrazol-3-ylamino)-2-[2-{3-(pyrid-2-yl)isoxazol-5-yl}pyrrolidin-1-yl]pyrimidine (Example 98) (200 mg, 0.39 mmol), methylacrylate (0.336 ml), 1,1'-bis(diphenylphosphino)ferrocene palladium (I) chloride (64 mg, 0.08 mmol), tetrabutylammonium iodide (288 mg, 0.78 mmol) in DMF (2.5 ml), water (0.5 ml) and triethylamine (0.5 ml) was heated at 130° C. in sealed vessel under microwave irradiation for 15 minutes. The mixture was extracted with ethyl acetate, the extracts combined and washed with water, dried (Na$_2$SO$_4$) and the volatiles removed by evaporation. The residue was purified by reverse phase HPLC using a C18 column eluting with water/acetonitrile/TFA (95:5:0.2 decreasing in polarity to 0:100:0.2) to give the title compound (50 mg, 28%).

NMR (DMSO): 2.05-2.18 (m, 3H), 2.20 (s, 3H), 2.38-2.45 (m, 1H), 3.73 (s, 3H), 3.75-3.89 (m, 2H), 5.48 (d, 1H), 6.10 (s, 1H), 6.48 (s, 1H), 6.70 (s, 1H), 6.80 (d, 1H), 7.23 (d, 1H), 7.48 (dd, 1H), 7.88-7.98 (m, 2H), 8.65 (d, 1H), 9.37 (s, 1H), 11.6 (s, 1H); m/z 473 [MH]+.

Example 114

S-6-Ethynyl-4-(5-methyl-1H-pyrazol-3-ylamino)-2-[2-{3-(pyrid-2-yl)isoxazol-5-yl}pyrrolidin-1-yl]pyrimidine Potassium carbonate (17 mg, 0.12 mmol) was added to a solution of S-6-[2-(trimethylsilyl)ethynyl]-4-(5-methyl-1H-pyrazol-3-ylamino)-2-[2-{3-(pyrid-2-yl)isoxazol-5-yl}pyrrolidin-1-yl]pyrimidine (Example 108) (50 mg, 0.1 mmol) in methanol (1 ml) and the mixture stirred at ambient temperature for 18 hours. The mixture was diluted with water and extracted with EtOAc. The extracts were combined, washed with brine, dried (Na$_2$SO$_4$) and the solvent removed by evaporation. The residue was triturated with ether and collected by filtration to give the title compound (21 mg, 50%).

NMR (DMSO): 2.01-2.15 (m, 3H), 2.20 (s, 3H), 2.30-2.45 (m, 1H), 3.65-3.80 (m, 2H), 3.94 (s, 1H), 5.45 (d, 1H), 6.05 (s, 1H), 6.50 (s, 1H), 6.69 (s, 1H), 7.48 (dd, 1H), 7.85-7.98 (m, 2H), 8.68 (d, 1H), 9.10 (s, 1H), 11.55 (s, 1H); m/z 413 [MH]+.

Example 115

6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine 4-Hydroxy-6-methoxymethyl-2-[2-{3-(pyrid-2-yl)isoxazol-5-yl}pyrrolidin-1-yl]pyrimidine (Method 34) and 3-amino-5-cyclopropyl-1H-pyrazole (Method 7 of WO 03/048133) were treated as described in Example 26 to give the title compound (245 mg, 48%).

NMR (DMSO): 0.68 (m, 2H), 0.84-0.88 (m, 2H), 1.85 (m, 1H), 2.02-2.10 (m, 2H), 2.12-2.19 (m, 1H), 2.31-2.42 (m, 1H), 3.36 (s, 3H), 3.66-3.79 (m, 2H), 4.17 (q, 2H), 5.46 (d, 1H), 6.0 (s, 1H), 6.38 (s, 1H), 6.65 (s, 1H), 7.44 (dd, 1H), 7.89-7.95 (m, 2H), 8.65 (d, 1H), 8.94 (s, 1H); m/z 459 [MH]+.

Example 116

S-6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 115) by chiral HPLC using a chiralpak AD column eluting with methanol/ethanol (85:15).

Example 117

S-6-Methoxymethyl-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 30) by chiral HPLC using a chiralpak AD column eluting with methanol/ethanol (85:15).

Example 118

S-6-[3-Aminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine Hydrazine hydrate (24 µl, 0.49 mmol) was added to S-6-[3-(N-phthalimido)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine (Method 60) (50 mg, 0.09 mmol) in THF (1 ml) and ethanol (0.1 ml) and the mixture stirred at ambient temperature for 1 hour then heated at 60° C. for 30 minutes. The mixture was extracted with EtOAc, the extracts combined, washed with water, dried (MgSO$_4$) and the solvent removed by evaporation. The residue was purified by reverse phase HPLC using a C18 column eluting with water/acetonitrile/TFA (95:5:0.2 decreasing in polarity to 0:100:0.2). Product containing fractions were neutralised with aqueous sodium hydrogen carbonate solution and extracted with DCM, dried (MgSO$_4$) and the solvent removed by evaporation to give the title compound (15 mg, 39%).

NMR (DMSO): 1.25-1.30 (m, 2H), 1.52-1.65 (m, 1H), 2.04-2.15 (m, 3H), 2.20 (s, 3H), 3.55 (s, 2H), 3.65-3.80 (m, 2H), 5.45 (d, 1H), 6.05 (s, 1H), 6.42 (s, 1H), 6.65 (s, 1H), 7.44 (dd, 1H), 7.85-7.95 (m, 2H), 8.65 (s, 1H), 9.0 (s, 1H), 11.50 (s, 1H); m/z 442 [MH]+.

Example 119

S-6-[2-(N-Methylcarbamoyl)ethyl]-4-(5-methyl-1H-pyrazol-3-ylamino)-2-[2-{3-(pyrid-2-yl)isoxazol-5-yl}pyrrolidin-1-yl]pyrimidine A mixture of S-6-[2-(ethoxycarbonyl)ethyl]-4-(5-methyl-1H-pyrazol-3-ylamino)-2-[2-{3-(pyrid-2-yl)isoxazol-5-yl}pyrrolidin-1-yl]pyrimidine (Example 112) (80 mg, 0.16 mmol), methylamine (3 ml of a 2M solution in methanol) and 1,8-diazobicyclo[5.4.0]undec-7-ene (DBU) (0.1 ml, 0.67 mmol) was heated at 105° C. in a sealed vessel under microwave irradiation for 1.5 hours. The mixture was extracted with EtOAc, the extracts combined, washed with water, dried (MgSO$_4$) and the solvent removed by evaporation. The residue was purified by reverse phase HPLC using a C18 column eluting with water/acetonitrile/TFA (95:5:0.2 decreasing in polarity to 0:100:0.2). Product containing fractions were neutralised with aqueous sodium hydrogen carbonate solution and extracted with DCM, dried (MgSO$_4$) and the solvent removed by evaporation to give the title compound (25 mg, 30%).

NMR (DMSO): 2.02-2.19 (m, 2H), 2.19 (s, 3H), 2.32-2.44 (m, 3H), 2.58 (s, 3H), 2.59-2.69 (m, 2H), 3.68-3.80 (m, 2H), 5.45 (d, 1H), 6.04 (s, 1H), 6.20 (s, 1H), 6.68 (s, 1H), 7.30 (s, 1H), 7.45 (dd, 1H), 7.88-7.98 (m, 2H), 8.68 (d, 1H), 8.78 (s, 1H), 11.5 (s, 1H); m/z 474 [MH]+.

Example 120

S-4-(5-Ethyl-1H-pyrazol-3-ylamino)-2-[2-[3-(2-methoxypyrid-3-yl)isoxazol-5-yl]pyrrolidin-1-yl]pyrimidine A mixture of 4-(5-ethyl-1H-pyrazol-3-ylamino)-2-chloropyrimidine (Method 65) (200 mg, 0.9 mmol), S-2-[3-(2-methoxypyrid-3-yl)isoxazol-5-yl]pyrrolidine (Method 64) (300 mg, 1.2 mmol) and diisopropylethylamine (0.22 ml, 1.4 mmol) in hexanol (10 ml) was heated at 150° C. for 24 hours. The residue was allowed to cool and diluted with EtOAc and washed with water. The organic solution was dried (MgSO$_4$) and the solvent removed by evaporation. The residue was purified by chromatography on silica gel eluting with EtOAc/hexane/methanol (50:50:0 increasing in polarity to 98:0:2) to give the title compound (212 mg, 55%).

NMR (DMSO): 1.19 (t, 3H), 2.06-2.19 (m, 3H), 2.30-2.40 (m, 1H), 2.56 (q, 2H), 3.66-3.80 (m, 2H), 3.94 (s, 3H), 5.45 (d, 1H), 6.12 (s, 1H), 6.30 (s, 1H), 6.59 (s, 1H), 7.08 (dd, 1H), 7.89 (d, 1H), 8.10 (d, 1H), 8.26 (d, 1H), 8.92 (s, 1H), 11.55 (s, 1H); m/z 433 [MH]+.

Examples 121 and 122

Examples 121 and 122 were prepared by an analogous method to that described for Example 120.

Example 121

S-4-(5-Methyl-1H-pyrazol-3-ylamino)-2-[2-[3-(2-methoxypyrid-3-yl)isoxazol-5-yl]pyrrolidin-1-yl]pyrimidine Starting materials: 2-chloro-4-(5-methyl-1H-pyrazol-3-ylamino)pyrimidine (Method 26) and S-2-[3-(2-methoxypyrid-3-yl)isoxazol-5-yl]pyrrolidine (Method 64). Yield: 147 mg, 49%.

NMR (DMSO): 2.05-2.18 (m, 3H), 2.20 (s, 3H), 2.32-2.40 (m, 1H), 3.66-3.78 (m, 2H), 3.94 (s, 3H), 5.45 (d, 1H), 6.08 (s, 1H), 6.30 (s, 1H), 6.59 (s, 1H), 7.09 (dd, 1H), 7.88 (d, 1H), 8.09 (d, 1H), 8.28 (d, 1H), 8.85 (s, 1H); m/z 419 [MH]+.

Example 122

S-4-(5-Cyclopropyl-1H-pyrazol-3-ylamino)-2-[2-[3-(2-methoxypyrid-3-yl)isoxazol-5-yl]pyrrolidin-1-yl]pyrimidine Starting materials: 2-chloro-4-(5-cyclopropyl-1H-pyrazol-3-ylamino)pyrimidine (Method 28) and S-2-[3-(2-methoxypyrid-3-yl)isoxazol-5-yl]pyrrolidine (Method 64). Yield: 143 mg, 51%.

NMR (DMSO): 0.64-0.69 (m, 2H), 0.84-0.90 (m, 2H), 1.80-1.90 (m, 1H), 2.02-2.19 (m, 3H), 2.30-2.41 (m, 1H), 3.67-3.80 (m, 2H), 3.96 (s, 3H), 5.48 (d, 1H), 6.02 (s, 1H), 6.30 (s, 1H), 6.59 (s, 1H), 7.09 (dd, 1H), 7.89 (d, 1H), 8.10 (d, 1H), 8.29 (d, 1H), 8.90 (s, 1H), 11.60 (s, 1H); m/z 445 [MH]+.

Example 123

6-(N-tert-Butoxycarbonyl)amino-2-{2-[3-(pyrid-2-yl)isoxazol-5-yl]pyrrolidin-1-yl}-4-(5-methyl-1H-pyrazol-3-ylamino)pyrimidine 2-{2-[3-(pyrid-2-yl)isoxazol-5-yl]pyrrolidin-1-yl}-4-(5-methyl-1H-pyrazol-3-ylamino)pyrimidin-6-yl carboxylic acid (Method 43) (300 mg, 0.69 mmol) was stirred in tert-butanol (30 ml) and diphenylphosphoryl azide (286 mg, 0.97 mmol) was added followed by triethylamine (140 µl, 0.99 mmol) and the mixture heated and stirred at 90° C. for 16 hours. The mixture was concentrated by evaporation and the residue purified by reverse phase HPLC using a C18 column eluting with water/acetonitrile/TFA (95:5:0.2 decreasing in polarity to 0:100:0.2). The product containing fractions were passed down a 20 g SCX-2 column, eluting with methanol then eluting the product with 2N methanolic ammonia. The solvent was removed by evaporation to give the title compound (40 mg, 12%) as a white powder.

NMR (DMSO-d$_6$+d$_4$-acetic acid at 100° C.): 1.45 (s, 9H), 2.00-2.15 (m, 3H), 2.15 (s, 3H), 2.35 (m, 1H), 3.60-3.80 (m, 2H), 5.42 (d, 1H), 6.00 (s, 1H), 6.68 (s, 1H), 7.40 (t, 1H), 7.85 (t, 1H), 7.95 (d, 1H), 8.65 (d, 1H); m/z 504 [MH]+.

Example 124

6-(4-(N-tert-Butoxycarbonylamino)piperidin-1-yl)-2-{2-[3-(pyrid-2-yl)isoxazol-5-yl]pyrrolidin-1-yl}-4-(5-methyl-1H-pyrazol-3-ylamino)pyrimidine A mixture of 6-chloro-2-{2-[3-(pyrid-2-yl)isoxazol-5-yl]pyrrolidin-1-yl}-4-(5-methyl-1H-pyrazol-3-ylamino)pyrimidine (Example 17) (150 mg, 0.35 mmol) and 4-(N-tert-butoxycarbonylamino)piperidine (700 mg, 3.5 mmol) were added to dioxane (4 ml) and heated in a sealed vessel under microwave irradiation at 150° C. for 60 minutes. The crude reaction mixture was purified by reverse phase HPLC using a C18 column eluting with water/acetonitrile/TFA (95:5:0.2 decreasing in polarity to 0:100:0.2). The product containing fractions were passed down an SCX-2 column eluting with methanol and then releasing the product with 2N methanolic ammonia. The solvent was removed by evaporation to give the title compound (134 mg, 64%) as a white solid.

NMR (DMSO-d$_6$+d$_4$-acetic acid at 100° C.): 1.20-1.30 (m, 1H), 1.35 (s, 9H), 1.7 (m, 2H), 2.10 (m, 3H), 2.15 (s, 3H), 2.35 (m, 1H), 2.90 (t, 2H), 3.45 (m, 1H), 3.67 (m, 1H), 3.75 (m, 1H), 4.00 (m, 2H), 5.34 (d, 1H), 6.65 (s, 1H), 7.40 (m, 1H), 7.85 (t, 1H), 7.90 (d, 1H), 8.60 (d, 1H); m/z 587 [MH]+.

Example 124a 6-(4-Aminopiperidin-1-yl)2-{2-[3-(pyrid-2-yl)isoxazol-5-yl]pyrrolidin-1-yl}-4-(5-methyl-1H-pyrazol-3-ylamino)pyrimidine 6-(4-(N-tert-Butoxycarbonylamino)piperidin-1-yl)-2-{2-[3-(pyrid-2-yl)isoxazol-5-yl]pyrrolidin-1-yl}-4-(5-methyl-1H-pyrazol-3-ylamino)pyrimidine (Example 124) (120 mg, 0.20 mmol) was stirred in DCM (10 ml) and trifluoroacetic acid (2 ml) was added and the mixture stirred at room temperature for 3 hours. The mixture was concentrated by evaporation and the residue dissolved in methanol (10 ml) and passed down a 20 g SCX-2 ion exchange column, eluting with methanol to elute impurities and then 2M methanolic ammonia to elute the product. The solvent was removed by evaporation to give the title compound (79 mg, 81%) as a cream powder.

NMR (DMSO-$d_6$+$d_4$-acetic acid at 100° C.): 1.35 (m, 1H), 1.45 (m, 1H), 1.90 (m, 2H), 2.00-2.10 (m, 3H), 2.15 (s, 3H), 2.35 (m, 1H), 2.82 (m, 2H), 3.20 (m, 1H), 3.65-3.80 (m, 2H), 4.10 (t, 2H), 5.35 (d, 1H), 6.3 (s, 1H), 7.40 (m, 1H), 7.85 (t, 1H), 7.95 (d, 1H), 8.60 (d, 1H); m/z 487 [MH]+.

Examples 125 to 132

Examples 125 to 132 were prepared by an analogous method to that described for Example 124.

Example 125

6-piperazin-1-yl-2-{2-[3-(pyrid-2-yl)isoxazol-5-yl]pyrrolidin-1-yl}-4-(5-methyl-1H-pyrazol-3-ylamino)pyrimidine Starting materials: 6-chloro-2-{2-[3-(pyrid-2-yl)isoxazol-5-yl]pyrrolidin-1-yl}-4-(5-methyl-1H-pyrazol-3-ylamino)pyrimidine (Example 17) and piperazine. Yield: 204 mg, 73% as a white powder.

NMR (DMSO-$d_6$+$d_4$-acetic acid at 100° C.): 2.00-2.15 (m, 3H), 2.20 (s, 3H), 2.35 (m, 1H), 3.00-3.15 (m, 5H), 3.60-3.80 (m, 6H), 5.40 (d, 1H), 5.50 (s, 1H), 6.00 (s, 1H), 6.70 (s, 1H), 7.40 (t, 1H), 7.85 (t, 1H), 7.95 (d, 1H), 8.65 (d, 1H); m/z 473 [MH]+.

Example 126

S-6-{4-[2-(2-Hydroxyethoxy)ethyl]piperazin-1-yl}-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine Example 96) and 2-[2-(hydroxyethoxy)ethyl]piperazine. Yield: 142 mg, 79% as a pale yellow solid.

NMR (DMSO-$d_6$+$d_4$-acetic acid at 100° C.): 2.00-2.15 (m, 3H), 2.15 (s, 3H), 2.35 (m, 1H), 2.70-2.90 (m, 6H), 3.45 (m, 2H), 3.35 (m, 6H), 3.65 (t, 2H), 3.68 (m, 1H), 3.75 (m, 1H), 5.35 (d, 1H), 5.95 (s, 1H), 6.65 (s, 1H), 7.38 (m, 1H), 7.85 (t, 1H), 7.95 (d, 1H), 8.65 (d, 1H); m/z 561 [MH]+.

Example 127

S-6-(1-Formyl-piperazin-4-yl)-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and 1-formylpiperazine. Yield: 55 mg, 31% as a pale yellow solid.

NMR (DMSO-$d_6$+$d_4$-acetic acid at 100° C.): 2.00-2.15 (m, 3H), 2.15 (s, 3H), 2.35 (m, 1H), 3.30-3.50 (m, 8H), 3.70 (m, 1H), 3.77 (m, 1H), 5.37 (d, 1H), 5.55 (s, 1H), 6.67 (s, 1H), 7.38 (t, 1H), 7.33 (t, 1H), 7.83 (t, 1H), 7.90 (d, 1H), 8.00 (s, 1H), 8.60 (d, 1H); m/z 501 [MH]+.

Example 128 was also isolated from the HLPC purification of Example 127:—

Example 128

S-6-piperazin-1-yl-2-{2-[3-(pyrid-2-yl)isoxazol-5-yl]pyrrolidin-1-yl}-4-(5-methyl-1H-pyrazol-3-ylamino)pyrimidine Yield: 64 mg, 38% as a pale yellow solid.

NMR (DMSO-$d_6$+$d_4$-acetic acid at 100° C.): 2.00-2.15 (m, 3H), 2.15 (s, 3H), 2.35 (m, 1H), 3.05 (m, 4H), 3.60 (m, 4H), 3.65-3.80 (m, 2H), 5.35 (d, 1H), 5.95 (s, 1H), 7.40 (m, 1H), 7.85 (t, 1H), 7.93 (d, 1H), 8.60 (d, 1H); m/z 473 [MH]+.

Example 129

S-6-(4-Isopropylpiperazin-1yl)-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5'-yl]pyrrolidin-1-yl}-4-(5-methyl-1H-pyrazol-3-ylamino)pyrimidine (Example 96) and 1-isopropylpiperazine. Yield: 94 mg, 52% as a cream powder.

NMR (DMSO-$d_6$+$d_4$-acetic acid at 100° C.): 1.05 (t, 6H), 2.00-2.15 (m, 3H), 2.20 (s, 3H), 2.35 (m, 1H), 2.65 (m, 4H), 3.00 (m, 1H), 3.50 (m, 4H), 3.60-3.80 (m, 2H), 5.45 (d, 1H), 5.95 (s, 1H), 6.65 (s, 1H), 7.40 (t, 1H), 7.85 (t, 1H), 8.90 (d, 1H), 8.60 (d, 1H); m/z 515 [MH]+.

Example 130

S-6-[(4-(2-Hydroxyethyl)piperazin-1-yl)]-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and 1-(2-hydroxyethyl)piperazine. Yield: 110 mg, 61% as a cream powder.

NMR (DMSO-$d_6$+$d_4$-acetic acid at 100° C.): 2.00-2.15 (m, 3H), 2.20 (s, 3H), 2.35 (m, 1H), 2.80-2.95 (m, 6H), 3.55 (t, 2H), 3.65 (t, 2H), 3.65-3.80 (m, 2H), 5.45 (d, 1H), 5.55 (s, 1H), 5.95 (s, 1H), 6.65 (s, 1H), 7.50 (t, 1H), 7.85 (t, 1H), 7.90 (d, 1H), 8.60 (d, 1H); m/z 517 [MH]+.

Example 131

S-6-[(3R)-3-Hydroxypyrrolidin-1-yl]-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine Example 96) and (3R)-3-hydroxypyrrolidine. Yield: 92 mg, 55% as purple powder.

NMR (DMSO-$d_6$+$d_4$-acetic acid at 100° C.) 1.75 (m, 1H), 1.95 (m, 1H), 2.00-2.15 (m, 3H), 2.20 (s, 3H), 2.35 (m, 1H), 3.25-3.45 (m, 4H), 3.65 (m, 1H), 3.75 (m, 1H), 4.30 (m, 1H), 5.40 (d, 1H), 5.55 (s, 1H), 6.70 (s, 1H), 7.35 (t, 1H), 7.80 (t, 1H), 7.90 (d, 1H), 8.60 (d, 1H); m/z 474 [MH]+.

Example 132

S-6-[(3R)-3-Dimethylamino-pyrrolidin-1-yl]-2-{2-[3-(pyrid-2-yl)isoxazol-5-yl]pyrrolidin-1-yl}-4-(5-methyl-1H-pyrazol-3-ylamino)pyrimidine

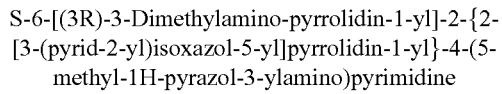

Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and (3R)-3-(dimethylamino)pyrrolidine. Yield: 128 mg, 73% as a brown powder.

NMR (DMSO-$d_6$+$d_4$-acetic acid at 100° C.): 1.75 (m, 1H), 2.00-2.15 (m, 4H), 2.18 (s, 3H), 2.22 (s, 6H), 2.35 (m, 1H), 2.77 (m, 1H), 3.15 (t, 1H), 3.27 (q, 1H), 3.40-3.50 (m, 2H), 3.75 (m, 2H), 5.40 (d, 1H), 5.50 (s, 1H), 5.95 (s, 1H), 6.20 (s, 1H), 7.45 (t, 1H), 7.90-8.00 (m, 1H), 8.65 (d, 1H); m/z 501 [MH]+.

Example 133

S-6-(4-Tetrahydropyranylamino)-2-{2-[3-(pyrid-2-yl)isoxazol-5-yl]pyrrolidin-1-yl}-4-(5-methyl-1H-pyrazol-3-ylamino)pyrimidine

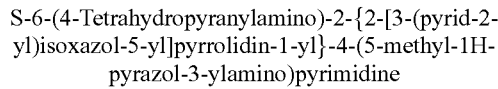

S-6-Chloro-2-{2-[3-(pyrid-2-yl)isoxazol-5-yl]pyrrolidin-1-yl}-4-(5-methyl-1H-pyrazol-3-ylamino)pyrimidine (Example 96) (150 mg, 0.35 mmol) was added to 4-aminotetrahydropyran (4 ml) and heated at 150° C. in a sealed vessel under microwave irradiation for 1 hour. The crude reaction mixture was purified by reverse phase HPLC using a C18 column eluting with water/acetonitrile/TFA (95:5:0.2 decreasing in polarity to 0:100:0.2). The product containing fractions passed down a 20 g SCX-2 column, eluting with methanol and then eluting the product with 2N methanolic ammonia. The solvent was removed by evaporation to give the title compound (52 mg, 30%) as a pale brown powder.

NMR (DMSO-$d_6$+$d_4$-acetic acid at 100° C.): 1.15 (m, 1H), 1.45 (m, 1H), 1.55 (m, 1H), 1.80 (m, 1H), 2.00-2.10 (m, 3H) 2.15 (s, 3H), 2.35 (m, 1H), 3.25 (t, 1H), 3.35 (m, 1H), 3.65 (m, 2H), 3.70-3.85 (m, 3H), 5.35 (d, 1H), 5.85 (s, 1H), 6.68 (s, 1H), 5.40 (t, 1H), 7.85 (t, 1H), 7.90 (d, 1H), 8.60 (d, 1H); m/z 488 [MH]+.

Example 134 to 139

Examples 134 to 139 were prepared by an analogous method to that described for Example 133.

Example 134

S-6-Morpholino-2-{2-[3-(pyrid-2-yl)isoxazol-5-yl]pyrrolidin-1-yl}-4-(5-methyl-1H-pyrazol-3-ylamino)pyrimidine

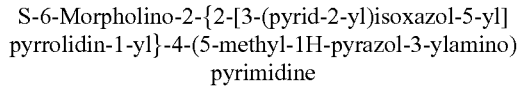

Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and morpholine. Yield: 119 mg, 71% as pale pink powder NMR (DMSO-$d_6$+$d_4$-acetic acid at 100° C.): 2.00-2.15 (m, 3H), 2.20 (s, 3H), 2.35 (m, 1H), 3.35 (m, 4H), 3.55 (m, 4H), 3.60-3.80 (m, 2H), 5.37 (d, 1H), 5.55 (s, 1H), 6.65 (s, 1H), 7.40 (m, 1H), 8.85 (t, 1H), 8.90 (d, 1H), 8.60 (d, 1H); m/z 474 [MH]+.

Example 135

S-6-(2-Methoxyethyl)amino-2-{2-[3-(pyrid-2-yl)isoxazol-5-yl]pyrrolidin-1-yl}-4-(5-methyl-1H-pyrazol-3-ylamino)pyrimidine

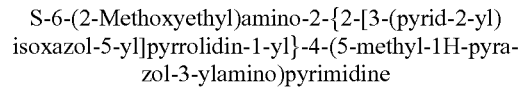

Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and 2-methoxyethylamine. Yield: 85 mg, 53% as a pale yellow powder.

NMR (DMSO-$d_6$+$d_4$-acetic acid at 100° C.): 2.00-2.15 (m, 3H), 2.20 (s, 3H), 2.35 (m, 1H), 3.20 (s, 3H), 3.20-3.40 (m, 4H), 3.60-3.80 (m, 2H), 5.40 (d, 1H), 6.68 (s, 1H), 7.40 (dd, 1H), 7.85 (t, 1H), 7.90 (d, 1H), 8.60 (d, 1H); m/z 462 [MH]+.

Example 136

S-6-[(N-2-Methoxyethyl)-N-methylamino]-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and N-(2-methoxyethyl)methylamine. Yield: 110 mg, 66% as a cream powder NMR (DMSO-$d_6$+$d_4$-acetic acid at 100° C.): 2.00-2.15 (m, 3H), 2.20 (s, 3H), 2.35 (m, 1H), 2.60-2.75 (m, 5H), 3.45 (t, 3H), 3.55 (t, 2H), 3.60-3.80 (m, 2H), 5.45 (d, 1H), 5.60 (s, 1H), 5.95 (s, 1H), 6.65 (s, 1H), 7.40 (t, 1H), 7.85 (t, 1H), 7.90 (d, 1H), 8.60 (d, 1H); m/z 476 [MH]+.

Example 137

S-6-((2R)-2-Hydroxyprop-1-ylamino)-2-{2-[3-(pyrid-2-yl)isoxazol-5-yl]pyrrolidin-1-yl}-4-(5-methyl-1H-pyrazol-3-ylamino)pyrimidine

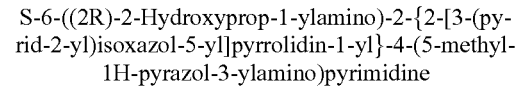

Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and (2R)-2-hydroxyprop-1-ylamine. Yield: 52 mg, 32% as a brown powder.

NMR (DMSO-$d_6$+$d_4$-acetic acid at 100° C.): 1.10 (d, 3H), 2.00-2.15 (m, 3H), 2.20 (s, 3H), 2.35 (m, 1H), 3.25-3.40 (m, 2H), 3.65 (m, 1H), 3.65-3.85 (m, 2H), 5.40 (d, 1H), 5.55 (s, 1H), 6.70 (s, 1H), 7.40 (t, 1H), 8.45 (t, 1H), 7.90 (d, 1H), 8.60 (d, 1H); m/z 462 [M]+.

Example 138

S-6-[N-(2-Hydroxyethyl)-N-ethylamino]-2-{2-[3-(pyrid-2-yl)isoxazol-5-yl]pyrrolidin-1-yl}-4-(5-methyl-1H-pyrazol-3-ylamino)pyrimidine

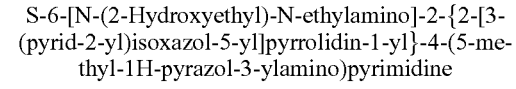

Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and N-(2-hydroxyethyl)ethylamine.

Yield: 113 mg, 70% as a yellow powder

NMR (DMSO-$d_6$+$d_4$-acetic acid at 100° C.): 1.05 (t, 2H), 2.00-2.15 (m, 3H), 2.20 (s, 3H), 2.35 (m, 1H), 3.30 (m, 4H), 3.55 (m, 2H), 3.67 (m, 1H), 3.77 (m, 1H), 5.40 (d, 1H), 5.55 (s, 1H), 6.70 (s, 1H0, 7.40 (t, 1H), 7.85 (t, 1H), 7.90 (d, 1H), 8.60 (d, 1H); m/z 476 [MH]+.

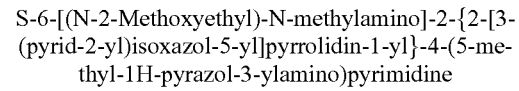

Example 139

S-6-Dimethylamino-2-{2-[3-(pyrid-2-yl)isoxazol-5-yl]pyrrolidin-1-yl}-4-(5-methyl-1H-pyrazol-3-ylamino)pyrimidine Starting materials: S-6-chloro-2-{2-[3-(pyrid-2-yl)isoxazol-5-yl]pyrrolidin-1-yl}-4-(5-methyl-1H-pyrazol-3-ylamino)pyrimidine (Example 96) and dimethylamine. Yield: 86 mg, 57% as a brown powder NMR (DMSO-$d_6$+$d_4$-acetic acid at 100° C.): 2.00-2.15 (m, 3H), 2.15 (s, 3H), 2.35 (m, 1H), 2.90 (s, 6H), 3.70 (m, 1H), 3.75 (m, 1H); 5.40 (d, 1H), 5.55 (s, 1H), 5.90 (s, 1H), 6.65 (s, 1H), 7.40 (t, 1H), 7.85 (t, 1H), 7.90 (d, 1H), 8.60 (d, 1H); m/z 432 [MH]+.

Example 140

S-6-Methylamino-2-{2-[3-(pyrid-2-yl)isoxazol-5-yl]pyrrolidin-1-yl}-4-(5-methyl-1H-pyrazol-3-ylamino)pyrimidine S-6-Chloro-2-{2-[3-(pyrid-2-yl)isoxazol-5-yl]pyrrolidin-1-yl}-4-(5-methyl-1H-pyrazol-3-ylamino)pyrimidine (Example 96) (150 mg, 0.35 mmol) was added to 2M methylamine in methanol (4 ml) and heated at 120° C. in a sealed vessel under microwave radiation for 90 minutes. The mixture was concentrated by evaporation and the residue purified by reverse phase HPLC using a C18 column eluting with water/acetonitrile/TFA (95:5:0.2 decreasing in polarity to 0:100:0.2). The product containing fractions were passed down a 20 g SCX-2 column, eluting with methanol then eluting the product with 2N ethanolic ammonia. The solvent was removed by evaporation to give the title compound 47 mg, 32%) as a white powder.

NMR (DMSO-$d_6$+$d_4$-acetic acid at 100° C.): 2.00-2.15 (m, 3H), 2.15 (s, 3H), 2.35 (m, 1H), 2.70 (s, 3H), 3.65-3.75 (m, 2H), 5.45 (d, 1H), 5.85 (s, 1H), 6.65 (s, 1H), 7.40 (m, 1H), 8.85 (t, 1H), 8.90 (d, 1H), 8.65 (s, 1H); m/z 418 [MH]+.

Example 141

S-6-Chloro-2-{2-[3-(pyrazin-2-yl)isoxazol-5-yl]pyrrolidin-1-yl}-4-(5-methyl-1H-pyrazol-3-ylamino)pyrimidine A mixture of S-2-[3-(2-pyrazinyl)isoxazol-5-yl]pyrrolidine (Method 55) (166 mg, 0.77 mmol), 2,6-dichloro-4-(5-methyl-1H-pyrazol-3-ylamino)pyrimidine (Method 29) (170 mg, 0.70) and N,N-diisopropylethylamine (134 μl, 0.77 mmol) in xylene was stirred and heated at 70° C. for 2 days. A second equivalent of N,N-diisopropylethylamine (134 μl, 0.77 mmol) was added and the mixture heated for a further 2 days. The mixture was concentrated by evaporation and the residue was purified by column chromatography on silica gel eluting with hexane/EtOAc (100:0 increasing in polarity to 0:100) to give the title compound (109 mg, 37%) as a cream powder.

NMR (DMSO-$d_6$+$d_4$-acetic acid at 100° C.): 2.00-2.15 (m, 3H), 2.15 (s, 3H), 2.40 (m, 1H), 3.65 (m, 1H), 3.75 (m, 1H), 5.43 (d, 1H), 5.60 (s, 1H), 6.00 (s, 1H), 6.35 (s, 1H), 6.75 (s, 1H), 8.65 (m, 2H), 9.10 (s, 1H); m/z 424 [MH]+.

Example 142

6-Mopholino-2-{2-[3-(pyrazin-2-yl)isoxazol-5-yl]pyrrolidin-1-yl}-4-(5-methyl-1H-pyrazol-3-ylamino)pyrimidine S-6-Chloro-2-{2-[3-(pyrazin-2-yl)isoxazol-5-yl]pyrrolidin-1-yl}-4-(5-methyl-1H-pyrazol-3-ylamino)pyrimidine (Example 141) (94 mg, 0.22 mmol) was added to morpholine (4 ml) and heated at 150° C. in a sealed vessel under microwave irradiation for 30 minutes. The reaction mixture was concentrated by evaporation and purified by column chromatography on silica gel eluting with DCM/2M methanolic ammonia (100:0 increasing in polarity to 95:5) to give the title compound (75 mg, 72%) as a pale yellow powder.

NMR (DMSO-$d_6$+$d_4$-acetic acid at 100° C.): 2.00-2.15 (m, 3H), 2.15 (s, 3H), 2.35 (m, 1H), 3.35 (m, 4H), 3.55 (m, 4H), 3.65-3.80 (m, 2H), 5.37 (d, 1H), 5.55 (s, 1H), 5.80 (s, 1H), 6.70 (s, 1H), 8.65 (m, 2H), 9.10 (s, 1H); m/z 475 [MH]+.

Example 143

6-Chloro-2-{2-[3-(pyrid-2-yl)isoxazol-5-yl]pyrrolidin-1-yl}-4-(5-cyclopropyl-1H-pyrazol-3-ylamino)pyrimidine S-2-(3-(2-pyridyl)isoxazol-5-yl)pyrrolidine (Method 42) (262 mg, 1.22 mmol) was stirred in n-butanol (40 ml) and 2,6-dichloro-4-(5-cyclopropyl-1H-pyrazol-3-ylamino)pyrimidine (Method 57) (300 mg, 1.1 mmol) was added followed by N,N-diisopropylamine (233 μl, 1.33) and the mixture stirred at 60° C. for 2 days. The mixture was concentrated by evaporation and saturated aqueous sodium bicarbonate solution (50 ml) was added and the mixture extracted with DCM (3×25 ml). The organic extracts were combined, washed with water (50 ml) and brine (50 ml), dried (MgSO$_4$) and the solvent removed by evaporation. The residue was purified by column chromatography on silica gel eluting with hexane/EtOAc (50:50 increasing in polarity to 0:100) to give the title compound (280 mg, 56%) as a white solid.

NMR (DMSO-$d_6$+$d_4$-acetic acid at 100° C.): 0.65 (m, 2H), 0.85 (m, 2H), 1.85 (m, 1H), 2.05 (m, 2H), 2.15 (m, 1H), 2.35 (m, 1H), 3.65 (m, 1H), 3.75 (m, 1H), 5.40 (d, 1H), 5.55 (s, 1H), 5.90 (s, 1H0, 6.35 (s, 1M), 6.65 (s, 1H), 7.40 (m, 1H), 7.85 (t, 1H), 7.90 (d, 1H), 8.60 (d, 1H); m/z 449 [MH]+.

Example 144

6-(2-Hydroxyethoxy)-2-{2-[3-(pyrid-2-yl)isoxazol-5-yl]pyrrolidin-1-yl}-4-(5-cyclopropyl-1H-pyrazol-3-ylamino)pyrimidine Sodium hydride (60% dispersion in oil, 71 mg, 1.78 mmol) was added to ethylene glycol (4 ml) and the mixture stirred for 5 minutes. S-6-Chloro-2-{2-[3-(pyrid-2-yl)isoxazol-5-yl]pyrrolidin-1-yl}-4-(5-cyclopropyl-1H-pyrazol-3-ylamino)pyrimidine (Example 143) (160 mg, 0.35 mmol) was added and the mixture heated at 150° C. in a sealed vessel under microwave irradiation for 45 minutes. The crude mixture was purified by reverse phase HPLC using a C18 column eluting with water/acetonitrile/TFA (95:5:0.2 decreasing in polarity to 0:100:0.2). The product containing fractions were poured onto a 20 g SCX-2 column, eluting with methanol then with 2N methanolic ammonia to elute the product. The solvent was removed by evaporation to give the title compound (23 mg, 14%) as a pale yellow powder.

NMR (DMSO-d$_6$+d$_4$-acetic acid at 100° C.): 0.65 (m, 2H), 0.85 (m, 2H), 1.85 (m, 1H), 2.00-2.15 (m, 3H), 2.35 (m, 1H), 3.55-3.80 (m, 4H), 4.15 (m, 2H), 5.40 (d, 1H), 5.55 (s, 1H), 5.75 (s, 1H), 5.90 (s, 1H), 6.67 (s, 1H), 7.45 (m, 1H), 7.85 (t, 1H), 7.95 (d, 1H), 8.65 (d, 1H). m/z 475 [MH]+.

Example 145

6-[4-(tert-Butoxycarbonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine A mixture of 6-chloro-4-(5-methyl-1H-pyrazol-3-ylamino)-2-[2-{3-(pyrid-2-yl)isoxazol-5-yl}pyrrolidin-1-yl]pyrimidine (Example 17) (250 mg, 0.6 mmol) and N-(tert-butoxycarbonyl)piperazine (222 mg, 6.0 mmol) in 1,4-dioxane (4 ml) was heated at 160° C. in a sealed vessel under microwave irradiation for 90 minutes. The crude reaction mixture was purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation to afford the desired product (85 mg, 25%) as a white solid.

NMR (DMSO-d$_6$ at 100° C.): 1.43 (s, 9H), 2.09 (m, 3H), 2.19 (s, 3H), 2.37 (m, 1H), 3.34 (m, 4H), 3.40 (m, 4H), 3.73 (m, 2H), 5.39 (d, 1H), 5.77 (br s, 1H), 5.97 (br s, 1H), 6.68 (s, 1H), 7.48 (dd, 1H), 7.92 (m, 2H), 8.32 (br s, 1H), 8.65 (d, 1H), 11.41 (br s, 1H); m/z 573 [MH]+.

Example 146

6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine The title compound was made by an analogous method to that described in Example 145 using 6-chloro-4-(5-methyl-1H-pyrazol-3-ylamino)-2-[2-{3-(pyrid-2-yl)isoxazol-5-yl}pyrrolidin-1-yl]pyrimidine (Example 17) and 4-acetylpiperazine. Yield: 182 mg, 60%.

NMR (DMSO-d$_6$ at 100° C.): 1.94 (s, 3H), 2.09 (m, 3H), 2.19 (s, 3H), 2.37 (m, 1H), 3.44 (m, 8H), 3.73 (m, 2H), 5.39 (d, 1H), 5.77 (br s, 1H), 5.97 (br s, 1H), 6.68 (s, 1H), 7.46 (dd, 1H), 7.92 (m, 2H), 8.30 (br s, 1H), 8.65 (d, 1H), 11.38 (br s, 1H); m/z 514 [MH]+.

Example 147

6-[2-(tert-Butoxycarbonyl)-2,7-diazaspiro[3.5]nonan-7-yl]-4-(5-methyl-1H-pyrazol-3-ylamino)-2-[2-{3-(pyrid-2-yl)isoxazol-5-yl}pyrrolidin-1-yl]pyrimidine A mixture of 6-chloro-N-(3-methyl-1H-pyrazol-5-yl)-2-[2-(3-pyridin-2-ylisoxazol-5-yl)pyrrolidin-1-yl]pyrimidin-4-amine (Example 17) (300 mg, 0.7 mmol) and 2-(tert-butoxycarbonyl)-2,7-diazaspiro[3.5]nonane (949 mg, 4.2 mmol) in 1,4-dioxane (8 ml) was heated at 160° C. in a sealed vessel under microwave irradiation for 120 minutes. The mixture was allowed to cool and the volatiles removed by evaporation. The residue was purified by column chromatography on silica gel eluting with DCM/methanol/aqueous ammonia (100:0:0 increasing in polarity to 90:10:1) to give the product (235 mg, 55%) as a mauve solid.

NMR (DMSO-d$_6$ at 100° C.): 1.42 (s, 9H), 1.59 (t, 4H), 2.07 (m, 3H), 2.16 (s, 3H), 2.37 (m, 1H), 3.37 (m, 4H), 3.52 (m, 4H), 3.71(m, 2H), 5.39 (d, 1H), 5.81 (br s, 1H), 5.94 (br s, 1H), 6.63 (s, 1H), 7.45 (dd, 1H), 7.92 (m, 2H), 8.24 (br s, 1H), 8.65 (d, 1H); m/z 614 [MH]+.

Example 148

6-(2,7-Diazaspiro[3.5]nonan-7-yl)-4-(5-methyl-1H-pyrazol-3-ylamino)-2-[2-{3-(pyrid-2-yl)isoxazol-5-yl}pyrrolidin-1-yl]pyrimidine A mixture of 6-[2-(tert-butoxycarbonyl)-2,7-diazaspiro[3.5]nonan-7-yl]-4-(5-methyl-1H-pyrazol-3-ylamino)-2-[2-{3-(pyrid-2-yl)isoxazol-5-yl}pyrrolidin-1-yl]pyrimidine (Example 147) (110 mg, 0.19 mmol) and TFA (2 ml) were stirred at ambient temperature for 60 minutes. The volatiles were removed by evaporation, the residue dissolved in DCM poured onto an isolute SCX-2 ion exchange column. The column was eluted with methanol to elute any neutrals, followed by 7M methanolic ammonia to elute the product. The solvent was removed by evaporation to afford the desired product as a yellow solid. (66 mg, 68%).

NMR (DMSO-d$_6$ at 100° C.): 1.51 (t, 4H), 2.07 (m, 3H), 2.16 (s, 3H), 2.37 (m, 1H), 3.22 (m, 4H), 3.36 (m, 4H), 3.71(m, 2H), 5.39 (d, 1H), 5.77 (br s, 1H), 5.94 (br s, 1H), 6.63 (s, 1H), 7.45 (dd, 1H), 7.92 (m, 2H), 8.24 (br s, 1H), 8.65 (d, 1H); m/z 513 [MH]+.

Example 149

S-6-[4-(2-Aminoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine A mixture of S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (100 mg, 0.24 mmol), 1-(2-aminoethyl)piperazine (186 mg, 1.4 mmol) in 1,4-dioxane (4 ml) was heated at 150° C. in a sealed vessel under microwave irradiation for 120 minutes. The crude reaction mixture was purified by reverse phase HPLC using a C18 column eluting with water/acetonitrile/TEA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation and the residue triturated diethyl ether and the product collected by filtration to give the title compound (68 mg, 55%) as a white solid.

NMR (DMSO-d$_6$ at 100° C.): 2.05 (m, 3H), 2.19 (s, 3H), 2.31 (m, 1H), 2.38 (m, 6H), 2.53 (m, 2H), 3.40 (t, 4H), 3.71 (m, 2H), 5.39 (d, 1H), 5.77 (br s, 1H), 5.95 (br s, 1H), 6.66 (s, 1H), 7.44 (dd, 1H), 7.92 (m, 2H), 8.30 (br s, 1H), 8.65 (d, 1H), 11.38 (br s, 1H); m/z 516 [MH]+.

Examples 150 to 159

Examples 150 to 159 were prepared by an analogous method to that described in Example 149.

Example 150

S-6-[4-(3-Hydroxypropyl)piperazin-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 1-(3-hydroxypropyl)piperazine. Yield: 84 mg, 66%.

NMR (DMSO-$d_6$ at 100° C.): 1.50 (m, 2H), 2.09 (m, 3H), 2.19 (s, 3H), 2.36 (m, 7H), 3.42 (t, 4H), 3.49 (t, 2H), 3.73 (m, 2H), 5.39 (d, 1H), 5.77 (br s, 1H), 5.95 (br s, 1H), 6.68 (s, 1H), 7.44 (dd, 1H), 7.94 (m, 2H), 8.30 (br s, 1H), 8.68 (d, 1H), 11.45 (br s, 1H); m/z 531 [MH]+.

Example 151

S-6-[4-(2-Cyanoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 1-(2-cyanoethyl)piperazine. Yield: 69 mg, 36%.

NMR (DMSO-$d_6$ at 100° C.): 2.08 (m, 3H), 2.19 (s, 3H), 2.39 (m, 1H), 2.42 (t, 4H), 2.59 (s, 4H), 3.42 (t, 4H), 3.71 (m, 2H), 5.39 (d, 1H), 5.77 (br s, 1H), 5.95 (br s, 1H), 6.68 (s, 1H), 7.44 (dd, 1H), 7.94 (m, 2H), 8.28 (br s, 1H), 8.68 (d, 1H), 11.40 (br s, 1H); m/z 527 [MH]+.

Example 152

S-6-[4-(2-Methoxyethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 1-(2-methoxyethyl)piperazine. Yield: 84 mg, 44%.

NMR (DMSO-$d_6$ at 100° C.): 2.08 (m, 3H), 2.19 (s, 3H), 2.36 (m, 7H), 3.25 (s, 3H), 3.43 (t, 4H), 3.46 (t, 2H), 3.71 (m, 2H), 5.39 (d, 1H), 5.77 (br s, 1H), 5.95 (br s, 1H), 6.68 (s, 1H), 7.48 (dd, 1H), 7.94 (m, 2H), 8.28 (br s, 1H), 8.68 (d, 1H), 11.40 (br s, 1H); m/z 532 [MH]+.

Example 153

S-6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 1-acetylpiperazine. Yield: 66 mg, 36%.

NMR (DMSO-$d_6$ at 100° C.): 2.01 (s, 3H), 2.08 (m, 3H), 2.19 (s, 3H), 2.36 (m, 1H), 3.48 (m, 8H), 3.71 (m, 2H), 5.39 (d, 1H), 5.77 (br s, 1H), 5.95 (br s, 1H), 6.68 (s, 1H), 7.48 (dd, 1H), 7.94 (m, 2H), 8.28 (br s, 1H), 8.68 (d, 1H), 11.40 (br s, 1H); m/z 515 [MH]+.

Example 154

S-6-[4-(Ethylsulphonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 1-(ethylsulphonyl)piperazine. Yield: 122 mg, 60%.

NMR (DMSO-$d_6$+$d_4$-acetic acid at 100° C.): 0.96 (t, 3H), 1.90 (m, 3H), 1.99 (s, 3H), 2.22 (m, 1H), 2.73 (m, 2H), 2.96 (m, 4H), 3.33 (m, 4H), 3.55 (m, 2H), 5.17 (d, 1H), 6.48 (s, 1H), 7.21 (dd, 1H), 7.72 (m, 2H), 8.44 (d, 1H); m/z 566 [MH]+.

Example 155

S-6-[2-(2-Hydroxyethoxy)ethylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 2-(2-hydroxyethoxy)ethylamine. Yield: 84 mg, 48%.

NMR (DMSO-$d_6$+$d_4$-acetic acid at 100° C.): 2.06 (m, 3H), 2.16 (s, 3H), 2.33 (m, 1H), 3.40 (m, 8H), 3.71 (m, 2H), 5.40 (d, 1H), 6.67 (s, 1H), 7.38 (dd, 1H), 7.89 (m, 2H), 8.62 (d, 1H); m/z 496 [MH]+.

Example 156

S-6-[2-(Acetoamido)ethylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 2-(acetoamido)ethylamine. Yield: 39 mg, 22%.

NMR (DMSO-$d_6$ at 100° C.): 1.80 (s, 3H), 2.07 (m, 3H), 2.17 (s, 3H), 2.36 (m, 1H), 3.19 (m, 4H), 3.71 (m, 2H), 5.42 (d, 1H), 5.52 (br s, 1H), 5.87 (br s, 1H), 6.06 (br s, 1H), 6.68 (s, 1H), 7.49 (br s, 1H), 7.43 (dd, 1H), 7.94 (m, 2H), 8.12 (br s, 1H), 8.66 (d, 1H), 11.40 (br s, 1H); m/z 489 [MH]+.

Example 157 was also isolated from the same reaction by the HPLC purification:—

Example 157

S-6-[2-Aminoethylamino]-4-(5-methyl-1H-pyrazol-3-ylamino)-2-[2-{3-(pyrid-2-yl)isoxazol-5-yl}pyrrolidin-1-yl]pyrimidine Yield: 15 mg, 9%.

NMR (DMSO-$d_6$ at 100° C.): 2.10 (m, 3H), 2.17 (s, 3H), 2.36 (m, 1H), 2.67 (t, 2H), 3.17 (m, 2H), 3.71 (m, 2H), 5.42 (d, 1H), 5.57 (br s, 1H), 5.90 (br s, 1H), 6.06 (br s, 1H), 6.68 (s, 1H), 7.48 (dd, 1H), 7.94 (m, 2H), 8.12 (br s, 1H), 8.68 (d, 1H); m/z 447 [MH]+.

Example 158

S-6-[4-Methylcyclohexylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 4-methylcyclohexylamine. Yield: 112 mg, 48%.

NMR (DMSO-$d_6$ at 100° C.): 0.84 (dd, 3H), 1.40 (m, 9H), 2.06 (m, 3H), 2.17 (s, 3H), 2.36 (m, 1H), 3.45 (m, 1H), 3.71 (m, 2H), 5.39 (m, 1H), 5.54 (br s, 1H), 5.82 (br s, 1H), 5.89 (br s, 1H), 6.63 (s, 1H), 7.42 (dd, 1H), 7.90 (m, 2H), 8.03 (br s, 1H), 8.64 (s, 1H), 11.41 (br s, 1H); m/z 500 [M]+.

Example 159

S-6-[4-Hydroxycyclohexylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 4-hydroxycyclohexylamine The title compound was made by an analogous method to Example 149 except that the reaction was heated for 6 hours at 180° C. Yield: 83 mg, 35%.

NMR (DMSO-$d_6$ at 100° C.): 1.16 (m, 4H), 1.81 (m, 4H), 2.06 (m, 3H), 2.17 (s, 3H), 2.36 (m, 1H), 3.38 (m, 1H), 3.50 (br s, 1H), 3.71 (m, 2H), 4.01 (d, 1H), 5.39 (d, 1H), 5.49 (br s, 1H), 5.82 (br s, 1H), 5.89 (br s, 1H), 6.63 (s, 1H), 7.42 (dd, 1H), 7.90 (m, 2H), 8.02 (br s, 1H), 8.64 (d, 1H), 11.35 (br s, 1H); m/z 502 [MH]+.

Example 160

S-6-[cis-3,4-Dihydroxypyrrolidin-1-yl]-4-(5-methyl-1H-pyrazol-3-ylamino)-2-[2-{3-(pyrid-2-yl)isoxazol-5-yl}pyrrolidin-1-yl]pyrimidine A mixture of S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (100 mg, 0.24 mmol), cis-3,3-dimethyl-2,4-dioxa-7-aza-bicyclo[3.3.0]octane (203 mg, 1.4 mmol) in 1,4-dioxane (3 ml) was heated at 150° C. in a sealed vessel under microwave irradiation for 120 minutes. The reaction mixture allowed to cool, the volatiles were removed by evaporation and the residue was purified by column chromatography on silica gel eluting with DCM/methanol/aqueous ammonia (100:0:0 increasing in polarity to 90:10:1). The purified product was dissolved in methanol (4 ml) and 2M hydrochloric acid (4 ml) and stirred at ambient temperature for 120 minutes. The crude reaction mixture was purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation, the residue triturated with ether and collected by filtration to give the desired product (22 mg, 19%) as a white solid.

NMR (DMSO-$d_6$ at 100° C.): 2.08 (m, 3H), 2.17 (s, 3H), 2.36 (m, 1H), 3.15 (m, 1H), 3.24 (m, 1H), 3.42 (m, 1H), 3.51 (m, 1H), 3.71 (m, 2H), 4.08 (s, 2H), 5.42 (d, 1H), 5.47 (br s, 1H), 5.90 (br s, 1H), 6.68 (s, 1H), 7.48 (dd, 1H), 7.94 (m, 2H), 8.38 (br s, 1H), 8.68 (d, 1H); m/z 491 [MH]+.

Example 161

S-6-Chloro-4-(5-methyl-1H-pyrazol-3-ylamino)-2-[2-{3-(pyrimid-2-yl)isoxazol-5-yl}pyrrolidin-1-yl]pyrimidine A mixture of 2,6-dichloro-4-(5-methyl-1H-pyrazol-3-ylamino)pyrimidine (Method 29) (134 mg, 0.55 mmol), S-2-[3-(pyrimid-2-yl)isoxazol-5-yl]pyrrolidine (Method 66) (130 mg, 0.6 mmol), N,N-diisopropylethylamine (78 mg, 0.6 mmol) and xylene (5 ml) was heated at 70° C. for 3 days. The crude reaction was passed through an isolute SCX-2 ion exchange column. The column was eluted with methanol to elute any neutrals, followed by 7M methanolic ammonia to elute the product. The solvent was removed by evaporation and residue was purified by column chromatography on silica gel eluting with EtOAc/hexane (0:100 increasingly in polarity to 100:0). The purified product triturated with ether and collected by filtration to give the title compound (110 mg, 47%) as a white solid.

NMR (DMSO-$d_6$ at 100° C.): 2.10 (m, 3H), 2.19 (s, 3H), 2.40 (m, 1H), 3.71 (m, 2H), 5.42 (d, 1H), 6.00 (s, 1H), 6.41(s, 1H), 6.73 (s, 1H), 7.52 (dd, 1H), 8.90 (d, 2H), 9.21 (s, 1H), 11.62 (br s, 1H); m/z 424 [MH]+.

Example 162

S-6-Chloro-4-(5-methyl-1H-pyrazol-3-ylamino)-2-[2-{3-(3-methoxypyrazin-2-yl)isoxazol-5-yl}pyrrolidin-1-yl]pyrimidine A mixture of 2,6-dichloro-4-(5-methyl-1H-pyrazol-3-ylamino)pyrimidine (Method 29) (162 mg, 0.66 mmol), S-2-[3-(2-methoxypyrazin-3-yl)isoxazol-5-yl]pyrrolidine (Method 68) (180 mg, 0.73 mmol), N,N-diisopropylethylamine (95 mg, 0.73 mmol) and 1-butanol (5 ml) was heated at 65° C. for 16 hours and then at 80° C. for 2 hours. The crude reaction mixture purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation, the residue triturated with ether and collected by filtration to give the title compound (117 mg, 39%) as a cream solid; m/z 454 [MH]+.

Example 163

S-6-Morpholino-4-(5-methyl-1H-pyrazol-3-ylamino)-2-[2-{3-(pyrimid-2-yl)isoxazol-5-yl}pyrrolidin-1-yl]pyrimidine A mixture S-6-chloro-4-(5-methyl-1H-pyrazol-3-ylamino)-2-[2-{3-(pyrimid-2-yl)isoxazol-5-yl}pyrrolidin-1-yl]pyrimidine (Example 161) (10 mg, 0.24 mmol) in morpholine (3 ml) was heated at 150° C. in a sealed vessel under microwave irradiation for 40 minutes. The crude reaction mixture was purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation and the residue triturated with ether to give the title compound (53 mg, 46%) as a white solid.

NMR (DMSO-d$_6$ at 100° C.): 2.10 (m, 3H), 2.17 (s, 3H), 2.36 (m, 1H), 3.44 (m, 4H), 3.60 (m, 4H), 3.71 (m, 2H), 5.42 (d, 1H), 5.57 (s, 1H), 5.90 (s, 1H), 6.68 (s, 1H), 7.52 (dd, 1H), 8.35 (br s, 1H), 8.90 (d, 2H), 11.40 (br s, 1H); m/z 476 [MH]+.

Example 164

S-6-Morpholino-4-(5-methyl-1H-pyrazol-3-ylamino)-2-[2-{3-(3-methoxypyrazin-2-yl)isoxazol-5-yl}pyrrolidin-1-yl]pyrimidine The title compound was made by an analogous method to that described in Example 163 starting from S-6-chloro-4-(5-methyl-1H-pyrazol-3-ylamino)-2-[2-{3-(3-methoxy-pyrazin-2-yl)isoxazol-5-yl}pyrrolidin-1-yl]pyrimidine (Example 162) and morpholine. Yield: 15 mg, 12%.

NMR (DMSO-d$_6$ at 100° C.): 2.07 (m, 3H), 2.17 (s, 3H), 2.36 (m, 1H), 3.47 (m, 4H), 3.60 (m, 4H), 3.71 (m, 2H), 4.01 (s, 3H), 5.42 (d, 1H), 5.75 (br s, 1H), 5.96 (br s, 1H), 6.66 (s, 1H), 8.31 (s, 2H), 11.40 (br s, 1H); m/z 506 [MH]+.

Example 165 was also isolated from the same reaction by the HPLC purification:—

Example 165

S-6-Morpholino-4-(5-methyl-1H-pyrazol-3-ylamino)-2-[2-{3-(3-hydroxypyrazin-2-yl)isoxazol-5-yl}pyrrolidin-1-yl]pyrimidine Yield: 32 mg, 26%.

NMR (DMSO-d$_6$ at 100° C.): 2.07 (m, 3H), 2.17 (s, 3H), 2.36 (m, 1H), 3.47 (m, 4H), 3.60 (m, 4H), 3.71 (m, 2H), 5.47 (d, 1H), 5.75 (s, 1H), 5.96 (s, 1H), 6.71 (s, 1H), 7.52 (m, 2H), 8.33 (s, 1H), 11.75 (br s, 1H); m/z 492 [MH]+.

Example 166

S-6-[4-Methylpiperazin-1-yl]-4-(5-methyl-1H-pyrazol-3-ylamino)-2-[2-{3-(pyrid-2-yl)isoxazol-5-yl}pyrrolidin-1-yl]pyrimidine A mixture of S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (150 mg, 0.36 mmol) in 1-methylpiperazine (3 ml) was heated at 150° C. in a sealed vessel under microwave irradiation for 40 minutes. The mixture was allowed to cool and was directly purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation, the residue triturated with hexane and collected by filtration to give the title compound (152 mg, 87%) as a white solid.

NMR (DMSO-d$_6$ at 100° C.): 2.08 (m, 3H), 2.16 (s, 3H), 2.38 (m, 1H), 3.34 (m, 4H), 3.60 (m, 4H), 3.71 (m, 2H), 5.39 (d, 1H), 5.74 (s, 1H), 5.95 (s, 1H), 6.68 (s, H), 7.50 (dd, 1H), 8.38 (br s, 1H), 8.92 (d, 2H); m/z 488 [MH]+.

Examples 167 to 171

Examples 167 to 171 were prepared by an analogous method to that described in Example 166.

Example 167

S-6-[Cyclobutylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and cyclobutylamine. Yield: 79 mg, 37%.

NMR (DMSO-d$_6$ at 100° C.): 1.87 (m, 6H), 2.06 (m, 3H), 2.17 (s, 3H), 2.36 (m, 1H), 3.71 (m, 2H), 4.14 (m, 1H), 5.39 (d, 1H), 5.49 (br s, 1H), 5.89 (br s, 1H), 6.22 (br s, 1H), 6.63 (s, 1H), 7.42 (dd, 1H), 7.90 (m, 2H), 8.12 (br s, 1H), 8.64 (d, 1H), 11.38 (br s, 1H); m/z 458 [MH]+.

Example 168

S-6-[3-Isopropoxyprop-1-ylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 3-isopropoxyprop-1-ylamine. Yield: 89 mg, 38%.

NMR (DMSO-d$_6$ at 100° C.): 1.04 (d, 6H), 1.65 (m, 2H), 2.06 (m, 3H), 2.17 (s, 3H), 2.36 (m, 1H), 3.18 (m, 2H), 3.35 (t, 2H), 3.49 (m, 1H), 3.70 (m, 2H), 5.39 (d, 1H), 5.54 (br s, 1H), 5.89 (br s, 1H), 5.99 (br s, 1H), 6.64 (s, 1H), 7.42 (dd, 1H), 7.90 (m, 2H), 8.02 (br s, 1H), 8.64 (d, 1H), 11.38 (br s, 1H); m/z 505 [MH]+.

Example 169

S-6-[2-Morpholin-4-yl)ethylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl 1H-pyrazol-3-ylamino)-2-[2-{3-(pyrid-2-yl)isoxazol-5-yl}pyrrolidin-1-yl]pyrimidine (Example 96) and 2-(morpholin-4-yl)ethylamine. The product was triturated with ether. Yield: 100 mg, 41%.

NMR (DMSO-d$_6$ at 100° C.): 2.06 (m, 3H), 2.17 (s, 3H), 2.36 (m, 5H), 2.41 (t, 2H), 3.26 (m, 2H), 3.54 (m, 4H), 3.70 (m, 2H), 5.40 (dd, 1H), 5.53 (br s, 1H), 5.91 (br s, 1H), 5.92 (br s, 1H), 6.64 (s, 1H), 7.42 (dd, 1H), 7.90 (m, 2H), 8.08 (br s, 1H), 8.64 (d, 1H); m/z 518 [MH]+.

Example 170

S-6-[2-(Dimethylamino)ethylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 2-(dimethylamino)ethylamine. Yield: 90 mg, 40%.

NMR (DMSO-d$_6$ at 100° C.): 2.06 (m, 3H), 2.12 (s, 6H), 2.17 (s, 3H), 2.36 (m, 3H), 3.26 (m, 2H), 3.70 (m, 2H), 5.43

(dd, 1H), 5.53 (br s, 1H), 5.91 (br s, 2H), 6.64 (s, 1H), 7.42 (dd, 1H), 7.90 (m, 2H), 8.08 (br s, 1H), 8.64 (d, 1H); m/z 476 [MH]+.

Example 171

S-6-[(2S)-2-Hydroxyprop-1-ylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and (2S)-2-Hydroxyprop-1-ylamine. Yield: 28 mg, 13%.

NMR (DMSO-$d_6$ at 100° C.): 1.06 (d, 3H), 2.06 (m, 3H), 2.17 (s, 3H), 2.36 (m, 1H), 3.08 (m, 1H), 3.18 (m, 1H), 3.70 (m, 3H), 4.27 (s, 1H), 5.39 (dd, 1H), 5.53 (br s, 1H), 5.90 (br s, 1H), 5.95 (br s, 1H), 6.64 (s, 1H), 7.42 (dd, 1H), 7.90 (m, 2H), 8.05 (br s, 1H), 8.64 (d, 1H), 11.39 (br s, 1H); m/z 463 [MH]+.

Example 172

S-6-[2-Methylprop-1-ylamino]-4-(5-methyl-1H-pyrazol-3-ylamino)-2-[2-{3-(pyrid-2-yl)isoxazol-5-yl}pyrrolidin-1-yl]pyrimidine A mixture of S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (200 mg, 0.47 mmol) and isobutylamine (2 ml) was heated at 150° C. in a sealed vessel under microwave irradiation for 30 minutes. The reaction was allowed to cool and poured into aqueous sodium bicarbonate solution. The resulting precipitate was collected by filtration, washed with water and dried under vacuum to give the title compound (170 mg, 79%) as an orange solid.

NMR (DMSO-$d_6$ at 100° C.): 0.85 (dd, 6H), 1.78 (m, 1H), 2.06 (m, 3H), 2.17 (s, 3H), 2.36 (m, 1H), 2.95 (m, 2H), 3.70 (m, 2H), 5.40 (d, 1H), 5.58 (br s, 1H), 5.89 (br s, 1H), 6.08 (br s, 1H), 6.64 (s, 1H), 7.42 (dd, 1H), 7.90 (m, 2H), 8.66 (d, 1H); m/z 460 [MH]+.

Examples 173 to 179

Examples 173 to 179 were prepared by an analogous method to that described in Example 172.

Example 173

S-6-[3-Methoxypropylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl]pyrimidine (Example 96) and 3-methoxypropylamine. Yield: 160 mg, 72%.

NMR (DMSO-$d_6$ at 100° C.): 1.68 (m, 2H), 2.06 (m, 3H), 2.17 (s, 3H), 2.36 (m, 1H), 3.18 (m, 2H), 3.20 (s, 3H), 3.33 (t, 2H), 3.70 (m, 2H), 5.39 (dd, 1H), 5.54 (s, 1H), 5.86 (s, 1H), 6.01 (br s, 1H), 6.64 (s, 1H), 7.42 (dd, 1H), 7.90 (m, 2H), 8.64 (dd, 1H); m/z 477 [MH]+.

Example 174

S-6-[4-Ethylpiperazin-1-yl]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl] pyrimidine (Example 96) and 1-ethylpiperazine. Yield: 200 mg, 85%.

NMR (DMSO-$d_6$ at 100° C.): 0.97 (t, 3H), 2.06 (m, 3H), 2.17 (s, 3H), 2.36 (m, 7H), 3.41 (m, 4H), 3.70 (m, 2H), 5.39 (dd, 1H), 5.75 (s, 1H), 5.94 (s, 1H), 6.64 (s, 1H), 7.42 (dd, 1H), 7.90 (m, 2H), 8.31 (br s, 1H), 8.64 (d, 1H); m/z 502 [MH]+.

Example 175

S-6-[3-Ethoxypropylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl] pyrimidine (Example 96) and 3-ethoxypropylamine. Yield: 105 mg, 46%.

NMR (DMSO-$d_6$ at 100° C.): 1.06 (t, 3H), 1.68 (m, 2H), 2.06 (m, 3H), 2.17 (s, 3H), 2.36 (m, 1H), 3.18 (m, 2H), 3.38 (m, 4H), 3.70 (m, 2H), 5.39 (dd, 1H), 5.53 (s, 1H), 5.88 (s, 1H), 6.01 (t, 1H), 6.64 (s, 1H), 7.42 (dd, 1H), 7.90 (m, 2H), 8.64 (d, 1H); m/z 491 [MH]+.

Example 176

S-6-[(2R)-Tetrahydrofuran-2-ylmethylamino]-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl-1H-pyrazol-3-ylamino)-2-[2-{3-(pyrid-2-yl)isoxazol-5-yl}pyrrolidin-1-yl] pyrimidine (Example 96) and (2R)-tetrahydrofuran-2-ylmethylamine. Yield: 196 mg, 86%.

NMR (DMSO-$d_6$ at 100° C.): 1.55 (m, 1H), 1.77 (m, 3H), 2.06 (m, 3H), 2.17 (s, 3H), 2.36 (m, 1H), 3.20 (m, 2H), 3.56 (m, 1H), 3.70 (m, 3H), 3.91 (m, 1H), 5.39 (dd, 1H), 5.56 (s, 1H), 5.88 (s, 1H), 6.00 (t, 1H), 6.64 (s, 1H), 7.42 (dd, 1H), 7.90 (m, 2H), 8.64 (d, 1H); m/z 488.5 [MH]+.

Example 177

S-6-(2-Isopropoxyethylamino)-4-(5-methyl-1H-pyrazol-3-ylamino)-2-[2-{3-(pyrid-2-yl)isoxazol-5-yl}pyrrolidin-1-yl]pyrimidine Starting materials: S-6-chloro-4-(5-methyl 1H-pyrazol-3-ylamino)-2-[2-{3-(pyrid-2-yl)isoxazol-5-yl}pyrrolidin-1-yl] pyrimidine (Example 96) and 2-isopropoxyethylamine. Yield: 180 mg, 78%.

NMR (DMSO-$d_6$ at 100° C.): 1.03 (dd, 6H), 2.06 (m, 3H), 2.17 (s, 3H), 2.36 (m, 1H), 3.30 (m, 4H), 3.48 (m, 1H), 3.70 (m, 2H), 5.40 (dd, 1H), 5.53 (s, 1H), 5.89 (s, 1H), 5.95 (t, 1H), 6.64 (s, 1H), 7.42 (dd, 1H), 7.90 (m, 2H), 8.66 (d, 1H); m/z 490 [MH]+.

Example 178

S-6-Morpholino-4-(5-cyclopropyl-1H-pyrazol-3-ylamino)-2-[2-{3-(pyrimid-2-yl)isoxazol-5-yl}pyrrolidin-1-yl]pyrimidine Starting materials: S-6-chloro-4-(5-cyclopropyl-1H-pyrazol-3-ylamino)-2-[2-{3-(pyrimid-2-yl)isoxazol-5-yl}pyrrolidin-1-yl]pyrimidine (Example 180) and morpholine. Yield: 145 mg, 66%.

NMR (DMSO-$d_6$ at 100° C.): 0.65 (m, 2H), 0.86 (m, 2H), 1.84 (m, 1H), 2.09 (m, 3H), 2.39 (m, 1H), 3.39 (m, 4H), 3.57 (m, 4H), 3.72 (m, 2H), 5.42 (dd, 1H), 5.72 (s, 1H), 5.89 (s, 1H), 6.69 (s, 1H), 7.55 (dd, 1H), 8.89 (d, 2H); m/z 502 [MH]+.

Example 179

S-6-Methylamino-4-(5-cyclopropyl-1H-pyrazol-3-ylamino)-2-[2-{3-(pyrimid-2-yl)isoxazol-5-yl}pyrrolidin-1-yl]pyrimidine Starting materials: S-6-chloro-4-(5-cyclopropyl-1H-pyrazol-3-ylamino)-2-[2-{3-(pyrimid-2-yl)isoxazol-5-yl}pyrrolidin-1-yl]pyrimidine (Example 180) and an excess of a 2M solution of methylamine in ethanol heated at 120° C. for 90 minutes. Yield: 125 mg, 64%.

NMR (DMSO-$d_6$ at 100° C.): 0.67 (m, 2H), 0.85 (m, 2H), 1.82 (m, 1H), 2.09 (m, 3H), 2.36 (m, 1H), 2.70 (d, 3H), 3.72 (m, 2H), 5.42 (dd, 1H), 5.50 (br s, 1H), 5.83 (br s, 1H), 5.97 (br s, 1H), 6.69 (s, 1H), 7.55 (dd, 1H), 8.12 (br s, 1H), 8.94 (d, 2H), 11.51 (br s, 1H); m/z 445 [MH]+.

Example 180

S-6-Chloro-4-(5-cyclopropyl-1H-pyrazol-3-ylamino)-2-[2-{3-(pyrimid-2-yl)isoxazol-5-yl}pyrrolidin-1-yl]pyrimidine A mixture of 2,6-dichloro-4-(5-cyclopropyl-1H-pyrazol-3-ylamino)pyrimidine (Method 57) (910 mgs, 3.4 mmol), S-2-[3-(pyrimid-2-yl)isoxazol-5-yl]pyrrolidine (Method 66) (800 mg, 0.37 mmol), N,N-diisopropylethylamine (480 mg, 0.37 mmol) and 1-butanol (20 ml) were heated at 75° C. for 16 hours. The volatiles were removed by evaporation and the residue purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation to give the title compound (850 mg, 55%).

NMR (DMSO-$d_6$ at 100° C.): 0.71 (m, 2H), 0.91 (m, 2H), 1.88 (m, 1H), 2.09 (m, 2H), 2.18 (m, 1H), 2.43 (m, 1H), 3.72 (m, 2H), 5.47 (dd, 1H), 5.98 (s, 1H), 6.40 (s, 1H), 6.74 (s, 1H), 7.55 (dd, 1H), 8.94 (d, 2H), 9.27 (s, 1H), 11.72 (br s, 1H); m/z 450 [MH]+.

Example 181

S-6-Methyl-4-(5-methyl-1H-pyrazol-3-ylamino)-2-[2-{3-(3-methoxypyrazin-2-yl)isoxazol-5-yl}pyrrolidin-1-yl]pyrimidine A mixture of 2-chloro-6-methyl-4-(5-methyl-1H-pyrazol-3-ylamino)pyrimidine (Method 56) (63 mg, 0.26 mmol), S-2-[3-(2-methoxypyrazin-3-yl)isoxazol-5-yl]pyrrolidine (Method 68) (70 mg, 0.28 mmol), diisopropylethylamine (0.09 ml, 0.52 mmol) and 1-hexanol (3 ml) were heated at 120° C. for 6 hours. The crude reaction mixture was purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation, the residue triturated with ether and collected by filtration to give the title compound (49 mg, 44%) as a white solid.

NMR (DMSO-$d_6$ at 100° C.): 12.06 (m, 3H), 2.12 (s, 3H), 2.17 (s, 3H), 2.36 (m, 1H), 3.70 (m, 2H), 4.00 (s, 3H), 5.45 (d, 1H), 6.01 (br s, 1H), 6.22 (br s, 1H), 6.64 (s, 1H), 8.30 (s, 2H), 8.74 (br s, 1H), 11.51 (br s, 1H); m/z 435 [MH]+.

Example 182

S-6-Methoxy-4-(5-cyclopropyl-1H-pyrazol-3-ylamino)-2-[2-{3-(pyrimidin-2-yl)isoxazol-5-yl}pyrrolidin-1-yl]pyrimidine Sodium hydride (88 mg, 1.1 mmol) was added to methanol (2 ml) and the mixture stirred for 5 minutes. S-6-chloro-4-(5-cyclopropyl-1H-pyrazol-3-ylamino)-2-[2-{3-(pyrimidin-2-yl)isoxazol-5-yl}pyrrolidin-1-yl]pyrimidine (Example 180) (200 mg, 0.44 mmol) was added and the mixture heated at 120° C. in a sealed vessel under microwave irradiation for 30 minutes. The reaction mixture was allowed to cool and was poured into cold aqueous ammonium chloride solution. The resulting precipitate was collected by filtration and dissolved in methanol. The solution was poured into water and precipitate collected by filtration, washed with water and dried in a vacuum oven to give the title compound (81 mg, 41%) as a white solid.

NMR (DMSO-$d_6$+$d_4$-acetic acid at 100° C.): 0.63 (m, 2H), 0.85 (m, 2H), 1.82 (m, 1H), 2.09 (m, 3H), 2.36 (m, 1H), 3.70 (s, 3H), 3.72 (m, 2H), 5.42 (dd, 1H), 6.69 (s, 1H), 7.49 (dd, 1H), 8.88 (d, 2H); m/z 446 [MH]+.

Example 183

S-6-(2-Methoxyethoxy)-4-(5-cyclopropyl-1H-pyrazol-3-ylamino)-2-[2-{3-(pyrimidin-2-yl)isoxazol-5-yl}pyrrolidin-1-yl]pyrimidine The title compound was made by an analogous method to that described in Example 182 starting from S-6-chloro-4-(5-cyclopropyl-1H-pyrazol-3-ylamino)-2-[2-{3-(pyrimidin-2-yl)isoxazol-5-yl}pyrrolidin-1-yl]pyrimidine (Example 180) and 2-methoxyethanol. Yield: 80 mg, 37%.

NMR (DMSO-$d_6$ at 100° C.): 0.67 (m, 2H), 0.85 (m, 2H), 1.82 (m, 1H), 2.09 (m, 3H), 2.36 (m, 1H), 3.24 (s, 3H), 3.52 (m, 2H), 3.72 (m, 2H), 4.25 (m, 2H), 5.42 (dd, 1H), 5.74 (s, 1H), 5.92 (s, 1H), 6.69 (s, 1H), 7.55 (dd, 1H), 8.68 (br s, 1H), 8.91 (d, 2H), 11.5 (br s, 1H); m/z 490 [MH]+.

Example 184

S-4-(5-Ethyl-1H-pyrazol-3-ylamino)-2-{2-[3-(pyrid-2-yl)isoxazol-5-yl]pyrrolidin-1-yl}pyrimidine A mixture of 4-(5-ethyl-1H-pyrazol-3-ylamino)-2-chloropyrimidine (Method 65) (224 mg, 11.0 mmol), S-2-(3-(2-pyridyl)isoxazol-5-yl)pyrrolidine (Method 42) (268 mg, 1.25 mmol) and N,N-diisopropylamine (322 mg, 0.43 ml, 2.5 mmol) in 1-hexanol (10 ml) was heated at 150° C. for 18 hours. The solvent was removed by evaporation, and the residue was suspended in aqueous sodium bicarbonate solution (25 ml) and extracted with EtOAc (4×25 ml). The organic extracts were combined, washed with brine (2×25 ml), dried (MgSO$_4$) and the solvent removed by evaporation. The residue was triturated with ether, collected by filtration and dried to give the title compound (202 mg, 50%) as a tan solid.

NMR (DMSO): 1.18 (m, 3H), 2.02 (m, 3H), 2.35 (m, 1H), 2.50 (m, 2H), 3.56 (m, 1H), 3.78 (m, 1H), 5.42 (d, 1H), 6.00 (br m, 1H), 6.25 (br m, 1H), 6.67 (s, 1H), 7.47 (m, 1H), 7.90 (m, 3H), 8.63 (d, 1H), 9.40 (br s, 1H), 11.80 (br s, 1H); m/z 403 [MH]+.

Example 185

S-4-(5-Cyclopropyl-1H-pyrazol-3-ylamino)-2-{2-[3-(pyrid-2-yl)isoxazol-5-yl]pyrrolidin-1-yl}pyrimidine 4-(5-Cyclopropyl-1H-pyrazol-3-ylamino)-2-chloropyrimidine (Method 28) (224 mg, 1.0 mmol) and S-2-(3-(2-pyridyl)isoxazol-5-yl)pyrrolidine (Method 42) were treated by the method described in Example 184, to give the title compound (210 mg, 50%) as a tan crystalline solid.

NMR (DMSO): 0.65 (m, 2H), 0.87 (m, 2H), 1.82 (br m, 1H), 2.02 (m, 3H), 2.35 (m, 1H), 3.55 (m, 1H), 3.80 (m, 1H), 5.40 (d, 1H), 5.90 (br m, 1H), 6.20 (br m, 1H), 6.65 (s, 1H), 7.47 (m, 1H), 7.85 (br s, 1H), 7.95 (m, 3H), 8.65 (m, 1H), 9.40 (br s, 1H), 11.85 (br s, 1H); m/z 415 [MH]+.

Example 186

S-4-(5-Ethyl-1H-pyrazol-3-ylamino)-5-fluoro-2-{2-[3-(pyrid-2-yl)isoxazol-5-yl]pyrrolidin-1-yl}pyrimidine 2-Chloro-4-(5-ethyl-1H-pyrazol-3-ylamino)-5-fluoropyrimidine (Method 69) and S-2-(3-(2-pyridyl)isoxazol-5-yl)pyrrolidine (Method 42) were treated by the method described in Example 184. The product was purified by column chromatography silica gel eluting with EtOAc/hexane mixture (50:50 increasing in polarity to 100:0) to give the title compound (221 mg, 53%) as a pale yellow solid.

NMR (DMSO): 1.17 (t, 3H), 2.08 (m, 3H), 2.38 (m, 1H), 2.57 (q, 2H), 3.65 (m, 1H), 3.75 (m, 1H), 5.37 (d, 1H), 6.18 (br s, 1H), 6.62 (s, 1H), 7.42 (m, 1H), 7.90 (m, 3H), 8.62 (d, 1H), 8.80 (br s, 1H), 11.60 (br s, 1H); m/z 421 [MH]+.

Example 187

S-4-(5-Cyclopropyl-1H-pyrazol-3-ylamino)-5-fluoro-2-{2-[3-(pyrid-2-yl)isoxazol-5-yl]pyrrolidin-1-yl}pyrimidine 2-Chloro-4-(5-cyclopropyl-1H-pyrazol-3-ylamino)-5-fluoropyrimidine (Method 27) and S-2-(3-(2-pyridyl)isoxazol-5-yl)pyrrolidine (Method 42) were treated by the method described in Example 184. The product was purified by column chromatography silica gel eluting with EtOAc/hexane mixture (50:50 increasing in polarity to 100:0) to give the title compound (192 mg, 44%) as a pale yellow solid.

NMR (DMSO): 0.67 (m, 2H), 0.87 (m, 2H), 1.85 (br m, 1H), 2.02 (m, 3H), 2.38 (m, 1H), 3.55 (m, 1H), 3.80 (m, 1H), 5.37 (d, 1H), 5.95 (br s, 1H), 6.70 (s, 1H), 7.50 (m, 1H), 7.95 (m, 3H), 8.66 (d, 1H), 9.45 (br s, 1H), 12.00 (br s, 1H); m/z 433 [MH]+.

Example 188

4-(5-Cyclopropyl-1H-pyrazol-3-ylamino)-6-methyl-2-{2-[3-(pyrimid-2-yl)isoxazol-5-yl]pyrrolidin-1-yl}pyrimidine A mixture of 2-chloro-6-methyl-4-(5-cyclopropyl-1H-pyrazol-3-ylamino)pyrimidine (Method 70) (210 mg, 0.84 mmol), S-2-[3-(pyrimid-2-yl)isoxazol-5-yl]pyrrolidine (Method 66) (200 mg, 0.92 mmol), N,N-diisopropylethylamine (0.16 ml, 1.18 mmol) and dry 1-hexanol (4.0 ml) was heated at 150° C. in a sealed vessel under microwave irradiation for 45 minutes. The reaction mixture was allowed to cool and was then directly purified by reverse phase HPLC using a C18 column eluting with water/acetonitrile/TFA (95:5:0.2 decreasing in polarity to 0:100:0.2). The product containing fractions were poured onto a 10 g isolute SCX-2 ion exchange column. The column was eluted with methanol to elute any neutrals, followed by 7M methanolic ammonia to elute the product. The solvent was removed by evaporation, the residue triturated with ether and collected by filtration to give the title compound (212 mg, 59%).

NMR (DMSO-d$_6$ at 100° C.): 0.65 (m, 2H), 0.85 (m, 2H), 1.85 (m, 1H), 2.05 (m, 2H), 2.10 (s, 3H), 2.15 (m, 1H), 2.35 (m, 1H), 3.70 (m, 1H), 3.75 (m, 1H), 5.47 (dd, 1H), 5.90 (br s, 1H), 6.15 (br s, 1H), 6.65 (s, 1H), 7.50 (t, 1H), 8.75 (br s, 1H), 8.90 (d, 2H), 11.55 (br s, 1H); m/z 430 [MH]+.

Example 189

4-(5-Cyclopropyl-1H-pyrazol-3-ylamino)-6-methyl-2-{2-[3-(pyrazin-2-yl)isoxazol-5-yl]pyrrolidin-1-yl}pyrimidine 2-Chloro-6-methyl-4-(5-cyclopropyl-1H-pyrazol-3-ylamino)pyrimidine (Method 70) and S-2-[3-(pyrazin-2-yl)isoxazol-5-yl]pyrrolidine (Method 55) were treated as described in Example 188 to give the title compound (218 mg, 71%).

NMR (DMSO-d$_6$ at 100° C.): 0.65 (m, 2H), 0.85 (m, 2H), 1.83 (heptet, 1H), 2.05 (m, 2H), 2.11 (s, 3H), 2.15 (m, 1H), 2.35 (m, 1H), 3.67 (m, 1H), 3.75 (m, 1H), 5.48 (dd, 1H), 5.95 (br s, 1H), 6.15 (br s, 1H), 8.65 (m, 2H), 8.75 (br s, 1H), 9.12 (br s, 1H), 11.55 (br s, 1H); m/z 430 [MH]+.

Example 190

4-(5-Cyclopropyl-1H-pyrazol-3-ylamino)-6-methyl-2-{2-[3-(pyrid-2-yl)isoxazol-5-yl]pyrrolidin-1-yl}pyrimidine 2-Chloro-6-methyl-4-(5-cyclopropyl-1H-pyrazol-3-ylamino)pyrimidine (Method 70) and S-2-(3-(2-pyridyl)isoxazol-5-yl)pyrrolidine (Method 42) were treated as described in Example 188 to give the title compound (242 mg, 66%).

NMR (DMSO-d$_6$ at 100° C.): 0.65 (m, 2H), 0.85 (m, 2H), 1.83 (heptet, 1H), 2.05 (m, 2H), 2.12 (s, 3H), 2.15 (m, 1H), 2.37 (m, 1H), 3.68 (m, 1H), 3.75 (m, 1H), 5.45 (dd, 1H), 5.95 (br s, 1H), 6.15 (br s, 1H), 7.60 (s, s, M1H), 7.43 (dd, 1H), 7.85 (dd, 1H), 7.92 (d, 1H), 8.61 (d, 1H), 8.75 (br s, 1H), 11.55 (br s, 1H); m/z 429 [MH]+.

Example 191

6-(3-Hydroxypropyl)-4-(5-methyl-1H-pyrazol-3-ylamino)-2-{2-[3-(pyrid-2-yl)isoxazol-5-yl]pyrrolidin-1-yl}pyrimidine 3-Amino-1H-5-methylpyrazole (87 mg, 0.894 mmol) was added to a stirred solution of 4-chloro-6-(3-hydroxypropyl)-2-{2-[3-(pyrid-2-yl)isoxazol-5-yl]pyrrolidin-1-yl}pyrimidine (Method 71) (230 mg, 0.596 mmol) in dry NMP (3 ml). 6M hydrogen chloride in dioxane (298 µl, 1.19 mmol) was added and the reaction stirred and heated at 120° C. under nitrogen for 20 hours. The reaction was allowed to cool and the reaction mixture applied to a 10 g isolute SCX2 ion exchange column. The column was washed with methanol to remove neutrals and then eluted with 2M methanolic ammonia to elute the product. The solvent from the product containing fractions was removed by evaporation and the residue purified by flash chromatography on silica eluting with methanol/DCM (5:95). The purified product was then dissolved in ethyl acetate and washed with water, dried ($Na_2SO_4$) and the solvent removed by evaporation. The residue was triturated with DCM/hexane and collected by filtration to give title compound (99 mg, 37%) as a white solid.

NMR (DMSO): 1.75 (m, 2H), 2.1 (m, 3H), 2.4 (s, 3H), 3.42 (m, 2H), 3.72 (m, 2H), 4.02 (s, 1H), 5.43 (d, 1H), 6.02 (s, 1H), 6.2 (s, 1H), 6.66 (s, 1H), 7.43 (t, 1H), 7.9 (m, 2H), 8.65 (d, 1H), 8.73 (s, 1H), 11.47 (s, 1H); m/z 447 [MH]+.

Example 192

S-6-(3-Hydroxypropyl)-4-(5-methyl-1H-pyrazol-3-ylamino)-2-{2-[3-(pyrid-2-yl)isoxazol-5-yl]pyrrolidin-1-yl}pyrimidine The S enantiomer of Example 191 was separated by chiral HPLC using a Chiralpak AD column with methanol as eluent.

Example 193

S-6-Propyl-2-{2-[3-(pyrid-2-yl)isoxazol-5-yl]pyrrolidin-1-yl}-4-(5-methyl-1H-pyrazol-3-ylamino)pyrimidine Bis(triphenylphosphine)palladium(II)chloride (34 mg) was added to a stirred solution of S-6-iodo-2-{2-[3-(pyrid-2-yl)isoxazol-5-yl]pyrrolidin-1-yl}-4-(5-methyl-1H-pyrazol-3-ylamino)pyrimidine (Example 98) (250 mg, 0.486 mmol) in dry dimethylacetamide (7.5 ml) and dry THF (2.5 ml). A 0.5M solution of n-propylzinc bromide in THF (3.9 ml, 1.94 mmol) was then added and the reaction stirred at ambient temperature for 24 hours. Further 0.5M solution of n-propylzinc bromide in THF (3.9 ml, 1.94 mmol) was added and the reaction stirred a further 24 hours. Water and ethyl acetate was then added to the reaction mixture and the mixture filtered to remove insoluble matter. The filtrate layers were separated and the organic layer washed with water and saturated brine, dried ($Na_2SO_4$), the solvent removed by evaporation. The residue was purified by reverse phase HPLC using a C18 column eluting with water/acetonitrile/TFA (95:5:0.2 decreasing in polarity to 0:100:0.2) to give the title (15 mg, 55%) as a white solid.

NMR (DMSO-$d_6$ at 373 deg K): 0.9 (t, 3H), 1.63 (m, 2H), 2.12 (m, 3H), 2.18 (s, 3H), 2.4 (m, 1H), 3.72 (m, 1H), 3.83 (m, 1H), 5.5 (d, 1H), 6.0 (s, 1H), 6.27 (s, 1H), 6.75 (s, 1H), 7.45 (t, 1H), 7.9 (m, 2H), 8.65 (d, 1H), 9.43 (s, 1H); m/z 431 [MH]+

Example 194

S-6-Chloro-4-(5-ethyl-1H-pyrazol-3-ylamino)-2-[2-{3-(pyrid-2-yl)isoxazol-5-yl}pyrrolidin-1-yl]pyrimidine 2,6-Dichloro-4-(5-ethyl-1H-pyrazol-3-ylamino)pyrimidine (Method 72) and S-2-(3-(2-pyridyl)isoxazol-5-yl)pyrrolidine (Method 42) were treated as described in Example 143 to give the title compound (80 mg, 48%);

NMR (DMSO-$d_6$ at 100° C.): 1.1 (t, 3H), 2.05 (m, 2H), 2.15 (m, 1H), 2.35 (m, 2H), 2.55 (q, 2H), 3.65 (m, 1H), 3.75 (m, 1H), 5.4 (d, 1H), 6.05 (br s, 1H), 6.4 (br s, 1H), 6.65 (s, 1H), 7.45 (m, 1H), 7.90 (m, 2H), 8.65 (d, 1H), 9.25 (br s, 1H), 11.65 (br s, 1H); m/z 438 [MH]+.

Example 195

S-6-(2-Hydroxyethoxy)-4-(5-ethyl-1H-pyrazol-3-ylamino)-2-[2-{3-(pyrid-2-yl)isoxazol-5-yl}pyrrolidin-1-yl]pyrimidine S-6-Chloro-4-(5-ethyl-1H-pyrazol-3-ylamino)-2-[2-{3-(pyrid-2-yl)isoxazol-5-yl}pyrrolidin-1-yl]pyrimidine (Example 194) and ethylene glycol were treated as described in Example 208 to give the title compound (80 mg, 49%).

NMR (DMSO-$d_6$ 100° C.): 1.17 (t, 3H), 2.10 (m, 3H), 2.45 (m, 1H), 2.55 (q, 2H), 3.60 (q, 2H), 3.75 (m, 2H), 4.18 (m, 2H), 4.35 (t, 1H), 5.42 (d, 1H), 5.75 (br s, 1H), 6.00 (br s, 1H), 6.66 (s, 1H), 7.45 (m, 1H), 7.92 (m, 2H), 8.65 (br s, 1H), 8.65 (d, 1H); m/z 464 [MH]+.

Example 196

S-6-(2-Methoxyethoxy)-4-(5-ethyl-1H-pyrazol-3-ylamino)-2-[2-{3-(pyrid-2-yl)isoxazol-5-yl}pyrrolidin-1-yl]pyrimidine S-6-Chloro-4-(5-ethyl-1H-pyrazol-3-ylamino)-2-[2-{3-(pyrid-2-yl)isoxazol-5-yl}pyrrolidin-1-yl]pyrimidine (Example 194) and 2-methoxyethanol were treated as described in Example 208 to give the title compound (122 mg, 56%).

NMR (DMSO-$d_6$ at 100° C.): 1.18 (t, 3H), 2.10 (m, 3H), 2.30 (m, 1H), 2.52 (q, 2H), 3.20 (s, 3H), 3.50 (q, 2H), 3.70 (m, 1H), 3.75 (m, 1H), 4.25 (t, 2H), 5.40 (d, 2H), 5.75 (br s, 1H), 6.00 (br s, 1H), 6.69 (s, 1H), 7.40 (m, 1H), 7.90 (m, 2H), 8.60 (d, 1H), 8.60 (br s, 1H), 11.50(br s, 1H); m/z 478 [MH]+.

Example 197

S-6-Morpholino-4-(5-ethyl-1H-pyrazol-3-ylamino)-2-[2-{3-(pyrid-2-yl)isoxazol-5-yl}pyrrolidin-1-yl]pyrimidine S-6-Chloro-4-(5-ethyl-1H-pyrazol-3-ylamino)-2-[2-{3-(pyrid-2-yl)isoxazol-5-yl}pyrrolidin-1-yl]pyrimidine (Example 194) and morpholine were treated as described in Example 166 to give the title compound (67 mg, 30%).

NMR (DMSO-$d_6$ at 100° C.): 1.20 (t, 3H), 2.10 (m, 3H), 2.35 (m, 1H), 2.55 (q, 2H), 3.40 (m, 4H), 3.60 (m, 4H), 3.75 (m, 2H), 5.40 (d, 1H), 5.80 (br s, 1H), 6.00 (br s, 1H), 6.65 (s, 1H), 7.45 (m, 1H), 7.95 (m, 1H), 8.35 (br s, 1H), 8.65 (d, 1H), 11.45 (br s, 1H); m/z 489 [MH]+.

Example 198

S-6-(4-Methylpiperazin-1-yl)-4-(5-ethyl-1H-pyrazol-3-ylamino)-2-[2-{3-(pyrid-2-yl)isoxazol-5-yl}pyrrolidin-1-yl]pyrimidine S-6-Chloro-4-(5-ethyl-1H-pyrazol-3-ylamino)-2-[2-{3-(pyrid-2-yl)isoxazol-5-yl}pyrrolidin-1-yl]pyrimidine (Example 194) and 1-methylpiperazine were treated as described in Example 166 to give the title compound (110 mg, 49%).

NMR (DMSO-$d_6$ at 100° C.): 1.15 (t, 3H), 2.00(m, 3H), 2.25 (s, 3H), 2.35 (m, 5H), 2.55 (q, 2H), 3.30 (m, 4H), 3.60 (m, 2H), 5.30 (q, 1H), 5.70 (br s, 1H), 5.90 (br s, 1H), 6.60 (s, 1H), 7.40 (m, 1H), 7.90 (m, 1H), 8.25 (br s, 1H), 8.65 (d, 1H), 11.30 (br s, 1H); m/z 502 [MH]+.

Example 199

S-6-Chloro-4-(5-ethyl-1H-pyrazol-3-ylamino)-2-[2-{3-(2-pyrazin-yl)isoxazol-5-yl}pyrrolidin-1-yl]pyrimidine 2,6-Dichloro-4-(5-ethyl-1H-pyrazol-3-ylamino)pyrimidine (Method 72) and S-2-[3-(2-pyrazinyl)isoxazol-5-yl]pyrrolidine (Method 55) were treated as described in Example 141 to give the title compound (800 mg, 48%).

NMR (DMSO-$d_6$ at 100° C.): 1.18 (t, 3H), 2.05 (m, 3H), 2.15 (m, 1H), 2.55 (q, 2H), 3.65 (m, 1H), 3.75 (m, 1H), 5.45 (d, 1H), 6.04 (br s, 1H), 6.40 (br s, 1H), 6.78 (s, 1H), 8.70 (m, 2H), 9.14 (s, 1H), 9.25 (br s, 1H); m/z 439 [MH]+.

Examples 200 to 207

The following single enantiomers were prepared by separation of the racemic compounds by chiral HPLC.

Example 200

S-6-Methoxy-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 48) by chiral HPLC using a chiralpak AD column eluting with methanol.

Example 201

S-6-(2-Methoxyethoxy)-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 214) by chiral HPLC using a Chiralpak AD column eluting with methanol.

Example 202

S-6-Pyrrolidin-1-yl-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 95) by chiral HPLC using a Chiralpak AS column eluting with methanol.

Example 203

S-6-Methoxymethyl-4-(5-cyclopropyl-1H-pyrazol-3-ylamino)-2-[2-(3-cyclopropylisoxazol-5-yl)pyrrolidin-1-yl]pyrimidine The title compound was prepared by separation of the racemic compound (Example 13) by chiral HPLC using a Chiralpak AS column eluting with methanol/ethanol (85:15).

Example 204

S-6-Morpholinocarbonyl-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 58) by chiral HPLC using a Chiralpak AD column eluting with methanol/ethanol (85:15).

Example 205

S-6-Carbamoyl-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 61) by chiral HPLC using a Chiralpak AD column eluting with methanol/ethanol (85:15).

Example 206

S-5-Fluoro-4-(5-methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 20) by chiral HPLC using a Chiralpak AS column eluting with methanol.

Example 207

S-4-(5-Methyl-1H-pyrazol-3-ylamino)-2-[2-{3-(pyrid-2-yl)isoxazol-5-yl}pyrrolidin-1-yl]pyrimidine The title compound was prepared by separation of the racemic compound (Example 23) by chiral HPLC using a Chiralpak AS column eluting with methanol.

Example 208

S-4-(5-Methyl-1H-pyrazol-3-ylamino)-6-(2-hydroxyethoxy)-2-[2-{3-(pyrid-2-yl)isoxazol-5-yl}pyrrolidin-1-yl]pyrimidine Sodium hydride (94 mg, 2.35 mmol) was added in portions to ethylene glycol (4 ml). The mixture was stirred for 10 minutes and S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (200 mg, 0.47 mmol) was added. The reaction was heated at 150° C. in a sealed vessel under microwave irradiation for 1 hour. The reaction was quenched with 2M hydrochloric acid then diluted with water and extracted with DCM. The extracts were combined, washed with brine, dried ($Na_2SO_4$) and the solvent removed by evaporation. The residue was purified by reverse phase HPLC using a C18 column eluting with water/acetonitrile/TFA (70:

30:0.2 decreasing in polarity to 30:70:0.2). Product containing fractions were poured onto a SCX-2 column, washed with methanol to elute neutral impurities then eluted with 3N methanolic ammonia to elute the product. The solvent was removed by evaporation and the residue triturated with ether to give the title compound (131 mg, 62%).

NMR (DMSO): 2.08 (m, 3H), 2.17 (s, 3H), 2.36 (m, 1H), 3.61 (m, 2H), 3.71 (m, 2H), 4.18 (m, 2H), 5.4 (d, 1H), 5.75 (s, 1H), 5.95 (s, 1H), 6.68 (s, 1H), 7.4 (m, 1H), 7.88 (m, 1H), 7.94 (d, 1H), 8.62 (d, 1H); m/z 449 [MH]+.

Examples 209 to 233

Examples 209 to 233 were prepared by an analogous method to that described for Example 208. Reaction times were between 30 minutes and 2 hours. In some cases, 10 equivalents of alcohol was used with 1 to 2 ml of 2-propanol as solvent. Reactions could be quenched with glacial acetic acid in place of hydrochloric acid; and reaction mixtures could be applied directly to HPLC purification without aqueous work-up.

| Ex No. | Starting material | Compound name | NMR (DMSO 373K+d4AcOH) | m/z (MH)+ |
|---|---|---|---|---|
| 209 | Example 96 and N,N-di(2-hydroxyethyl) methylamine | S-4-(5-Methyl-1H-pyrazol-3-ylamino)-6-(2-{N-[2-hydroxyethyl]-N-methyl-amino}ethoxy)-2-[2-{3-(pyrid-2-yl)isoxazol-5-yl}pyrrolidin-1-yl]pyrimidine | 2.10(m, 3H), 2.19(s, 3H), 2.27(s, 3H), 2.4(m, 1H), 2.69(t, 2H), 3.95(m, 2H), 3.45(t, 2H), 3.72(m, 2H), 4.23(t, 2H), 5.4(d, 1H), 5.75(s, 1H), 5.96(s, 1H), 6.69(s, 1H), 7.43(m, 1H), 7.9(m, 2H), 8.6(s, 1H), 8.63(d, 1H), 11.45(br s, 1H) not deuterated | 506 |
| 210 | Example 96 and 2-morpholino ethanol | S-4-(5-Methyl-1H-pyrazol-3-ylamino)-6-(2-morpholinoethoxy)-2-[2-{3-(pyrid-2-yl)isoxazol-5-yl}pyrrolidin-1-yl]pyrimidine | 2.08(m, 3H), 2.19(s, 3H), 2.36(m, 5H), 2.58(t, 2H), 3.51(t, 4H), 3.92(m, 2H), 4.23(m, 2H), 5.4(d, 1H), 5.77(s, 1H), 5.97(s, 1H), 6.68(s, 1H), 7.43(m, 1H), 7.91(m, 2H), 8.6(s, 1H), 8.63(d, 1H), 11.48(br s, 1H) not deuterated | 518 |
| 211 | Example 96 and methane thiol | S-4-(5-Methyl-1H-pyrazol-3-ylamino)-6-(methylthio)-2-[2-{3-(pyrid-2-yl)isoxazol-5-yl}pyrrolidin-1-yl]pyrimidine | 2.08(m, 3H), 2.17(s, 3H), 2.35(m, 4H), 3.7(m, 1H), 3.79(m, 1H), 5.42(d, 1H), 5.99(s, 1H), 6.27(s, 1H), 6.65(s, 1H), 7.4(m, 1H), 7.86(m, 1H), 7.93(d, 1H), 8.62(d, 1H) | 435 |
| 212 | Example 17 and tetrahydrofuran-3-ylmethanol | 4-(5-Methyl-1H-pyrazol-3-ylamino)-6-(tetrahydrofuran-3-ylmethoxy)-2-[2-{3-(pyrid-2-yl)isoxazol-5-yl}pyrrolidin-1-yl]pyrimidine | 1.57(m, 1H), 1.92(m, 1H), 2.09(m, 3H), 2.2(s, 3H), 2.36(m, 1H), 3.44(m, 1H), 2.52(m, 1H), 3.58(m, 1H), 3.6-3.8(m, 4H), 4.09(m, 2H), 5.38(d, 1H), 5.74(s, 1H), 5.99(s, 1H), 6.68(s, 1H), 7.41(m, 1H), 7.87(m, 1H), 7.95(d, 1H), 8.64(d, 1H) | 489 |
| 213 | Example 96 and 2-(2-hydroxy ethoxy)ethanol | S-4-(5-Methyl-1H-pyrazol-3-ylamino)-6-(2-(2-hydroxyethoxy)ethoxy)-2-[2-{3-(pyrid-2-yl)isoxazol-5-yl}pyrrolidin-1-yl]pyrimidine | 2.07(m, 3H), 2.16(s, 3H), 2.35(m, 1H), 3.41(m, 2H), 2.46(m, 2H), 3.61(m, 2H), 3.72(m, 2H), 4.25(t, 2H), 5.49(d, 1H), 5.74(s, 1H), 5.95(s, 1H), 6.66(s, 1H), 7.4(m, 1H), 7.85(m, 1H), 7.93(d, 1H), 8.62(d, 1H) | 493 |
| 214 | Example 17 and 2-methoxyethanol | 4-(5-Methyl-1H-pyrazol-3-ylamino)-6-(2-methoxyethoxy)-2-[2-{3-(pyrid-2-yl)isoxazol-5- | 2.08(m, 3H), 2.16(s, 3H), 2.36(m, 1H), 3.19(s, 3H), 3.47(m, 2H), 3.66(m, 1H), 3.77(m, 1H), 4.24(m, 2H), | 463 |

-continued

| Ex No. | Starting material | Compound name | NMR (DMSO 373K+d4AcOH) | m/z (MH)+ |
|---|---|---|---|---|
| | | yl}pyrrolidin-1-yl]pyrimidine | 5.38(d, 1H), 5.68(s, 1H), 5.96(s, 1H), 6.66(s, 1H), 7.38(m, 1H), 7.83(m, 1H), 7.92(d, 1H), 8.61(d, 1H) | |
| 215 | Example 96 and 1,3-propanediol | S-4-(5-Methyl-1H-pyrazol-3-ylamino)-6-(3-hydroxypropyloxy)-2-[2-{3-(pyrid-2-yl)isoxazol-5-yl}pyrrolidin-1-yl]pyrimidine | 1.68(m, 2H), 2.0(m, 3H), 2.09(s, 3H), 2.29(m, 1H), 3.39(t, 2H), 3.63(m, 2H), 4.14(m, 2H), 5.32(d, 1H), 5.65(s, 1H), 5.85(s, 1H), 6.58(s, 1H), 7.34(t, 1H), 7.78(t, 1H), 7.84(d, 1H), 8.55(d, 1H) | 463 |
| 216 | Example 96 and 2-(2-methoxy ethoxy)ethanol | S-4-(5-Methyl-1H-pyrazol-3-ylamino)-6-[2-(2-methoxyethoxy)ethoxy]-2-[2-{3-(pyrid-2-yl)isoxazol-5-yl}pyrrolidin-1-yl]pyrimidine | 2.07(m, 3H), 2.16(s, 3H), 2.47(m, 1H), 3.2(s, 3H), 3.38(m, 2H), 3.48(m, 2H), 3.59(m, 2H), 3.72(m, 2H), 4.24(t, 2H), 5.39(d, 1H), 5.72(s, 1H), 5.95(s, 1H), 6.66(s, 1H), 7.4(m, 1H), 7.86(m, 1H), 7.92(d, 1H), 8.63(d, 1H) | 507 |
| 217 | Example 96 and 2-ethoxyethanol | S-4-(5-Methyl-1H-pyrazol-3-ylamino)-6-(2-ethoxyethoxy)-2-[2-{3-(pyrid-2-yl)isoxazol-5-yl}pyrrolidin-1-yl]pyrimidine | 1.05(t, 3H), 2.08(m, 3H), 2.17(s, 3H), 2.39(m, 1H), 3.4(q, 2H), 3.56(m, 2H), 3.73(m, 2H), 4.25(m, 2H), 5.4(d, 1H), 5.77(s, 1H), 5.97(s, 1H), 6.69(s, 1H), 7.45(m, 1H), 7.92(m, 2H), 8.63(m, 2H), 11.5(br s, 1H) | 477 |
| 218 | Example 96 and 3-morpholino propan-1-ol | S-4-(5-Methyl-1H-pyrazol-3-ylamino)-6-(3-morpholinoprop-1-yloxy)-2-[2-{3-(pyrid-2-yl)isoxazol-5-yl}pyrrolidin-1-yl]pyrimidine | 1.84(m, 2H), 2.09(m, 3H), 2.17(s, 3H), 2.38(m, 1H), 2.65(m, 4H), 2.94(br s, 2H), 3.62(m, 4H), 3.73(m, 2H), 4.22(m, 2H), 5.4(d, 1H), 5.77(s, 1H), 5.98(s, 1H), 6.69(s, 1H), 7.45(m, 1H), 7.92(m, 2H), 8.65(m, 2H) | 532 |
| 219 | Example 96 and 3-methoxy propan-1-ol | S-4-(5-Methyl-1H-pyrazol-3-ylamino)-6-(3-methoxyprop-1-yloxy)-2-[2-{3-(pyrid-2-yl)isoxazol-5-yl}pyrrolidin-1-yl]pyrimidine | 1.83(m, 2H), 2.08(m, 3H), 2.17(s, 3H), 2.32(m, 1H), 3.2(s, 3H), 3.37(t, 2H), 3.72(m, 2H), 4.19(t, 2H), 5.4(d, 1H), 5.76(s, 1H), 5.96(s, 1H), 6.67(s, 1H), 7.45(m, 1H), 7.92(m, 2H), 8.61(s, 1H), 8.65(d, 1H) | 477 |
| 220 | Example 96 and N-(2-hydroxyethyl)-pyrrolidin-2-one | S-4-(5-Methyl-1H-pyrazol-3-ylamino)-6-[2-(2-oxopyrrolidin-1-yl)ethoxy]-2-[2-{3-(pyrid-2-yl)isoxazol-5-yl}pyrrolidin-1-yl]pyrimidine | 1.87(m, 2H), 2.1(m, 3H), 2.17(m, 5H), 2.38(m, 1H), 3.33(t, 2H), 3.45(m, 2H), 3.75(m, 2H), 4.27(m, 2H), 5.41(d, 1H), 5.76(s, 1H), 5.96(s, 1H), 6.69(s, 1H), 7.44(m, 1H), 7.93(m, 2H), 8.65(d, 2H), 11.5(br s, 1H) | 516 |
| 221 | Example 96 and (2S)-2-methoxy propan-1-ol | S-4-(5-Methyl-1H-pyrazol-3-ylamino)-6-[(2S)-2-methoxyprop-1-yloxy]-2-[2-{3-(pyrid-2-yl)isoxazol-5-yl}pyrrolidin-1-yl]pyrimidine | 1.04(d, 3H), 2.1(m, 3H), 2.19(s, 3H), 2.39(m, 1H), 3.21(s, 3H), 3.53(m, 1H), 3.74(m, 2H), 4.11(d, 2H), 5.39(d, 1H), 5.79(s, 1H), 5.97(s, 1H), 6.68(s, 1H), 7.45(m, 1H), 7.91(m, 2H), 8.65(d, 2H), 11.5(br s, 1H) | 477 |

-continued

| Ex No. | Starting material | Compound name | NMR (DMSO 373K+d4AcOH) | m/z (MH)+ |
|---|---|---|---|---|
| 222 | Example 96 and 3-methylthio propan-1-ol | S-4-(5-Methyl-1H-pyrazol-3-ylamino)-6-[3-(methylthio)prop-1-yloxy]-2-[2-{3-(pyrid-2-yl)isoxazol-5-yl}pyrrolidin-1-yl]pyrimidine | 1.88(m, 2H), 2.01(s, 3H), 2.09(m, 3H), 2.18(s, 3H), 2.37(m, 1H), 2.5(under DMSO peak, 2H), 3.72(m, 2H), 4.22(t, 2H), 5.4(d, 1H), 5.76(s, 1H), 5.96(s, 1H), 6.68(s, 1H), 7.44(m, 1H), 7.92(m, 2H), 8.59(s, 1H), 8.63(d, 1H), 11.47(br s, 1H) | 493 |
| 223 | Example 96 and (5S)-5-hydroxy methyl-pyrrolidin-2-one | S-4-(5-Methyl-1H-pyrazol-3-ylamino)-6-[(2S)-5-oxopyrrolidin-2-yl)methoxy]-2-[2-{3-(pyrid-2-yl)isoxazol-5-yl}pyrrolidin-1-yl]pyrimidine | 1.74(m, 1H), 2.1(m, 6H), 2.18(s, 3H), 2.39(m, 1H), 3.73(m, 3H), 4.1(m, 2H), 5.4(d, 1H), 5.78(s, 1H), 5.94(s, 1H), 6.7(s, 1H), 7.25(s, 1H), 7.44(m, 1H), 7.92(m, 2H), 8.63(d, 2H) | 502 |
| 224 | Example 96 and (5R)-5-hydroxy methyl-pyrrolidin-2-one | S-4-(5-Methyl-1H-pyrazol-3-ylamino)-6-[(2R)-5-oxopyrrolidin-2-yl)methoxy]-2-[2-{3-(pyrid-2-yl)isoxazol-5-yl}pyrrolidin-1-yl]pyrimidine | 1.75(m, 1H), 2.1(m, 6H), 2.18(s, 3H), 2.38(m, 1H), 3.74(m, 3H), 4.1(m, 2H), 5.4(d, 1H), 5.8(s, 1H), 5.97(s, 1H), 6.71(s, 1H), 7.3(s, 1H), 7.45(m, 1H), 7.91(m, 2H), 8.65(d, 2H), 11.5(br s, 1H) | 502 |
| 225 | Example 96 and 2-1-(2-hydroxyethyl) imidazolid-2-one | S-4-(5-Methyl-1H-pyrazol-3-ylamino)-6-[2-(imidazolid-2-on-1-yl)ethoxy]-2-[2-{3-(pyrid-2-yl)isoxazol-5-yl}pyrrolidin-1-yl]pyrimidine | 2.08(m, 3H), 2.17(s, 3H), 2.37(m, 1H), 3.18(t, 2H), 3.32(m, 4H), 3.72(m, 2H), 4.25(m, 2H), 5.41(d, 1H), 5.78(s, 1H), 5.86(s, 1H), 5.97(s, 1H), 6.7(s, 1H), 7.44(m, 1H), 7.92(m, 2H), 8.65(d, 2H), 11.5(br s, 1H) | 517 |
| 226 | Example 96 and ethanol Sub-method a | S-4-(5-Methyl-1H-pyrazol-3-ylamino)-6-ethoxy-2-[2-{3-(pyrid-2-yl)isoxazol-5-yl}pyrrolidin-1-yl]pyrimidine | 1.2(t, 3H), 2.09(m, 3H), 2.17(s, 3H), 2.38(m, 1H), 3.72(m, 2H), 4.19(q, 2H), 5.39(d, 1H), 5.75(s, 1H), 5.97(s, 1H), 6.68(s, 1H), 7.45(m, 1H), 7.91(m, 2H), 8.57(s, 1H), 8.65(d, 1H), 11.46(br s, 1H) | 433 |
| 227 | Example 96 and (2R)-1,2-propane diol Sub-method a | S-4-(5-Methyl-1H-pyrazol-3-ylamino)-6-hydroxy-2-[2-{3-(pyrid-2-yl)isoxazol-5-yl}pyrrolidin-1-yl]pyrimidine | 2.1(m, 3H), 2.18(s, 3H), 2.36(m, 1H), 3.62(m, 1H), 3.8(m, 1H), 5.45(s, 1H), 5.53(s, 1H), 5.84(s, 1H), 6.77(s, 1H), 7.47(m, 1H), 7.94(m, 2H), 8.34(s, 1H), 8.68(d, 1H) | 405 |
| 228 | Example 242 and 2-methoxyethanol | S-4-(5-Methyl-1H-pyrazol-3-ylamino)-6-(2-methoxyethoxy)-2-[2-{3-(thiazol-2-yl)isoxazol-5-yl}pyrrolidin-1-yl]pyrimidine | 2.07(m, 3H), 2.13(s, 3H), 2.37(m, 1H), 3.18(s, 3H), 3.48(m, 2H), 3.68(m, 1H), 3.75(m, 1H), 4.24(m, 2H), 5.37(d, 1H), 5.75(s, 1H), 5.93(s, 1H), 6.65(s, 1H), 7.81(s, 1H), 7.98(s, 1H), 8.6(s, 1H), 11.43(s, 1H) | 469 |
| 229 | Example 242 and ethylene glycol | S-4-(5-Methyl-1H-pyrazol-3-ylamino)-6-(2-hydroxyethoxy)-2-[2-{3-(thiazol-2-yl)isoxazol-5-yl}pyrrolidin-1- | 2.09(m, 3H), 2.17(s, 3H), 2.38(m, 1H), 3.61(m, 2H), 3.72(m, 2H), 4.17(m, 2H), 4.33(s, 1H), 5.4(d, 1H), 5.78(s, 1H), 5.94(s, 1H), | 455 |

-continued

| Ex No. | Starting material | Compound name | NMR (DMSO 373K+d4AcOH) | m/z (MH)+ |
|---|---|---|---|---|
| | | yl]pyrimidine | 6.68(s, 1H), 7.85(d, 1H), 7.99(d, 1H), 8.62(s, 1H), 11.48(s, 1H) | |
| 230 | Example 96 and (2R)-1,2-propanediol sub-method b | S-4-(5-Methyl-1H-pyrazol-3-ylamino)-6-[(2R)-2-hydroxyprop-1-yloxy]-2-[2-{3-(pyrid-2-yl)isoxazol-5-yl}pyrrolidin-1-yl]pyrimidine | 1.07(d, 3H), 2.09(m, 3H), 2.18(s, 3H), 2.38(m, 1H), 3.42(m, 1H), 3.71(m, 2H), 3.85-4.07(m, 2H), 4.3(d, 1H), 5.4(d, 1H), 5.76(br d, 1H), 5.94(s, 1H), 6.67(s, 1H), 7.43(m, 1H), 7.9(m, 2H), 8.6(s, 1H), 8.64(d, 1H), 11.45(br s, 1H) | 463 |
| 231 | Example 199 and 2-methoxyethanol Sub-method c | S-4-(5-Ethyl-1H-pyrazol-3-ylamino)-6-(2-methoxyethoxy)-2-[2-{3-(pyrazin-2-yl)isoxazol-5-yl}pyrrolidin-1-yl]pyrimidine | 1.18(t, 3H), 2.1(m, 3H), 2.4(m, 1H), 2.55(q, 2H), 3.21(s, 3H), 3.53(m, 2H), 3.73(m, 2H), 4.25(t, 2H), 5.41(d, 1H), 5.77(s, 1H), 6.0(s, 1H), 6.77(s, 1H), 8.65(s, 1H), 8.7(m, 2H), 9.16(s, 1H), 11.51(s, 1H) | 478 |
| 232 | Example 199 and Methanol Sub-method c | S-4-(5-Ethyl-1H-pyrazol-3-ylamino)-6-methoxy-2-[2-{3-(pyrazin-2-yl)isoxazol-5-yl}pyrrolidin-1-yl]pyrimidine | 1.2(t, 3H), 2.12(m, 3H), 2.42(m, 1H), 2.56(q, 2H), 3.75(s, 3H), 3.78(m, 2H), 5.47(d, 1H), 5.8(s, 1H), 6.02(s, 1H), 6.7(s, 1H), 8.66(s, 1H), 8.72(m, 2H), 9.16(s, 1H) | 434 |
| 233 | Example 243 and ethylene glycol Sub-method c | S-4-(5-Cyclopropyl-1H-pyrazol-3-ylamino)-6-(2-hydroxyethoxy)-2-[2-{3-(thiazol-2-yl)isoxazol-5-yl}pyrrolidin-1-yl]pyrimidine | 0.64(d, 2H), 0.87(d, 2H), 1.82(m, 1H), 2.07(m, 3H), 2.38(m, 1H), 3.62(m, 2H), 3.71(m, 2H), 4.15(m, 2H), 4.33(t, 1H), 5.4(d, 1H), 5.75(s, 1H), 5.9(s, 1H), 6.67(s, 1H), 7.83(d, 1H), 7.98(d, 1H), 8.64(s, 1H), 11.55(s, 1H) | 481 |

Sub-methods
a. Reaction quenched with glacial acetic acid mixture purified directly by hplc.
b. Reaction quenched with glacial acetic acid, diluted with water then extracted with DCM, dried ($Na_2SO_4$), evaporated then purified by hplc.
c. Reaction quenched with saturated ammonium chloride solution then extracted with DCM, dried ($Na_2SO_4$), evaporated then purified by hplc.

Example 234

S-4-(5-Methyl-1H-pyrazol-3-ylamino)-6-(tetrahydropyran-4-yloxy)-2-[2-{3-(pyrid-2-yl)isoxazol-5-yl}pyrrolidin-1-yl]pyrimidine Cesium fluoride (681 mg, 3.5 mmol) and S-6-chloro-4-(5-methyl-1H-pyrazol-3-ylamino)-2-[2-{3-(pyrid-2-yl)isoxazol-5-yl}pyrrolidin-1-yl]pyrimidine (Example 96) (300 mg, 0.71 mmol) in tetrahydro-4-pyranol (3 ml) were heated at 200° C. in a sealed vessel under microwave irradiation for 2 hours. The reaction mixture was diluted with water and extracted with DCM. The extracts were combined, washed with brine, dried ($Na_2SO_4$) and the solvent removed by evaporation. The residue was purified by reverse phase HPLC using a C18 column eluting with water/acetonitrile/TFA (70:30:0.2 decreasing in polarity to 30:70:0.2). Product containing fractions were poured onto a SCX-2 column and washed with methanol then eluted with 7N methanolic ammonia to elute the product. The solvent was removed by evaporation to give the title compound (107 mg, 31%).

NMR (DMSO): 1.41 (m, 1H), 1.61 (m, 2H), 1.94 (m, 1H), 2.05 (m, 3H), 2.17 (s, 3H), 2.35 (m, 1H), 3.29 (t, 1H), 3.44 (m, 1H), 3.65 (m, 2H), 3.8 (m, 2H), 4.96 (m, 1H), 5.33 (d, 1H), 5.7 (s, 1H), 5.96 (s, 1H), 6.65 (s, 1H), 7.4 (m, 1H), 7.84 (m, 1H), 7.91 (d, 1H), 8.61 (d, 1H); m/z 489 [MH]+.

Example 235

S-5-Fluoro-4-(5-methyl-1H-pyrazol-3-ylamino)-2-[2-{3-(thiazol-2-yl)isoxazol-5-yl}pyrrolidin-1-yl]pyrimidine A mixture of 2-chloro-4-(5-methyl-1H-pyrazol-3-ylamino)-5-fluoropyrimidine (Method 27(b)) (175 mg, 0.77 mmol), S-2-(3-(thiazol-2-yl)isoxazol-5-yl)pyrrolidine (Method 77) (187 mg, 0.85 mmol) and diisopropylethylamine (0.28 ml, 1.6 mmol) in 1-hexanol (3 ml) was heated at 130° C. for 48 hours. The solvent was removed by evaporation and the residue purified by column chromatography eluting with EtOAc/hexane (1:1 increasing in polarity to 2:1). The purified product was triturated with diethylether and collected by filtration to give the title compound (79 mg, 25%)

NMR (DMSO): 2.06 (m, 3H), 2.18 (s, 3H), 2.38 (m, 1H), 3.64 (m, 1H), 3.76 (m, 1H), 5.36 (d, 1H), 6.11 (s, 1H), 6.62 (s, 1H), 7.85 (d, 1H), 7.9 (d, 1H), 7.98 (d, 1H), 8.82 (br s, 1H), 11.64 (br s, 1H); m/z 413 [MH]+.

Examples 236 to 241

Examples 236 to 241 were prepared by an analogous method to that described in Example 235.

| Ex No. | Starting material | Compound name | NMR (DMSO 373K+d4AcOH) | m/z (MH)+ |
|---|---|---|---|---|
| 236 | Method 73 and 2,5-dichloro-4-(5-methyl-1H-pyrazol-3-ylamino)pyrimidine | S-5-Chloro-4-(5-methyl-1H-pyrazol-3-ylamino)-2-[2-{3-(thiazol-4-yl)isoxazol-5-yl}pyrrolidin-1-yl]pyrimidine | 2.09(m, 3H), 2.18(s, 3H), 2.35(m, 1H), 3.65(m, 1H), 3.75(m, 1H), 5.35(d, 1H), 6.17(s, 1H), 6.51(s, 1H), 7.95(s, 1H), 8.06(s, 1H), 9.04(s, 1H) | 429 |
| 237 | Method 77 and Method 69 | S-5-Fluoro-4-(5-ethyl-1H-pyrazol-3-ylamino)-2-[2-{3-(thiazol-2-yl)isoxazol-5-yl}pyrrolidin-1-yl]pyrimidine | 1.19(t, 3H), 2.09(m, 3H), 2.38(m, 1H), 2.58(q, 2H), 3.64(m, 1H), 3.75(m, 1H), 5.38(d, 1H), 6.17(s, 1H), 6.62(s, 1H), 7.85(d, 1H), 7.91(d, 1H), 7.98(d, 1H), 8.85(br s, 1H), 11.69(br s, 1H) | 427 |
| 238 | Method 77 and Method 26 | S-4-(5-Methyl-1H-pyrazol-3-ylamino)-2-[2-{3-(thiazol-2-yl)isoxazol-5-yl}pyrrolidin-1-yl]pyrimidine | 2.09(m, 3H), 2.17(s, 3H), 2.36(m, 1H), 3.66(m, 1H), 3.78(m, 1H), 5.43(d, 1H), 6.0(s, 1H), 6.29(d, 1H), 6.64(s, 1H), 7.77(d, 1H), 7.85(d, 1H), 7.95(d, 1H) | 395 |
| 239 | Method 77 and Method 65 Sub-method d | S-4-(5-Ethyl-1H-pyrazol-3-ylamino)-2-[2-{3-(thiazol-2-yl)isoxazol-5-yl}pyrrolidin-1-yl]pyrimidine | 1.18(t, 3H), 2.09(m, 3H), 2.3(m, 1H), 2.55(q, 2H), 3.68(m, 1H), 3.77(m, 1H), 5.43(d, 1H), 6.07(s, 1H), 6.3(s, 1H), 6.64(s, 1H), 7.86(m, 2H), 7.98(d, 1H), 8.92(s, 1H), 11.57(s, 1H) | 409 |
| 240 | Method 77 and Method 28 Sub-method d | S-4-(5-Cyclopropyl-1H-pyrazol-3-ylamino)-2-[2-{3-(thiazol-2-yl)isoxazol-5-yl}pyrrolidin-1-yl]pyrimidine | 0.65(d, 2H), 0.87(d, 2H), 1.85(m, 1H), 2.06(m, 3H), 2.37(m, 1H), 3.67(m, 2H), 5.43(d, 1H), 5.96(s, 1H), 6.27(s, 1H), 6.59(s, 1H), 7.82(m, 2H), 7.97(d, 1H), 8.89(s, 1H), 11.55(s, 1H) | 421 |
| 241 | Method 77 and Method 27 Sub-method d | S-4-(5-Cyclopropyl-1H-pyrazol-3-ylamino)-5-fluoro-2-[2-{3-(thiazol-2-yl)isoxazol-5-yl}pyrrolidin-1-yl]pyrimidine | 0.67(m, 2H), 0.88(m, 2H), 1.83(m, 1H), 2.08(m, 3H), 2.35(m, 1H), 3.64(m, 1H), 3.75(m, 1H), 5.38(d, 1H), 6.09(s, 1H), 6.61(s, 1H), 7.86(d, 1H), 7.91(d, 1H), 7.99(d, 1H), 8.83(s, 1H) | 439 |

Sub-method d. Crude product was purified by hplc, product containing fractions were poured onto a SCX-2 ion exchange column, eluted with methanol to remove neutral impurities and then with methanolic ammonia to elute the product.

Example 242

S-6-Chloro-4-(5-methyl-1H-pyrazol-3-ylamino)-2-[2-{3-(thiazol-2-yl)isoxazol-5-yl}pyrrolidin-1-yl]pyrimidine 2,6-Dichloro-4-(5-methyl-1H-pyrazol-3-ylamino)pyrimidine (Method 29) and S-2-(3-(thiazol-2-yl)isoxazol-5-yl)pyrrolidine (Method 77) were treated as described in Example 96. The crude product was purified by column chromatography on silica gel eluting with EtOAc/hexane (7:3). The purified product was triturated with diethylether and collected by filtration to give the title compound (0.89 g, 57%) as a white solid.

NMR (DMSO): 2.09 (m, 3H), 2.18 (s, 3H), 2.39 (m, 1H), 3.66 (m, 1H), 3.75 (m, 1H), 5.42 (d, 1H), 5.97 (s, 1H), 6.39 (s, 1H), 6.71 (s, 1H), 7.85 (d, 1H), 7.98 (d, 1H), 9.22 (s, 1H), 11.62 (s, 1H); m/z 429 [MH]+.

Example 243

S-6-Chloro-4-(5-cyclopropyl-1H-pyrazol-3-ylamino)-2-[2-{3-(thiazol-2-yl)isoxazol-5-yl}pyrrolidin-1-yl]pyrimidine 2,6-Dichloro-4-(5-cyclopropyl-1H-pyrazol-3-ylamino)pyrimidine (Method 57) and S-2-(3-(thiazol-2-yl)isoxazol-5-yl)pyrrolidine (Method 77) were treated as described in Example 242 to give the title compound (183 mg, 29%) as a white solid.

NMR (DMSO 373K+ d4AcOH): 0.65 (m, 2H), 0.88 (m, 2H), 1.8 (m, 1H), 2.04 (m, 2H), 2.13 (m, 1H), 2.37 (m, 1H), 3.65 (m, 1H), 3.72 (m, 1H), 5.42 (d, 1H), 5.94 (s, 1H), 6.38 (s, 1H), 6.67 (s, 1H), 7.81 (d, 1H), 7.97 (s, 1H); m/z 455 [MH]+.

Example 244

S-6-Morpholino-4-(5-methyl-1H-pyrazol-3-ylamino)-2-[2-{3-(thiazol-2-yl)isoxazol-5-yl}pyrrolidin-1-yl]pyrimidine S-6-Chloro-4-(5-methyl-1H-pyrazol-3-ylamino)-2-[2-{3-(thiazol-2-yl)isoxazol-5-yl}pyrrolidin-1-yl]pyrimidine (Example 242) (150 mg, 0.35 mmol) and morpholine (3 ml) were heated at 120° C. in a sealed vessel under microwave irradiation for 30 minutes. The reaction mixture was purified by reverse phase HPLC using a C18 column eluting with water/acetonitrile/TFA (97.5:2.5:0.2 decreasing in polarity to 60:40:0.2). Product containing fractions were poured on to a SCX-2 column, washed with methanol to elute neutral impurities then with 3.5N methanolic ammonia to elute the product. The solvent was removed by evaporation, the residue triturated with ether and collected by filtration to give the title compound (72 mg, 43%) as a cream solid.

NMR (DMSO): 2.07 (m, 3H), 2.16 (s, 3H), 2.37 (m, 1H), 3.35 (m, 4H), 3.57 (m, 4H), 3.71 (m, 2H), 5.37 (d, 1H), 5.75 (s, 1H), 5.94 (s, 1H), 6.64 (s, 1H), 7.85 (d, 1H), 7.99 (d, 1H), 8.34 (s, 1H), 11.42 (s, 1H); m/z 480 [MH]+.

Examples 245 to 248

Examples 245 to 248 were prepared by an analogous method to that described in Example 244.

| Ex No. | Starting material | Compound name | NMR (DMSO 373K+d4AcOH) | m/z (MH)+ |
|---|---|---|---|---|
| 245 | Example 199 and morpholine | S-6-Morpholino-4-(5-ethyl-1H-pyrazol-3-ylamino)-2-[2-{3-(pyrazin-2-yl)isoxazol-5-yl}pyrrolidin-1-yl]pyrimidine | 1.18(t, 3H), 2.07(m, 3H), 2.37(m, 1H), 2.53(q, 2H), 3.37(m, 4H), 3.58(m, 4H), 3.72(m, 2H), 5.41(d, 1H), 5.76(s, 1H), 5.98(s, 1H), 6.73(s, 1H), 8.35(s, 1H), 8.7(m, 2H), 9.14(s, 1H), 11.45(s, 1H) | 489 |
| 246 | Example 242 and 2-methoxyethylamine Sub-method e | S-6-(2-Methoxyethylamino)-4-(5-methyl-1H-pyrazol-3-ylamino)-2-[2-{3-(thiazol-2-yl)isoxazol-5-yl}pyrrolidin-1-yl]pyrimidine | 2.05(m, 3H), 2.15(s, 3H), 2.33(m, 1H), 2.68(s, 3H), 3.71(m, 2H), 5.4(d, 1H), 5.49(s, 1H), 5.83(s, 1H), 5.99(s, 1H), 6.65(s, 1H), 7.83(d, 1H), 7.97(d, 1H), 8.19(br s, 1H) | 424 |
| 247 | Example 242 and methylamine Sub-method f | S-6-Methylamino-4-(5-methyl-1H-pyrazol-3-ylamino)-2-[2-{3-(thiazol-2-yl)isoxazol-5-yl}pyrrolidin-1-yl]pyrimidine | 2.05(m, 3H), 2.14(s, 3H), 2.35(m, 1H), 3.19(s, 3H), 3.3(m, 4H), 3.69(m, 2H), 5.37(d, 1H), 5.54(s, 1H), 5.86(s, 1H), 6.62(s, 1H), 7.8(d, 1H), 7.95(d, 1H) | 468 |
| 248 | Example 242 and 1-methylpiperazine Sub-method g | S-6-(4-Methylpiperazin-1yl)-4-(5-methyl-1H-pyrazol-3-ylamino)-2-[2-{3-(thiazol-2-yl)isoxazol-5- | 2.05(m, 3H), 2.15(s, 3H), 2.26(m, 4H), 2.36(m, 1H), 3.37(m, 4H), 3.71(m, 2H), 5.35(d, 1H), 5.77(s, 1H), 5.94(s, 1H), 6.64(s, 1H), 7.85(d, | 493 |

-continued

| Ex No. | Starting material | Compound name | NMR (DMSO 373K+d4AcOH) | m/z (MH)+ |
|---|---|---|---|---|
| | | yl{pyrrolidin-1-yl]pyrimidine | 1H), 7.98(d, 1H), 8.26(br s, 1H) | |

Sub-Methods
e. Heated at 150 °C. for 90 minutes.
f. Methylamine solution in ethanol. Heated at 130 °C. for 90 minutes.
g. Reaction work-up:- diluted with water, extracted with EtOAc, dried ($Na_2SO_4$) and volatiles evaporated. The residue purified by column chromatography, on silica gel eluting with methanol/DCM/aqueous ammonia (5:95:0 and then 5:94:1).

Example 249

S-6-Methyl-4-(5-methyl-1H-pyrazol-3-ylamino)-2-[2-{3-(thiazol-2-yl)isoxazol-5-yl}pyrrolidin-1-yl]pyrimidine 2-Chloro-6-methyl-4-(5-methyl-1H-pyrazol-3-ylamino)-pyrimidine (Method 56) (200 mg, 0.89 mmol), S-2-(3-(thiazol-2-yl)isoxazol-5-yl)pyrrolidine (Method 77) (218 mg, 0.98 mmol) and N,N-diisopropylethylamine (0.37 ml, 2.1 mmol) were suspended in 1-hexanol (4 ml) and heated at 150 C in a sealed vessel under microwave irradiation for 3 hours. Reaction mixture was purified by reverse phase HPLC using a C18 column eluting with water/acetonitrile/TFA (97.5:2.5:0.2 decreasing in polarity to 60:40:0.2). Product containing fractions were poured onto a SCX-2 ion exchange column and washed with methanol to remove neutrals and then with 3.5N methanolic ammonia to elute product. The solvent was removed by evaporation, the residue triturated with ether and collected by filtration to give title compound (164 mg, 45%) as a white solid.

NMR (DMSO): 2.07 (m, 3H), 2.12 (s, 3H), 2.18 (s, 3H), 2.36 (m, 1H), 3.71 (m, 2H), 5.43 (d, 1H), 5.99 (s, 1H), 6.19 (s, 1H), 6.64 (s, 1H), 7.85 (d, 1H), 7.98 (d, 1H), 8.73 (s, 1H), 11.5 (s, 1H); m/z 409 [MH]+.

Example 250

S-6-[3-(Methylsulphonyl)propyl-1-oxy]-4-(5-methyl-1H-pyrazol-3-ylamino)-2-[2-{3-(pyrid-2-yl)isoxazol-5-yl}pyrrolidin-1-yl]pyrimidine A solution of potassium peroxymonosulphate, potassium hydrogen sulphate, potassium sulphate complex (oxone™) (227 mg, 0.37 mmol) in water (1.3 ml) was added dropwise to a stirred solution S-4-(5-methyl-1H-pyrazol-3-ylamino)-6-[3-(methylthio)prop-1-yloxy]-2-[2-{3-(pyrid-2-yl)isoxazol-5-yl}pyrrolidin-1-yl]pyrimidine (Example 222) (130 mg, 0.26 mmol) in THF (1.3 ml). The mixture was stirred at ambient temperature for 2 hours then diluted with water and adjusted to pH 8 with 1M aqueous potassium hydroxide solution. The mixture was extracted with ethyl acetate (×3) and the organic extracts were combined, washed with brine and dried ($Na_2SO_4$). The solvent was removed by evaporation and the residue was purified by reverse phase HPLC using a C18 column eluting with water/acetonitrile/TFA (70:30:0.2 decreasing in polarity to 30:70:0.2). Product containing fractions were poured onto a SCX-2 ion exchange column which was washed with methanol then eluted with 3.5N methanolic ammonia to elute the product. The solvent was removed by evaporation, the residue triturated with diethylether and collected by filtration to give the title compound (45 mg, 33%) as a cream solid.

NMR (DMSO): 2.09 (m, 5H), 2.17 (s, 3H), 2.37 (m, 1H), 2.94 (s, 3H), 3.13 (t, 2H), 3.72 (m, 2H), 4.28 (m, 2H), 5.4 (d, 1H), 5.78 (s, 1H), 5.95 (s, 1H), 6.7 (s, 1H), 7.44 (m, 1H), 7.92 (m, 2H), 8.66 (d, 2H), 11.5 (br s, 1H); m/z 525 [MH]+.

Example 251

S-6-(2-Methoxyethoxy)-2-{2-[3-(pyrazin-2-yl)isoxazol-5-yl]pyrrolidin-1-yl}-4-(5-cyclopropyl-1H-pyrazol-3-ylamino)pyrimidine S-6-Chloro-2-{2-[3-(pyrazin-2-yl)isoxazol-5-yl]pyrrolidin-1-yl}-4-(5-cyclopropyl-1H-pyrazol-3-ylamino)pyrimidine (Example 91) and 2-methoxyethanol were treated by analogous method to that described in Example 208 except that the crude product was purified by column chromatography on silica gel eluting with hexane/EtOAc (80:20 increasing in polarity to 0:100) to give the title compound (70 mg, 21%) a pale yellow powder.

NMR (DMSO-$d_6$+$d_4$-acetic acid at 100° C.): 0.65 (m, 2H), 0.85 (m, 2H), 1.85 (m, 1H), 2.00-2.15 (m, 3H), 2.40 (m, 1H), 3.20 (s, 3H), 3.50 (m, 2H), 3.70 (m, 1H), 3.75 (m, 1H), 4.25 (t, 2H), 5.40 (d, 1H), 5.55 (s, 1H), 5.70 (s, 1H), 5.90 (s, 1H), 6.70 (s, 1H), 8.65 (m, 2H), 9.10 (s, 1H); m/z 490 [MH]+.

Example 252

S-6-Chloro-2-{2-[3-(pyrimid-2-yl)isoxazol-5-yl]pyrrolidin-1-yl}-4-(5-ethyl-1H-pyrazol-3-ylamino)pyrimidine 2,6-Dichloro-4-(5-ethyl-1H-pyrazol-3-ylamino)pyrimidine (Method 72) and S-2-[3-(pyrimid-2-yl)isoxazol-5-yl]pyrrolidine (Method 66) were treated by an analogous method to that described in Example 161 to give the title compound (364 mg, 49%) as a white powder.

NMR (DMSO-$d_6$+$d_4$-acetic acid at 100° C.): 1.15 (m, 3H), 2.00-2.20 (m. 3H), 2.40 (m, 1H), 2.55 (m, 2H), 3.65 (m, 1H), 3.75 (m, 1H), 5.45 (d, 1H), 6.05 (br s, 1H), 6.47 (s, 1H), 6.70 (s, 1H), 7.48 (t, 1H), 8.85 (d, 2H); m/z 438 [MH]+.

Example 253

S-6-Methoxy-2-{2-[3-(pyrimid-2-yl)isoxazol-5-yl]pyrrolidin-1-yl}-4-(5-ethyl-1H-pyrazol-3-ylamino)pyrimidine S-6-Chloro-2-{2-[3-(pyrimid-2-yl)isoxazol-5-yl]pyrrolidin-1-yl}-4-(5-ethyl-1H-pyrazol-3-ylamino)pyrimidine (Example 252) was treated by an analogous method to that described in Example 94 to give the title compound (118 mg, 80%) as a pink powder.

NMR (DMSO-d$_6$+d$_4$-acetic acid at 100° C.): 1.15 (t, 3H), 2.00-2.15 (m, 3H), 2.35 (m, 1H), 2.55 (q, 2H), 3.70 (m, 4H), 3.75 (m, 1H), 5.40 (d, 1H), 5.55 (s, 1H), 6.67 (s, 1H), 7.45 (t, 1H), 8.85 (d, 2H); m/z 434 [MH]+.

Example 254

S-6-Ethyl-2-{2-[3-(pyrimid-2-yl)isoxazol-5-yl]pyrrolidin-1-yl}-4-(5-ethyl-1H-pyrazol-3-ylamino)pyrimidine A mixture of S-2-[3-(pyrimid-2-yl)isoxazol-5-yl]pyrrolidine (Method 66) (198 mg, 0.91 mmol), 6-ethyl-2-chloro-4-(5-ethyl-1H-pyrazol-3-ylamino)pyrimidine (Method 79) (210 mg, 0.83 mmol), and di-isopropylethylamine were heated in hexanol (4 ml) at 150° C. for 60 minutes under microwave irradiation. The crude reaction mixture was passed down a 10 g SCX column, eluting with methanol and then eluting the product with 2M methanolic ammonia and the solvent removed by evaporation. The residue was purified by column chromatography eluting with DCM/2M methanolic ammonia (100:0 increasing in polarity to 90:10) to give the title compound (78 mg, 22%) as a pale brown powder.

NMR (DMSO-d$_6$+d$_4$-acetic acid at 100° C.): 1.00-1.20 (m, 6H), 2.00-2.15 (m, 3H), 2.35-2.45 (m, 3H), 2.55 (q, 2H), 3.65-3.80 (m, 2H), 5.45 (d, 1H), 5.60 (s, 1H), 6.10 (s, 1H), 6.20 (s, 1H), 6.70 (s, 1H), 7.50 (t, 1H), 8.90 (d, 2H); m/z 432 [MH]+.

Example 255

S-6-Aminomethyl-2-{2-[3-(pyrimid-2-yl)isoxazol-5-yl]pyrrolidin-1-yl}-4-(5-ethyl-1H-pyrazol-3-ylamino)pyrimidine S-6-Chloro-2-{2-[3-(pyrimid-2-yl)isoxazol-5-yl]pyrrolidin-1-yl}-4-(5-ethyl-1H-pyrazol-3-ylamino)pyrimidine (Example 252) was treated by an analogous method to that described in Example 140 to give the title compound (20 mg, 13%) as a brown solid.

NMR (DMSO-d$_6$+d$_4$-acetic acid at 100° C.): 1.15 (t, 3H), 2.00-2.15 (m, 3H), 0.35 (m, 1H), 2.55 (q, 2H), 2.65 (s, 3H), 3.60-3.80 (m, 2H), 5.45 (d, 1H), 5.60 (s, 1H), 5.90 (s, 1H), 6.70 (s, 1H), 7.45 (, 1H), 8.85 (d, 2H); m/z 433 [MH]+.

Example 256

S-6-Ethyl-2-{2-[3-(pyrimid-2-yl)isoxazol-5-yl]pyrrolidin-1-yl}-4-(5-cyclopropyl-1H-pyrazol-3-ylamino)pyrimidine 6-Ethyl-2-chloro-4-(5-cyclopropyl-1H-pyrazol-3-ylamino)pyrimidine (Method 80) and S-2-[3-(pyrimid-2-yl)isoxazol-5-yl]pyrrolidine (Method 66) were treated by an analogous method to that described in Example 254 to give the title compound (230 mg, 68%) as a brown powder.

NMR (DMSO-d$_6$+d$_4$-acetic acid at 100° C.): 0.65 (m, 2H), 0.85 (m, 2H), 1.10 (t, 3H), 1.80 (m, 1H), 2.05 (m, 2H), 2.15 (m, 1H), 2.30-2.45 (m, 3H), 3.67 (m, 1H), 3.75 (m, 1H), 5.45 (dd, 1H), 5.55 (s, 1H), 5.95 (s, 1H), 6.15 (s, 1H), 7.48 (t, 1H), 8.85 (d, 2H); m/z 444 [MH]+.

Example 257

S-6-Cyclopropyl-2-{2-[3-(pyrimid-2-yl)isoxazol-5-yl]pyrrolidin-1-yl}-4-(5-cyclopropyl-1H-pyrazol-3-ylamino)pyrimidine 6-Cyclopropyl-2-chloro-4-(5-cyclopropyl-1H-pyrazol-3-ylamino)pyrimidine (Method 81) and S-2-[3-(pyrimid-2-yl)isoxazol-5-yl]pyrrolidine (Method 66) were treated by an analogous method to that described in Example 254 to give the title compound (89 mg, 27%) as a brown powder.

NMR (DMSO-d$_6$+d$_4$-acetic acid at 100° C.): 0.65-0.90 (m, 7H), 0.95 (m, 1H), 1.70 (m, 1H), 1.85 (m, 1H), 2.00-2.15 (m, 3H), 2.35 (m, 1H), 3.65 (m, 1H), 3.75 (m, 1H), 5.35 (dd, 1H), 5.65 (s, 1H), 6.00 (s, 1H), 6.20 (s, 1H), 6.65 (s, 1H), 7.50 (t, 1H), 8.90 (d, 1H); m/z 456 [MH]+.

Example 258

S-6-Cyclopropyl-2-{2-[3-(pyrimid-2-yl)isoxazol-5-yl]pyrrolidin-1-yl}-4-(5-ethyl-1H-pyrazol-3-ylamino)pyrimidine 6-Cyclopropyl-2-chloro-4-(5-ethyl-1H-pyrazol-3-ylamino)pyrimidine (Method 82) and S-2-[3-(pyrimid-2-yl)isoxazol-5-yl]pyrrolidine (Method 66) were treated by an analogous method to that described in Example 254 to give the title compound (80 mg, 49%) as a brown powder.

NMR (DMSO-d$_6$+d$_4$-acetic acid at 100° C.): 0.70-0.80 (m, 3H), 0.95 (m, 1H), 1.15 (t, 3H), 1.70 (m, 1H), 2.00-2.15 (m, 3H), 2.35 (m, 1H), 2.55 (q, 2H), 3.65 (m, H), 3.75 (m, 1H), 5.35 (dd, 1H), 5.60 (s, 1H), 6.05 (s, 1H), 6.20 (s, 1H), 6.65 (s, 1H), 7.45 (t, 1H), 8.90 (d, 2H); m/z 444 [MH]+.

Example 259

S-6-(2-Methoxyethoxy)-2-{2-[3-(pyrimid-2-yl)isoxazol-5-yl]pyrrolidin-1-yl}-4-(5-ethyl 1H-pyrazol-3-ylamino)pyrimidine S-6-Chloro-2-{2-[3-(pyrimid-2-yl)isoxazol-5-yl]pyrrolidin-1-yl}-4-(5-ethyl-1H-pyrazol-3-ylamino)pyrimidine (Example 252) and 2-methoxyethanol were treated by analogous method to that described in Example 208 except that the crude product was purified by column chromatography on silica gel eluting with DCM/2M methanolic ammonia (100:0 increasing in polarity to 95:5) to give the title compound (118 mg, 47%) as a white solid.

NMR (DMSO-d$_6$+d$_4$-acetic acid at 100° C.): 1.15 (t, 3H), 2.00-2.20 m, 3H), 2.40 (m, 1H), 2.55 (q, 2H), 3.20 (s, 3H), 3.50 (m, 2H), 3.65 (m, 1H), 3.75 (m, 1H), 4.25 (t, 2H), 5.40 (dd, 1H), 5.55 (s, 1H), 5.70 (s, 1H), 6.00 (s, 1H), 6.70 (s, 1H), 7.45 (t, 1H), 8.85 (d, 2H); m/Z 478 [MH]+.

Example 260

S-6-Methyl-2-{2-[3-(3-methoxypyrazin-2-yl)isoxazol-5-yl]pyrrolidin-1-yl}-4-(5-ethyl-1H-pyrazol-3-ylamino)pyrimidine A mixture of 2-chloro-6-methyl-4-(5-ethyl-1H-pyrazol-3-ylamino)pyrimidine (Method 83) (105 mg, 0.44 mmol), S-2-[3-(2-methoxypyrazin-3-yl)isoxazol-5-yl]pyrrolidine (Method 68) (120 mg, 0.49 mmol), diisopropylethylamine (0.12 ml, 0.69 mmol) and hexanol (3 ml) was heated at 150° C. in a sealed vessel under microwave irradiation for 1 hour. The crude reaction mixture was poured onto an isolute SCX-2 ion exchange column. The column was eluted with methanol to elute any neutrals, followed by 7M methanolic ammonia to elute the product. The solvent was removed by evaporation and the residue was purified by column chromatography on silica gel eluting with DCM/2M methanolic ammonia (100:0 increasing in polarity to 90:10) to give the title compound (86 mg, 44%) as a fawn solid.

NMR (DMSO-$d_6$ at 100° C.): 1.21 (t, 3H), 2.07 (m, 3H), 2.16 (s, 3H), 2.37 (m, 1H), 2.58 (q, 2H), 3.71(m, 2H), 4.01 (s, 3H), 5.50 (dd, 1H), 6.08 (s, 1H), 6.22 (s, 1H), 6.63 (s, 1H), 8.33 (s, 2H), 8.78 (br s, 1H), 11.51 (br s, 1H); m/z 449 [MH]+.

Example 261

S-6-Chloro-2-{2-[3-(3-methoxypyrazin-2-yl)isoxazol-5-yl]pyrrolidin-1-yl}-4-(5-ethyl-1H-pyrazol-3-ylamino)pyrimidine A mixture of 2,6-dichloro-4-(5-ethyl-1H-pyrazol-3-ylamino)pyrimidine (Method 72) (570 mg, 2.2 mmol), S-2-[3-(2-methoxypyrazin-3-yl)isoxazol-5-yl]pyrrolidine (Method 68) (600 mgs, 2.4 mmol), diisopropylethylamine (310 mg, 2.4 mmol) in 1-butanol (10 ml) was heated at 75° C. for 16 hours. The solvent was removed by evaporation and the residue was purified by column chromatography on silica gel eluting with hexane/EtOAc (80:20 increasing in polarity to 0:100) to give the title compound (450 mg, 44%) as a white foam.

NMR (DMSO-$d_6$ at 100° C.): 1.21 (t, 3H), 2.07 (m, 3H), 2.37 (m, 1H), 2.58 (q, 2H), 3.71(m, 2H), 4.01 (s, 3H), 5.50 (dd, 1H), 6.08 (s, 1H), 6.42 (s, 1H), 6.66 (s, 1H), 8.33 (s, 2H), 9.27 (s, 1H), 11.61 (s, 1H); m/z 469 [MH]+.

Example 262

S-6-Methyl-2-{2-[3-(3-methoxypyrazin-2-yl)isoxazol-5-yl]pyrrolidin-1-yl}-4-(5-cyclopropyl-1H-pyrazol-3-ylamino)pyrimidine 2-Chloro-6-methyl-4-(5-cyclopropyl-1H-pyrazol-3-ylamino)pyrimidine (Method 70) and S-2-[3-(2-methoxypyrazin-3-yl)isoxazol-5-yl]pyrrolidine (Method 68) were treated by an analogous method to that described in Example 260 to give the title compound (88 mg, 40%).

NMR (DMSO-$d_6$ at 100° C.): 0.68 (m, 2H), 0.89 (m, 2H), 1.89 (m, 1H), 2.07 (m, 3H), 2.18 (s, 3H), 2.37 (m, 1H), 3.71(m, 2H), 4.01 (s, 3H), 5.50 (dd, 1H), 5.97 (s, 1H), 6.17 (s, 1H), 6.66 (s, 1H), 8.33 (s, 2H), 8.72 (br s, 1H), 11.58 (br s, 1H); m/z 461 [MH]+.

Example 263

S-6-Morpholino-2-{2-[3-(3-methoxypyrazin-2-yl)isoxazol-5-yl]pyrrolidin-1-yl}-4-(5-ethyl-1H-pyrazol-3-ylamino)pyrimidine A mixture of S-6-chloro-2-{2-[3-(3-methoxypyrazin-2-yl)isoxazol-5-yl]pyrrolidin-1-yl}-4-(5-ethyl-1H-pyrazol-3-ylamino)pyrimidine (Example 261) (250 mg, 0.5 mmol) in morpholine (3 ml) was heated at 70° C. in a sealed vessel under microwave irradiation for 2 hours. The crude reaction mixture was purified by reverse phase HPLC using a C18 column eluting with water/acetonitrile/TFA (95:5:0.2 decreasing in polarity to 0:100:0.2). Product containing fractions were combined and passed through an isolute SCX-2 ion exchange column. The column was eluted with methanol to elute any neutrals, followed by 7M methanolic ammonia to elute the product. The solvent was removed by evaporation and the residue triturated hexane and collected by filtration to give the title compound (81 mg, 31%) as a white solid.

NMR (DMSO-$d_6$ at 100° C.): 1.20 (t, 3H), 2.07 (m, 3H), 2.37 (m, 1H), 2.58 (q, 2H), 3.39 (m, 4H), 3.59 (m, 4H), 3.71 (m, 2H), 4.01 (s, 3H), 5.44 (dd, 1H), 5.77 (br s, 1H), 6.01 (br s, 1H), 6.62 (s, 1H), 8.27 (s, 3H), 11.42 (br s, 1H); m/z 520 [MH]+.

Example 264

S-6-Morpholino-2-[2-{3-(3-hydroxypyrazin-2-yl) isoxazol-5-yl}pyrrolidin-1-yl]-4-(5-ethyl-1H-pyrazol-3-ylamino)-pyrimidine The title compound was isolated as a by-product from the preparation of Example 263 (30 mg, 11%).

NMR (DMSO-$d_6$ at 100° C.): 1.20 (t, 3H), 2.07 (m, 3H), 2.37 (m, 1H), 2.58 (q, 2H), 3.39 (m, 4H), 3.59 (m, 4H), 3.71 (m, 2H), 5.40 (dd, 1H), 5.81 (s, 1H), 6.03 (s, 1H), 6.71 (s, 1H), 7.58 (s, 2H), 8.31 (s, 1H), 11.42 (br s, 1H); m/z 505 [MH]+.

Example 265

S-6-Methyl-2-{2-[3-(2-methoxypyrid-3-yl)isoxazol-5-yl]pyrrolidin-1-yl}-4-(5-methyl-1H-pyrazol-3-ylamino)pyrimidine A mixture of 6-methyl-2-chloro-4-(5-methyl-1H-pyrazol-3-ylamino)pyrimidine (Method 56) (200 mg, 0.9 mmol), S-2-[3-(2-methoxypyrid-3-yl)isoxazol-5-yl]pyrrolidine (Method 64) (262 mg, 1.1 mmol) and diisopropylethylamine (0.22 ml, 1.25 mmol), in hexanol (5 ml) was heated at 150° C. in a sealed vessel under microwave irradiation for 105 minutes. The volatiles were removed by evaporation, the residue was dissolved in EtOAc, washed with water, dried (MgSO$_4$), and the solvent removed by evaporation. The residue was purified by column chromatography on silica gel eluting with EtOAc/hexane (1:1) to give the title compound (160 mg, 42%).

NMR (DMSO): 2.0-2.2 (m, 9H), 2.30-2.40 (m, 1H), 3.65-3.70 (m, 2H), 3.90 (s, 3H), 5.40 (dd, 1H), 6.0 (s, 1H), 6.19 (s, 1H), 6.60 (s, 1H), 7.10 (dd, 1H), 8.10 (dd, 1H), 8.25 (d, 1H), 8.70 (s, 1H), 11.45 (s, 1H); m/z 433 [MH]+.

Example 266

S-5-Fluoro-2-{2-[3-(2-methoxypyrid-3-yl)isoxazol-5-yl]pyrrolidin-1-yl}-4-(5-cyclopropyl-1H-pyrazol-3-ylamino)pyrimidine A mixture of 2-chloro-4-(5-cyclopropyl-1H-pyrazol-3-ylamino)-5-fluoropyrimidine (Method 27) (150 mg, 0.6 mmol), S-2-[3-(2-methoxypyrid-3-yl)isoxazol-5-yl]pyrrolidine (Method 64) (194 mg, 0.8 mmol), diisopropylethylamine (0.29 ml, 1.6 mmol) in hexanol (10 ml) was heated at 150° C. for 24 hours. The mixture was allowed to cool, the volatiles removed by evaporation, the residue dissolved in EtOAc, washed with water, dried (MgSO$_4$) and solvent removed by evaporation. The residue was purified by column chromatography on silica gel eluting with EtOAc/hexane (50:50 increasing in polarity to 70:30) to give the title compound (95 mg, 35%).

NMR (DMSO): 0.65 (m, 2H), 0.89 (m, 2H), 1.85 (s, 1H), 1.98-2.10 (m, 3H), 2.30-2.40 (m, 1H), 3.50-3.60 (m, 1H), 3.70-3.80 (m, 1H), 3.90 (s, 3H), 5.35 (d, 1H), 6.00 (s, 1H), 6.60 (s, 1H), 7.10 (dd, 1H), 7.90 (s, 1H), 8.20 (dd, 1H), 8.30 (d, 1H), 9.45 (s, 1H), 12.0 (s, 1H); m/z 463 [MH]+.

Example 267

S-5-Fluoro-4-(5-ethyl-1H-pyrazol-3-ylamino)-2-[2-[3-(2-methoxypyrid-3-yl)isoxazol-5-yl]pyrrolidin-1-yl]pyrimidine

2-Chloro-4-(5-ethyl-1H-pyrazol-3-ylamino)-5-fluoropyrimidine (Method 69) and S-2-[3-(2-methoxypyrid-3-yl)isoxazol-5-yl]pyrrolidine (Method 64) were treated by an analogous method to that described in Example 266 to give the title compound (67 mg, 24%).

NMR (DMSO): 1.40 (t, 3H), 2.02-2.20 (m, 3H), 2.32-2.40 (m, 1H), 2.50-2.60 (m, 2H), 3.63-3.70 (m, 1H), 3.73-3.80 (m, 1H), 3.95 (s, 3H), 5.38 (dd, 1H), 6.20 (s, 1H), 6.65 (s, 1H), 7.06 (dd, 1H), 7.90 (s, 1H), 8.10 (d, 1H), 8.28 (d, 1H), 8.80 (s, 1H), 11.70 (s, 1H); m/z 451 [MH]+.

Example 268

S-5-Fluoro-4-(5-Methyl-1H-pyrazol-3-ylamino)-2-[2-[3-(2-methoxypyrid-3-yl)isoxazol-5-yl]pyrrolidin-1-yl]pyrimidine

2-Chloro-4-(5-methyl-1H-pyrazol-3-ylamino)-5-fluoropyrimidine (Method 27(b)) and S-2-[3-(2-methoxypyrid-3-yl)isoxazol-5-yl]pyrrolidine (Method 64) were treated by an analogous method to that described in Example 266 to give the title compound (140 mg, 37%).

NMR (DMSO): 2.01-2.15 (m, 3H), 2.20 (s, 3H), 2.30-2.40 (m, 1H), 3.61-3.69 (m, 1H), 3.70-3.78 (m, 1H), 3.95 (s, 3H), 5.38 (d, 1H), 6.18 (s, 1H), 6.58 (s, 1H), 7.08 (dd, 1H), 7.90 (s, 1H), 8.10 (dd, 1H), 8.28 (d, 1H), 8.82 (s, 1H), 11.65 (s, 1H); m/z 437 [MH]+.

Example 269

S-6-Chloro-4-(5-cyclopropyl-1H-pyrazol-3-ylamino)-2-[2-[3-(2-methoxypyrid-3-yl)isoxazol-5-yl]pyrrolidin-1-yl]pyrimidine

A mixture of 2,6-dichloro-4-(5-cyclopropyl-1H-pyrazol-3-ylamino)pyrimidine (Method 57) (300 mg, 1.1 mmol), S-2-[3-(2-methoxypyrid-3-yl)isoxazol-5-yl]pyrrolidine (Method 64) (299 mg, 1.22 mmole), diisopropylethylamine (0.46 ml) in xylene (10 ml) was heated at 80° C. for 18 hours. The solvent was removed by evaporation, the residue dissolved in EtOAc, washed with water, dried (MgSO$_4$) and the solvent removed by evaporation. The residue was purified by column chromatography on silica gel eluting with EtOAc/hexane (45:55) to give the title compound (300 mg, 57%).

NMR (DMSO): 0.62-0.70 (m, 2H), 0.86-0.90 (m, 2H), 1.80-1.89 (m, 1H), 2.05-2.20 (m, 2H), 2.31-2.42 (m, 1H), 3.62-3.78 (m, 2H), 3.95 (s, 1H), 5.44 (dd, 1H), 6.00 (s, 1H), 6.39 (s, 1H), 6.65 (s, 1H), 7.08 (dd, 1H), 8.10 (d, 1H), 8.28 (dd, 1H), 9.25 (s, 1H); m/z 479 [MH]+.

Example 270

S-6-Chloro-4-(5-ethyl-1H-pyrazol-3-ylamino)-2-[2-[3-(2-methoxypyrid-3-yl)isoxazol-5-yl]pyrrolidin-1-yl]pyrimidine

2,6-Dichloro-4-(5-ethyl-1H-pyrazol-3-ylamino)pyrimidine (Method 72) and S-2-[3-(2-methoxypyrid-3-yl)isoxazol-5-yl]pyrrolidine (Method 64) were treated by an analogous method to that described in Example 269 to give the title compound (240 mg, 44%).

NMR (DMSO): 1.2 (t, 3H), 2.02-2.20 (m, 3H), 2.32-2.45 (m, 1H), 2.55 (q, 2H), 3.62-3.80 (m, 2H), 3.95 (s, 3H), 5.45 (dd, 1H), 6.08 (s, 1H), 6.40 (s, 1H), 6.65 (s, 1H), 7.09 (dd, 1H), 9.10 (d, 1H), 8.28 (d, 1H), 9.35 (s, 1H), 11.65 (s, 1H); m/z 467 [MH]+.

Example 271

S-6-Chloro-4-(5-methyl-1H-pyrazol-3-ylamino)-2-[2-[3-(2-methoxypyrid-3-yl)isoxazol-5-yl]pyrrolidin-1-yl]pyrimidine

2,6-Dichloro-4-(5-methyl-1H-pyrazol-3-ylamino)pyrimidine (Method 29) and S-2-[3-(2-methoxypyrid-3-yl)isoxazol-5-yl]pyrrolidine (Method 64) were treated by an analogous method to that described in Example 269 to give the title compound (240 mg, 44%). m/z 463 [MH]+.

Example 272

S-6-(2-Hydroxyethoxy)-4-(5-methyl-1H-pyrazol-3-ylamino)-2-[2-[3-(2-methoxypyrid-3-yl)isoxazol-5-yl]pyrrolidin-1-yl]pyrimidine

Sodium hydride (106 mg, 2.65 mmol) was added to ethylene glycol (4 ml) and the mixture stirred for 10 minutes. S-6-Chloro-4-(5-methyl-1H-pyrazol-3-ylamino)-2-[2-[3-(2-methoxypyrid-3-yl)isoxazol-5-yl]pyrrolidin-1-yl]pyrimidine (Example 271) (180 mg, 0.4 mmol) was added and mixture was heated at 150° C. in a sealed vessel under microwave irradiation for 30 minutes. The mixture was allowed to cool, diluted with aqueous ammonium chloride solution and extracted with EtOAc. The extracts were combined, dried (MgSO$_4$), and the solvent removed by evaporation. The residue was purified by column chromatography on silica gel eluting with EtOAc/hexane (50:50 increasing in polarity to 90:10) to give the title compound (60 mg, 32%).

NMR (DMSO): 2.01-2.18 (m, 3H), 2.14 (s, 3H), 2.35-2.42 (m, 1H), 3.64 (s, 2H), 3.68-3.77 (m, 2H), 3.96 (s, 3H), 4.10-4.18 (m, 1H), 4.19-4.28 (m, 1H), 4.34 (s, 1H), 5.41 (dd, 1H), 5.79 (s, 1H), 6.00 (s, 1H), 6.65 (s, 1H), 7.10 (dd, 1H), 8.10 (dd, 1H), 8.28 (d, 1H), 8.62 (s, 1H); m/z 479 [MH]+.

Example 273

S-6-(2-Hydroxyethoxy)-4-(5-cyclopropyl-1H-pyrazol-3-ylamino)-2-[2-[3-(2-methoxypyrid-3-yl)isoxazol-5-yl]pyrrolidin-1-yl]pyrimidine

S-6-Chloro-4-(5-cyclopropyl-1H-pyrazol-3-ylamino)-2-[2-[3-(2-methoxypyrid-3-yl)isoxazol-5-yl]pyrrolidin-1-yl]pyrimidine (Example 269) and ethylene glycol were treated by an analogous method to that described in Example 272 to give the title compound (50 mg, 20%).

NMR (DMSO): 0.62-0.70 (m, 2H), 0.82-0.90 (m, 2H), 1.30-1.35 (m, 1H), 1.81-1.90 (m, 1H), 2.05-2.20 (m, 2H), 2.37-2.45 (m, 1H), 3.45 (s, 2H), 3.59-3.65 (m, 1H), 3.65-3.75 (m, 1H), 3.95 (s, 3H), 4.14-4.25 (m, 2H), 4.35 (t, 1H), 5.40 (d, 1H), 5.75 (s, 1H), 5.91 (s, 1H), 6.62 (s, 1H), 7.10 (s, 1H), 7.70 (dd, 1H), 8.10 (dd, 1H), 8.25 (d, 1H), 8.60 (s, 1H), 11.55 (s, 1H); m/z 505 [MH]+.

Example 274

S-6-(2-Hydroxyethoxy)-4-(5-ethyl-1H-pyrazol-3-ylamino)-2-[2-[3-(2-methoxypyrid-3-yl)isoxazol-5-yl]pyrrolidin-1-yl]pyrimidine S-6-Chloro-4-(5-ethyl-1H-pyrazol-3-ylamino)-2-[2-[3-(2-methoxypyrid-3-yl)isoxazol-5-yl]pyrrolidin-1-yl]pyrimidine (Example 270) and ethylene glycol were treated by an analogous method to that described in Example 272 to give the title compound (37 mg, 16%).

NMR (DMSO): 1.15 (t, 3H), 2.02-2.18 (m, 3H), 2.32-2.42 (m, 1H), 3.60-3.65 (m, 2H), 3.68-3.77 (m, 2H), 3.96 (s, 3H), 4.10-4.18 (m, 1H), 4.18-4.25 (m, 1H), 4.33 (s, 1H), 5.40 (d, 1H), 5.80 (s, 1H), 6.00 (s, 1H), 6.61 (s, 1H), 7.08 (dd, 1H), 8.10 (d, 1H), 8.28 (d, 1H), 8.65 (s, 1H), 11.5 (s, 1H); m/z 493 [MH]+.

Example 275

S-6-Methyl-4-(5-ethyl-1H-pyrazol-3-ylamino)-2-[2-{3-(pyrimid-2-yl)isoxazol-5-yl}pyrrolidin-1-yl]pyrimidine 2-Chloro-6-methyl-4-(5-ethyl-1H-pyrazol-3-ylamino)pyrimidine (Method 83) and S-2-[3-(pyrimid-2-yl)isoxazol-5-yl]pyrrolidine (Method 66) were treated by an analogous method to that described in Example 260 to give the title compound (77 mg, 56%).

NMR (DMSO-$d_6$+$d_4$-acetic acid at 100° C.): 1.15 (t, 3H), 2.00-2.15 (m, 6H), 2.35 (m, 1H), 2.55 (q, 2H), 3.65 (m, 1H), 3.75 (m, 1H), 5.40 (dd, 1H), 5.60 (s, 1H), 6.05 (s, 1H), 6.20 (s, 1H), 6.65 (s, 1H), 7.40 (t, 1H), 8.90 (t, 2H); m/z 418 [MH]+.

Example 276

S-6-Methyl-4-(5-ethyl-1H-pyrazol-3-ylamino)-2-[2-{3-(pyrid-2-yl)isoxazol-5-yl}pyrrolidin-1-yl]pyrimidine 2-Chloro-6-methyl-4-(5-ethyl-1H-pyrazol-3-ylamino)pyrimidine (Method 83) and S-2-(3-(2-pyridyl)isoxazol-5-yl)pyrrolidine (Method 42) were treated by an analogous method to that described in Example 260 to give the title compound (134 mg, 51%).

NMR (DMSO-$d_6$ at 100° C.): 1.15 (t, 3H), 2.00-2.15 (m, 6H), 2.35 (m, 1H), 2.55 (q, 2H), 2.65-3.80 (m, 2H), 5.45 (dd, 1H), 6.05 (br s, 1H), 6.20 (br s, 1H), 6.65 (s, 1H), 7.40 (m, 1H), 7.90 (m, 2H), 8.65 (d, 1H), 8.70 (br s, 1H), 11.50 (br s, 1H); m/z 417 [MH]+.

Example 277

S-6-(3-Methoxypropyl)-2-{2-[3-(pyrid-2-yl)isoxazol-5-yl]pyrrolidin-1-yl}-4-(5-methyl-1H-pyrazol-3-ylamino)pyrimidine 2-Chloro-6-(3-methoxypropyl)-4-(5-methyl-1H-pyrazol-3-ylamino)pyrimidine (Method 87) and S-2-(3-(2-pyridyl)isoxazol-5-yl)pyrrolidine (Method 42) were treated as described in Example 249 to give the title compound (60 mg, 19%).

NMR (DMSO): 1.75-1.81 (m, 2H), 2.03-2.20 (m, 3H), 2.21 (s, 3H), 2.30-2.42 (m, 3H), 3.20 (s, 3H), 3.30 (t, 2H), 3.65-3.80 (m, 2H), 5.44 (dd, 1H), 6.01 (s, 1H), 6.18 (s, 1H), 6.65 (s, 1H), 7.43, (dd, 1H), 7.88-7.97 (m, 2H), 8.65 (d, 1H), 8.74 (s, 1H), 11.45 (s, 1H); m/z 461 [MH]+.

METHODS

Preparation of Starting Materials

The starting materials for the examples above are either commercially available or are readily prepared by standard methods from known materials. For example, the following reactions are an illustration, but not a limitation, of some of the starting materials used in the above reactions.

Methods 1 and 2

The following compounds were prepared by analogous method to that described for 3-methoxybenzaldehyde oxime in method 35 of WO 03/048133.

| Method | Starting material | Compound name | NMR (CDCl$_3$) | m/z (MH)+ |
|---|---|---|---|---|
| 1[a] | # | Cyclopropylcarboxaldehyde oxime | 0.60(m, 2H), 0.90(m, 2H), 1.60(m, 0.25H), 2.30(m, 0.75H), 6.05(d, 0.75H), 6.95(d, 0.25H), 8.60(br s, 0.25H), 9.00(br s, 0.75H) | n/a |
| 2[b] | # | Thiazol-2-ylcarboxaldehyde oxime | 7.75(d, 0.4H), 7.91(d, 0.4H), 7.97(d, 0.6H), 8.00(m, 1.2H), 8.33(s, 0.4H), 11.95(br s, 0.4H), 12.18(br s, 0.6H) | n/a |

[a] approximate 3:1 mixture of E/Z isomers
commercially available
[b] approximate 3:1 mixture of E/Z isomers

Method 3

5-(tert-Butoxycarbonylaminomethyl)-3-cyclopropyl-isoxazole

The title compound was prepared starting from cyclopropylcarboxaldehyde oxime (Method 1) by an analogous method to that described for Method 69 of WO 03/048133 and used without purification.

Method 4

5-(tert-Butoxycarbonylaminomethyl)-3-(thiazol-2-yl)isoxazole

The title compound was prepared starting from thiazol-2-ylcarboxaldehyde oxime (Method 2) in two steps by analogous methods to that described in Methods 22 and 43 of WO 03/048133.

NMR: 1.40 (s, 9H), 4.35 (d, 2H), 6.77 (s, 1H), 7.60 (br t, 1H), 7.98 (d, 1H), 8.07 (d, 1H); m/z 226 [MH–$C_4H_8$]+.

Method 5

5-Aminomethyl-3-cyclopropylisoxazole

Crude 5-(tert-butoxycarbonylaminomethyl)-3-cyclopropylisoxazole (Method 3) (37.4 g, 0.157 mol) and 3M hydrochloric acid (80 ml) in methanol (100 ml) was heated at 50° C. for 2 hours. The methanol was removed by evaporation and aqueous residue washed with DCM. The aqueous layer was adjusted to pH 12 by careful addition of 40% aqueous sodium hydroxide solution and then extracted with DCM (×4). The extracts were combined, washed with brine, then dried ($Na_2SO_4$) and the volatiles removed by evaporation to give the title compound (11.5 g, 53%) as oil.

NMR ($CDCl_3$): 0.80 (m, 2H), 1.00 (m, 2H), 2.00 (m, 1H), 3.90 (s, 2H), 5.78 (s, 1H); m/z 277 [2M+H]+.

Method 6

5-Aminomethyl-3-(thiazol-2-yl)isoxazole

The title compound was prepared starting from 5-(tert-butoxycarbonylaminomethyl)-3-(thiazol-2-yl)isoxazole (Method 4) by an analogous method to that described in Method 56 of W0 03/048133.

NMR: 4.41 (s, 2H), 7.14 (s, 1H), 8.03 (d, 1H), 8.11 (d, 1H), 8.62 (s, 3H); m/z 182 [MH]+.

Method 7

[3-(Pyridin-2-yl)isoxazol-5-yl]methyl[(1E)-phenyl-methylene]amine

Freshly distilled benzaldehyde (373 mg, 3.5 mmol) was added to a solution of 5-aminomethyl-3-(pyrid-2-yl)isoxazole (Method 70 of WO 03/048133) (0.614 mg, 3.5 mmol) in dry DCM (18 ml). 4 Å molecular sieve (1.75 g) was then added and the mixture stirred gently under nitrogen for 20 hours. The molecular sieve was removed by filtration and the filtrate evaporated. The residue was dissolved in toluene and the solution concentrated by evaporation. The product crystallised and was collected by filtration to give the title compound (900 mg, 97%).

NMR ($CDCl_3$): 4.97 (s, 2H), 6.87 (s, 1H), 7.32 (m, 1H), 7.43 (m, 3H), 7.77 (m, 3H), 8.06 (d, 1H), 8.44 (s, 1H), 8.67 (d, 1H); m/z 264 [MH]+.

Methods 8 to 11

Examples 8 to 11 were prepared using the same method as Example 7:—

| Method | Starting material | Compound name | NMR | m/z (MH)+ |
|---|---|---|---|---|
| 8 | # | (3-Methylisoxazol-5-yl)methyl[(1E)-phenylmethylene]amine | 2.20(s, 3H), 4.84(s, 2H), 6.28(s, 1H), 7.42-7.48(m, 3H), 7.78(dd, 2H), 8.50(s, 1H) | n/a |
| 9 | Method 5 | (3-Cyclopropylisoxazol-5-yl)methyl[(1E)-phenylmethylene]amine | $CDCl_3$ 0.80(m, 2H), 1.00(m, 2H), 2.00(m, 1H), 4.80(s, 2H), 5.85(s, 1H), 7.42(m, 2H), 7.78(dd, 2H), 8.38(s, 1H) | 227 |
| 10 | Method 6 | [3-(thiazol-2-yl)isoxazol-5-yl]methyl[(1E)-phenylmethylene]amine2- | 5.0(s, 2H), 6.95(s, 1H), 7.47(m, 3H), 7.77(m, 2H), 7.96(d, 1H), 8.05(d, 1H), 8.56(s, 1H) | n/a |
| 11 | 5-aminomethyl-3-(pyrid-3-yl)isoxazole ## | [3-(Pyridin-3-yl)isoxazol-5-yl]methyl[(1E)-phenylmethylene]amine | 4.97(s, 2H), 6.6(s, 1H), 7.43(m, 4H), 7.82(d, 2H), 8.15(d, 1H), 8.47(s, 1H), 8.67(d, 1H), 9.02(S, 1H) | n/a | described in Method 68 of WO03/048133
commercially available

Method 12

2-[3-(Pyrid-2-yl)isoxazol-5-yl]pyrrolidine n-Butyllithium (7.5 ml of a 1.82M solution in hexane, 13.74 mmol) was added to a solution of 2,2,6,6-tetramethylpiperidine (2.5 ml, 14.9 mmol) in THF (99 ml) stirred at −78° C. under nitrogen such that the temperature was maintained below −65° C. The solution was then stirred at −78° C. for 15 minutes. A solution of [3-(pyridin-2-yl)isoxazol-5-yl]methyl[(1E)-phenylmethylene]amine (Method 7) (3.0 g, 11.45 mmol) in dry THF (5 ml) was then added over 5 minutes, keeping the temperature at or below −70° C., and the mixture stirred at −78° C. for 15 minutes. 1-Chloro-3-iodopropane (1.53 ml, 14.31 mmol) was then added dropwise over 1 minute, the mixture was then stirred at −78° C. for 15 minutes, then allowed to warm to ambient temperature and stirred at ambient temperature for 18 hours. Diethyl ether, followed by water was added to the reaction mixture and the mixture stirred vigorously for 5 minutes. The layers were separated, the organic layer was washed with water and then brine, dried ($Na_2SO_4$), and evaporated to give the crude alkylated imine. This imine was directly dissolved in ethanol (24 ml) and 2 M hydrochloric acid (48 ml) added. The mixture was stirred 18 hours at ambient temperature. The ethanol was removed by evaporation and further water added and the aqueous layer washed with diethyl ether (×2). The aqueous solution was adjusted to pH 11.5 by addition of solid sodium carbonate and 40% aqueous sodium hydroxide solution near the end point. This aqueous solution was stirred for 2 hours at ambient temperature during this period additional 40% sodium hydroxide was added to maintain the solution at pH 11.5.

The resulting solution of crude product is purified by one of two process:—

Purification Process A

DCM (70 ml) and di-t-butyl dicarbonate (2.74 g, 12.57 mmol) were then added to the aqueous solution of crude product and the mixture stirred vigorously at ambient temperature for 2.5 hours. The layers were separated and the organic layer washed with water and then brine dried ($Na_2SO_4$), and the volatiles removed by evaporation. The residue was purified by column chromatography on a Biotage 40M silica cartridge eluting with DCM/EtOAc (93:7) to give 1-(tert-butoxycarbonyl)-2-[3-(pyrid-2-yl)isoxazol-5-yl]pyrrolidine (1.81 g, 50%) as a waxy solid.

NMR (Mixture of rotamers—peaks assigned to major rotamer): 1.24 (s, 9H), 1.95 (m, 3H), 2.28 (m, 1H), 3.35 (m, 1H), 3.5 (m, 1H), 5.0 (m, 1H), 6.76 (s, 1H), 7.5 (m, 1H), 7.97 (m, 2H), 8.68 (d, 1H); m/z 316 [MH]+.

1-(tert-butoxycarbonyl)-2-[3-(pyrid-2-yl)isoxazol-5-yl]pyrrolidine (0.56 g, 1.78 mmol) was stirred at ambient temperature in a mixture of ethanol (5 ml) and 2M hydrochloric acid (1.5 ml) for 18 hours and then heated at 60° C. for a further 2 hours. The reaction was concentrated by evaporation and water added. The solution was adjusted to pH 12.5 by addition of solid sodium carbonate and 40% aqueous sodium hydroxide solution near the end point. The aqueous solution was extracted with DCM (×4), the organic extracts combined, dried ($Na_2SO_4$) and evaporated to give the title compound (183 mg, 48%) as a brown oil.

NMR: 1.8 (m, 3H), 2.13 (m, 1H), 2.9 (t, 2H), 4.35 (t, 1H), 6.8 (s, 1H), 7.48 (t, 1H); 7.96 (m, 2H), 8.67 (d, 1H); m/z 216 [MH]+.

Purification Process B

The aqueous solution of crude product was extracted with DCM (×4) the organic extracts combined, dried ($Na_2SO_4$) and solvent removed by evaporation. The residue was purified by column chromatography on silica gel eluting with diethyl ether and then DCM/Methanol (100:0 increasing in polarity to 95:5) to give the title compound.

Methods 13 to 16a

Examples 13 to 16a were prepared using the same method as Example 12:—

| Method | Starting material | Compound name | NMR | m/z (MH)+ |
|---|---|---|---|---|
| 13[b,c] | Method 8 | 2-(3-Methylisoxazol-5-yl)pyrrolidine | 1.97-1.73(m, 3H), 2.02-2.12(m, 1H), 2.18(s, 3H), 2.82-2.90(m, 2H), 4.18-4.22(m, 1H), 6.14(s, 1H) | 153 |
| 14[b] | Method 9 | 2-(3-Cyclopropylisoxazol-5-yl)pyrrolidine | $CDCl_3$ 0.78(m, 2H), 0.98(m, 2H), 1.95(m, 4H), 2.15(m, 1H), 3.15(m, 2H), 4.25(m, 1H), 5.75(s, 1H) | 179 |
| 15[b] | Method 10 | 2-[3-(Thiazol-2-yl)isoxazol-5-yl]pyrrolidine | 1.75(m, 3H), 2.10(m, 1H), 2.89(t, 2H), 4.33(m, 1H), 6.78(s, 1H), 7.95(d, 1H), 8.03(d, 1H) | 222 |
| 16[a,d] | Method 11 | 2-[3-(Pyrid-3-yl)isoxazol-5-yl]pyrrolidine | 1.77(m, 3H), 2.1(m, 1H), 2.88(t, 2H), 4.35(m, 1H), 6.93(s, 1H), 7.5(t, 1H), 8.22(d, 1H), 8.65(d, 1H), 9.02(s, 1H) | 216 |
| 16(a)[b,e,f] | Method 7 | 2-[3-(Pyrid-2-yl)isoxazol-5-yl]piperidine | 1.43(m, 4H), 1.75(m, 1H), 1.93(m, 1H), 2.63(m, 2H), 2.95(d, 1H), | 230 |

| Method | Starting material | Compound name | NMR | m/z (MH)+ |
|--------|-------------------|---------------|-----|-----------|
| | | | 3.87(d, 1H), 6.8(s, 1H), 7.47(t, 1H), 7.93(m, 2H), 8.67(d, 1H) | |

[a] purified by purification process A
[b] purified by purification process B
[c] purified by chromatography eluting with diethyl ether and then DCM/Methanol (100:0 increasing in polarity to 90:10)
[d] prepared via 1-(tert-butoxycarbonyl)-2-[3-(pyrid-3-yl)isoxazol-5-yl]pyrrolidine - NMR (Mixture of rotamers - peaks assigned to major rotamer): 1.27(s, 9H), 1.93(m, 3H), 2.27(m, 1H), 3.35(m, 2H), 5.0(m, 1H), 7.0(s, 1H), 7.53(t, 1H), 8.23(d, 1H), 8.07(d, 1H), 9.05(s, 1H); m/z 316 [MH]+.
[f] prepared using 4-chloro-1-iodobutane
[e] prepared via 1-(tert-butoxycarbonyl)-2-[3-(pyrid-3-yl)isoxazol-5-yl]piperidine - NMR 1.36 (m, 11H), 1.62(m, 2H), 1.8(m, 1H), 2.17(d, 1H), 2.72(t, 1H), 3.92(d, 1H), 6.88(s, 1H), 7.47 (dd, 1H), 7.9(t, 1H), 8.0(d, 1H), 8.07(d, 1H); m/z 330 [MH]+.

Method 17

2-(3-Cyclopropylisoxazol-5-yl)pyrrolidine-1-carboximidamide

A mixture of 2-(3-cyclopropylisoxazol-5-yl)pyrrolidine (Method 14) (2.05 g, 11.5 mmol) and formamidinesulphonic acid (1.425 g, 11.5 mmol) in dry methanol (30 ml) was heated at 60° C. for 18 hours. The solvent was removed by evaporation and the residue dissolved in water. The aqueous solution was washed with water and then the water removed by evaporation. The residue was triturated with ether/DCM, the solid product was collected and dried under vacuum at 50° C. for 18 hours to give the title compound monosulphate salt (1.839 mg, 41%); m/z 221 [MH]+.

Method 18

2-[2-(3-Cyclopropylisoxazol-5-yl)pyrrolidin-1-yl]-4-hydroxy-6-methoxymethylpyrimidine Sodium bis-(trimethylsilyl)amide (3.65 ml of a 2M solution in THF, 7.3 mmol) was added to a solution of 2-(3-cyclopropylisoxazol-5-yl)pyrrolidine-1-carboximidamide mono sulphate (Method 17) (1.83 g, 6.09 mmol) and methyl 4-methoxyacetoacetate (0.867 ml, 6.7 mmol) in methanol (30 ml) and the mixture heated at reflux for 4 hours. The solvent was removed by evaporation and the residue purified by chromatography on silica gel eluting with DCM/Methanol (100:0 increasing in polarity to 95:5). The purified product was triturated with ether and the solid then recrystallised from methanol to give the title compound (565 mg, 29%) as white solid.

NMR (DMSO-$d_6$+$d_4$-acetic acid): 0.67 (m, 2H), 0.90 (m, 2H), 1.93 (m, 4H), 3.25 (s, 3H), 3.40 (m, 1H), 3.64 (m, 1H), 3.98 (dd, 2H), 5.24 (d, 1H), 5.61 (s, 1H), 5.95 (s, 1H); m/z 317 [MH]+.

Method 19

4-Chloro-2-[2-(3-cyclopropylisoxazol-5-yl)pyrrolidin-1-yl]-6-methoxymethylpyrimidine A mixture of 2-[2-(3-cyclopropylisoxazol-5-yl]pyrrolidin-1-yl]-4-hydroxy-6-methoxymethylpyrimidine (Method 18) (563 mg, 1.78 mmol) and phosphoryl chloride (1 ml, 10.7 mmol) was heated at reflux for 45 minutes. The volatiles were removed by evaporation, the residue dissolved in DCM, washed with saturated aqueous sodium hydrogen carbonate solution, dried ($Na_2SO_4$) and evaporated. The residue was purified by chromatography on silica gel eluting with DCM/diethyl ether (100:0 and then 80:20) to give the title compound (511 mg, 81%) as a yellow oil.

NMR: 0.67 (m, 2H), 0.95 (m, 2H), 1.95 (m, 4H), 2.25 (m, 1H), 3.30 (m, 3H), 3.52 (m, 1H), 3.65 (m, 1H), 4.30 (m, 2H), 5.25 (d, 1H), 6.00 (s, 1H), 6.70 (s, 1H); m/z 335 [MH]+.

Method 21

5-Aminomethyl-3-(tetrahydrofuran-3-yl)isoxazole

This compound was prepared by a method analogous to that described in Methods 3 and 5 using the appropriate starting materials.

NMR (DMSO): 1.88 (m, 3H), 2.25 (m, 1H), 3.44 (m, 1H), 3.62 (m, 1H), 3.7-3.82 (m, 4H), 3.96 (m, 1H), 6.25 (s, 1H); m/z 169 [MH]+.

Method 22

[3-(Tetrahydrofuran-3-yl)isoxazol-5-yl]methyl[(1E)-phenylmethylene]amine

This compound was prepared by a method analogous to that described in Method 7 starting from the compound of method 21.

NMR (DMSO): 1.99 (m, 1H), 2.25 (m, 1H), 3.45 (m, 1H), 3.65 (m, 1H), 3.8 (m, 2H), 3.96 (m, 1H), 4.85 (s, 2H), 6.37 (s, 1H), 7.47 (m, 3H), 7.75 (m, 2H), 8.51 (s, 1H).

Method 23

[3-(2-Methoxypyrid-3-yl)isoxazol-5-yl]methyl[(1E)-phenylmethylene]amine

This compound was prepared by a method analogous to that described in Method 7, starting from 5-aminomethyl-3-(2-methoxypyrid-3-yl)isoxazole (prepared as described in WO 03/048133).

NMR (DMSO): 4.02 (s, 3H), 4.95 (s, 2H), 6.8 (s, 1H), 7.0 (t, 1H), 7.45 (m, 2H), 7.8 (m, 2H), 8.24 (m, 2H), 8.45 (s, 1H); m/z 294 [MH]+.

Method 24

2-[3-(Tetrahydrofuran-3-yl)isoxazol-5-yl]pyrrolidine

This compound was prepared by a method analogous to that described in Method 12, starting from the compound of Method 22.

NMR (DMSO): 1.7 (m, 3H), 1.9-2.15 (m, 2H), 2.15 (m, 1H), 2.84 (m, 2H), 3.18 (br s, 1H), 3.45 (m, 1H), 3.62 (m, 1H), 3.78 (m, 2H), 3.97 (m, 2H), 4.2 (t, 1H), 6.04 (s, 1H).

Method 25

2-[3-(2-Methoxypyrid-3-yl)isoxazol-5-yl]pyrrolidine

This compound was prepared by a method analogous to that described in Method 12, starting from the compound of Method 23.

NMR (DMSO): 1.75 (m, 3H), 2.13 (m, 1H), 2.9 (m, 2H), 3.96 (s, 3H), 4.3 (t, 1H), 6.69 (s, 1H), 7.1 (t, 1H), 8.13 (d, 1H), 8.28 (d, 1H); m/z 246 [MH]+.

Method 26

2-Chloro-4-(5-methyl-1H-pyrazol-3-ylamino)pyrimidine

A mixture of 2,4-dichloropyrimidine (2.97 g, 20 mmol), 3-amino-5-methyl-1H-pyrazole (2.14 g, 22 mmol), and N,N-diisopropylethylamine (2.82 g, 22 mmol) in dry THF (75 ml) was stirred at 50° C. for 18 hours. The solvent was removed by evaporation, and the residue partitioned between DCM (75 ml) and water (50 ml). The resulting precipitate was collected by filtration washed with water and then ether, and dried under vacuum at 50° C. to give the title compound (1.08 g, 26%) as a colourless crystalline solid.

NMR (DMSO): 2.20 (s, 3H), 6.05 (s, 1H), 7.10 (d, 1H), 8.10 (d, 1H), 9.80 (br s, 1H), 11.85 (br s, 1H); m/z 210 [MH]+.

Methods 27, 27(b) and 28

The compounds of Methods 27, 27(b) and 28 were prepared by methods analogous to that described in Method 26 using the appropriate starting materials.

Method 27

2-Chloro-4-(5-cyclopropyl-1H-pyrazol-3-ylamino)-5-fluoropyrimidine

Yield: 546 mg, 23%.

NMR (DMSO): 0.7 (m, 2H), 0.93 (m, 2H), 1.9 (m, 2H), 6.22 (s, 1H), 8.2 (d, 1H), 10.3 (s, 1H), 12.2 (s, 1H); m/z 254 [MH]+.

Method 27(b)

2-Chloro-4-(5-methyl-1H-pyrazol-3-ylamino)-5-fluoropyrimidine

Yield: 3.02 g, 66%.

NMR (DMSO): 2.2 (s, 3H), 6.3 (s 1H), 8.2 (d, 1H), 10.3 (br s, 1H), 12.2 (br s, 1H); m/z 228 [MH]+.

Method 28

2-Chloro-4-(5-cyclopropyl-1H-pyrazol-3-ylamino)pyrimidine

Yield: 323 mg, 14%.

NMR (DMSO): 0.66 (m, 2H), 0.92 (m, 2H), 1.86 (m, 1H), 5.90 (br m 1H), 8.14 (d, 1H), 10.22 (br s, 1H), 12.14 (br s, 1H); m/z 236 [MH]+.

Method 29

2,6-Dichloro-4-(5-methyl-1H-pyrazol-3-ylamino)pyrimidine

A mixture of 2,4,6-trichloropyrimidine (1.0 g, 5.4 mmol), 3-amino-5-methyl-1H-pyrazole (0.53 g, 5.4 mmol), and sodium carbonate (0.57 g, 5.4 mmol) in ethanol (25 ml) was stirred at ambient temperature for 18 hours. Water was added and the resulting precipitate was collected by filtration washed with water and a small amount of methanol, and dried to give the title compound (1.15 g, 88%) as a colourless crystalline solid.

NMR (DMSO) 2.23 (s, 3H), 6.01 (s, 1H), 7.24 (s, 1H), 10.25 (br s, 1H), 11.9 (br s, 1H); m/z 244 [MH]+.

Method 30

4-Hydroxy-6-methyl-2-[2-{3-(pyrid-2-yl)isoxazol-5-yl}pyrrolidin-1-yl]pyrimidine A mixture of 4-hydroxy-6-methyl-2-thiomethylpyrimidine (362 mg, 2.3 mmol) and 2-[3-(2-pyridyl)isoxazol-5-yl]pyrrolidine (500 mg, 2.3 mmol) was placed under a nitrogen atmosphere and heated at 150° C. for 18 hours. The mixture was purified by chromatography on silica gel eluting with DCM/methanol (100:0 increasing in polarity to 96:4) to give the title compound (420 mg, 56%).

NMR (DMSO): 1.94-2.1 (m, 6H), 2.10-2.14 (m, 1H), 3.45 (q, 1H), 3.75 (q, 1H), 5.42-5.55 (m, 2H), 2.74 (s, 1H), 7.50 (t, 1H), 7.88-7.99 (m, 2H), 8.64 (d, 2H); m/z 324 [MH]+

Method 31

4-Hydroxy-6-methyl-2-[2-(3-methylisoxazol-5-yl)pyrrolidin-1-yl]pyrimidine

This compound was prepared by an analogous method to that described in Method 30 using the appropriate starting materials to give the title compound (270 mg, 81%).

NMR (DMSO): 1.84-2.0 (m, 6H), 2.16 (s, 3H), 2.20-2.28 (m, 1H), 3.38-3.45 (m, 1H), 3.62-3.72 (m, 1H), 5.39 (d, 1H), 5.54 (s, 1H), 6.10 (s, 1H); m/z 261 [MH]+.

Method 32

6-Ethyl-4-hydroxy-2-[2-{3-(pyrid-2-yl)isoxazol-5-yl}pyrrolidin-1-yl]pyrimidine A mixture of ethyl propionylacetate (350 mg, 2.4 mmol), 2-[3-(pyrid-2-yl)isoxazol-5-yl]pyrrolidine-1-carboximidamide trifluoroacetate salt (Method 38) (901 mg, 2.43 mmol), sodium methoxide (144 mg, 7.7 mmol), in butanol (10 ml) was heated at 120° C. for 18 hours. The mixture was allowed to cool and poured directly on to an isolute SCX2 ion exchange column. The column was eluted with DCM/methanol (4:1) to remove neutrals and then with 7M methanolic ammonia to elute the product. The solvent was evaporated and the residue purified by chromatography on silica gel eluting with DCM/methanol (98:2 increasing in polarity to 95:5) to give the title compound (360 mg, 46%).

NMR (DMSO): 0.99 (t, 3H), 2.0-2.1 (m, 3H), 2.2-2.3 (m, 3H), 3.48 (m, 1H), 3.74-3.80 (m, 1H), 5.43 (d, 1H), 5.49 (s, 1H), 6.76 (s, 1H), 7.48 (dd, 1H), 7.88-7.99 (m, 2H), 8.64 (d, 1H), 11.0 (s, 1H); m/z 338 [MH]+.

Methods 33 to 35

The compounds of Methods 33 to 35 were prepared by analogous methods to that described in Method 32 using the appropriate starting materials.

Method 33

4-Hydroxy-6-(3-methoxypropyl)-2-[2-{3-(pyrid-2-yl)isoxazol-5-yl}pyrrolidin-1-yl]pyrimidine Yield: 575 mg, 35%.
NMR (DMSO): 1.60-1.68 (m, 1H), 2.0-2.1 (m, 2H), 2.20-2.35 (m, 2H), 3.08 (s, 3H), 3.10-3.15 (m, 1H), 3.50 (q, 1H), 3.78 (t, 1H), 5.40 (d, 1H), 5.49 (s, 1H), 6.76 (s, 1H), 7.50 (dd, 1H), 7.89-7.99 (m, 2H), 8.64 (d, 1H), 11.10 (s, 1H); m/z 382 [MH]+.

Method 34

4-Hydroxy-6-(methoxymethyl)-2-[2-{3-(pyrid-2-yl)isoxazol-5-yl}pyrrolidin-1-yl]pyrimidine Yield: 1 g, 48%.
NMR (DMSO): 2.0-2.14 (m, 3H), 2.13-2.38 (m, 1H), 3.28 (s, 3H), 3.46 (q, 1H), 3.78 (t, 1H), 4.01 (q, 2H), 5.42 (d, 1H), 5.62 (s, 1H), 6.78 (s, 1H), 7.50 (dd, 1H), 7.9-8.0 (m, 2H), 8.64 (d, 1H); m/z 354 [MH]+.

Method 35

4-Hydroxy-6-(pent-3-en-1-yl)-2-[2-{3-(pyrid-2-yl)isoxazol-5-yl}pyrrolidin-1-yl]pyrimidine Yield: 1 g, 33%.
NMR (DMSO): 1.42 (s, 3H), 2.0-2.15 (m, 5H), 2.2-2.38 (m, 3H), 3.52 (q, 1H), 3.73-3.80 (m, 1H), 5.22 (s, 2H), 5.42 (d, 1H), 5.48 (s, 1H), 6.75 (s, 1H), 7.48 (dd, 1H), 7.89-7.99 (m, 2H), 8.63 (d, 1H), 11.05 (s, 1H); m/z 378 [MH]+.

Methods 35(a) to 37

The compounds of Methods 35(a) to 37 were prepared by analogous methods to that described in Method 30 using the appropriate starting materials.

Method 35(a)

4-Hydroxy-6-(methoxymethyl)-2-[2-{3-(pyrid-3-yl)isoxazol-5-yl}pyrrolidin-1-yl]pyrimidine Made using 4-hydroxy-6-methoxymethyl-2-methylthiopyrimidine as starting material.
Yield: 804 mg, 61%.
NMR (DMSO): 2.02 (m, 3H), 2.27 (m, 1H), 3.30 (s, 3H), 3.50 (m, 1H), 3.73 (m, 1H), 4.00 (q, 2H), 5.42 (d, 1H), 5.43 (d, 1H), 5.65 (s, 1H), 6.79 (s, 1H), 7.50 (dd, 1H), 8.22 (d, 1H), 8.65 (d, 1H), 9.02 (s, 1H); m/z 354 [MH]+.

Method 36

4-Hydroxy-6-methoxymethyl-2-[2-{3-(thiazol-2-yl)isoxazol-5-yl}pyrrolidin-1-yl]pyrimidine Made using 4-hydroxy-6-methoxymethyl-2-methylthiopyrimidine as starting material.
Yield: 451 mg, 31%.
NMR (DMSO): 2.04 (m, 3H), 2.28 (m, 1H), 3.25 (s, 3H), 3.47 (m, 2H), 3.75 (m, 1H), 4.0 (m, 1H), 5.41 (d, 1H), 5.62 (s, 1H), 6.8 (s, 1H), 7.95 (d, 1H), 8.02 (d, 1H); m/z 360 [MH]+.

Method 37

4-Hydroxy-2-[2-{3-(pyrid-2-yl)isoxazol-5-yl}pyrrolidin-1-yl]-6-trifluoromethylpyrimidine Made using 2-ethylthio-4-hydroxy-6-trifluoromethylpyrimidine as starting material.
Yield: 710 mg, 30%.
NMR (CDCl$_3$): 2.30 (m, 4H), 3.65 (m, 1H), 3.94 (m, 1H), 5.60 (m, 1H), 6.10 (s, 1H), 6.80 (s, 1H), 6.80 (s, 1H), 7.34 (t, 1H), 7.78 (t, 1H), 8.02 (d, 1H), 8.64 (d, 1H); m/z 378 [MH]+.

Method 38

2-[3-(Pyrid-2-yl)isoxazol-5-yl]pyrrolidine-1-carboximidamide (trifluoroacetate salt)

TFA (30 ml) was added to a cooled solution of N,N'-di(tert-butyloxycarbonyl)-2-[3-(pyrid-2-yl)isoxazol-5-yl]pyrrolidine-1-carboximidamide (Method 39) in DCM (150 ml) at 0° C. The mixture was stirred 0° C. for one hour, allowed to warm to ambient temperature and stirred for a further 18 hours. The volatiles were removed by evaporation and the residue triturated from DCM/ether/hexane. The product was collected by filtration to give the title compound (2.2 g, >100%).

NMR (DMSO): 1.9-2.2 (m,3H), 2.3-2.4 (m, 1H), 3.42 (q, 1H), 3.72 (t, 1H), 5.35 (d, 1H), 6.95 (s, 1H), 7.41 (s, 2H), 7.50 (t, 1H), 7.92-8.02 (m, 2H), 8.7(d, 1H); m/z 258 [MH]+.

Method 39

N,N'-Di(tertbutyloxycarbonyl)-2-[3-(pyrid-2-yl)isoxazol-5-yl]pyrrolidine-1-carboximidamide 2-[3-(Pyrid-2-yl)isoxazol-5-yl]pyrrolidine (Method 12) (1.5 g, 7 mmol) was added to a solution of N,N'-di(tertbutyloxycarbonyl)-N''-(trifluoromethylsulphonyl)guanidine (2.59 g, 6.6 mmol) and triethylamine (0.975 ml) in DCM and the mixture stirred at ambient temperature for 8 hours. The mixture was then washed with water, dried (MgSO$_4$) and the volatiles removed by evaporation. The residue was purified by chromatography on silica gel eluting with DCM/methanol (100:0 increasing in polarity to 98:2) to give the title compound (2.3 g, 70%).

NMR (DMSO): 1.32 (s, 18H), 1.9-2.1 (m, 3H), 2.25-2.35 (m, 1H), 3.41-3.50 (m, 1H), 3.72-3.80 (m, 1H), 5.41 (s, 1H), 6.79 (s, 1H), 7.50 (dd, 1H), 7.9-8.0 (m, 2H), 8.68 (d, 1H), 9.48 (s, 1H).

Method 40

S-2-(3-Methylisoxazol-5-yl)pyrrolidine n-Butyl lithium (6.29 ml of a 1.6M solution in hexanes, 10.1 mmol) was added to a solution of acetone oxime (368 mg, 5.0 mmol) in anhydrous THF (20 ml) under nitrogen cooled to −5° C. such that the reaction temperature was maintained below 0° C. On completion of addition the mixture was stirred at 0° C. for one hour. Then a solution of N-(tert-butoxycarbonyl)-L-proline N'-methoxy-N'-methylamide (1.0 g, 3.87 mmol) in anhydrous THF (30 ml) was added at such a rate to maintain reaction temperature below 0° C. On completion of addition the mixture was stirred at 0° C. for 3.5 hours. The reaction mixture was quenched with saturated aqueous ammonium chloride solution, the organic solvent was removed by evaporation and the aqueous residue extracted with dichloromethane. The extracts were combined and the solvent removed by evaporation. The residue was triturated with isohexane to give a solid intermediate oxime (617 mg). This oxime (617 mg, 2.28 mmol) and triethylamine (0.41 ml, 2.96 mmol) were dissolved in anhydrous THF (20 ml) and methanesulphonyl chloride (0.19 ml, 2.54 mmol) added at ambient temperature and the mixture stirred at ambient temperature for 30 minutes. The volatiles were removed by evaporation, the residue dissolved in water and extracted with dichloromethane. The extracts were combined and the solvent removed by evaporation to give the intermediate mesylate as an oil. This mesylate was added to 4M hydrogen chloride in 1,4-dioxane (15 ml, 90 mmol) and the mixture heated at reflux for 30 minutes. The mixture was allowed to cool and then poured on to a 50 g isolute SCX-2 ion exchange column. The column was eluted with methanol to elute any neutrals, followed by 7M methanolic ammonia to elute the product. The solvent was removed by evaporation and the residue purified by chromatography on silica gel eluting with DCM/methanol (100:0 increasing in polarity to 90:10) to give the title compound (273 mg, 46%) as an oil.

NMR (CDCl$_3$): 1.90 (m, 3H), 2.17 (m, 1H), 3.05 (m, 1H), 3.10 (m, 1H), 4.30 (m, 1H), 5.95 (s, 1H); m/z 153 [MH]+.

Method 41

S—N-tert-Butyloxycarbonyl-2-(3-(2-pyridyl)isoxazol-5-yl)pyrrolidine

A 13% solution of sodium hypochlorite in water (4.6 ml) was added over 2 hours to a vigorously stirred solution of S—N-tert-butoxycarbonyl-2-ethynylpyrrolidine (prepared as described in Bull. Soc. Chim. Fr. 1997, 134, 141-144 and J. Med. Chem. 1994, 37, 4455-4463) (1.0 g, 5.2 mmol) and pyrid-2-ylcarboxaldehyde oxime (577 mg, 4.72 mmol) in dichloromethane (15 ml) at −3° C. After the addition was complete, the reaction was stirred at 0° C. for 2.5 hours. The mixture was then diluted with water and dichloromethane and the layers partitioned and separated. The organic layer was washed in turn with water and brine, dried (Na$_2$SO$_4$) and the volatiles removed by evaporation. The residue was purified by chromatography on silica gel eluting with 10% isohexane/ethyl acetate (90:10 increasing in polarity to 75:25) to give the title compound (0.69 g, 47%) as a waxy solid.

NMR (DMSO) (Major rotamer): 1.4 (s, 9H), 1.95 (m, 3H), 2.28 (m, 1H), 3.35 (m, 1H), 3.5 (m, 1H), 5.0 (s, 1H), 6.76 (s, 1H), 7.5 (m, 1H), 7.97 (m, 2H), 8.68 (d, 1H); m/z 316 [MH]+. Rotation α$_D$=−104.8 (c=1.0, methanol).

Method 42

S-2-(3-(2-Pyridyl)isoxazol-5-yl)pyrrolidine

Trifluoroacetic acid (2.3 ml) was added over 10 minutes to a stirred solution of S—N-tert-butyloxycarbonyl-2-(3-(2-pyridyl)isoxazol-5-yl)pyrrolidine (Method 41) (0.744 g, 2.36 mmol) in dichloromethane (12 ml) at 0° C. The reaction was stirred at 0° C. for 1 hour and then at ambient temperature for 18 hours. The volatiles were removed by evaporation and the residue dissolved in distilled water (23 ml). The solution was adjusted to pH 10.5 by careful addition of solid sodium carbonate and then 40% aqueous sodium hydroxide solution near the end point. The aqueous solution was the extracted with dichloromethane (×4), the organic extracts were combined, dried (Na$_2$SO$_4$) and the solvent removed by evaporation to give the title compound (0.446 g, 88%) as a gum.

NMR (DMSO): 1.8 (m, 3H), 2.13 (m, 1H), 2.9 (t, 2H), 4.35 (t, 1H), 6.8 (s, 1H), 7.48 (t, 1H); 7.96 (m, 2H), 8.67 (d, 1H); m/z 216 [MH]+. Rotation α$_D$=−15.2 (c=1.0, methanol).

Method 43

2-{2-[3-(Pyrid-2-yl)isoxazol-5-yl]pyrrolidin-1-yl}-4-(5-methyl-1H-pyrazol-3-ylamino)pyrimidin-6-yl carboxylic acid A solution of 2-chloro-4-(5-methyl-1H-pyrazol-3-ylamino)pyrimidin-6-yl carboxylic acid sodium salt (Method 44) (58 mg, 0.21 mmol) and 2-[3-(pyrid-2-yl)isoxazol-5-yl]pyrrolidine (Method 12) (54 mg, 0.25 mmol) in water (4 ml) was heated at 110° C. for 18 hours. The solid product was isolated by filtration from the hot reaction mixture, washed with cold water and dried. The product was then triturated with diethyl ether to give the title compound (48.1 mg, 53%).

NMR (DMSO-d$_6$+d$_4$-acetic acid at 100° C.): 2.05 (m, 3H), 2.17 (s, 3H), 2.35 (m, 1H), 3.75 (m, 1H), 3.85 (m, 1H), 5.50 (dd, 1H), 6.07 (s, 1H), 6.70 (s, 1H), 6.88 (s, 1H), 7.40 (m, 1H), 7.85 (t, 1H), 7.95 (d, 1H), 8.65 (d, 1H); m/z 433 [MH]+.

Method 44

2-Chloro-4-(5-methyl-1H-pyrazol-3-ylamino)pyrimidin-6-yl carboxylic acid sodium salt A mixture of 2,4-dichloropyrimidin-6-yl carboxylic acid (Method 45) (528 mg, 2.73 mmol), 3-amino-5-methylpyrazole (279 mg, 2.87 mmol) and sodium carbonate (578 mg, 5.46 mmol) was heated in water (10 ml) at 50° C. for 18 hours. The mixture was allowed to cool and the product was collected by filtration, washed with water and dried to give the title compound (430 mg, 77%).

NMR (DMSO-d$_6$+d$_4$-acetic acid at 100° C.): 2.20 (s, 3H), 6.03 (s,1H), 7.28 (s, 1H); m/z 254 [MH]+.

Method 45

2,4-Dichloropyrimidine-6-carboxylic acid

A mixture of 2,4-dihydroxypyrimidine-6-carboxylic acid (50 g, 0.32 mol), phosphoryl chloride (298 ml, 3.2 mol) and N,N-dimethylaniline (44.7 ml, 0.35 mol) was heated at reflux for 5 hours. The mixture was allowed to cool, the volatiles were removed by evaporation and the residue poured into an ice-water mixture. The aqueous mixture was extracted with diethyl ether, treated with decolourising charcoal, filtered and the volatiles removed from the filtrate by evaporation. The residue was treated with hot iso-hexane, the insoluble material removed by filtration and solvent removed by evaporation of the filtrate to give the title compound. (29.05 g, 47.6%).

NMR (DMSO-$d_6$): 8.15 (s, 1H); m/z 191 [MH]–.

Method 46

1-tert-Butyloxy-2-(2-methyl-2H-tetrazol-5-yl)pyrrolidine

A mixture of 1-tert-butyloxy-2-(2H-tetrazol-5-yl)pyrrolidine (Method 47) (500 mg, 2.2 mmol), cesium carbonate (1.43 g, 4.4 mmol), methyl iodide (0.41 ml, 6.6 mmol) in acetonitrile (15 ml) was stirred at ambient temperature for 12 hours. The solution were decanted from the solid material and the solution then partitioned between water and ethyl acetate. The organics were separated, dried (MgSO$_4$) and the volatiles removed by evaporation. The residue was purified by chromatography on silica gel eluting with isohexane/ethyl acetate (100:0 increasing in polarity to 0:100) to give the title compound (175 mg, 33%) as a clear oil.

NMR (CDCl$_3$): 1.35 (d, 9H), 2.03 (m, 3H), 2.31 (m, 1H), 3.50 (m, 1H), 3.66 (m, 1H), 4.31 (s, 3H), 5.17 (m, 1H).

Method 47

1-tert-Butyloxy-2-(2H-tetrazol-5-yl)pyrrolidine

A mixture of tert-butyloxy-2-cyanopyrrolidine (3 g, 15.3 mmol), sodium azide (1.49 g, 23.0 mmol) and ammonium chloride (1.22 g, 23 mmol) in DMF (15 ml) were heated at 95° C. for 48 hours. The reaction was then partitioned between ethyl acetate and water. The organics were separated, dried (MgSO$_4$) and the volatiles removed by evaporation. The residue was triturated with diethyl ether and collected by filtration to give the title compound (0.79 g, 22%) as a white solid.

NMR (CDCl$_3$): 1.50 (s, 9H), 2.06 (m, 2H), 2.34 (m, 1H), 2.94 (m, 1H), 3.43 (m, 2H), 5.07 (dd, 1H).

Method 48

2,6-Dibromo-4-(5-methyl-1H-pyrazol-3-ylamino) pyrimidine

A mixture of 2,4,6-tribromopyrimidine (3.5 g, 11 mmol), 5-methyl-1H-pyrazole (1.077 g, 1 mmol), sodium carbonate (1 g) in ethanol (50 ml) was stirred at ambient temperature under nitrogen for 18 hours. The volatiles were removed by evaporation and the residue dissolved in DCM and the minimum methanol. The resulting solution was washed with water, dried (Na$_2$SO$_4$) and the solvent volume reduced by evaporation. The product precipitated and was collected by filtration to give the title compound (1.7 g, 47%).

NMR (DMSO): 2.20 (s, 3H), 5.80 (s, 1H), 7.92 (s, 1H); m/z 334 [MH]+.

Method 49

6-Bromo-4-(5-methyl-1H-pyrazol-3-ylamino)-2-(2-(3-(pyrid-2-yl)isoxazol-5-yl)pyrrolidine)pyrimidine A mixture of 2,6-dibromo-4-(5-methyl-1H-pyrazol-3-ylamino)pyrimidine (Method 48) (235 mg, 0.7 mmol), 2-(3-(2-pyridyl)isoxazol-5-yl)pyrrolidine (Method 12) (167 mg, 0.77 mmol) and DIPEA (0.272 ml, 1.55 mmol) in xylene (2.5 ml) was heated at 80° C. for 18 hours. The volatiles were removed by evaporation and the residue dissolved in ethyl acetate and the minimum methanol. The resulting solution was washed with water, dried (MgSO$_4$) and the solvent removed by evaporation. The residue was dissolved in the minimum DCM and stored at –10° C. for 18 hours. The resulting precipitate was collected by filtration to give the title compound (140 mg, 50%).

NMR (DMSO): 1.98-2.40 (m, 7H), 3.50-3.60 (m, 1H), 3.64-3.80 (m, 1H), 5.38 (d, 1H), 5.85 (s, 1H), 6.75 (s, 1H), 7.50 (t, 1H), 7.88-8.0 (m, 2H), 8.64 (s, 1H), 9.68 (s, 1H); m/z 468 [MH]+.

Method 50

S-2-{2-[3-(Pyrid-2-yl)isoxazol-5-yl]pyrrolidin-1-yl}-4-(5-methyl-1H-pyrazol-3-ylamino)pyrimidin-6-yl carboxylic acid 2-Chloro-4-(5-methyl-1H-pyrazol-3-ylamino)pyrimidin-6-yl carboxylic acid sodium salt (Method 44) and S-2-[3-(pyrid-2-yl)isoxazol-5-yl]pyrrolidine (Method 42) were treated as described in Method 43 to give the title compound.

NMR (DMSO-$d_6$+$d_4$-acetic acid at 100° C.): 2.05 (m, 3H), 2.17 (s, 3H), 2.35 (m, 1H), 3.75 (m, 1H), 3.85 (m, 1H), 5.50 (dd, 1H), 6.07 (s, 1H), 6.70 (s, 1H), 6.88 (s, 1H), 7.40 (m, 1H), 7.85 (t, 1H), 7.95 (d, 1H), 8.65 (d, 1H); m/z 433 [MH]+.

Method 51

6-[N-(Acetylamino)carbamoyl]-2-{2-[3-(pyrid-2-yl) isoxazol-5-yl]pyrrolidin-1-yl}-4-(2-acetyl-5-methyl-1H-pyrazol-3-ylamino)pyrimidine Acetyl chloride (0.28 ml, 3.94 mmol) was added to a mixture of 6-hydrazide-2-{2-[3-(pyrid-2-yl)isoxazol-5-yl]pyrrolidin-1-yl}-4-(5-methyl-1H-pyrazol-3-ylamino)pyrimidine (Example 77) (800 mg, 1.79 mmol) and triethylamine (0.6 ml, 4.13 mmol) in anhydrous THF (20 ml) at 0° C. The reaction was allowed to warm to ambient temperature and stirred for a further 1 hour. The volatiles were removed by evaporation and the residue triturated with water and collected by filtration to give the title compound (911 mg, 96%).

NMR (DMSO-$d_6$+$d_4$-acetic acid at 100° C.): 1.90 (s, 3H), 2.10 (m, 3H), 2.18 (s, 3H), 2.42 (m, 1H), 2.52 (s, 3H), 3.76 (m, 1H), 3.85 (m, 1H), 5.55 (dd, 1H), 6.50 (s, 1H), 6.70 (s, 1H), 7.05 (s, 1H), 7.38 (m, 1H), 7.85 (t, 1H), 7.92 (d, 1H), 8.61 (d, 1H); m/z 531 [MH]+.

Method 52

6-[(4-Methylphenylsulphonyloxy)methyl]-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine p-Toluenesulphonyl chloride (3.0 g, 15.7 mmol) was added to a mixture of 6-hydroxymethyl-2-{2-[3-(pyrid-2-yl)isoxazol-5-yl]pyrrolidin-1-yl}-4-(5-methyl-1H-pyrazol-3-ylamino)pyrimidine (Example 80) (3.13 g, 7.49 mmol), triethylamine (2.5 ml, 18 mmol) in anhydrous THF (50 ml). The resulting mixture was stirred at ambient temperature for 1 hour then heated at reflux for 4 hours. The volatiles were removed by evaporation and the residue dissolved in water and extracted with DCM. The organic extracts were combined and the solvent removed by evaporation. The residue was purification by chromatography on silica gel, eluting with DCM (100%) and then with diethylether (100%) to give the title compound (contaminated with 31% of the 6-chloromethyl derivative) (1.69 g, 31%).

NMR (DMSO-$d_6$+$d_4$-acetic acid at 100° C.): 2.10 (m, 3H), 2.20 (s, 3H), 2.29 (s, 3H), 2.35 (s, 3H), 2.38 (m, 1H), 3.70 (m, 1H), 3.75 (m, 1H), 4.40 (s, 2H), 5.45 (dd, 1H), 6.45 (s, 1H), 6.68 (s, 1H), 6.75 (s, 1H), 7.10 (d, 2H), 7.38 (d, 2H), 7.42 (m, 1H), 7.55 (d, 2H), 7.75 (d, 2H), 7.90 (m, 2H), 8.62 (d, 1H); m/z 727 [MH]+.

Method 53

S-6-Chloromethyl-2-{2-[3-(pyrid-2-yl)isoxazol-5-yl]pyrrolidin-1-yl}-4-(5-methyl-2-N-[4-methylphenylsulphonyl]-1H-pyrazol-3-ylamino)pyrimidine p-Toluenesulphonyl chloride (624 mg, 3.26 mmol) was added to a mixture of S-6-hydroxymethyl-2-{2-[3-(pyrid-2-yl)isoxazol-5-yl]pyrrolidin-1-yl}-4-(5-methyl-1H-pyrazol-3-ylamino)pyrimidine (Example 86) (570.4 mg, 1.36 mmol) and N,N-diisopropylethylamine (0.467 ml, 3.40 mmol) in anhydrous THF (20 ml). The mixture was stirred at ambient temperature for 1 hour then heated at reflux for 4 hours. The volatiles were removed by evaporation, the residue dissolved in water and extracted with DCM. The extracts were combined, the solvent removed by evaporation and the residue purified by chromatography on silica gel, eluting with dichloromethane (100%) and then diethylether (100%) to give the title compound (403 mg, 50%).

NMR (DMSO-$d_6$+$d_4$-acetic acid at 100° C.): 2.05 (m, 3H), 2.20 (s, 3H), 2.35 (s, 3H), 2.38 (m, 1H), 3.65 (m, 1H), 3.76 (m, 1H), 4.35 (s, 2H), 5.40 (dd, 1H), 6.43 (s, 1H), 6.50 (s, 1H), 6.65 (s, 1H), 7.35 (d, 2H), 7.42 (m, 1H), 7.72 (d, 2H), 7.85 (t, 1H), 7.90 (m, 1H), 8.62 (d, 1H); m/z 591 [MH]+.

Method 54

Pyrazine-2-carboxaldehyde oxime

A 1N solution of lithium aluminium hydride in THF (73.8 ml, 73.8 mmol) was added to a suspension of methylpyrazine-2-carboxylate (20 g, 145 mmol) in anhydrous THF (300.0 ml) at −78° C. keeping the reaction temperature below −72° C. On completion of addition the reaction mixture was left to stir at −78° C. for a further 20 minutes and then quenched with glacial acetic acid (20.0 ml). The resulting mixture was warmed to room temperature and the volatiles removed by evaporation. The residue was dissolved in 3N hydrochloric acid (116 ml) and extracted with DCM. The extracts were combined, washed with saturated aqueous sodium hydrogen carbonate solution and the solvent evaporated. The residue was purified by chromatography on silica gel eluting with DCM/diethylether (100:0 then 80:20 and then 0:100) to give pyrazine-2-carboxaldehyde (15.67 g, 100%). This was immediately dissolved in chloroform (200 ml) cooled to 0° C. and hydroxylamine mono-hydrochloride (11.02 g, 159.5 mmol) and triethylamine (24.2 ml, 117.4 mmol) were added. The reaction mixture was then stirred at ambient temperature for 0.5 hour, and the solvent removed by evaporation. The residue suspended in diethylether (500 ml) and the insolubles removed by filtration. The filtrate was evaporated and the residue purified by chromatography eluting with DCM/diethylether (100:0 then 80:20 and then 0:100) to give the title compound (5.5 g, 31%) as a solid.

NMR (DMSO-$d_6$): 8.15 (s, 1H), 8.62 (dd, 2H), 8.99 (s, 1H).

Method 55

S-2-[3-(2-Pyrazinyl)isoxazol-5-yl]pyrrolidine

A 13% solution of sodium hypochlorite in water (5.95 ml, 12.51 mmol) was added to a mixture of S—N-tert-butoxycarbonyl-2-ethynlpyrrolidine (1.344 g, 6.88 mmol), pyrazine-2-carboxaldehyde oxime (770 mg, 6.26 mmol) and DCM (50 ml) keeping the reaction temperature below −3° C. The reaction mixture was then stirred at ambient temperature for 5 hours. Water was added and the organic layer separated and the solvent evaporated. The residue was dissolved in 4M hydrogen chloride in 1,4-dioxane (20 ml) and methanol (30 ml) the mixture heated at reflux for 1 hour. The mixture was allowed to cool, the volatiles were removed by evaporation, the residue dissolved in water and the solution adjusted to pH 12 with 10M aqueous sodium hydroxide solution. The aqueous mixture was extracted with DCM, the extracts combined and evaporated and the residue purified by chromatography on silica gel, eluting with DCM and then with diethylether/DCM (20:80) and finally with methanol/DCM (2:98 increasing in polarity to 10:90). The purified product was then triturated with diethylether and collected by filtration to give the title compound (344 mg, 25%).

NMR (DMSO-$d_6$): 1.78 (m, 3H), 2.17 (m, 1H), 4.38 (dd, 1H), 6.87 (s, 1H), 8.78 (dd, 2H), 9.21 (s, 1H); m/z 217 [MH]+.

Method 56

2-Chloro-6-methyl-4-(5-methyl-1H-pyrazol-3-ylamino)pyrimidine

Solid sodium carbonate (1.2 g, 11.3 mmol) was added to a solution of 2,4-dichloro-6-methylpyrimidine (1.7 g, 10.3 mmol) and 5-amino-3-methyl-1H-pyrazole (1.0 g, 10.3 mmol) in dry ethanol (50 ml) and the mixture heated and stirred at 42° C. for 3 days. The mixture was allowed to cool, the insoluble material was removed by filtration and the filter pad washed with ethanol (10 ml). The volatiles were removed from the filtrate by evaporation, keeping the bath temperature below 40° C. The residue was immediately purified by chromatography on silica gel eluting with methanol/DCM (5:95 increasing in polarity to 20:80) to give the title compound (758 mg, 33%) as a white solid.

NMR (CDCl$_3$): 2.17 (s, 3H), 2.11 (s, 3H), 5.88 (br s, 1H), 7.85 (br s, 1H), 8.80 (br s, 1H); m/z 224 [MH]+.

Method 57

2,6-Dichloro-4-(5-cyclopropyl-1H-pyrazol-3-ylamino)pyrimidine 2,4,6-Trichloropyrimidine and 3-amino-5-cyclopropyl-1H-pyrazole (Method 7 of WO 03/048133) were treated as described in Method 29 to give the title compound (12 g, 55%).

NMR (DMSO): 0.75 (m, 2H), 0.95 (m, 2H), 1.95 (m, 1H), 1.35 (m, 1H), 5.65 (br s, 1H), 7.70 (br s, 1H), 10.60 (s, 1H), 12.20 (s, 1H); m/z 270 [MH]+.

Method 58

3-(tert-Butoxycarbonylamino)prop-1-en-1-yl boronate[2,3-dihydroxy-2,3-dimethylbutane]ester Borane methyl sulphide complex (8.4 ml of a 2M solution in THF) was added dropwise to a solution of α-pinene (5.4 ml, 34 mmol) in THF (10 ml) at 0° C. and the mixture stirred for 1 hour. The mixture was allowed to warm to ambient temperature, stirred for 2 hours then cooled to 0° C. A solution of 3-(tert-butoxycarbonylamino)prop-1-yne (2.0 g, 13 mmol) in THF (5 ml) was then added slowly and the mixture stirred at ambient temperature for 18 hours. The mixture was cooled to 0° C. and acetaldehyde (14.3 ml, 0.25 mmol) was added dropwise. The mixture was stirred for 5 hours and then excess acetaldehyde and solvent were removed by evaporation. 2,3-Dihydroxy-2,3-dimethylbutane (2.4 g, 20 mmol) in heptane was added and the mixture stirred at ambient temperature for 18 hours. The mixture was washed with water, dried ($Na_2SO_4$) and the solvent evaporated. The residue was purified by column chromatography on silica gel eluting with EtOAc/hexane (10:90 increasing in polarity to 18:82) to give the title compound which was used directly.

Method 59

3-(N-Methylacetamido)prop-1-yne

Acetic anhydride (1.2 ml, 12.7 mmol) was added dropwise to a solution of N-methyl propargylamine (400 mg, 5.8 mmol) and 4-dimethylaminopyridine (70 mg, 0.67 mmol) in pyridine (15 ml). The mixture was stirred at ambient temperature for 18 hours and the solvent was removed by evaporation. The residue was dissolved in EtOAc, washed with water and dried ($MgSO_4$) and the solvent removed by evaporation. The residue was purified by chromatography on silica gel eluting with methanol/DCM (5:95 and then 10:90) to give the title compound (136 mg, 22%).
NMR (DMSO): 1.99 (s, 3H), 2.98 (s, 3H), 4.12 (s, 2H), 4.15 (s, 1H).

Method 60

S-6-[3-(N-Phthalimido)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine S-6-iodo-4-(5-methyl-1H-pyrazol-3-ylamino)-2-[2-{3-(pyrid-2-yl)isoxazol-5-yl}pyrrolidin-1-yl]pyrimidine (Example 98) and 3-(N-phthalimido)prop-1-yne were reacted by the method described for Example 105 to give the title compound (150 mg, 45%).
NMR (DMSO): 2.00-2.12 (m, 3H), 2.18 (s, 3H), 2.32-2.41 (m, 1H), 3.61-3.69 (m, 1H), 3.70-3.78 (m, 1H), 4.61 (s, 2H), 5.45 (s, 1H), 5.68 (s, 1H), 6.01 (s, 1H), 6.45 (s, 1H), 6.65 (s, 1H), 7.44 (dd, 1H), 7.84-7.96 (m, 7H), 8.65 (d, 1H), 9.05 (s, 1H), 11.55 (s, 1H); m/z 572 [MH]+.

Method 61

2-Chloropyrid-3-ylcarboxaldehyde oxime

A solution of hydroxylamine hydrochloride (533 mg, 7.6 mmol) in water (1.8 ml) was added dropwise to sodium hydroxide (708 mg, 17 mmol) in water (2 ml). The resulting solution was then added to a solution of 2-chloropyrid-3-ylcarboxaldehyde (1 g, 7 mmol) in ethanol (7 ml), water (7 ml) and ice (15 g). The mixture was stirred at ambient temperature for 18 hours. The mixture was neutralised to pH7 with 6M hydrochloric acid. The solid product was collected by filtration, washed with water and dried to give the title compound (800 mg, 73%).
NMR (DMSO): 7.45 (dd, 1H), 8.18 (dd, 1H), 8.32 (s, 1H), 8.42 (dd, 1H); m/z 157 [MH]+.

Method 62

S—N-(tert-Butoxycarbonyl)-2-[3-(2-chloropyrid-3-yl)isoxazol-5-yl]pyrrolidine

Sodium hypochlorite (5.3 ml of a 13% aqueous solution) was added dropwise to a vigorously stirred suspension of 2-chloropyrid-3-ylcarboxaldehyde oxime (Method 61) (800 mg, 5.1 mmol) and S—N-tert-butoxycarbonyl-2-ethynlpyrrolidine (prepared as described in Bull. Soc. Chim. Fr. 1997, 134, 141-144 and J. Med. Chem. 1994, 37, 4455-4463) (1.99 g, 10.2 mmol) in DCM (20 ml) at about 0 to 5° C. The mixture was allowed to warm and stirred at ambient temperature for 18 hours. The volatiles were removed by evaporation and the residue purified by chromatography on silica gel eluting with EtOAc/hexane (20:80) to give the title compound (955 mg, 54%).
NMR (DMSO): 1.22-1.42 (m, 9H), 1.95-2.0 (m, 3H), 2.22-2.38 (m, 1H), 3.30-3.40 (m, 1H), 3.43-3.55 (m, 1H), 5.0 (s, 1H), 6.78 (s, 1H), 7.58 (s, 1H), 8.12 (d, 1H), 8.55 (dd, 1H); m/z 350 [MH]+.

Method 63

S—N-(tert-Butoxycarbonyl)-2-[3-(2-methoxypyrid-3-yl)isoxazol-5-yl]pyrrolidine

A mixture of S—N-(tert-butoxycarbonyl)-2-[3-(2-chloropyrid-3-yl)isoxazol-5-yl]pyrrolidine (Method 62) (950 mg, 2.7 mmol) and sodium methoxide (740 mg, 13.7 mmol) in methanol (25 ml) was heated at reflux for 18 hours. The reaction mixture was allowed to cool, diluted with EtOAc. The solution was washed with water, dried ($Na_2SO_4$) and the solvent removed by evaporation. The residue was purified by chromatography on silica gel eluting with EtOAc/hexane (15:85) to give the title compound (675 mg, 72%).
NMR (DMSO): 1.22-1.42 (m, 2H), 1.88-2.0 (m, 3H), 2.22-2.34 (m, 1H), 3.34-3.42 (m, 1H), 3.42-3.53 (m, 1H), 3.95 (s, 3H), 4.98 (s, 1H), 6.67 (s, 1H), 7.12 (dd, 1H), 8.14 (dd, 1H), 8.30 (dd, 1H); m/z 346 [MH]+.

Method 64

S-2-[3-(2-Methoxypyrid-3-yl)isoxazol-5-yl]pyrrolidine

2M Hydrochloric acid (25 ml) was added to a solution of S—N-(tert-butoxycarbonyl)-2-[3-(2-methoxypyrid-3-yl)isoxazol-5-yl]pyrrolidine (Method 63) (670 mg, 2 mmol) in methanol (25 ml) and the mixture stirred at ambient temperature for 2.5 days. The mixture was concentrated by evaporation, adjusted to pH7 with 40% aqueous sodium hydroxide solution and extracted with DCM. The extracts were combined, dried ($MgSO_4$) and the solvent removed by evaporation to give the title compound (300 mg, 65%) as an oil.
NMR (DMSO): 1.70-1.82 (m, 3H), 1.98-2.07 (m, 1H), 2.86-2.91 (m, 2H), 3.96 (s, 3H), 4.29-4.38 (m, 1H), 6.70 (s, 1H), 7.10 (dd, 1H), 8.13 (dd, 1H), 8.28 (dd, 1H); m/z 246 [MH]+.

Method 65

4-(5-Ethyl-1H-pyrazol-3-ylamino)-2-chloropyrimidine

A mixture of 2,4-dichloropyrimidine (2.97 g, 20 mmol), 5-amino-3-ethyl-1H-pyrazole (2.44 g, 22 mmol) and N,N- diisopropylethylamine (3.8 ml, 22 mmol) in dry THF (75 ml) was heated at 60° C. for 18 hours. The volatiles were removed by evaporation, and the residue was triturated with a mixture of DCM and water. The solid product was collected by filtration, washed with water and ether, and dried to give the title compound (1.55 g, 35%) as a colourless crystalline solid.

NMR (DMSO): 1.20 (t, 3H), 2.60 (q, 2H), 6.06 (s, 1H), 7.15 (s, 1H), 8.10 (d, 1H), 9.80 (s, 1H), 11.83 (br s, 1H); m/z 224 [MH]+.

Method 66

S-2-[3-(Pyrimid-2-yl)isoxazol-5-yl]pyrrolidine

13% Aqueous sodium hypochlorite solution (4.25 ml, 7.45 mmol) was slowly added to a mixture of S—N-tert-butoxycarbonyl-2-ethynlpyrrolidine (prepared as described in Bull. Soc. Chim. Fr. 1997, 134, 141-144 and J. Med. Chem. 1994, 37, 4455-4463) (1.45 g, 7.45 mmol) and pyrimidine-2-carbaldehyde oxime (0.47 g, 3.82 mmol, Khimiya Geterotsiklicheskikh Soedinenii (1972), 10, 1422-4) in DCM (15 ml) cooled to 0° C. The reaction mixture was allowed to warm to ambient temperature and then stirred for 12 hours. The mixture diluted with ethyl acetate, the layers were separated the solvent was removed from the organic layer by evaporation. The residue was purified by column chromatography on silica gel eluting with EtOAc/hexane (0:100 increasingly in polarity to 100:0). The product fractions were evaporated to give a golden oil which solidified to a solid on standing (250 mgs, 20%). This solid was then dissolved in TFA (2 ml) and stirred at ambient temperature for 45 minutes. The reaction was evaporated to dryness and the residue dissolved in DCM and poured onto an isolute SCX-2 ion exchange column. The column was eluted with methanol to elute any neutrals, followed by 7M methanolic ammonia to elute the product. The product containing fractions were evaporated to give the title compound (125 mg, 15%) as an orange solid.

NMR (DMSO-$d_6$): 1.78 (m, 3H), 2.14 (m, 1H), 2.92 (t, 2H), 4.36 (t, 1H), 6.82 (s, 1H), 7.60 (t, 1H), 8.96 (d, 2H); m/z 217 [MH]+.

Method 67

3-Methoxypyrazine-2-carboxaldehyde oxime

A mixture of 3-methoxypyrazine-2-carboxaldehyde (Tetrahedron (1999), 56(2), 265-273) (2.1 g, 15 mmol), hydroxylamine hydrochloride (1.27 g, 18 mmol), ethanol (20 ml) and triethylamine (4.17 ml, 30 mmol) was heated at 60° C. for 90 minutes. The volatiles were removed by evaporation and residue was purified by column chromatography on silica gel eluting with hexane/EtOAc (100:0 increasing in polarity 0:100) to give the title compound (740 mg, 32%) as a white solid.

NMR (DMSO-$d_6$): 3.96 (s, 3H), 8.22 (s, 2H), 8.23 (m, 1H), 11.89 (s, 1H).

Method 68

S-2-[3-(2-Methoxypyrazin-3-yl)isoxazol-5-yl]pyrrolidine

Sodium hypochlorite (5.23 ml of a 13% aqueous solution, 9.16 mmol) was slowly added to a stirred mixture of S—N-tert-butoxycarbonyl-2-ethynylpyrrolidine (prepared as described in Bull. Soc. Chim. Fr. 1997, 134, 141-144 and J. Med. Chem. 1994, 37, 4455-4463) (1.07 g, 5.50 mmol), 3-methoxypyrazine-2-carboxaldehyde oxime (Method 67) (0.7 g, 4.58 mmol) in DCM (40 ml) cooled to 0° C. The reaction was allowed to warm to ambient temperature and then stirred for 12 hours. The layers were separated, the solvent removed from the organic layer and the residue purified by column chromatography on silica gel eluting with hexane/EtOAc (100:0 increasing in polarity 0:100). The purified product solidified to a solid on standing and was dissolved in TFA (10 ml) and the mixture stirred at ambient temperature for 30 minutes. The volatiles were removed by evaporation and the residue dissolved in DCM and poured onto an isolute SCX-2 ion exchange column. The column was eluted with methanol to elute any neutrals, followed by 7M methanolic ammonia to elute the product. The solvent was removed by evaporation to give the title compound (260 mgs, 23%) as a brown oil.

NMR (DMSO-$d_6$): 1.78 (m, 3H), 2.14 (m, 1H), 2.92 (t, 2H), 4.01 (s, 3H), 4.36 (dd, 1H), 6.78 (s, 1H), 8.36 (s, 2H); m/z 247 [MH]+.

Method 69

2-Chloro-4-(5-ethyl-1H-pyrazol-3-ylamino)-5-fluoropyrimidine

5-Amino-1H-3-ethylpyrazole and 2,4-dichloro-5-fluoropyrimidine were treated by the method described in Method 65 to give the title compound (1.89 g, 78%) as an off-white crystalline solid.

NMR (DMSO): 1.20 (t, 3H), 2.62 (q, 2H), 6.35 (s, 1H), 8.22 (d, 1H), 10.35 (s, 1H), 12.25 (br s, 1H); m/z 242 [MH]+.

Method 70

2-Chloro-6-methyl-4-(5-cyclopropyl-1H-pyrazol-3-ylamino)pyrimidine

Sodium carbonate (2.15 g, 20.25 mmol) was added to a stirred solution of 2,4-dichloro-6-methylpyrimidine (3 g, 18.4 mmol) and 3-amino-1H-5-cyclopropylpyrazole (2.25 g, 18.4 mmol) in dry ethanol (40 ml) and the mixture stirred at 40° C. for 4 days. The insoluble material was removed by filtration, the filter pad washed with ethanol. The volatiles were removed from the filtrate by evaporation keeping the bath below 40° C. The residue was immediately purified by column chromatography on silica gel eluting with methanol/DCM (0:100 increasing in polarity to 20:80) to give the title product (1.9 g, 46%) obtained as a white solid.

NMR (DMSO): 0.65 (m, 2H), 0.90 (m, 2H), 2.25 (s, 3H), 5.90 (br s, 1H), 7.05 (br s, 1H), 10.15 (br s, 1H), 12.10 (br s, 1H); m/z 250 [MH]+.

Method 71

4-Chloro-6-(3-hydroxypropyl)-2-{2-[3-(pyrid-2-yl)isoxazol-5-yl]pyrrolidin-1-yl}pyrimidine A solution of 2.5% w/v osmium tetroxide in tert-butanol (0.47 ml) was added to a vigorously stirred solution of 4-chloro-6-(pent-3-en-1-yl)-2-{2-[3-(pyrid-2-yl)isoxazol-5-yl]pyrrolidin-1-yl}pyrimidine (prepared as described in Example 34) in THF (10.5 ml) and water (2.8 ml). Solid sodium periodate (951 mg, 4.44 mmol) was then added. The reaction was stirred at ambient temperature for 2 hours. The reaction mixture was diluted with water and extracted with ethyl acetate. The ethyl acetate layer was washed with water and saturated brine, dried ($Na_2SO_4$), and the solvent removed by evaporation. The residue was dissolved in THF (13.5 ml) and distilled water (5.0 ml) and sodium borohydride (59 mg, 1.59 mmol) was added. The reaction was stirred at ambient temperature for 18 hours. The reaction mixture was diluted with ethyl acetate and water and the layers partitioned and separated. The ethyl acetate layer was washed with water and saturated brine, dried (Na$_2$SO$_4$) and the solvent removed by evaporation. The residue was purified by flash chromatography on silica gel eluting with methanol/DCM (1.5:98.5) to give the title compound (205 mg, 36%).

NMR (DMSO-d$_6$/300 MH): 1.67 (m, 2H), 2.06 (m, 3H), 2.42 (m, 3H), 3.35 (m, 2H), 3.58 (m, 1H), 3.78(m, 1H), 4.4 (d, 1H), 5.4 (d, 1H), 6.67(s, 1H), 6.73(s, 1H), 7.47 (t, 1H), 7.95 (m, 1H), 8.66 (d, 1H); m/z 386 [MH]+.

Method 72

2,6-Dichloro-4-(5-ethyl-1H-pyrazol-3-ylamino)pyrimidine 2,4,6-Trichloropyrimidine and 3-amino-5-ethyl-1H-pyrazole (Method 6 of WO 03/048133) were treated as described in Method 29 to give the title compound (2.48 g, 51%).

NMR (DMSO-d$_6$ at 100° C.): 1.2 (t, 3H), 2.6 (q, 2H), 6.0 (s, 1H), 7.3 (br s, 1H), 10.2 (br s, 1H), 12.0 (br s, 1H); m/z 259 [MH]+.

Method 73

S-2-(3-(Thiazol-4-yl)isoxazol-5-yl)pyrrolidine

S—N-tert-Butyloxycarbonyl-2-(3-(thiazol-4-yl)isoxazol-5-yl)pyrrolidine (Method 74) (334 mg, 1.04 mmol) was treated as described in Method 42 to give the title compound (217 mg, 94%) a yellow solid.

NMR (DMSO): 1.75 (m, 3H), 2.1 (m, 1H), 2.9 (t, 2H), 4.32 (t, 1H), 6.72 (s, 1H), 8.29 (s, 1H), 9.24 (s, 1H); m/z 222 [MH]+

Method 74

S—N-Tert-butyloxycarbonyl-2-(3-(thiazol-4-yl)isoxazol-5-yl)pyrrolidine

A solution of triethylamine (0.7 ml, 5.4 mmol) in THF (2 ml) was added dropwise to stirred solution of thiazole-4-chlorocarboxaldehyde oxime (Method 75) (730 mg, 4.5 mmol) and S—N-tert-butoxycarbonyl-2-ethynlpyrrolidine (prepared as described in Bull. Soc. Chim. Fr. 1997, 134, 141-144 and J. Med. Chem. 1994, 37, 4455-4463) (0.96 g, 4.95 mmol) in THF (20 ml) cooled to 0° C. The mixture was allowed to warm to ambient temperature and stirred for 18 hours. The solvent was removed by evaporation and the residue partitioned between DCM and water and insoluble material was removed by filtration. The layers were separated, the solvent removed from the organic layer and the residue purified by column chromatography on silica gel eluting with hexane/EtOAc (3:1 increasing in polarity 3:2) to give recovered acetylene (634 mg) and the title compound (334 mg, 23%) as a white solid.

NMR (DMSO): 1.25 (s, 5H), 1.38 (s, 4H), 1.93 (m, 3H), 2.26 (m, 1H), 3.37 (m, 1H), 3.48 (m, 1H), 5.0 (s, 1H), 6.71 (br d, 1H), 8.32 (s, 1H), 9.23 (s, 1H); m/z 344 [M+Na]+

Method 75

Thiazole-4-chlorocarboxaldehyde oxime

N-Chlorosuccinimide (600 mg, 4.5 mmol) was added to a solution of thiazole-4-carboxaldehyde oxime (Method 76) (579 mg, 4.5 mmol) in DMF (4 ml) cooled to 0° C. The reaction was stirred at 0° C. for 1 hour, allowed to warm to ambient temperature and stirred for a further 2 hours. The mixture was diluted with ether and water. The ether layer was separated washed with water and brine, the solid product was collected by filtration and the filtrate was dried (Na$_2$SO$_4$) and the solvent removed by evaporation to give solid product. The two batches of solid were combined to give the crude title compound (730 mg, 100%).

NMR (DMSO): 8.12 (s, 1H), 9.15 (s, 1H), 12.42 (s, 1H); m/z 163 [MH]+

Method 76

Thiazole-4-carboxaldehyde oxime

Thiazole-4-carboxaldehyde (Synthesis 1987, 998) was treated by the method described in Method 67 to give the title compound.

NMR (DMSO): 7.93 (s, 1H), 8.22 (s, 1H), 9.13 (s, 1H), 11.28 (s, 1H).

Method 77

S-2-(3-(Thiazol-2-yl)isoxazol-5-yl)pyrrolidine

3M Hydrochloric acid (26 ml) was added to a solution of S—N-tert-butyloxycarbonyl-2-(3-(thiazol-2-yl)isoxazol-5-yl)pyrrolidine (Method 78) (8.32 g, 26 mmol) in methanol (26 ml) and the mixture stirred at ambient temperature for 18 hours and then at 60° C. for 1 hour. The volatiles were removed by evaporation, the aqueous layer was washed with DCM, adjusted to pH 11-12 with 40% aqueous sodium hydroxide solution and extracted with DCM (x6). The extracts were combined, dried (Na$_2$SO$_4$) and the solvent removed by evaporation. The residue was purified by column chromatography on silica gel eluting with methanol/DCM (5:95) to give the title compound (4.01 g, 70%) as a yellow oil.

NMR (DMSO): 1.75 (m, 3H), 2.10 (m, 1H), 2.89 (t, 2H), 4.33 (m, 1H), 6.78 (s, 1H), 7.95(d, 1H), 8.03 (d, 1H); m/z 222 [MH]+.

Method 78

S—N-tert-Butyloxycarbonyl-2-(3-(thiazol-2-yl)isoxazol-5-yl)pyrrolidine

N-Chlorosuccinimide (10.6 g, 80 mmol) was added in portions to a solution of thiazole-2-carboxaldehyde oxime (Method 2) (10.35 g, 80 mmol) in DMF (30 ml) cooled to −5° C. The reaction was stirred at −5° C. for 1 hour, allowed to warm slowly to ambient temperature over 3 hours. The mixture was diluted with ether, EtOAc and water. The solid product was collected by filtration. The organic layer was separated washed with water and brine, dried (Na$_2$SO$_4$) and the solvent removed by evaporation, keeping the bath temperature at ambient temperature, to give solid product. The two batches of solid were combined and directly dissolved in THF (200 ml) and the solution added dropwise to a solution of S—N-tert-butoxycarbonyl-2-ethynlpyrrolidine (prepared as described in Bull. Soc. Chim. Fr. 1997, 134, 141-144 and J. Med. Chem. 1994, 37, 4455-4463) (31 g, 160 mmol) and triethylamine (13.4 ml, 96 mmol) in THF (200 ml) cooled to 0° C., the mixture was allowed to slowly warm to ambient temperature and stirred for 18 hours. The solvent was removed by evaporation, water added to the residue and the mixture extracted with DCM. The extracts were combined, washed with brine, dried ($Na_2SO_4$) and the solvent removed by evaporation. The residue was purified by column chromatography on silica gel eluting with EtOAc/hexane (1:4 increasing in polarity to 1:1) to elute first recovered starting acetylene and then to give the title compound (8.32 g, 32%) as an orange oil.

NMR (DMSO): 1.22 and 1.38 (2×br s, 9H), 1.85 (m, 3H), 2.15 (br m, 1H), 3.37 (m, 1H), 3.50 (m, 1H), 5.00 (br m, 1H), 6.78 and 6.83 (2×br s, 1H), 7.97 (d, 1H), 8.05 (d, 1H); m/z 266 [MH–$C_4H_9$]+.

Method 79

6-Ethyl-2-chloro-4-(5-ethyl-1H-pyrazol-3-ylamino)pyrimidine 2,4-Dichloro-6-ethyl-pyrimidine (J. Am. Chem. Soc. 1936, 58, 78) (1.33 g 7.53 mmol) was stirred in ethanol (50 ml) and 5-ethyl-1H-3-amino-pyrazole (Method 6 of WO 03/048133) (0.836 g, 7.53 mmol) was added followed by sodium carbonate (1.25 g) and the mixture stirred at 40° C. for 4 days then at 55° C. overnight. The insoluble inorganics were removed by filtration and solvent removed from the filtrate by evaporation. Water (100 ml) was added and the mixture extracted with EtOAc (3×50 ml). The extracts were combined and washed with water (50 ml), brine (50 ml), dried ($MgSO_4$) and solvent removed by evaporation. The residue was purified by column chromatography on silica gel eluting with hexane/EtOAc (100:0 increasing in polarity to 0:100) to give the title compound (210 mg, 11%) a white solid.

NMR (DMSO-$d_6$ at 100° C.): 1.20 (m, 6H), 2.50-2.70 (m, 4H), 6.05 (s, 1H), 7.05 (br s, 1H), 9.70 (br s, 1H), 11.85 (br s, 1H); m/z 252 [MH]+.

Method 80

6-Ethyl-2-chloro-4-(5-cyclopropyl-1H-pyrazol-3-ylamino)pyrimidine 2,4-Dichloro-6-ethyl-pyrimidine (J. Am. Chem. Soc. 1936, 58, 78) and 5-cyclopropyl-1H-3-amino-pyrazole (Method 7 of WO 03/048133) were treated by analogous that described in Method 79 to give the title compound (464 mg, 32%) as a yellow powder.

NMR (DMSO-$d_6$ at 100° C.): 0.65 (m, 2H), 0.90 (m, 2H), 1.15 (t, 3H), 1.90 (m, 1H), 2.55 (q, 2H), 5.95 (br s, 1H), 7.05 (br s, 1H), 9.70 (br s, 1H); m/z 264 [MH]+.

Method 81

6-Cyclopropyl-2-chloro-4-(5-cyclopropyl-1H-pyrazol-3-ylamino)pyrimidine 2,4-Dichloro-6-cyclopropylpyrimidine (Chem. Abs. 1969, 71, 61412y) and 5-cyclopropyl-1H-3-amino-pyrazole (Method 7 of WO 03/048133) were treated by an analogous method to that described in Method 79 to give the title compound (200 mg, 23%) as a pink solid.

NMR (DMSO-$d_6$ at 100° C.): 0.85 (m, 2H), 0.95 (m, 6H), 1.90 (m, 2H), 5.90 (s, 1H), 7.05 (br s, 1H), 9.60 (br s, 1H), 11.90 (br s, 1H); m/z 276 [MH]+.

Method 82

6-Cyclopropyl-2-chloro-4-(5-ethyl-1H-pyrazol-3-ylamino)pyrimidine 2,4-Dichloro-6-cyclopropylpyrimidine (Chem. Abs. 1969, 71, 61412y) and 5-ethyl-1H-3-amino-pyrazole (Method 6 of WO 03/048133) were treated by an analogous method to that described in Method 79 to give the title compound (200 mg, 23%) as a pink solid.

NMR (DMSO-$d_6$ at 100° C.): 0.95 (m, 4H), 1.20 (t, 3H), 1.90 (m, 1H), 2.60 (q, 2H), 5.65 (s, 1H), 6.05 (br s, 1H), 7.05 (br s, 1H), 9.60 (br s, 1H), 11.85 (br s, 1H); m/z 264 [MH]+.

Method 83

2-Chloro-6-methyl-4-(5-ethyl-1H-pyrazol-3-ylamino)pyrimidine 2,4-dichloro-6-methylpyrimidine and 5-amino-3-ethyl-1H-pyrazole (Method 6 of WO 03/048133) were treated by an analogous method to that described in Method 56 to give the title compound (450 mg, 42%).

NMR (DMSO-$d_6$ at 100° C.): 1.20 (t, 3H), 2.25 (s, 1H), 3.60 (q, 2H), 6.05 (s, 1H), 7.00 (br s, 1H), 9.70 (br s, 1H), 11.85 (br s, 1H); m/z 238 [MH]+.

Method 84

4-Hydroxy-4-mercapto-6-(3-methoxypropyl)pyrimidine

A solution of methyl 6-methoxy-3-oxohexanoate (5.33 g, 30.6 mmol) in ethanol (20 ml) was added to a mixture of thiourea (3.29 g, 43.3 mmol) and sodium ethoxide in ethanol (22.4 ml of 21% wt/wt solution) heated at 80° C. and the mixture stirred at 75° C. for 18 hours. The volatiles were removed by evaporation and the residue was dissolved in water and the solution adjusted to pH 3 with 2M hydrochloric acid. The mixture was cooled in ice and the precipitated product collected by filtration and dried to give the title compound (2.52 g, 43%).

NMR (DMSO): 1.78 (q, 2H), 2.39 (t, 2H), 3.22 (s, 3H), 3.28 (q, 2H), 5.64 (s, 1H); m/z 201 [MH]+.

Method 85

2,4-Dihydroxy-6-(3-methoxypropyl)pyrimidine

A suspension of 4-hydroxy-4-mercapto-6-(3-methoxypropyl)pyrimidine (Method 84) (3.9 g, 19.5 mmol) and chloroacetic acid (1.89 g, 19.9 mmol) in water (20 ml) was heated at 120° C. for 24 hours. The mixture was allowed to cool, adjusted to pH7 with sodium hydroxide solution and extracted with EtOAc. The extracts were combined, dried ($Na_2SO_4$) and the solvent removed by evaporation to give the title compound (1.9 g, 55%) as a solid.

NMR (DMSO): 1.78 (q, 2H), 2.31 (t, 2H), 3.21 (s, 3H), 3.30 (q, 2H), 5.29 (s, 1H); m/z 185 [MH]+.

Method 86

2,4-Dichloro-6-(3-methoxypropyl)pyrimidine

A solution of 2,4-dihydroxy-6-(3-methoxypropyl)pyrimidine (Method 85) (1.9 g 10.2 mmol) and N,N-dimethylaniline (2 ml) in phosphoryl chloride (20 ml) was heated at 90° C. for 30 minutes. The mixture was allowed to cool, ice water was added and the mixture extracted with EtOAc. The extracts were combined, washed with 2M hydrochloric acid, dried (Na$_2$SO$_4$) and the solvent removed by evaporation. The residue was purified by column chromatography on silica gel eluting with hexane/EtOAc (50:50) to give the title compound (1.5 g, 68%).

NMR (DMSO): 1.88 (q, 2H), 2.78 (t, 2H), 3.21 (s, 3H), 3.32 (t, 2H), 7.72 (s, 1H); m/z 221 [MH]+.

Method 87

2-Chloro-6-(3-methoxypropyl)-4-(5-methyl-1H-pyrazol-3-ylamino)pyrimidine 2,4-Dichloro-6-(3-methoxypropyl)pyrimidine (Method 86) and 3-amino-1H-5-methylpyrazole were treated as described in Method 70 to give the title compound (200 mg, 32%).

NMR (DMSO): 1.88 (q, 2H), 2.20 (s, 3H), 2.59 (t, 2H), 3.21 (s, 3H), 3.32 (t, 2H), 3.38 (t, 2H), 6.05 (s, 1H), 7.04, (s, 1H), 9.65 (s, 1H), 11.80 (s, 1H); m/z 282 [MH]+.

Pharmacological Analysis

Methods for Detecting Inhibition Of Ipf-1r Kinase Activity and Downstream Signalling and Selectivity Over Insulin Receptor Kinase and Egfr Signalling Abbreviations Used:
PBS (PBS/T) is Phosphate buffered saline, pH7.4 (with 0.05% Tween 20)
HEPES is N-[2-Hydroxyethyl]piperazine-N-[2-ethanesulphonic acid]
DTT is dithiothreitol
TMB is tetramethyl benzidine
DMSO is dimethyl sulphoxide
BSA is bovine serum albumin
ATP is adenosine tri-phosphate
DMEM is Dulbecco's modified Eagle's Medium
FBS/FCS is foetal bovine/calf serum
HBSS is Hanks Balanced Salts Solution
HRP is horse-radish peroxidase
SDS is sodium dodecyl sulphate
IGF-I (IGF-1R) is insulin-like growth factor-I (IGF-1 receptor)
EGF is Epidermal growth factor IGF-1R Kinase Assay a) Protein Cloning, Expression and Purification A DNA molecule encoding a fusion protein containing glutathione-S-transferase (GST), thrombin cleavage site and IGF-1R intracellular domain (amino-acids 930-1367) and subsequently referred to as GST-IGFR, was constructed and cloned into pFastBac1 (Life Technologies Ltd, UK) using standard molecular biology techniques (Molecular Cloning—A Laboratory Manual, Second Edition 1989; Sambrook, Fritsch and Maniatis; Cold Spring Harbour Laboratory Press).

Production of recombinant virus was performed following the manufacturer's protocol.

Briefly, the pFastBac-1 vector containing GST-IGFR was transformed into *E. coli* DH10Bac cells containing the baculovirus genome (bacmid DNA) and via a transposition event in the cells, a region of the pFastBac vector containing gentamycin resistance gene and the GST-IGFR expression cassette including the baculovirus polyhedrin promoter was transposed directly into the bacmid DNA. By selection on gentamycin, kanamycin, tetracycline and X-gal, resultant white colonies should contain recombinant bacmid DNA encoding GST-IGFR. Bacmid DNA was extracted from a small scale culture of several BH10Bac white colonies and transfected into *Spodoptera frugiperda* Sf21 cells grown in TC100 medium (Life Technologies Ltd, UK) containing 10% serum using CellFECTIN reagent (Life Technologies Ltd, UK) following the manufacturer's instructions. Virus particles were harvested by collecting cell culture medium 72 hrs post transfection. 0.5 ml of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant GST-IGFR.

The GST-IGFR protein was purified by affinity chromatography on Glutathione-Sepharose followed by elution with glutathione. Briefly, cells were lysed in 50 mM HEPES pH 7.5 (Sigma, H3375), 200 mM NaCl (Sigma, S7653), Complete Protease Inhibitor cocktail (Roche, 1 873 580) and 1 mM DTT (Sigma, D9779), hereinafter referred to as lysis buffer. Clarified lysate supernatant was loaded through a chromatography column packed with Glutathione Sepharose (Amersham Pharmacia Biotech UK Ltd.). Contaminants were washed from the matrix with lysis buffer until the UV absorbance at 280 nm returned to the baseline. Elution was carried out with lysis buffer containing 20 mM reduced glutathione (Sigma, D2804) and fractions containing the GST fusion protein were pooled and dialysed into a glycerol-containing buffer comprising 50 mM HEPES, pH 7.5, 200 mM NaCl, 10% glycerol (v/v), 3 mM reduced glutathione and 1 mM DTT.

b) Kinase Activity Assay

The activity of the purified enzyme was measured by phosphorylation of a synthetic poly GluAlaTyr (EAY) 6:3:1 peptide (Sigma-Aldrich Company Ltd, UK, P3899) using an ELISA detection system in a 96-well format.

b.i) Reagents Used

| | Stock solutions | | |
|---|---|---|---|
| 200 mM | HEPES, pH 7.4 | stored at 4° C. | (Sigma, H3375) |
| 1M | DTT | stored at −20° C. | (Sigma, D9779) |
| 100 mM | Na$_3$VO$_4$ | stored at 4° C. | (Sigma, S6508) |
| 1M | MnCl$_2$ | stored at 4° C. | (Sigma, M3634) |
| 1 mM | ATP | stored at −20° C. | (Sigma, A3377) |
| Neat | Triton X-100 | stored at room temperature | (Sigma, T9284) |
| 10 mg/ml | BSA | stored at 4° C. | (Sigma, A7888) |

Enzyme Solution

GST-IGF-1R fusion protein at 75 ng/ml in 100 mM HEPES, pH 7.4, 5 mM DTT, 0.25 mM $Na_3VO_4$, 0.25% Triton X-100, 0.25 mg/ml BSA, freshly prepared.

Co-factor Solution 100 mM HEPES, pH 7.4, 60 mM $MnCl_2$, 5 mM ATP.

Poly EAY Substrate

Sigma substrate poly (Glu, Ala, Tyr) 6:3:1 (P3899). Made up to 1 mg/ml in PBS and stored at −20° C.

Assay Plates

Nunc Maxisorp 96 well immunoplates (Life Technologies Ltd, UK).

Antibodies

Anti-phosphotyrosine antibody, monoclonal from Upstate Biotechnology Inc., NY, USA (UBI 05-321). Dilute 3 µl in 11 ml PBS/T+0.5% BSA per assay plate.

Sheep—anti-mouse IgG HRP-conjugated secondary antibody from Amersham Pharmacia Biotech UK Ltd. (NXA931). Dilute 20 µl of stock into 11 ml PBS/T+0.5% BSA per assay plate.

TMB Solution

Dissolve 1 mg TMB tablet (Sigma T5525) into 1 ml DMSO (Sigma, D8779) in the dark for 1 hour at room temperature. Add this solution to 9 ml of freshly prepared 50 mM phosphate-citrate buffer pH 5.0+0.03% sodium perborate [1 buffer capsule (Sigma P4922) per 100 ml distilled water].

Stop solution is 1M $H_2SO_4$ (Fisher Scientific UK. Cat. No. S/9200/PB08).

Test Compound

Dissolve in DMSO to 10 mM then dilutions in distilled water to give a range from 200 to 0.0026 µM in 1-2% DMSO final concentration in assay well.

b.ii) Assay Protocol

The poly EAY substrate was diluted to 1 g/ml in PBS and then dispensed in an amount of 100 µl per well into a 96-well plate. The plate was sealed and incubated overnight at 4° C. Excess poly EAY solution was discarded and the plate was washed (2×PBS/T; 250 µl PBS per well), blotting dry between washes. The plate was then washed again (1×50 mM HEPES, pH 7.4; 250 µl per well) and blotted dry (this is important in order to remove background phosphate levels). 10 µl test compound solution was added with 40 µl of kinase solution to each well. Then 50 µl of co-factor solution were added to each well and the plate was incubated for 60 minutes at room temperature.

The plate was emptied (i.e. the contents were discarded) and was washed twice with PBS/T (250 µl per well), blotting dry between each wash. 100 µl of diluted anti-phosphotyrosine antibody were added per well and the plate was incubated for 60 minutes at room temperature.

The plate was again emptied and washed twice with PBS/T (250 µl per well), blotting dry between each wash. 100 µl of diluted sheep—anti-mouse IgG antibody were added per well and the plate was left for 60 minutes at room temperature. The contents were discarded and the plate washed twice with PBS/T (250 µl per well), blotting dry between each wash. 100 µl of TMB solution were added per well and the plate was incubated for 5-10 minutes at room temperature (solution turns blue in the presence horse radish peroxidase).

Reaction was stopped with 50 µl of $H_2SO_4$ per well (turns the blue solution yellow) and the plate was read at 450 nm in Versamax plate reader (Molecular Devices Corporation, CA, USA) or similar.

The compounds of the Examples were found to have an $IC_{50}$ in the above test of less than 100 µM.

c) Inhibition of IGF-stimulated Cell Proliferation

The construction of murine fibroblasts (NIH3T3) overexpressing human IGF-1 receptor has been described by Lammers et al (EMBO J, 8, 1369-1375, 1989). These cells show a proliferative response to IGF-I which can be measured by BrdU incorporation into newly synthesised DNA. Compound potency was determined as causing inhibition of the IGF-stimulated proliferation in the following assay:

c.i) Reagents Used:

Cell Proliferation ELISA, BrdU (colorimetric) [Boehringer Mannheim (Diagnostics and Biochemicals) Ltd, UK. Cat no. 1 647 229].

DMEM, FCS, Glutamine, HBSS (all from Life Technologies Ltd., UK).

Charcoal/Dextran Stripped FBS (HyClone SH30068.02, Perbio Science UK Ltd).

BSA (Sigma, A7888).

Human recombinant IGF-1 Animal/media grade (GroPep Limited ABN 78 008 176 298, Australia. Cat No. IU 100).

Preparation and Storage of IGF

100 µg of lyophilised IGF was reconstituted in 100 ul of 10 mM HCl.
Add 400 µl of 1 mg/ml BSA in PBS
25 µl aliquots @ 200 µg/ml IGF-1
Stored at −20° C.

For Assay:

10 µl of stock IGF+12.5 ml growth medium to give 8× stock of 160 ng/ml.

Complete Growth Medium

DMEM, 10% FCS, 2 mM glutamine.

Starvation Medium

DMEM, 1% charcoal/dextran stripped FCS, 2 mM glutamine.

Test Compound

Compounds are initially dissolved in DMSO to 10 mM, followed by dilutions in DMEM+1% FCS+glutamine to give a range from 100 to 0.0.45 µM in 1-0.00045% DMSO final concentration in assay well.

c.ii) Assay Protocol

Day 1

Exponentially growing NIH3T3/IGFR cells were harvested and seeded in complete growth medium into a flat-bottomed 96 well tissue culture grade plate (Costar 3525) at $1.2 \times 10^4$ cells per well in a volume of 100 µl.

Day 2

Growth medium was carefully removed from each well using a multi-channel pipette. Wells were carefully rinsed three times with 200 µl with HBSS. 100 µl of starvation medium was added to each well and the plate was re-incubated for 24 hours.

Day 3

50 µl of a 4× concentrate of test compound was added to appropriate wells. Cells were incubated for 30 minutes with compound alone before the addition of IGF. For cells treated with IGF, an appropriate volume (i.e. 25 µl) of starvation medium was added to make a final volume per well up to 200 µl followed by 25 µl of IGF-1 at 160 ng/ml (to give a final concentration of 20 ng/ml). Control cells unstimulated with IGF also had an appropriate volume (i.e. 50 µl) of starvation medium added to make final volume per well up to 200 µl. The plate was re-incubated for 20 hours.

Day 4

The incorporation of BrdU in the cells (after a 4 h incorporation period) was assessed using the BrdU Cell Proliferation Elisa according to the manufacturer's protocol.

The compounds of the Examples were found to have an $IC_{50}$ in the above test of less than 50 µM.

d) Mechanism of Action Assay

Inhibition of IGF-IR mediated signal transduction was determined by measuring changes in phosphorylation of IGF-IR, Akt and MAPK (ERK1 and 2) in response to IGF-I stimulation of MCF-7 cells (ATCC No. HTB-22). A measure of selectivity was provided by the effect on MAPK phosphorylation in response to EGF in the same cell line.

d.i) Reagents Used:

RPMI 1640 medium, RPMI 1640 medium without Phenol Red, FCS, Glutamine (all from Life Technologies Ltd., UK).

Charcoal/Dextran Stripped FBS (HyClone SH30068.02, Perbio Science UK Ltd).

SDS (Sigma, L4390).

2-mercaptoethanol (Sigma, M6250).

Bromophenol blue (Sigma, B5525).

Ponceau S (Sigma, P3504).

Tris base (TRIZMA™ base, Sigma, T1503).

Glycine (Sigma, G7403).

Methanol (Fisher Scientific UK. Cat. No. M/3950/21).

Dried milk powder (Marvel™, Premier Brands UK Ltd.).

Human recombinant IGF-1 Animal/media grade (GroPep Limited ABN 78 008 176 298, Australia. Cat No. IU 100).

Human recombinant EGF (Promega Corporation, WI, USA. Cat. No. G5021).

Complete Growth Medium

RPMI 1640, 10% FCS, 2 mM glutamine

Starvation Medium

RPMI1640 medium without Phenol Red, 1% charcoal/dextran stripped FCS, 2 mM glutamine.

Test Compound

Compounds were initially dissolved in DMSO to 10 mM, followed by dilutions in RPMI 1640 medium without Phenol Red+1% FCS+2 mM glutamine to give a range from 100 to 0.0.45 µM in 1-0.00045% DMSO final concentration in assay well.

Western Transfer Buffer 50 mM Tris base, 40 mM glycine, 0.04% SDS, 20% methanol.

Laemmli Buffer ×2:

100 mM Tris-HCl pH6.8, 20% glycerol, 4% SDS.

Sample Buffer ×4:

200 mM 2-mercaptoethanol, 0.2% bromophenol blue in distilled water.

Primary Antibodies

Rabbit anti-human IGF-1Rβ (Santa Cruz Biotechnology Inc., USA, Cat. No sc-713) Rabbit anti-insulin/IGF-1R [pYpY$^{1162/1163}$] Dual Phosphospecific (BioSource International Inc, CA, USA. Cat No. 44-8041).

Mouse anti-PKBα/Akt (Transduction Laboratories, KY, USA. Cat. No. P67220) Rabbit anti-Phospho-Akt (Ser473) (Cell Signalling Technology Inc, MA, USA. Cat. No. #9271).

Rabbit anti-p44/p42 MAP kinase (Cell Signalling Technology Inc, MA, USA. Cat. No. #9102).

Rabbit anti-Phospho p44/p42 MAP kinase (Cell Signalling Technology Inc. MA, USA. Cat. No. #9101).

Mouse anti-actin clone AC-40 (Sigma-Aldrich Company Ltd, UK, A4700).

Antibody dilutions

| Antibody | Dilution in PBST | Secondary antibody in PBST |
|---|---|---|
| IGFR | 1:200 with 5% milk | Anti-rabbit with 5% milk |
| Phospho-IGFR | 1:1000 with 5% milk | Anti-rabbit with 5% milk |
| Akt | 1:1000 with 5% milk | Anti-mouse with 5% milk |
| PhosphoAkt | 1:1000 with 5% milk | Anti-rabbit with 5% milk |
| MAPK | 1:1000 with 5% milk | Anti-rabbit with 5% milk |
| Phospho-MAPK | 1:1000 with 5% milk | Anti-rabbit with 5% milk |
| Actin | 1:1000 with 5% milk | Anti-mouse with 5% milk |

Secondary antibodies

Goat anti-rabbit, IP linked (Cell Signalling Technology Inc, MA, USA. Cat. No. #7074).

Sheep—anti-mouse IgG HRP-conjugated (Amersham Pharmacia Biotech UK Ltd. Cat. No. NXA931).

Dilute anti-rabbit to 1:2000 in PBST+5% milk.

Dilute anti-mouse to 1:5000 in PBST+5% milk.

d.ii) Assay Protocol

Cell Treatment

MCF-7 cells were plated out in a 24 well plate at 1×10$^5$ cells/well in 1 ml complete growth medium. The plate was incubated for 24 hours to allow the cells to settle. The medium was removed and the plate was washed gently 3 times with PBS 2 ml/well. 1 ml of starvation medium was added to each well and the plate was incubated for 24 hours to serum starve the cells.

Then 25 µl of each compound dilution was added and the cells and compound were incubated for 30 minutes at 37° C. After 30 minutes incubation of the compound, 25 µl of IGF (for 20 ng/ml final concentration) or EGF (for 0.1 ng/ml final concentration) was added to each well as appropriate and the cells incubated with the IGF or EGF for 5 minutes at 37° C. The medium was removed (by pipetting) and then 100 µl of 2× Laemmli buffer was added. The plates were stored at 4° C. until the cells were harvested. (Harvesting should occur within 2 hours following addition of Laemmli buffer to the cells.)

To harvest the cells, a pipette was used to repeatedly draw up and expel the Laemmli buffer/cell mix and transfer into a 1.5 ml Eppendorf tube. The harvested cell lysates were kept at −20° C. until required. The protein concentration of each lysate could be determined using the DC protein assay kit (Bio-Rad Laboratories, USA, according to manufacturer's instructions).

Western Blot Technique

Cell samples were made up with 4× sample buffer, syringed with a 21 gauge needle and boiled for 5 minutes. Samples were loaded at equal volumes and a molecular weight ladder on 4-12% Bis-Tris gels (Invitrogen BV, The Netherlands) and the gels were run in an Xcell SureLock™ Mini-Cell apparatus (Invitrogen) with the solutions provided and according to the manufacturer's instructions. The gels were blotted onto Hybond C Extra™ membrane (Amersham Pharmacia Biotech UK Ltd.) for 1 hour at 30 volts in the Xcell SureLock™ Mini-Cell apparatus, using Western transfer buffer. The blotted membranes were stained with 0.1% Ponceau S to visualise transferred proteins and then cut into strips horizontally for multiple antibody incubations according to the molecular weight standards. Separate strips were used for detection of IGF-1R, Akt, MAPK and actin control.

The membranes were blocked for 1 hour at room temperature in PBST+5% milk solution. The membranes were then placed into 3 ml primary antibody solution in 4 well plates and the plates were incubated overnight at 4° C. The membranes were washed in 5 ml PBST, 3 times for 5 minutes each wash. The HRP-conjugated secondary antibody solution was prepared and 5 ml was added per membrane. The membranes were incubated for 1 hour at room temperature with agitation. The membranes were washed in 5 ml PBST, 3 times for 5 minutes each wash. The ECL solution (SuperSignal ECL, Pierce, Perbio Science UK Ltd) was prepared and incubated with the membranes for 1 minute (according to manufacturer's instructions), followed by exposure to light sensitive film and development.

The compounds of the Examples were found to have an $IC_{50}$ in the above test of less than 20 µl By way of example, the following Table illustrates the activity of representative compounds according to the invention. Column 2 of the Table shows $IC_{50}$ data from Test (c) described above for the inhibition of IGF-stimulated proliferation in murine fibroblasts (NIH3T3) over-expressing human IGF-1 receptor:

| Example Number | $IC_{50}$ (µM) - Test (c) |
|---|---|
| 5 | 0.13 |
| 23 | 0.11 |
| 35 | 0.56 |
| 38 | 0.054 |

The invention claimed is:
1. A compound of formula (I)

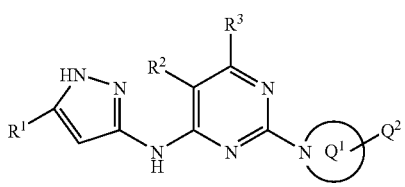

(I)

or a pharmaceutically acceptable salt thereof,
wherein:
$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;
$R^2$ represents hydrogen, halogen or trifluoromethyl;
$R^3$ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)$R^{3b}$, —O$R^{3b}$, —S$R^{3b}$, —NH$R^{3b}$, —N[(C1-C6)alkyl]$R^{3b}$, —S(O)$_m$ $R^{3a}$ or —N($R^{3c}$)C(O)$R^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, $R^{3b}$ represents a saturated monocyclic 4-, 5- or 6-membered heterocyclic ring comprising at least one ring heteroatom selected from nitrogen, oxygen and sulphur and $R^{3c}$ represents hydrogen or (C1-C6)alkyl,
or $R^3$ represents a saturated monocyclic 5- to 6-membered heterocyclic ring comprising at least one ring heteroatom selected from nitrogen, oxygen and sulphur,
or $R^3$ represents a 5- to 6-membered heteroaromatic ring comprising at least one ring heteroatom selected from nitrogen, oxygen and sulphur,
or $R^3$ represents a 2, 7-diazaspiro[3.5]nonane group,
each of which groups or rings within $R^3$ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[((C1-C4)alkyl]silyl, cyano, amino, (C1-C6)alkylamino, di-[(C1-C6)alkyl]amino, (C3-C8)cycloalkylamino, (C3-C6)cycloalkyl(C1-C3)alkylamino, amino(C1-C6)alkyl, (C1-C6)alkylamino (C1-C6)alkyl, di-[(C1-C6)alkyl]amino(C1-C6)alkyl, (C3-C8)cycloalkylamino(C1-C6)alkyl, (C3-C6)cycloalkyl(C1-C3)alkylamino(C1-C6)alkyl, (C1-C6)alkoxycarbonyl, carbamoyl, (C1-C6)alkylcarbamoyl, di-[(C 1-C6)alkyl]carbamoyl, (C1-C6)alkylthio, (C1-C6)alkylsulphonyl, (C1-C6)alkylsulphinyl, (C1-C6)alkanoyl, an alkanoylamino group —N($R^{3c}$)C(O)$R^{3a}$ wherein $R^{3a}$ and $R^{3c}$ are as defined above, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups;
—N$Q^1$ represents an N-linked saturated monocyclic 5- to 6-membered ring containing one nitrogen heteroatom and optionally comprising one or more additional ring heteroatoms selected from nitrogen, oxygen and sulphur;
$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —N$R^4R^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)N$R^6R^7$ and —SO$_2$N$R^8R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;
$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6) alkyl or (C1-C6)alkoxy (either of which may be optionally substituted by one or more substituents independently selected from halogen, amino, hydroxyl and trifluoromethyl), halogen, nitro, cyano, —$NR^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —$S(O)_n$(C1-C6)alkyl, —$C(O)NR^{12}R^{13}$ and -$SO_2NR^{14}R^{15}$, wherein $R^{10}$, $R^{11}$, $R^{12}$, $R^{13}$, $R^{14}$ and $R^{15}$ each independently represent hydrogen or (C1-C6)alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2; and wherein any saturated monocyclic ring optionally bears 1 or 2 oxo or thioxo substituents.

2. A compound according to claim 1 wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by one or more substituents independently selected from halogen and (C1-C6)alkoxy;

$R^2$ represents hydrogen, halogen or trifluoromethyl;

$R^3$ represents hydrogen or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C2-C6)alkanoylamino, —$C(O)R^{3b}$, —$OR^{3b}$, —$SR^{3b}$, —$NHR^{3b}$, —$N[(C1-C6)alkyl]R^{3b}$ or —$S(O)_mR^{3a}$ group, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2, and $R^{3b}$ represents a saturated monocyclic 5- to 6- membered ring containing one or more heteroatoms selected from nitrogen, oxygen and sulphur, or $R^3$ represents a saturated monocyclic 5- to 6- membered heterocyclic ring, which ring comprises at least one ring heteroatom selected from nitrogen, oxygen and sulphur, each of which groups or rings within $R^3$ may be optionally substituted by one or more substituents independently selected from (C1-C6)alkyl, (C1-C6)alkoxy, (C1-C6)alkoxy(C1-C6)alkoxy, halogen, hydroxyl, trifluoromethyl, cyano, amino, (C1-C6)alkylamino, di-[(C1-C6)alkyl]amino, (C3-C8)cycloalkylamino, (C3-C6)cycloalkyl(C1-C3)alkylamino, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-6)alkanoylamino or a saturated monocyclic 4-, 5-, 6- or 7-membered ring, which ring may optionally comprise one or more heteroatoms selected from nitrogen, oxygen and sulphur;

—$NQ^1$ represents an N-linked saturated monocyclic 5- to 6-membered ring containing one nitrogen heteroatom and optionally comprising one or more additional ring heteroatoms selected from nitrogen, oxygen and sulphur;

$Q^2$ represents a 5- to 6-membered heteroaromatic ring comprising at least one ring heteroatom selected from nitrogen, oxygen and sulphur, which ring is substituted by $Q^3$ and is optionally substituted, on any available ring atom, by one or more further substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —$NR^4R^5$, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —$S(O)_p$(C1-C4)alkyl, —$C(O)NR^6R^7$ and —$SO_2NR^8R^9$, wherein $R^4$, $R^5$, $R^6$, $R^7$, $R^8$ and $R^9$ each independently represent hydrogen or (C1-C6)alkyl, or $R^4$ and $R^5$, or $R^6$ and $R^7$, or $R^8$ and $R^9$, when taken together with the nitrogen atom to which they are attached, may each independently form a saturated heterocyclic ring and p is 0, 1 or 2;

$Q^3$ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein $Q^3$ is optionally substituted by one or more substituents independently selected from (C1-C6)alkyl or (C1-C6)alkoxy (either of which may be optionally substituted by one or more substituents independently selected from halogen, amino, hydroxyl and trifluoromethyl), halogen, nitro, cyano, —N $R^{10}R^{11}$, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —$S(O)$—(C1-C6)alkyl, —$C(O)NR^{12}R^{13}$ and —$S_2NR^{14}R^{15}$, wherein $R^{10}$, $R^{11}$, $R^{12}$, $R^{13}$, $R^{14}$ and $R^{15}$ each independently represent hydrogen or (C1-C6) alkyl, or $R^{10}$ and $R^{11}$, or $R^{12}$ and $R^{13}$, or $R^{14}$ and $R^{15}$, when taken together with the nitrogen atom to which they are attached, may each independently form a saturated heterocyclic ring and n is 0, 1 or 2.

3. A compound according to claim 1, wherein:

$R^1$ represents trifluoromethyl, or a (C1-C6)alkyl, (C3-C8)cycloalkyl or (C3-C8)cycloalkyl(C1-C6)alkyl group, each of which groups may be optionally substituted by halogen or a (C1-C6)alkoxy group;

$R^2$ represents hydrogen, halogen or trifluoromethyl;

$R^3$ represents hydrogen or a (C1-C6)alkyl, (C3-C8)cycloalkyl, (C3-C8)cycloalkyl(C1-C6)alkyl, (C1-C6)alkoxy, (C1-C6)alkylcarbonyl, (C3-C8)cycloalkylcarbonyl, (C3-C8)cycloalkyl(C1-C6)alkylcarbonyl, (C1-C6)alkoxycarbonyl, (C1-C6)alkylamino, (C3-C8)cycloalkylamino, (C3-C8)cycloalkyl(C1-C6)alkylamino, (C1-C6)alkoxyamino or —$S(O)_mR^{3a}$ group, each of which groups may be optionally substituted by at least one substituent selected from (C1-C6)alkoxy, (C1-C6)alkoxy(C1-C6)alkoxy, halogen, hydroxyl, trifluoromethyl, or a saturated monocyclic 4- to 7-membered ring, which ring may optionally comprise one or more heteroatoms selected from nitrogen, oxygen and sulphur, wherein $R^{3a}$ represents a (C1-C6)alkyl, (C3-C8)cycloalkyl, (C3-C8)cycloalkyl(C1-C6)alkyl or (C1-C6)alkoxy group, m is 0, 1 or 2;

—$NQ^1$ represents an N-linked saturated monocyclic 5- to 6-membered ring containing one nitrogen heteroatom and optionally comprising one or more additional ring heteroatoms selected from nitrogen, oxygen and sulphur;

Q² represents a 5- to 6-membered heteroaromatic ring comprising at least one ring heteroatom selected from nitrogen, oxygen and sulphur, which ring is substituted by Q³ and is optionally substituted, on any available ring atom, by one or more further substituents, which may be the same or different, selected from (C1-C6)alkyl or (C1-C6)alkoxy (either of which may be optionally substituted by at least one substituent selected from halogen, amino, hydroxyl and trifluoromethyl), halogen, nitro, cyano, —NR⁴R⁵, carboxyl, hydroxyl, (C2-C6)alkenyl, (C3-C8)cycloalkyl, (C3-C8)cycloalkyl(C1-C6)alkyl, (C1-C4)alkoxycarbonyl, (C1-C4)alkylcarbonyl, (C1-C4)alkylcarbonylamino, phenylcarbonyl, —S(O)$_p$(C1-C4)alkyl, —C(O)NR⁶R⁷ and —SO₂NR⁸R⁹, wherein R⁴, R⁵, R⁶, R⁷, R⁸ and R⁹ each independently represent hydrogen or (C1-C6)alkyl, or R⁴ and R⁵, or R⁶ and R⁷, or R⁸ and R⁹, when taken together with the nitrogen atom to which they are attached, may each independently form a saturated heterocyclic ring and p is 0, 1 or 2;

Q³ represents a (C1-C6)alkyl, (C3-C6)cycloalkyl or (C3-C6)cycloalkyl(C1-C6)alkyl group or a saturated or unsaturated 5- to 6-membered monocyclic ring which may comprise at least one ring heteroatom selected from nitrogen, oxygen and sulphur, and wherein Q³ is optionally substituted by at least one substituent selected from (C1-C6)alkyl or (C1-C6)alkoxy (either of which may be optionally substituted by at least one substituent selected from halogen, amino, hydroxyl and trifluoromethyl), halogen, nitro, cyano, —NR¹⁰R¹¹, carboxyl, hydroxyl, (C2-C6)alkenyl, (C3-C8)cycloalkyl, (C1-C6)alkoxycarbonyl, (C1-C6)alkylcarbonyl, (C1-C6)alkylcarbonylamino, phenylcarbonyl, —S(O)—(C1-C6)alkyl, -C(O)NR¹²R¹³ and —S₂NR¹⁴R¹⁵, wherein R¹⁰, R¹¹, R¹², R¹³, R¹⁴ and R¹⁵ each independently represent hydrogen or (C1-C6)alkyl, or R¹⁰ and R¹¹, or R¹² and R¹³, or R¹⁴ and R¹⁵, when taken together with the nitrogen atom to which they are attached, may each independently form a saturated heterocyclic ring and n is 0, 1 or 2.

4. A compound according to claim 1, wherein R¹ represents a (C1-C4)alkyl or (C3-C6)cycloalkyl group.

5. A compound according to claim 1, wherein R² represents hydrogen or halogen.

6. A compound according to claim 5, wherein R² represents halogen.

7. A compound according to claim 1, wherein R³ represents hydrogen, hydroxyl or halogen, or a (C1-C6)alkyl, (C2-C6)alkenyl, (C2-C6)alkynyl, (C3-C8)cycloalkyl, (C3-C8)cycloalkyl(C1-C6)alkyl, (C1-C6)alkoxy, (C3-C8)cycloalkyl(C1-C6)alkoxy, (C1-C6)alkylcarbonyl, (C1-C6)alkoxycarbonyl, amino, (C1-C6)alkylamino, di-[(C1-C6)alkyl]amino, (C3-C8)cycloalkylamino, (C3-C8)cycloalkyl(C1-C6)alkylamino, (C1-C6)alkoxyamino, carbamoyl, (C1-C6)alkylcarbamoyl, di-[(C1-C6)alkyl]carbamoyl, —C(O)R³ᵇ, —OR³ᵇ, —NHR³ᵇ, —N[(C1-C6)alkyl]R³ᵇ, —S(O)$_m$R³ᵃ or —N(R³ᶜ)C(O)R³ᵃ group, wherein R³ᵃ represents a (C1-C6)alkyl or (C1-C6)alkoxy group, m is 0, 1 or 2, R³ᵇ represents a saturated monocyclic 4-, 5- or 6-membered heterocyclic ring comprising at least one ring heteroatom selected from nitrogen, oxygen and sulphur and R³ᶜ represents hydrogen or (C1-C6)alkyl, or R³ represents a saturated monocyclic 5- to 6-membered heterocyclic ring comprising at least one ring heteroatom selected from nitrogen, oxygen and sulphur, or R³ represents a 5- to 6-membered heteroaromatic ring comprising at least one ring heteroatom selected from nitrogen, oxygen and sulphur, or R³ represents a 2,7-diazaspiro[3.5]nonane group, each of which groups or rings within R³ may be optionally substituted by one or more substituents independently selected from (C1-C6)alkyl, (C1-C6)alkoxy, (C1-C6)alkoxy(C1-C6)alkyl, (C1-C6)alkoxy(C1-C6)alkoxy, halogen, hydroxyl, trifluoromethyl, tri-[(C1-C4)alkyl]silyl, cyano, amino, (C1-C6)alkylamino, di-[(C1-C6)alkyl]amino, amino(C1-C6)alkyl, (C1-C6)alkylamino(C1-C6)alkyl, di-[(C1-C6)alkyl]amino(C1-C6)alkyl, (C1-C6)alkoxycarbonyl, carbamoyl, (C1-C6)alkylcarbamoyl, di-[(C1-C6)alkyl]carbamoyl, (C1-C6)alkylthio, (C1-C6)alkylsulphonyl, (C1-C6)alkylsulphinyl, (C1-C6)alkanoyl, an alkanoylamino group —N(R³ᶜ)C(O)R³ᵃ wherein R³ᵃ and R³ᶜ are as defined in claim 1, or a saturated monocyclic 3-, 4-, 5-, 6- or 7-membered ring, which ring may optionally comprise one or more heteroatoms selected from nitrogen, oxygen and sulphur, any of which substituents may be optionally substituted by one or more (C1-C4)alkyl, hydroxyl or cyano groups, and wherein any saturated monocyclic ring optionally bears 1 or 2 oxo or thioxo substituents.

8. A compound according to claim 1, wherein R³ represents hydrogen or halogen, or a (C1-C6)alkyl, (C2-C6)alkenyl, (C2-C6)alkynyl, (C1-C6)alkoxy, (C1-C6)alkylcarbonyl, (C1-C6)alkoxycarbonyl, amino, (C1-C6)alkylamino, di-[(C1-C6)alkyl]amino, carbamoyl, —C(O)R³ᵇ, —OR³ᵇ, —SR³ᵇ, —NHR³ᵇ, —N[(C1-C6)alkyl]R³ᵇ or —S(O)$_m$R³ᵃ group wherein R³ᵃ and R³ᵇ are as defined in claim 1,
or R³ represents a saturated monocyclic 5- or 6- membered heterocyclic ring, which ring comprises at least one ring heteroatom selected from nitrogen, oxygen and sulphur,
each of which groups or rings may be optionally substituted by one or more substituents as defined in claim 1.

9. A compound according to claim 1, wherein R³ represents hydrogen or a (C1-C4)alkyl, (C1-C3)alkoxy or (C3-C5)cycloalkyl group,
or R³ represents a saturated monocyclic 5- to 6-membered heterocyclic ring comprising at least one ring heteroatom selected from nitrogen and oxygen,
each of which groups or rings may be optionally substituted by one or more substituents independently selected from hydroxyl and (C1-C3)alkoxy.

10. A compound according to claim 1, wherein R³ represents hydrogen.

11. A compound according to claim 1, wherein NQ¹ represents a saturated monocyclic 5- to 6-membered ring containing one nitrogen heteroatom and optionally at least one additional ring heteroatom, which may be the same or different, selected from nitrogen, oxygen and sulphur.

12. A compound according to claim 11, wherein NQ¹ is pyrrolidinyl or piperidinyl.

13. A compound according to claim 1, wherein Q² represents a 5- to 6-membered heteroaromatic ring comprising one or two ring heteroatoms, which may be the same or different, selected from nitrogen and oxygen, which ring is substituted by Q³ and optionally by at least one substituent independently selected from (C1-C6)alkyl, (C1-C6)alkoxy, halogen and (C3-C8)cycloalkyl.

14. A compound according to claim 13, wherein the heteroaromatic ring is selected from isoxazolyl and tetrazolyl.

15. A compound according to claim 14, wherein the heteroaromatic ring is isoxazolyl.

16. A compound according to claim 1, wherein Q³ represents (C1-C6)alkyl, (C3-C8)cycloalkyl or an optionally substituted saturated or unsaturated 5- to 6-membered monocyclic ring comprising optionally at least one ring heteroatom selected from nitrogen, oxygen and sulphur.

17. A compound according to claim 16, wherein Q³ represents a (C1-C4)alkyl or (C3-C6)cycloalkyl group or an optionally substituted unsaturated 5- to 6-membered monocyclic ring comprising one or two ring heteroatoms, which may be the same or different, selected from nitrogen, oxygen and sulphur.

18. A compound according to claim 16, wherein $Q^3$ represents an optionally substituted unsaturated 5- to 6-membered monocyclic ring comprising one or two ring heteroatoms, which may be the same or different, selected from nitrogen, oxygen and sulphur.

19. A compound according to claim 18, wherein $Q^3$ represents thiazolyl, pyrazinyl, pyrimidinyl or pyridyl.

20. A compound according to claim 1, wherein $R^1$ represents a (C1-C4)alkyl or (C3-C6)cycloalkyl group; $R^2$ represents halogen; $R^3$ represents hydrogen; —NO$^1$ represents a saturated monocyclic five or six membered ring containing one nitrogen heteroatom and optionally at least one additional ring heteroatom selected from nitrogen, oxygen and sulphur; $Q^2$ represents a substituted 5- to 6-membered heteroaromatic ring comprising one or two ring heteroatoms, which may be the same or different, selected from nitrogen and oxygen; and $Q^3$ represents a (C1-C4)alkyl or (C3-C6)cycloalkyl group or an optionally substituted unsaturated 5- to 6-membered monocyclic ring comprising one or two ring heteroatoms, which may be the same or different, selected from nitrogen, oxygen and sulphur.

21. A compound according to claim 20, wherein —NO$^1$ represents pyrrolidinyl or piperidinyl; $Q^1$ represents isoxazolyl or tetrazolyl; and $Q^3$ represents methyl, cyclopropyl, thiazolyl, tetrahydrofuranyl, pyrazinyl, thiazolyl, pyrimidinyl or pyridyl.

22. A compound according to claim 20, wherein —NQ$^1$ represents pyrrolidinyl; $Q^2$ represents isoxazolyl; and $Q^3$ represents thiazolyl, pyrazinyl, pyrimidinyl or pyridyl.

23. A compound according to claim 20, wherein —NQ$^1$ represents pyrrolidinyl or piperidinyl; $Q^2$ represents isoxazolyl; and $Q^3$ represents methyl, cyclopropyl, thiazolyl or pyridyl.

24. A compound of formula (I) according to claim 1 selected from one or more of:

5-Chloro-2-{2-[3-(pyrid-2-yl)isoxazol-5-yl]pyrrolidin-1-yl}-4-(5-methyl-1H-pyrazol-3-ylamino)pyrimidine;
5-Chloro-2-[2-(3-methylisoxazol-5-yl]pyrrolidin-1-yl]-4-(5-tert-butyl-1H-pyrazol-3-ylamino)pyrimidine;
5-Chloro-2-[2-(3-methylisoxazol-5-yl]pyrrolidin-1-yl]-4-(5-cyclopropyl-1H-pyrazol-3-ylamino)pyrimidine;
5-Chloro-2-[2-(3-cyclopropylisoxazol-5-yl]pyrrolidin-1-yl]-4-(5-cylopropyl-1H-pyrazol-3-ylamino)pyrimidine;
5-Chloro-2-[2-(3-cyclopropylisoxazol-5-yl]pyrrolidin-1-yl]-4-(5-methyl-1H-pyrazol-3-ylamino)pyrimidine;
5-Chloro-2-[2-(3-methylisoxazol-5-yl]pyrrolidin-1-yl]-4-(5-methyl-1H-pyrazol-3-ylamino)pyrimidine;
5-Chloro-2-{2-[3-(thiazol-2-yl)isoxazol-5-yl]pyrrolidin-1-yl}-4-(5-methyl-1H-pyrazol-3-ylamino)pyrimidine;
5-Chloro-2-{2-[3-(thiazol-2-yl)isoxazol-5-yl]pyrrolidin-1-yl}-4-(5-cyclopropyl-1H-pyrazol-3-ylamino)pyrimidine;
5-Chloro-2-{2-[3-(pyrid-2-yl)isoxazol-5-yl]pyrrolidin-1-yl}-4-(5-cyclopropyl-1H-pyrazol-3-ylamino)pyrimidine;
5-Chloro-2-{2-[3-(pyrid-3-yl)isoxazol-5-yl]pyrrolidin-1-yl}-4-(5-methyl-1H-pyrazol-3-ylamino)pyrimidine;
5-Chloro-2-{2-[3-(pyrid-3-yl)isoxazol-5-yl]pyrrolidin-1-yl}-4-(5-cyclopropyl-1H-pyrazol-3-ylamino)pyrimidine;
2-[2-(3-Cyclopropylisoxazol-5-yl)pyrrolidin-1-yl]-6-methoxymethyl-4-(5-methyl-1H-pyrazol-3-ylamino)pyrimidine;
2-[2-(3-Cyclopropylisoxazol-5-yl)pyrrolidin-1-yl]-6-methoxymethyl-4-(5-cyclopropyl-1H-pyrazol-3-ylamino)pyrimidine;
5-Chloro-2-(2-(3-(pyrid-2-yl)isoxazol-5-yl)piperidin-1-yl)-4-(5-methyl-1H-pyrazol-3-ylamino)pyrimidine;
5-Chloro-2-[2-(3-{tetrahydrofuran-3-yl}isoxazol-5-yl]pyrrolidin-1-yl]-4-(5-methyl-1H-pyrazol-3-ylamino)pyrimidine;
5-Chloro-4-(5-cyclopropyl-1H-pyrazol-3-ylamino)-2-[2-(3-{tetrahydrofuran-3-yl}isoxazol-5-yl]pyrrolidin-1-yl]-pyrimidine;
6-Chloro-4-(5-methyl-1H-pyrazol-3-ylamino)-2-{2-[3-(pyrid-2-yl)isoxazol-5-yl]pyrrolidin-1-yl}pyrimidine;
5-Chloro-4-(5-cyclopropyl-1H-pyrazol-3-ylamino)-2-{2-[3-(pyrid-2-yl)isoxazol-5-yl]piperidin-1-yl}pyrimidine;
5-Chloro-2-{2-[3-(2-methoxypyrid-3-yl)isoxazol-5-yl]pyrrolidin-1-yl}-4-(5-methyl-1H-pyrazol-3-ylamino)pyrimidine;
5- Fluoro-4-(5-methyl-1H-pyrazol-3-ylamino)-2-{2-[3-(pyrid-2-yl)isoxazol-5-yl]pyrrolidin-1-yl}-pyrimidine;
4-(5-Cyclopropyl-1H-pyrazol-3-ylamino)-5-fluoro-2-{2-[3-(pyrid-2-yl)isoxazol-5-yl]pyrrolidin-1-yl}pyrimidine;
S-5-Chloro-2-{2-[3-methylisoxazol-5-yl]pyrrolidin-1-yl}-4-(5-cyclopropyl-1H-pyrazol-3-ylamino)pyrimidine;
4-(5-Methyl-1H-pyrazol-3-ylamino)-2-{2-[3-(pyrid-2-yl)isoxazol-5-yl]pyrrolidin-1-yl}pyrimidine;
4-(5-Cyclopropyl-1H-pyrazol-3-ylamino)-2-{2-[3-(pyrid-2-yl)isoxazol-5-yl]pyrrolidin-1-yl}pyrimidine;
4-(5-Cyclopropyl-1H-pyrazol-3-ylamino)-6-methyl-2-[2-{3-(pyrid-2-yl)isoxazol-5-yl}pyrrolidin-1-yl]pyrimidine;
4-(5-Methyl-1H-pyrazol-3-ylamino)-6-methyl-2-[2-{3-(pyrid-2-yl)isoxazol-5-yl}pyrrolidin-1-yl]pyrimidine;
4-(5-Cyclopropyl-1H-pyrazol-3-ylamino)-6-methyl-2-[2-(3-methylisoxazol-5-yl)pyrrolidin-1-yl]pyrimidine;
6-Ethyl-4-(5-methyl-1H-pyrazol-3-ylamino)-2-[2-{3-(pyrid-2-yl)isoxazol-5-yl}pyrrolidin-1-yl]pyrimidine;
6-(3-Methoxypropyl)-4-(5-methyl-1H-pyrazol-3-ylamino)-2-[2-{3-(pyrid-2-yl)isoxazol-5-yl}pyrrolidin-1-yl]pyrimidine;
6-Methoxymethyl-4-(5-methyl-1H-pyrazol-3-ylamino)-2-[2-{3-(pyrid-2-yl)isoxazol-5-yl}pyrrolidin-1-yl]pyrimidine;
4-(5-Cyclopropyl-1H-pyrazol-3-ylamino)-6-methoxymethyl-2-[2-{3-(pyrid-2-yl)isoxazol-5-yl}pyrrolidin-1-yl]pyrimidine;
6-Methoxymethyl-4-(5-methyl-1H-pyrazol-3-ylamino)-2-{2-[3-(thiazol-2-yl)isoxazol-5-yl]pyrrolidin-1-yl}pyrimidine;
6-Methoxymethyl-4-(5-methyl-1H-pyrazol-3-ylamino)-2-[2-{3-(pyrid-3-yl)isoxazol-5-yl}pyrrolidin-1-yl]pyrimidine; 4-(5-Methyl-1H-pyrazol-3-ylamino)-6-(pent-3-en-1-yl)-2-[2-{3-(pyrid-2-yl)isoxazol-5-yl}pyrrolidin-1-yl]pyrimidine;
4-(5-Methyl-1H-pyrazol-3-ylamino)-2-{2-[3-(pyrid-2-yl)isoxazol-5-yl]pyrrolidin-1-yl}-6-trifluoromethylpyrimidine;
4-(5-Cyclopropyl-1H-pyrazol-3-ylamino)-2-{2-[3-(pyrid-2-yl)isoxazol-5-yl]pyrrolidin-1-yl}-6-trifluoromethylpyrimidine;
S-6-Ethyl-4-(5-methyl-1H-pyrazol-3-ylamino)-2-[2-{3-(pyrid-2-yl)isoxazol-5-yl}pyrrolidin-1-yl]pyrimidine;

S-5-Chloro-2-{2-[3-(thiazol-2-yl)isoxazol-5-yl]pyrrolidin-1-yl}-4-(5-methyl-1H-pyrazol-3-ylamino)pyrimidine;

S-5-Chloro-2-{2-[3-(pyrid-2-yl)isoxazol-5-yl]pyrrolidin-1-yl}-4-(5-cyclopropyl-1H-pyrazol-3-ylamino)pyrimidine;

S-4-(5-Methyl-1H-pyrazol-3-ylamino)-6-methyl-2-[2-{3-(pyrid-2-yl)isoxazol-5-yl}pyrrolidin-1-yl]pyrimidine;

S-5-Chloro-2-{2-[3-(pyrid-2-yl)isoxazol-5-yl]pyrrolidin-1-yl}-4-(5-methyl-1H-pyrazol-3-ylamino)pyrimidine;

S-5-Chloro-2-{2-[3-(2-methoxypyrid-3-yl)isoxazol-5-yl]pyrrolidin-1-yl}-4-(5-methyl-1H-pyrazol-3-ylamino)pyrimidine;

6-(3-N,N-Dimethylaminopropyl)-4-(5-methyl-1H-pyrazol-3-ylamino)-2-[2-{3-(pyrid-2-yl)isoxazol-5-yl}pyrrolidin-1-yl]pyrimidine;

6-(3-Pyrrolidin-1-ylpropyl)-4-(5-methyl-1H-pyrazol-3-ylamino)-2-[2-{3-(pyrid-2-yl)isoxazol-5-yl}pyrrolidin-1-yl]pyrimidine;

6-Methoxycarbonyl-4-(5-methyl-1H-pyrazol-3-ylamino)-2-{2-[3-(pyrid-2-yl)isoxazol-5-yl]pyrrolidin-1-yl}pyrimidine;

6-(2- Hydroxyethylcarbamoyl)-4-(5-methyl-1H-pyrazol-3-ylamino)-2-{2-[3-(pyrid-2-yl)isoxazol-5-yl]pyrrolidin-1-yl}pyrimidine;

4-(5-Methyl-1H-pyrazol-3-ylamino)-2-{2-[3-(pyrid-2-yl)isoxazol-5-yl]pyrrolidin-1-yl}-6-(pyrrolidin-1-ylcarbonyl)pyrimidine;

6-Methoxy-4-(5-methyl-1H-pyrazol-3-ylamino)-2-{2-[3-(pyrid-2-yl))isoxazol-5-yl]pyrrolidin-1-yl}pyrimidine;

5-Chloro-4-(3-cyclopropyl-1H-pyrazol-5-ylamino)-2-[2-(2-methyl-2H-tetrazol-5-yl)pyrrolidin-1-yl]pyrimidine;

6-N-Ethylpiperazinyl-4-(5-methyl-1H-pyrazol-3-ylamino)-2-{2-[3-(pyrid-2-yl)isoxazol-5-yl]pyrrolidin-1-yl}pyrimidine;

6-N-Methylpiperazyl-2-{2-[3-(pyrid-2-yl)isoxazol-5-yl]pyrrolidin-1-yl}-4-(5-methyl-1H-p yrazol-3-ylamino)pyrimidine; 6-Morpholino-4-(5-methyl-1H-pyrazol-3-ylamino)-2-{2-[3-(pyrid-2-yl)isoxazol-5-yl]pyrrolidin-1-yl}pyrimidine;

6-(3-(N,N-Dimethylamino)propyn-1-yl)-4-(5-methyl-1H-pyrazol-3-ylamino)-2-(2-(3-(pyrid-2-yl)isoxazol-5-yl)pyrrolidin-1-yl)pyrimidine;

6-Methylamino-4-(5-methyl-1H-pyrazol-3-ylamino)-2-[2-(3-pyridin-2-ylisoxazol-5-yl)pyrrolidin-1-yl]pyrimidine;

6-(2-Methoxyethyl)amino-4-(5-methyl-1H-pyrazol-3-ylamino)-2-{2-[3-(pyrid-2-yl)isoxazol-5-yl]pyrrolidin-1-yl}pyrimidine;

6-Methoxycarbonyl-2-{2-[3-(pyrid-2-yl)isoxazol-5-yl]pyrrolidin-1-yl}-4-(5-methyl-1H-pyrazol-3-ylamino)pyrimidine;

6-(N-Methylcarbamoyl)-2-{2-[3-(pyrid-2-yl)isoxazol-5-yl]pyrrolidin-1-yl}-4-(5-methyl-1H-pyrazol-3-ylamino)pyrimidine;

6-Morpholinocarbonyl-2-{2-[3-(pyrid-2-yl)isoxazol-5-yl]pyrrolidin-1-yl}-4-(5-methyl-1H-pyrazol-3-ylamino)pyrimidine;

6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine;

6-(N-Hydroxycarbamoyl)-2-{2-[3-(pyrid-2-yl)isoxazol-5-yl]pyrrolidin-1-yl}-4-(5-methyl-1H-pyrazol-3-ylamino)pyrimidine;

6-Carbamoyl-2-{2-[3-(pyrid-2-yl)isoxazol-5-yl]pyrrolidin-1-yl}-4-(5-methyl-1H-pyrazol-3-ylamino)pyrimidine;

S-6-Methoxycarbonyl-2-{2-[3-(pyrid-2-yl)isoxazol-5-yl]pyrrolidin-1-yl}-4-(5-methyl-1H-pyrazol-3-ylamino)pyrimidine;

S-6-(N-(2-Methoxyethyl)carbamoyl)-2-{2-[3-(pyrid-2-yl)isoxazol-5-yl]pyrrolidin-1-yl}-4-(5-methyl-1H-pyrazol-3-ylamino)pyrimidine;

S-6-[N-(2-Methoxyethyl)-N-methylcarbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-(2-(Acetylamino)ethyl)carbamoyl]-2-{2-[3-(pyrid-2-yl)isoxazol-5-yl]pyrrolidin-1-yl}-4-(5-methyl-iH-pyrazol-3-ylamino)pyrimidine;

S-6-{N-[2-(2-Hydroxyethoxy)ethyl]carbamoyl}-2-{2-[3-(pyrid-2-yl)isoxazol-5-yl]pyrrolidin-1-yl}-4-(5-methyl-1H-pyrazol-3-ylamino)pyrimidine;

S-6-[N-((R)-2-Hydroxypropyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-(4-Hydroxybutyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-[N-((2R)-2,3-Dihydroxypropyl)carbamoyl]-2-{2-[3-(pyrid-2-yl)isoxazol-5-yl]pyrrolidin- 1-yl}-4-(5-methyl-1H-pyrazol-3-ylamino)pyrimidine;

S-6-[N-(Carbamoylmethyl)carbamoyl]-2-{2-[3-(pyrid-2-yl)isoxazol-5-yl]pyrrolidin-1-yl}-4-(5-methyl-1H-pyrazol-3-ylamino)pyrimidine;

S-6-((3R)-3- Hydroxypyrrolidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine;

S-6-{N-[2-(Methylthio)ethyl]carbamoyl}-2-{2-[3-(pyrid-2-yl)isoxazol-5-yl]pyrrolidin-1-yl}-4-(5-methyl-1H-pyrazol-3-ylamino)pyrimidine;

S-6-(N-Cyclopropylcarbamoyl)-2-{2-[3-(pyrid-2-yl)isoxazol-5-yl]pyrrolidin-1-yl}-4-(5-methyl-1H-pyrazol-3-ylamino)pyrimidine;

S-6-(N-Cyclopentylcarbamoyl)-2-{2-[3-(pyrid-2-yl)isoxazol-5-yl]pyrrolidin-1-yl}-4-(5-methyl-1H-pyrazol-3-ylamino)pyrimidine;

S-6-(Azetidin-1-ylcarbonyl)-2-{2-[3-(pyrid-2-yl)isoxazol-5-yl]pyrrolidin-1-yl}-4-(5-methyl-1H-pyrazol-3-ylamino)pyrimidine;

S-6-(N-Methylcarbamoyl)-2-{2-[3-(pyrid-2-yl)isoxazol-5-yl]pyrrolidin-1-yl}-4-(5-methyl-1H-pyrazol-3-ylamino)pyrimidine;

6-(N-Aminocarbamoyl)-2-{2-[3-(pyrid-2-yl)isoxazol-5-yl]pyrrolidin-1-yl}-4-(5-methyl-1H-1 pyrazol-3-ylamino)pyrimidine;

6-[N-(Acetylamino)carbamoyl]-2-{2-[3-(pyrid-2-yl)isoxazol-5-yl]pyrrolidin-1-yl}-4-(5-methyl-1H-pyrazol-3-ylamino)pyrimidine;

6-(5-Methyl-[1,3,4]-oxadiazol-2-yl)-2-{2-[3-(pyrid-2-yl)isoxazol-5-yl]pyrrolidin-1-yl}-4-(5-methyl-1H-pyrazol-3-ylamino)pyrimidine;

6-Hydroxymethyl-2-{2-[3-(pyrid-2-yl)isoxazol-5-yl]pyrrolidin-1 -yl}-4-(5-methyl-1H-pyrazol-3-ylamino)pyrimidine;

6-(Morpholinomethyl)-2-{2-[3-(pyrid-2-yl)isoxazol-5-yl]pyrrolidin-1-yl}-4-(5-methyl-1H-pyrazol-3-ylamino)pyrimidine;

6-(4-Methylpiperazin-1-ylmethyl)-2-{2-[3-(pyrid-2-yl)isoxazol-5-yl]pyrrolidin-1-yl}-4-(5-methyl-1H-pyrazol-3-ylamino)pyrimidine;

6-(Methylaminomethyl)-2-{2-[3-(pyrid-2-yl)isoxazol-5-yl]pyrrolidin-1-yl}-4-(5-methyl-1H-pyrazol-3-ylamino)pyrimidine;

6-(Pyrrolidin-1-ylmethyl)-2-{2-[3-(pyrid-2-yl)isoxazol-5-yl]pyrrolidin-1-yl}-4-(5-methyl-1H-pyrazol-3-ylamino)pyrimidine;

6-Aminomethyl-2-{2-[3-(pyrid-2-yl)isoxazol-5-yl]pyrrolidin-1-yl}-4-(5-methyl-1H-pyrazol-3-ylamino)pyrimidine;

S-6-Hydroxymethyl-2-{2-[3-(pyrid-2-yl)isoxazol-5-yl]pyrrolidin-1-yl}-4-(5-methyl-1H-pyrazol-3-ylamino)pyrimidine;

S-6-Ethoxymethyl-2-{2-[3-(pyrid-2-yl)isoxazol-5-yl]pyrrolidin-1-yl}-4-(5-methyl-1H-pyrazol-3-ylamino)pyrimidine;

S-6-[(2-Methoxyethoxy) methyl]-2-{2-[3-(pyrid-2-yl)isoxazol-5-yl]pyrrolidin-1-yl}-4-(5-methyl-1H-pyrazol-3-ylamino)pyrimidine;

S-5-Chloro-2-{2-[3-(pyrazin-2-yl)isoxazol-5-yl]pyrrolidin-1-yl}-4-(5-cyclopropyl-1H-pyrazol-3-ylamino)pyrimidine;

S-6-Methyl-4-(5-methyl-1H-pyrazol-3-ylamino)-2-{2-[3-(pyrazin-2-yl)isoxazol-5-yl]pyrrolidin-1-yl}pyrimidine;

S-6-Chloro-4-(5-cyclopropyl-1H-pyrazol-3-ylamino)-2-{2-[3-(pyrazin-2-yl)isoxazol-5-yl]pyrrolidin-1-yl}pyrimidine;

S-4-(5-Cyclopropyl-1H-pyrazol-3-ylamino)-2-{2-[3-(pyrazin-2-yl)isoxazol-5-yl]pyrrolidin-1-yl-6-(2-methoxyethylamino)pyrimidine;

S-6-Methylamino-{2-[3-(pyrazin-2-yl)isoxazol-5-yl]pyrrolidin-1-yl}-4-(5-cyclopropyl-1H-pyrazol-3-ylamino)pyrimidine;

S-4-(5-Cyclopropyl-1H-pyrazol-3-ylamino)-6-methoxy-{2-[3-(pyrazin-2-yl)isoxazol-5-yl]pyrrolidin-1-yl}pyrimidine;

6-Pyrrolidin-1-yl-2-{2-[3-(pyrid-2-yl)isoxazol-5-yl]pyrrolidin-1-yl}-4-(5-methyl-1H-pyrazol-3-ylamino)pyrimidine;

S-6-Chloro-4-(5-methyl-1H-pyrazol-3-ylamino)-2-[2-{3-(pyrid-2-yl)isoxazol-5-yl}pyrrolidin-1-yl]pyrimidine;

S-6-(2,2,6,6-Tetramethylpiperidin-4-ylamino)-2-{2-[3-(pyrid-2-yl)isoxazol-5-yl]pyrrolidin-1-yl-4-(5-methyl-1H-pyrazol-3-ylamino)pyrimidine;

S-6-Iodo-4-(5-methyl-1H-pyrazol-3-ylamino)-2-[2-{3-(pyrid-2-yl)isoxazol-5-yl}pyrrolidin-1-yl]pyrimidine;

S-E-6-[3-(tert-Butoxycarbonylamino)prop-1-en-1-yl]-4-(5-methyl-1H-pyrazol-3-ylamino)-2-[2-{3-(pyrid-2-yl)isoxazol-5-yl}pyrrolidin-1-yl]pyrimidine;

S-6-Ethenyl-4-(5-methyl-1H-pyrazol-3-ylamino)-2-[2-{3-(pyrid-2-yl)isoxazol-5-yl}pyrrolidin-1-yl]pyrimidine;

S-E-6-(3-Hydroxyprop-1-en-1-yl)-4-(5-methyl-1H-pyrazol-3-ylamino)-2-[2-{3-(pyrid-2-yl)isoxazol-5-yl}pyrrolidin-1-yl]pyrimidine;

S-6-[3-(tert-Butoxycarbonylamino)prop-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Aminoprop-1-yl]-4-(5-methyl-1H-pyrazol-3-ylamino)-2-[2-{3-(pyrid-2-yl)isoxazol-5-yl}pyrrolidin-1-yl]pyrimidine;

S-E-6-[3-Aminoprop-1-en-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Methylaminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Methoxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3- Hydroxyprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(Trimethylsilyl)ethynyl]-4-(5-methyl-1H-pyrazol-3-ylamino)-2-[2-{3-(pyrid-2-yl)isoxazol-5-yl}pyrrolidin-1-yl]pyrimidine;

S-6-[3-(N-Methylacetamido)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-(Dimethylamino)prop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[3-Acetamidoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-( Ethoxycarbonyl)ethyl]-4-(5-methyl-1H-pyrazol-3-ylamino)-2-[2-{3-(pyrid-2-yl)isoxazol-5-yl}pyrrolidin-1-yl]pyrimidine;

S-E-6-[2-(Methoxycarbonyl)ethen-1-yl]-4-(5-methyl-1H-pyrazol-3-ylamino)-2-[2-{3-(pyrid-2-yl)isoxazol-5-yl}pyrrolidin-1-yl]pyrimidine;

S-6- Ethynyl-4-(5-methyl-1H-pyrazol-3-ylamino)-2-[2-{3-(pyrid-2-yl)isoxazol-5-yl}pyrrolidin-1-yl]pyrimidine;

6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine;

S-6-Methoxymethyl-4-(5-cyclopropyl-1H-pyrazol-3-ylamino)-2-[2-{3-(pyrid-2-yl)isoxazol-5-yl}pyrrolidin-1-yl]pyrimidine;

S-6-Methoxymethyl-4-(5-methyl-1H-pyrazol-3-ylamino)-2-[2-{3-(pyrid-2-yl)isoxazol-5-yl}pyrrolidin-1-yl]pyrimidine;

S-6-[3-Aminoprop-1-yn-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(N-Methylcarbamoyl)ethyl]-4-(5-methyl-1H-pyrazol-3-ylamino)-2-[2-{3-(pyrid-2-yl)isoxazol-5-yl}pyrrolidin-1-yl]pyrimidine;

S-4-(5- Ethyl-1H-pyrazol-3-ylamino)-2-[2-[3-(2-methoxypyrid-3-yl)isoxazol-5-yl]pyrrolidin-1-yl]pyrimidine;

S-4-(5-Methyl-1H-pyrazol-3-ylamino)-2-[2-[3-(2-methoxypyrid-3-yl)isoxazol-5-yl]pyrrolidin-1-yl]pyrimidine;

S-4-(5-Cyclopropyl-1H-pyrazol-3-ylamino)-2-[2-[3-(2-methoxypyrid-3-yl)isoxazol-5-yl]pyrrolidin-1-yl]pyrimidine;

6-(N-tert- Butoxycarbonyl)amino-2-{2-[3-(pyrid-2-yl)isoxazol-5-yl]pyrrolidin-1-yl}-4-(5-methyl-1H-pyrazol-3-ylamino)pyrimidine;

6-(4-Aminopiperidin-1-yl)2-{2-[3-(pyrid-2-yl)isoxazol-5-yl]pyrrolidin-1-yl}-4-(5-methyl-1-pyrazol-3-ylamino)pyrimidine;

6-(4-(N-tert-Butoxycarbonylamino)piperidin-1-yl)-2-{2-[3-(pyrid-2-yl)isoxazol-5-yl]pyrrolidin-1-yl}-4-(5-methyl-1H-pyrazol-3-ylamino)pyrimidine;

6-Piperazin-1-yl-2-{2-[3-(pyrid-2-yl)isoxazol-5-yl]pyrrolidin-1-yl}-4-(5-methyl-1H-pyrazol-3-ylamino)pyrimidine;

S-6-{4-[2-(2-Hydroxyethoxy)ethyl]piperazin-1-yl}-2-{2-[3-(pyrid-2-yl)isoxazol-5-yl]pyrrolidin-1-yl}-4-(5-methyl-1H-pyrazol-3-ylamino)pyrimidine;

S-6-(1-Formyl-piperazin-4-yl)-2-{2-[3-(pyrid-2-yl)isoxazol-5-yl]pyrrolidin-1-yl}-4-(5-methyl-1H-pyrazol-3-ylamino)pyrimidine;

S-6-Piperazin-1-yl-2-{2-[3-(pyrid-2-yl)isoxazol-5-yl]pyrrolidin-1-yl}-4-(5-methyl-1H-pyrazol-3-ylamino)pyrimidine;

S-6-(4-Isopropylpiperazin-1yl)-2-{2-[3-(pyrid-2-yl)isoxazol-5-yl]pyrrolidin-1-yl}-4-(5-methyl-1H-pyrazol-3-ylamino)pyrimidine;

S-6-[(4-(2-Hydroxyethyl)piperazin-1-yl)]-2-{2-[3-(pyrid-2-yl)isoxazol-5-yl]pyrrolidin-1-yl}-4-(5-methyl-iH-pyrazol-3-ylamino)pyrimidine;

S-6-[(3R)-3-Hydroxypyrrolidin-1-yl]-2-{2-[3-(pyrid-2-yl)isoxazol-5-yl]pyrrolidin-1-yl}-4-(5-methyl-iH-pyrazol-3-ylamino)pyrimidine;

S-6-[(3R)-3-Dimethylamino-pyrrolidin-1-yl]-2-{2-[3-(pyrid-2-yl)isoxazol-5-yl]pyrrolidin-1-yl}-4-(5-methyl-iH-pyrazol-3-ylamino)pyrimidine;

S-6-(4-Tetrahydropyranylamino)-2-{2-[3-(pyrid-2-yl)isoxazol-5-yl]pyrrolidin-1-yl}-4-(5-methyl-1H-pyrazol-3-ylamino)pyrimidine;

S-6-Morpholino-2-{2-[3-(pyrid-2-yl)isoxazol-5-yl]pyrrolidin-1-yl}-4-(5-methyl-1H-pyrazol-3-ylamino)pyrimidine;

S-6-(2-Methoxyethyl)amino-2-{2-[3-(pyrid-2-yl)isoxazol-5-yl]pyrrolidin-1-yl}-4-(5-methyl-1H-pyrazol-3-ylamino)pyrimidine;

S-6-[(N-2-Methoxyethyl)-N-methylamino]-2-{2-[3-(pyrid-2-yl)isoxazol-5-yl]pyrrolidin-1-yl}-4-(5-methyl-iH-pyrazol-3-ylamino)pyrimidine;

S-6-((2 R)-2-Hydroxyprop-1-ylamino)-2-{2-[3-(pyrid-2-yl)isoxazol-5-yl]pyrrolidin-1-yl}-4-(5-methyl-iH-pyrazol-3-ylamino)pyrimidine;

S-6-[N-(2-Hydroxyethyl)-N-ethylamino]-2-{2-[3-(pyrid-2-yl)isoxazol-5-yl]pyrrolidin-1-yl}-4-(5-methyl-1H-pyrazol-3-ylamino)pyrimidine;

S-6-Dimethylamino-2-{2-[3-(pyrid-2-yl)isoxazol-5-yl]pyrrolidin-1-yl}-4-(5-methyl-1H-pyrazol-3-ylamino)pyrimidine;

S-6-Methylamino-2-{2-[3-(pyrid-2-yl)isoxazol-5-yl]pyrrolidin-1-yl}-4-(5-methyl-1H-pyrazol-3-ylamino)pyrimidine;

S-6-Chloro-2-{2-[3-(pyrazin-2-yl)isoxazol-5-yl]pyrrolidin-1-yl}-4-(5-methyl-1H-pyrazol-3-ylamino)pyrimidine;

6-Mopholino-2-{2-[3-(pyrazin-2-yl)isoxazol-5-yl]pyrrolidin-1-yl}-4-(5-methyl-1H-pyrazol-3-ylamino)pyrimidine;

6-Chloro-2-{2-[3-(pyrid-2-yl)isoxazol-5-yl]pyrrolidin-1-yl}-4-(5-cyclopropyl-1H-pyrazol-3-ylamino)pyrimidine;

6-(2-Hydroxyethoxy)-2-{2-[3-(pyrid-2-yl)isoxazol-5-yl]pyrrolidin-1-yl}-4-(5-cyclopropyl-1H-pyrazol-3-ylamino)pyrimidine;

6-[4-(tert-Butoxycarbonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine;

6-[2-(tert-Butoxycarbonyl)-2,7-diazaspiro[3.5]nonan-7-yl]-4-(5-methyl-1H-pyrazol-3-ylamino)-2-[2-{3-(pyrid-2-yl)isoxazol-5-yl}pyrrolidin-1-yl]pyrimidine;

6-(2,7-Diazaspiro[3.5]nonan-7-yl)-4-(5-methyl-1H-pyrazol-3-ylamino)-2-[2-{3-(pyrid-2-yl)isoxazol-5-yl}pyrrolidin-1-yl]pyrimidine;

S-6-[4-(2-Aminoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(3-Hydroxypropyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(2-Cyanoethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[4-(2-Methoxyethyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-(4-Acetylpiperazin-1-yl)-4-(5-methyl-1H-pyrazol-3-ylamino)-2-[2-{3-(pyrid-2-yl)isoxazol-5-yl}pyrrolidin-1-yl]pyrimidine;

S-6-[4-(Ethylsulphonyl)piperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[2-(2-Hydroxyethoxy)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[2-(Acetoamido)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[2-Aminoethylamino]-4-(5-methyl-1H-pyrazol-3-ylamino)-2-[2-{3-(pyrid-2-yl)isoxazol-5-yl}pyrrolidin-1-yl]pyrimidine;

S-6-[4-Methylcyclohexylamino]-4-(5-methyl-1H-pyrazol-3-ylamino)-2-[2-{3-(pyrid-2-yl)isoxazol-5-yl}pyrrolidin-1-yl]pyrimidine;

S-6-[4-Hydroxycyclohexylamino]-4-(5-methyl-1H-pyrazol-3-ylamino)-2-[2-{3-(pyrid-2-yl)isoxazol-5-yl}pyrrolidin-1-yl]pyrimidine;

S-6-[cis-3,4-Dihydroxypyrrolidin-1-yl]-4-(5-methyl-1H-pyrazol-3-ylamino)-2-[2-{3-(pyrid-2-yl)isoxazol-5-yl}pyrrolidin-1-yl]pyrimidine;

S-6-Chloro-4-(5-methyl-1H-pyrazol-3-ylamino)-2-[2-{3-(pyrimid-2-yl)isoxazol-5-yl}pyrrolidin-1-yl]pyrimidine;

S-6-Chloro-4-(5-methyl-1H-pyrazol-3-ylamino)-2-[2-{3-(3-methoxypyrazin-2-yl)isoxazol-5-yl}pyrrolidin-1-yl]pyrimidine;

S-6-Morpholino-4-(5-methyl-1H-pyrazol-3-ylamino)-2-[2-{3-(pyrimid-2-yl)isoxazol-5-yl}pyrrolidin-1-yl]pyrimidine;

S-6-Morpholino-4-(5-methyl-1H-pyrazol-3-ylamino)-2-[2-{3-(3-methoxypyrazin-2-yl)isoxazol-5-yl}pyrrolidin-1-yl]pyrimidine;

S-6-Morpholino-4-(5-methyl-1H-pyrazol-3-ylamino)-2-[2-{3-(3-hydroxypyrazin-2-yl)isoxazol-5-yl}pyrrolidin-1-yl]pyrimidine;

S-6-[4-Methylpiperazin-1-yl]-4-(5-methyl-1H-pyrazol-3-ylamino)-2-[2-{3-(pyrid-2-yl)isoxazol-5-yl}pyrrolidin-1-yl]pyrimidine;

S-6-[Cyclobutylamino]-4-(5-methyl-1H-pyrazol-3-ylamino)-2-[2-{3-(pyrid-2-yl)isoxazol-5-yl}pyrrolidin-1-yl]pyrimidine;

S-6-[3-Isopropoxyprop-1-ylamino]-4-(5-methyl-1H-pyrazol-3-ylamino)-2-[2-{3-(pyrid-2-yl)isoxazol-5-yl}pyrrolidin-1-yl]pyrimidine;

S-6-[2-(Morpholin-4-yl)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[2-(Dimethylamino)ethylamino]-4-(5-methyl-1H-pyrazol-3-ylamino)-2-[2-{3-(pyrid-2-yl)isoxazol-5-yl}pyrrolidin-1-yl]pyrimidine;

S-6-[(2S)-2-Hydroxyprop-1-ylamino]-4-(5-methyl-1H-pyrazol-3-ylamino)-2-[2-{3-(pyrid-2-yl)isoxazol-5-yl}pyrrolidin-1-yl]pyrimidine;
S-6-[2-Methylprop-1-ylamino]-4-(5-methyl-1H-pyrazol-3-ylamino)-2-[2-{3-(pyrid-2-yl)isoxazol-5-yl}pyrrolidin-1-yl]pyrimidine;
S-6-[3-Methoxypropylamino]-4-(5-methyl-1H-pyrazol-3-ylamino)-2-[2-{3-(pyrid-2-yl)isoxazol-5-yl}pyrrolidin-1-yl]pyrimidine;
S-6-[4-Ethylpiperazin-1-yl]-4-(5-methyl-1H-pyrazol-3-ylamino)-2-[2-{3-(pyrid-2-yl)isoxazol-5-yl}pyrrolidin-1-yl]pyrimidine;
S-6-[3-Ethoxypropylamino]-4-(5-methyl-1H-pyrazol-3-ylamino)-2-[2-{3-(pyrid-2-yl)isoxazol-5-yl}pyrrolidin-1-yl]pyrimidine;
S-6-[(2R)-Tetrahydrofuran-2-ylmethylamino]-4-(5-methyl-1H-pyrazol-3-ylamino)-2-[2-{3-(pyrid-2-yl)isoxazol-5-yl}pyrrolidin-1-yl]pyrimidine;
S-6-(2-Isopropoxyethylamino)-4-(5-methyl-1H-pyrazol-3-ylamino)-2-[2-{3-(pyrid-2-yl)isoxazol-5-yl}pyrrolidin-1-yl]pyrimidine;
S-6-Morpholino-4-(5-cyclopropyl-1H-pyrazol-3-ylamino)-2-[2-{3-(pyrimid-2-yl)isoxazol-5-yl}pyrrolidin-1-yl]pyrimidine;
S-6-Methylamino-4-(5-cyclopropyl-1H-pyrazol-3-ylamino)-2-[2-{3-(pyrimid-2-yl)isoxazol-5-yl}pyrrolidin-1-yl]pyrimidine;
S-6-Chloro-4-(5-cyclopropyl-1H-pyrazol-3-ylamino)-2-[2-{3-(pyrimid-2-yl)isoxazol-5-yl}pyrrolidin-1-yl]pyrimidine;
S-6-Methyl-4-(5-methyl-1H-pyrazol-3-ylamino)-2-[2-{3-(3-methoxypyrazin-2-yl)isoxazol-5-yl}pyrrolidin-1-yl]pyrimidine;
S-6-Methoxy-4-(5-cyclopropyl-1H-pyrazol-3-ylamino)-2-[2-{3-(pyrimidin-2-yl)isoxazol-5-yl}pyrrolidin-1-yl]pyrimidine;
S-6-(2-Methoxyethoxy)-4-(5-cyclopropyl-1H-pyrazol-3-ylamino)-2-[2-{3-(pyrimidin-2-yl)isoxazol-5-yl}pyrrolidin-1-yl]pyrimidine;
S-4-(5-Ethyl-1H-pyrazol-3-ylamino)-2-{2-[3-(pyrid-2-yl)isoxazol-5-yl]pyrrolidin-1-yl}pyrimidine;
S-4-(5-Cyclopropyl-1H-pyrazol-3-ylamino)-2-{2-[3-(pyrid-2-yl)isoxazol-5-yl]pyrrolidin-1-yl}pyrimidine;
S-4-(5- Ethyl-1H-pyrazol-3-ylamino)-5-fluoro-2-{2-[3-(pyrid-2-yl)isoxazol-5-yl]pyrrolidin-1-yl}pyrimidine;
S-4-(5-Cyclopropyl-1H-pyrazol-3-ylamino)-5-fluoro-2-{2-[3-(pyrid-2-yl)isoxazol-5-yl]pyrrolidin-1-yl}pyrimidine;
4-(5-Cyclopropyl-1H-pyrazol-3-ylamino)-6-methyl-2-{2-[3-(pyrimid-2-yl)isoxazol-5-yl]pyrrolidin-1-yl}pyrimidine;
4-(5-Cyclopropyl-1H-pyrazol-3-ylamino)-6-methyl-2-{2-[3-(pyrazin-2-yl)isoxazol-5-yl]pyrrolidin-1-yl}pyrimidine;
4-(5-Cyclopropyl-1H-pyrazol-3-ylamino)-6-methyl-2-{2-[3-(pyrid-2-yl)isoxazol-5-yl]pyrrolidin-1-yl}pyrimidine;
6-(3-Hydroxypropyl)-4-(5-methyl-1H-pyrazol-3-ylamino)-2-{2-[3-(pyrid-2-yl)isoxazol-5-yl]pyrrolidin-1-yl}pyrimidine;
S-6-(3- Hydroxypropyl)-4-(5-methyl-1H-pyrazol-3-ylamino)-2-{2-[3-(pyrid-2-yl)isoxazol-5-yl]pyrrolidin-1-yl}pyrimidine;
S-6- Propyl-2-{2-[3-(pyrid-2-yl)isoxazol-5-yl]pyrrolidin-1-yl}-4-(5-methyl-1H-pyrazol-3-ylamino)pyrimidine;
S-6-Chloro-4-(5-ethyl-1H-pyrazol-3-ylamino)-2-[2-{3-(pyrid-2-yl)isoxazol-5-yl}pyrrolidin-1-yl]pyrimidine;
S-6-(2-Hydroxyethoxy)-4-(5-ethyl-1H-pyrazol-3-ylamino)-2-[2-{3-(pyrid-2-yl)isoxazol-5-yl}pyrrolidin-1-yl]pyrimidine;
S-6-(2-Methoxyethoxy)-4-(5-ethyl-1H-pyrazol-3-ylamino)-2-[2-{3-(pyrid-2-yl)isoxazol-5-yl}pyrrolidin-1-yl]pyrimidine;
S-6-Morpholino-4-(5-ethyl-1H-pyrazol-3-ylamino)-2-[2-{3-(pyrid-2-yl)isoxazol-5-yl}pyrrolidin-1-yl]pyrimidine;
S-6-(4-Methylpiperazin-1-yl)-4-(5-ethyl-1H-pyrazol-3-ylamino)-2-[2-{3-(pyrid-2-yl)isoxazol-5-yl}pyrrolidin-1-yl]pyrimidine;
S-6-Chloro-4-(5-ethyl-1H-pyrazol-3-ylamino)-2-[2-{3-(2-pyrazinyl)isoxazol-5-yl}pyrrolidin-1-yl]pyrimidine;
S-6-Methoxy-4-(5-methyl-1H-pyrazol-3-ylamino)-2-[2-{3-(pyrid-2-yl)isoxazol-5-yl}pyrrolidin-1-yl]pyrimidine;
S-6-(2-Methoxyethoxy)-4-(5-methyl-1H-pyrazol-3-ylamino)-2-[2-{3-(pyrid-2-yl)isoxazol-5-yl}pyrrolidin-1-yl]pyrimidine;
S-6-Pyrrolidin-1-yl-4-(5-methyl-1H-pyrazol-3-ylamino)-2-[2-{3-(pyrid-2-yl)isoxazol-5-yl}pyrrolidin-1-yl]pyrimidine;
S-6-Methoxymethyl-4-(5-methyl-1H-pyrazol-3-ylamino)-2-[2-{3-(pyrid-2-yl)isoxazol-5-yl}pyrrolidin-1-yl]pyrimidine;
S-6-Morpholinocarbonyl-4-(5-methyl-1H-pyrazol-3-ylamino)-2-[2-{3-(pyrid-2-yl)isoxazol-5-yl}pyrrolidin-1-yl]pyrimidine;
S-6-Carbamoyl-4-(5-methyl-1H-pyrazol-3-ylamino)-2-[2-{3-(pyrid-2-yl)isoxazol-5-yl}pyrrolidin-1-yl]pyrimidine;
S-5-Fluoro-4-(5-methyl-1H-pyrazol-3-ylamino)-2-[2-{3-(pyrid-2-yl)isoxazol-5-yl}pyrrolidin-1-yl]pyrimidine;
S-4-(5-Methyl-1H-pyrazol-3-ylamino)-2-[2-{3-(pyrid-2-yl)isoxazol-5-yl}pyrrolidin-1-yl]pyrimidine;
S-4-(5-Methyl-1H-pyrazol-3-ylamino)-6-(2-hydroxyethoxy)-2-[2-{3-(pyrid-2-yl)isoxazol-5-yl}pyrrolidin-1-yl]pyrimidine;
S-4-(5-Methyl-1H-pyrazol-3-ylamino)-6-(2-{N-[2-hydroxyethyl]-N-methyl-amino}ethoxy)-2-[2-{3-(pyrid-2-yl)isoxazol-5-yl}pyrrolidin-1-yl]pyrimidine;
S-4-(5-Methyl-1H-pyrazol-3-ylamino)-6-(2-morpholinoethoxy)-2-[2-{3-(pyrid-2-yl)isoxazol-5-yl}pyrrolidin-1-yl]pyrimidine;
S-4-(5-Methyl-1H-pyrazol-3-ylamino)-6-(methylthio)-2-[2-{3-(pyrid-2-yl)isoxazol-5-yl}pyrrolidin-1-yl]pyrimidine;
4-(5-Methyl-1H-pyrazol-3-ylamino)-6-(tetrahydrofuran-3-ylmethoxy)-2-[2-{3-(pyrid-2-yl)isoxazol-5-yl}pyrrolidin-1-yl]pyrimidine;
S-4-(5-Methyl-1H-pyrazol-3-ylamino)-6-(2-(2-hydroxyethoxy)ethoxy)-2-[2-{3-(pyrid-2-yl)isoxazol-5-yl}pyrrolidin-1-yl]pyrimidine;
4-(5-Methyl-1H-pyrazol-3-ylamino)-6-(2-methoxyethoxy)-2-[2-{3-(pyrid-2-yl)isoxazol-5-yl}pyrrolidin-1-yl]pyrimidine;
S-4-(5-Methyl-1H-pyrazol-3-ylamino)-6-(3-hydroxypropyloxy)-2-[2-{3-(pyrid-2-yl)isoxazol-5-yl}pyrrolidin-1-yl]pyrimidine;
S-4-(5-Methyl-1H-pyrazol-3-ylamino)-6-[2-(2-methoxyethoxy)ethoxy]-2-[2-{3-(pyrid-2-yl)isoxazol-5-yl}pyrrolidin-1-yl]pyrimidine;
S-4-(5-Methyl-1H-pyrazol-3-ylamino)-6-(2-ethoxyethoxy)-2-[2-{3-(pyrid-2-yl)isoxazol-5-yl}pyrrolidin-1-yl]pyrimidine;

S-4-(5-Methyl-1H-pyrazol-3-ylamino)-6-(3-morpholinoprop-1-yloxy)-2-[2-{3-(pyrid-2-yl)isoxazol-5-yl}pyrrolidin-1-yl]pyrimidine;

S-4-(5-Methyl-1H-pyrazol-3-ylamino)-6-(3-methoxyprop-1-yloxy)-2-[2-{3-(pyrid-2-yl)isoxazol-5-yl}pyrrolidin-1-yl]pyrimidine;

S-4-(5-Methyl-1H-pyrazol-3-ylamino)-6-[2-(2-oxopyrrolidin-1-yl)ethoxy]-2-[2-{3-(pyrid-2-yl)isoxazol-5-yl}pyrrolidin-1-yl]pyrimidine;

S-4-(5-Methyl-1H-pyrazol-3-ylamino)-6-[(2S)-2-methoxyprop-1-yloxy]-2-[2-{3-(pyrid-2-yl)isoxazol-5-yl}pyrrolidin-1-yl]pyrimidine;

S-4-(5-Methyl-1H-pyrazol-3-ylamino)-6-[3-(methylthio)prop-1-yloxy]-2-[2-{3-(pyrid-2-yl)isoxazol-5-yl}pyrrolidin-1-yl]pyrimidine;

S-4-(5-Methyl-1H-pyrazol-3-ylamino)-6-[(2S)-5-oxopyrrolidin-2-yl)methoxy]-2-[2-{3-(pyrid-2-yl)isoxazol-5-yl}pyrrolidin-1-yl]pyrimidine;

S-4-(5-Methyl-1H-pyrazol-3-ylamino)-6-[(2R)-5-oxopyrrolidin-2-yl)methoxy]-2-[2-{3-(pyrid-2-yl)isoxazol-5-yl}pyrrolidin-1-yl]pyrimidine;

S-4-(5-Methyl-1H-pyrazol-3-ylamino)-6-[2-(imidazolid-2-on-1-yl) ethoxy]-2-[2-{3-(pyrid-2-yl)isoxazol-5-yl}pyrrolidin-1-yl]pyrimidine;

S-4-(5-Methyl-1H-pyrazol-3-ylamino)-6-ethoxy-2-[2-{3-(pyrid-2-yl)isoxazol-5-yl}pyrrolidin-1-yl]pyrimidine;

S-4-(5-Methyl-1H-pyrazol-3-ylamino)-6-hydroxy-2-[2-{3-(pyrid-2-yl)isoxazol-5-yl}pyrrolidin-1-yl]pyrimidine;

S-4-(5-Methyl-1H-pyrazol-3-ylamino)-6-(2-methoxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-(2-hydroxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-[(2R)-2-hydroxyprop-1-yloxy]-2-[2-{3-(pyrid-2-yl)isoxazol-5-yl}pyrrolidin-1-yl]pyrimidine;

S-4-(5-Ethyl-1H-pyrazol-3-ylamino)-6-(2-methoxyethoxy)-2-[2-{3-(pyrazin-2-yl)isoxazol-5-yl}pyrrolidin-1-yl]pyrimidine;

S-4-(5-Ethyl-1H-pyrazol-3-ylamino)-6-methoxy-2-[2-{3-(pyrazin-2-yl)isoxazol-5-yl}pyrrolidin-1-yl]pyrimidine;

S-4-(5-Cyclopropyl-1H-pyrazol-3-ylamino)-6-(2-hydroxyethoxy)-2-[2-{3-(thiazol-2-yl)isoxazol-5-yl}pyrrolidin-1-yl]pyrimidine;

S-4-(5-Methyl-1H-pyrazol-3-ylamino)-6-(tetrahydropyran-4-yloxy)-2-[2-{3-(pyrid-2-yl)isoxazol-5-yl}pyrrolidin-1-yl]pyrimidine;

S-5-Fluoro-4-(5-methyl-1H-pyrazol-3-ylamino)-2-[2-{3-(thiazol-2-yl)isoxazol-5-yl}pyrrolidin-1-yl]pyrimidine;

S-5-Chloro-4-(5-methyl-1H-pyrazol-3-ylamino)-2-[2-{3-(thiazol-4-yl)isoxazol-5-yl}pyrrolidin-1-yl]pyrimidine;

S-5-Fluoro-4-(5-ethyl-1H-pyrazol-3-ylamino)-2-[2-{3-(thiazol-2-yl)isoxazol-5-yl}pyrrolidin-1-yl]pyrimidine;

S-4-(5-Methyl-1H-pyrazol-3-ylamino)-2-[2-{3-(thiazol-2-yl)isoxazol-5-yl}pyrrolidin-1-yl]pyrimidine;

S-4-(5-Ethyl-1H-pyrazol-3-ylamino)-2-[2-{3-(thiazol-2-yl)isoxazol-5-yl}pyrrolidin-1-yl]pyrimidine;

S-4-(5-Cyclopropyl-1H-pyrazol-3-ylamino)-2-[2-{3-(thiazol-2-yl)isoxazol-5-yl}pyrrolidin-1-yl]pyrimidine;

S-4-(5-Cyclopropyl-1H-pyrazol-3-ylamino)-5-fluoro-2-[2-{3-(thiazol-2-yl)isoxazol-5-yl}pyrrolidin-1-yl]pyrimidine;

S-6-Chloro-4-(5-methyl-1H-pyrazol-3-ylamino)-2-[2-{3-(thiazol-2-yl)isoxazol-5-yl}pyrrolidin-1-yl]pyrimidine;

S-6-Chloro-4-(5-cyclopropyl-1H-pyrazol-3-ylamino)-2-[2-{3-(thiazol-2-yl)isoxazol-5-yl}pyrrolidin-1-yl]pyrimidine;

S-6-Morpholino-4-(5-methyl-1H-pyrazol-3-ylamino)-2-[2-{3-(thiazol-2-yl)isoxazol-5-yl}pyrrolidin-1-yl]pyrimidine;

S-6-Morpholino-4-(5-ethyl-1H-pyrazol-3-ylamino)-2-[2-{3-(pyrazin-2-yl)isoxazol-5-yl}pyrrolidin-1-yl]pyrimidine;

S-6-(2-Methoxyethylamino)-4-(5-methyl-1H-pyrazol-3-ylamino)-2-[2-{3-(thiazol-2-yl)isoxazol-5-yl}pyrrolidin-1-yl]pyrimidine;

S-6-Methylamino-4-(5-methyl-1H-pyrazol-3-ylamino)-2-[2-{3-(thiazol-2-yl)isoxazol-5-yl}pyrrolidin-1-yl]pyrimidine;

S-6-(4-Methylpiperazin-1yl)-4-(5-methyl-1H-pyrazol-3-ylamino)-2-[2-{3-(thiazol-2-yl)isoxazol-5-yl}pyrrolidin-1-yl]pyrimidine;

S-6-Methyl-4-(5-methyl-1H-pyrazol-3-ylamino)-2-[2-{3-(thiazol-2-yl)isoxazol-5-yl}pyrrolidin-1-yl]pyrimidine;

S-6-[3-(Methylsulphonyl)propyl-1-oxy]-4-(5-methyl-1H-pyrazol-3-ylamino)-2-[2-{3-(pyrid-2-yl)isoxazol-5-yl}pyrrolidin-1-yl]pyrimidine;

S-4-(5-Cyclopropyl-1H-pyrazol-3-ylamino)-6-(2-methoxyethoxy)-2-[2-{3-(pyrazin-2-yl)isoxazol-5-yl}pyrrolidin-1-yl]pyrimidine;

S-6-Methyl-4-(5-Ethyl-1H-pyrazol-3-ylamino)-2-[2-{3-(3-methoxypyrazin-2-yl)isoxazol-5-yl}pyrrolidin-1-yl]pyrimidine;

S-6-Chloro-4-(5-Ethyl-1H-pyrazol-3-ylamino)-2-[2-{3-(3-methoxypyrazin-2-yl)isoxazol-5-yl}pyrrolidin-1-yl]pyrimidine;

S-6-Chloro-4-(5-ethyl-1H-pyrazol-3-ylamino)-2-[2-{3-(pyrimid-2-yl)isoxazol-5-yl}pyrrolidin-1-yl]pyrimidine;

S-6-Methoxy-4-(5-ethyl-1H-pyrazol-3-ylamino)-2-[2-{3-(pyrimid-2-yl)isoxazol-5-yl}pyrrolidin-1-yl]pyrimidine;

S-6-Ethyl-4-(5-ethyl-1H-pyrazol-3-ylamino)-2-[2-{3-(pyrimid-2-yl)isoxazol-5-yl}pyrrolidin-1-yl]pyrimidine;

S-6-Methylamino-4-(5-ethyl-1H-pyrazol-3-ylamino)-2-[2-{3-(pyrimid-2-yl)isoxazol-5-yl}pyrrolidin-1-yl]pyrimidine;

S-6-Ethyl-4-(5-cyclopropyl-1H-pyrazol-3-ylamino)-2-[2-{3-(pyrimid-2-yl)isoxazol-5-yl}pyrrolidin-1-yl]pyrimidine;

S-6-Cyclopropyl-4-(5-cyclopropyl-1H-pyrazol-3-ylamino)-2-[2-{3-(pyrimid-2-yl)isoxazol-5-yl}pyrrolidin-1-yl]pyrimidine;

S-6-Cyclopropyl-4-(5-ethyl-1H-pyrazol-3-ylamino)-2-[2-{3-(pyrimid-2-yl)isoxazol-5-yl}pyrrolidin-1-yl]pyrimidine;

S-6-(2-Methoxyethoxy)-4-(5-ethyl-1H-pyrazol-3-ylamino)-2-[2-{3-(pyrimid-2-yl)isoxazol-5-yl}pyrrolidin-1-yl]pyrimidine;

S-6-Methyl-4-(5-Methyl-1H-pyrazol-3-ylamino)-2-[2-[3-(2-methoxypyrid-3-yl)isoxazol-5-yl]pyrrolidin-1-yl]pyrimidine;

S-5-Fluoro-4-(5-cyclopropyl-1H-pyrazol-3-ylamino)-2-
[2-[3-(2-methoxypyrid-3-yl)isoxazol-5-yl]pyrrolidin-
1-yl]pyrimidine;
S-5-Fluoro-4-(5-ethyl-1H-pyrazol-3-ylamino)-2-[2-[3-
(2-methoxypyrid-3-yl)isoxazol-5-yl]pyrrolidin-1-yl]
pyrimidine;
S-6-(2-Hydroxyethoxy)-4-(5-methyl-1H-pyrazol-3-
ylamino)-2-[2-[3-(2-methoxypyrid-3-yl)isoxazol-5-yl]
pyrrolidin-1-yl]pyrimidine;
S-6-Chloro-4-(5-cyclopropyl-1H-pyrazol-3-ylamino)-2-
[2-[3-(2-methoxypyrid-3-yl)isoxazol-5-yl]pyrrolidin-
1-yl]pyrimidine;
S-6-Chloro-4-(5-ethyl-1H-pyrazol-3-ylamino)-2-[2-[3-
(2-methoxypyrid-3-yl)isoxazol-5-yl]pyrrolidin-1-yl]
pyrimidine;
S-6-(2- Hydroxyethoxy)-4-(5-cyclopropyl-1H-pyrazol-3-
ylamino)-2-[2-[3-(2-methoxypyrid-3-yl)isoxazol-5-yl]
pyrrolidin-1-yl]pyrimidine;
S-5-Fluoro-4-(5-methyl-1H-pyrazol-3-ylamino)-2-[2-[3-
(2-methoxypyrid-3-yl)isoxazol-5-yl]pyrrolidin-1-yl]
pyrimidine;
S-6-(2- Hydroxyethoxy)-4-(5-ethyl-1H-pyrazol-3-
ylamino)-2-[2-[3-(2-methoxypyrid-3-yl)isoxazol-5-yl]
pyrrolidin-1-yl]pyrimidine;
S-6-Methyl-4-(5-cyclopropyl-1H-pyrazol-3-ylamino)-2-
[2-{3-(3-methoxypyrazin-2-yl)isoxazol-5-
yl}pyrrolidin-1-yl]pyrimidine;
S-6-Morpholino-4-(5-ethyl-1H-pyrazol-3-ylamino)-2-[2-
{3-(3-methoxypyrazin-2-yl)isoxazol-5-yl}pyrrolidin-
1-yl]pyrimidine;
S-6-Chloro-4-(5-methyl-1H-pyrazol-3-ylamino)-2-[2-[3-
(2-methoxypyrid-3-yl)isoxazol-5-yl]pyrrolidin-1-yl]
pyrimidine;
S-6-Methyl-4-(5-ethyl-1H-pyrazol-3-ylamino)-2-[2-{3-
(pyrimid-2-yl)isoxazol-5-yl}pyrrolidin-1-yl]pyrimi-
dine;
S-6-Methyl-4-(5-ethyl-1H-pyrazol-3-ylamino)-2-[2-{3-
(pyrid-2-yl)isoxazol-5-yl}pyrrolidin-1-yl]pyrimidine;
S-6-Morpholino-4-(5-ethyl-1H-pyrazol-3-ylamino)-2-[2-
{3-(3-hydroxypyrazin-2-yl)isoxazol-5-yl}pyrrolidin-1-
yl]pyrimidine; and
S-6-(3-Methoxypropyl)-4-(5-methyl-1H-pyrazol-3-
ylamino)-2-[2-{3-(pyrid-2-yl)isoxazol-5-
yl}pyrrolidin-1-yl]pyrimidine;
and pharmaceutically acceptable salts thereof.

25. A pharmaceutical composition comprising a compound of formula (I), or a pharmaceutically acceptable salt thereof, as claimed in claim 1, in association with a pharmaceutically acceptable adjuvant, diluent or carrier.

26. A process for the preparation of a pharmaceutical composition as claimed in claim 25 which comprises mixing a compound of formula (I), or a pharmaceutically acceptable salt thereof, as defined in claim 1 with a pharmaceutically acceptable adjuvant, diluent or carrier.

27. A method of treating cancer which comprises administering to a patient a therapeutically effective amount of a compound of formula (I) or a pharmaceutically acceptable salt thereof as claimed in claim 1, wherein said cancer is selected from breast, prostate, and colon cancer.

28. A process for preparing a compound of formula (I) as defined in claim 1, or a pharmaceutically acceptable salt thereof, which comprises (i) reacting a compound of formula (II)

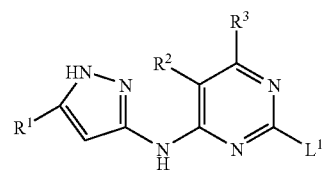

(II)

wherein $L^1$ represents a leaving group and $R^1$, $R^2$ and $R^3$ are as defined in formula (I) except that any functional group is protected if necessary, with a compound of formula (III),

(III)

wherein $Q^1$ and $Q^2$ are as defined in formula (I) except that any functional group is protected if necessary;

or (ii) reacting a compound of formula (IV)

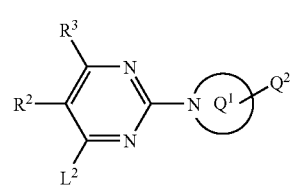

(IV)

wherein $L^2$ represents a leaving group and $R^2$, $R^3$, $Q^1$ and $Q^2$ are as defined in formula (I) except that any functional group is protected if necessary, with a compound of formula (V),

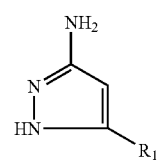

(V)

wherein $R^1$ is as defined in formula (I) except that any functional group is protected if necessary;

or (iii) reacting a compound of formula (VI)

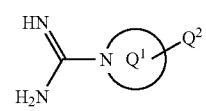

(VI)

wherein $Q^1$ and $Q^2$ are as defined in formula (I) except that any functional group is protected if necessary, with a compound of formula (VII)

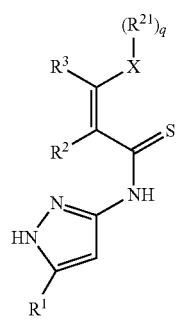

(VII)

wherein X represents an oxygen atom and q is 1 or X represents a nitrogen atom and q is 2, $R^{21}$ independently represents a (C1-C6)alkyl group and $R^2$ and $R^3$ are as defined in formula (I) except that any functional group is protected if necessary;

or (iv) reacting a compound of formula (VIII)

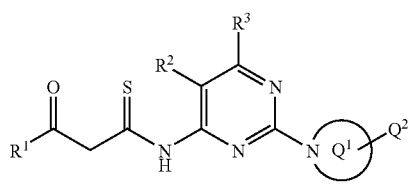

(VIII)

wherein $R^1$, $R^2$, $R^3$, $NQ^1$ and $Q^2$ are as defined in formula (I) except that any functional group is protected if necessary with hydrazine;

or (v) for compounds of formula (I) wherein $R^3$ is a (C1-C6) alkoxy, amino, (C1-C6)alkylamino, di-[(C1-C6)alkyl] amino, amino, —$OR^{3b}$, —$SR^{3b}$, —$NHR^{3b}$, —$N[(C1-C6)alkyl]R^{3b}$ or —$S(O)_mR^{3a}$ group wherein m is 0 and $R^{3a}$ and $R^{3b}$ are as defined above (and the group $R^3$ is optionally substituted by at least one group as defined above), reacting a compound of formula (IX)

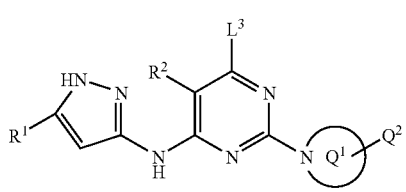

(IX)

wherein $L^3$ represents a leaving group and $R^1$, $R^2$, $Q^1$ and $Q^2$ are as defined in formula (I) except that any functional group is protected if necessary, with a compound of formula H-Xa, wherein Xa is selected from $OR^{22}$, $NH_2$, $NHR^{22}$, $N(R^{22})_2$, $NH_2$, $OR^{3b}$, $SR^{3b}$, $NHR^{3b}$, $N[(C1-C6)alkyl]R^{3b}$ and $SR^{3a}$, wherein $R^{22}$ is an, optionally substituted, (C1-C6)alkyl group and $R^{3a}$ and $R^{3b}$ are each as defined above except that any functional group is protected if necessary;

or (vi) for compounds of formula (I) wherein $R^3$ is an, optionally substituted, saturated monocyclic 5- or 6-membered heterocyclic ring comprising at least one ring nitrogen and, optionally, one or more additional heteroatoms selected from nitrogen, oxygen and sulphur, reacting a compound of formula (IX), with a compound of formula (Xb)

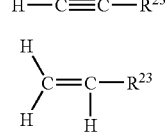

(Xb)

wherein $Q^4$ is a saturated monocyclic 5- or 6-membered heterocyclic ring optionally comprising one or more heteroatoms selected from nitrogen, oxygen and sulphur in addition to the nitrogen atom shown above, which ring is optionally substituted by at least one group as defined above, or with an optionally substituted 2,7-diazaspiro[3.5]nonane group; or (vii) for compounds of formula (I) wherein $R^3$ is a (C2-C6) alkenyl or (C2-C6)alkynyl group, and the group $R^3$ is optionally substituted by at least one group as defined above, reacting a compound of formula (IX), with a compound of formula (Xc) or of formula (Xc')

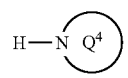

(Xc)

(Xc')

wherein $R^{23}$ is selected from hydrogen and an, optionally substituted, (1-4C)alkyl or (C1-C4)alkoxy carbonyl group;

or (viii) for compounds of formula (I) wherein $R^3$ is attached to the pyrimidine ring through a carbon atom, reacting a compound of formula (IX), with a compound of the formula M-$R^3$, wherein $R^3$ is appropriately selected from the $R^3$ groups as defined above and M is a metallic group;

(ix) for compounds of formula (I) wherein $R^3$ is a (C1-C6) alkoxycarbonyl group (and the group $R^3$ is optionally substituted by at least one group as defined above), reacting a compound of formula (X)

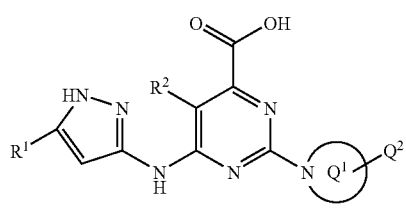

(X)

wherein $R^1$, $R^2$, $Q^1$ and $Q^2$ are as defined in formula (I) except that any functional group is protected if necessary, with a compound of formula H—O—(C1-C6) alkyl, wherein the (C1-C6)alkyl group is optionally substituted by at least one group as defined above and any functional group is protected if necessary; or (x) for compounds of formula (I) wherein $R^3$ is a 5-membered heteroaromatic ring comprising at least one heteroatom selected from nitrogen, oxygen and sulphur (and the group $R^3$ is optionally substituted by at least one group as defined above), conducting an internal condensation reaction using an appropriate starting material and a suitable dehydrating agent; or (xi) for compounds of formula (I) wherein $R^3$ is a (C1-C6) alkyl, (C3-C6)alkenyl, (C3-C6)alkynyl or (C1-C6) alkoxy group substituted by at least one group as defined above, reacting a compound of formula (XII)

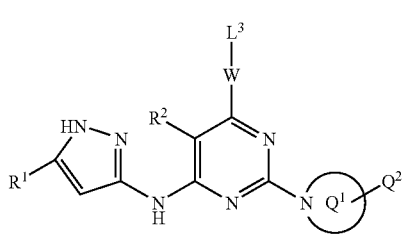

(XII)

wherein $L^3$ represents a leaving group as defined above, W represents an optionally substituted (C1-C6)alkyl, (C3-C6)alkenyl, (C3-C6)alkynyl or (C1-C6)alkoxy group and $R^1$, $R^2$ $Q^1$ and $Q^2$ are as defined in formula (I) except that any functional group is protected if necessary, with a compound of formula H-Xa, (Xb), (Xc), (Xc') or M-$R^3$ as defined above; and optionally after (i), (ii), (iii), (iv) (v), (vi), (vii), (viii), (ix), (x) or (xi) carrying out one or more of the following:
converting the compound obtained to a further compound of the invention forming a pharmaceutically acceptable salt of the compound.

29. The method of claim 28, wherein said leaving group is selected from halogen and sulphonyloxy.

30. The method of claim 29, wherein said sulphonyloxy is selected from methanesulphonyloxy or toluene-4-sulphonyloxy.

31. The method of claim 28, wherein said metallic group is selected from ZnBr, B(OH)$_2$, CuCN, and SnBu$_3$.

32. The method of claim 28, wherein for compounds of formula (I) wherein $R^3$ is a 1,3,4-oxadiazole group, reacting a compound of formula (XI)

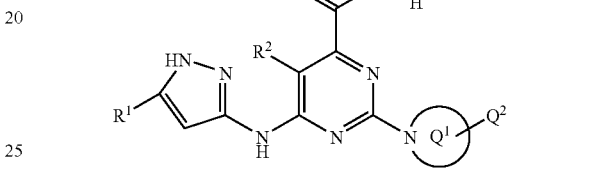

(XI)

wherein Z represents any suitable substituent for $R^3$ as defined above and $R^1$, $R^2$, $Q^1$ and $Q^2$ are as defined in formula (I), except that any functional group is protected if necessary, with a suitable dehydrating agent.

33. The method of claim 32, wherein said dehydrating agent is (methoxycarbonylsulphamoyl)triethylammonium hydroxide.

* * * * *